(12) United States Patent
Haefner et al.

(10) Patent No.: US 7,968,699 B2
(45) Date of Patent: Jun. 28, 2011

(54) MULTIPLE PROMOTERS AND THE USE THEREOF FOR GENE EXPRESSION

(75) Inventors: Stefan Haefner, Speyer (DE); Hartwig Schroder, Nussloch (DE); Oskar Zelder, Speyer (DE); Corinna Klopprogge, Mannheim (DE); Andrea Herold, Ketsch (DE)

(73) Assignee: BASF Aktiengesellschaft (DE)

( * ) Notice: Subject to any disclaimer, the term of this patent is extended or adjusted under 35 U.S.C. 154(b) by 177 days.

(21) Appl. No.: 12/048,599

(22) Filed: Mar. 14, 2008

(65) Prior Publication Data

US 2008/0268502 A1   Oct. 30, 2008

Related U.S. Application Data

(62) Division of application No. 11/793,909, filed as application No. PCT/EP2005/013809 on Dec. 21, 2005, now abandoned.

(30) Foreign Application Priority Data

Dec. 22, 2004   (DE) .......................... 10 2004 061 846

(51) Int. Cl.
  *C07H 21/04*   (2006.01)
  *C12N 15/85*   (2006.01)
(52) U.S. Cl. .................. 536/24.1; 435/320.1; 435/252.3
(58) Field of Classification Search .................. None
See application file for complete search history.

(56) References Cited

U.S. PATENT DOCUMENTS 7,141,388 B2 *   11/2006   Crafton et al. ............... 435/69.1

FOREIGN PATENT DOCUMENTS

| CA | 2 548 306 A1 | 6/2005 |
|---|---|---|
| CA | 2 549 171 A1 | 6/2005 |
| WO | WO-2005/059143 A1 | 6/2005 |
| WO | WO-2005/059144 A1 | 6/2005 |

OTHER PUBLICATIONS

Ivanov, I., et al., Expression of Human Alpha 1 Interferon Genes in Vectors Containing Tandemly Located Promoters Recognized by Two Different RNA Polymerases (*Escherichia coli* and T7), FEMS Microbiology Letters, 1993, vol. 108, pp. 231-236.
Follettie, M. T., et al., "Gene Structure and Expression of the *Corynebacterium flavum* N13 *ask-asd* Operon", Journal of Bacteriology, 1993, vol. 175, No. 13, pp. 4096-4103.
Murakami, Y., et al, "Construction of New Excretion Vectors: Two and Three Tandemly Located Promoters are Active for Extracellular Protein Production from *Escherichia coli*", Appl. Microbial. Biotechnol., 1989, vol. 30, pp. 619-623.
Kalinowski, J., et al., "The Complete *Corynebacterium glutamicum* ATCC 13032 Genome Sequence and its Impact on the Production of L-Aspartate-Derived Amino Acids and Vitamins", Journal of Biotechnology, 2003, vol. 104, pp. 5-25.

* cited by examiner

*Primary Examiner* — Celine X Qian
(74) *Attorney, Agent, or Firm* — Connolly Bove Lodge & Hutz LLP

(57) ABSTRACT

The present invention relates to multiple promoters and to expression units comprising them; to the use thereof for regulating transcription and expression of genes; to expression cassettes which comprise multiple promoters or expression units of this kind; to vectors which comprise such expression cassettes; to genetically modified microorganisms which comprise vectors and/or expression units of this kind; and to processes for preparing biosynthetic products by culturing said genetically modified microorganisms.

13 Claims, 1 Drawing Sheet

Figure 1

A) pEFTu

>EFTU\rxa01284\
ggccgttaccctgcgaatgtccacagggtagctgg<u>tagttt</u>gaaaatcaacgccgttgccc<u>taggatt</u>ca
gtaactggcacattttgtaat<u>gcgct</u>agatctgtgtgctcagtcttcaggctgcttatcacagtgaaagc
aaaaccaattcgtggctgcgaaagtcgtagccaccacgaagtcc*aggagga*cataca ggccgttaccctgcgaatgtccacagggtagctgg<u>tagttt</u>gaaaatcaacgccgttgccc<u>taggatt</u>ca
gtaactggcacattttgtaat<u>gcgct</u>agatctgtgtgctcagtcttcaggctgcttatcacagtgaaagc
aaaaccaattcgtggctgcgaaagtcgtagccaCACGAAGTCC

B) pGRO

>groES\rxa00497\
cggcttaaagtttggctgccatgtgaattttagcaccctcaacagttgagtgctggcactctcgggg
<u>tagagt</u>gccaaataggttgtttgacacacagttgttcacccgcgacgacggctgtgctggaaacccacaa
ccggcacacacaaaatttttctcat*ggaggga*ttcatc cggcttaaagtttggctgccatgtgaattttagcaccctcaacagttgagtgctggcactctcgggg
<u>tagagt</u>gccaaataggttgtttgacacacagttgttcacccgcgacgacggctgtgctggaaacccacaa
ccggcacacacaaaatTTTTCTCAT

C) pEFTs

>elongationsfaktor \rxa01913\
cccccacgacaatggaactttgacttttaaaatttcatcgccgtgggggcttttgggcacagcccgc
cgtgtcgcaacgtaatcgactgaatacctgtacgatcacttttagacgggcggtagggctactgtgcc
ctaacc<u>taagct</u>tgtaaagca<u>ttaatt</u>atccatacata*aggagga*tcgcccgta cccccacgacaatggaactttgacttttaaaatttcatcgccgtgggggcttttgggcagccagcccgc
cgtgtcgcaacgtaatcgactgaatacctgtacgatcacttttagacgggcgggtagggctactgtgcc
ctaacc<u>taagct</u>tgtaaagca<u>ttaatt</u>atccatacata

D) pSOD

>superoxid\dismutase\rxa03119\
agctgccaattattccgggcttgtgacccgctacccgataaataggtcggctgaaaatttcgt<u>tgcaat</u>
atcaacaaaaaggcc<u>tatcatt</u>gggaggtgtcgcaccaagtacttttggaagcgccatctgacggattt
tcaaaagatgtatatgctcggtgcggaaacctac*gaaagga*ttttttaccc agctgccaattattccgggcttgtgacccgctacccgataaataggtcggctgaaaaatttcgt<u>tgcaat</u>
atcaacaaaaaggcc<u>tatcatt</u>gggaggtgtcgcaccaagtacttttgcgaagcgccatctgacggattt
tcaaaagatgtatatgctcggtgcggaaacctaC

MULTIPLE PROMOTERS AND THE USE THEREOF FOR GENE EXPRESSION

RELATED APPLICATIONS

This application is a divisional of U.S. application Ser. No. 11/793,909, filed Jun. 21, 2007 which is a 35 U.S.C. 371 National stage filing of International Application No. PCT/EP2005/013809, filed Dec. 21, 2005, which claims priority to German Application No. 10 2004 061 846.1, filed Dec. 22, 2004. The entire contents of each of these applications are hereby incorporated by reference herein.

SEQUENCE LISTING SUBMISSION

The Sequence Listing associated with this application is filed in electronic format via EFS-Web and hereby incorporated by reference into the specification in its entirety. The name of the text file containing the Sequence Listing is Sequence_List_12810_00672_US. The size of the text file is 174 KB, and the text file was created on Jun. 16, 2008.

DESCRIPTION

The present invention relates to multiple promoters and to expression units comprising them; to the use thereof for regulating transcription and expression of genes; to expression cassettes which comprise multiple promoters or expression units of this kind; to vectors which comprise such expression cassettes; to genetically modified microorganisms which comprise vectors and/or expression units of this kind; and to processes for preparing biosynthetic products by culturing said genetically modified microorganisms.

BACKGROUND OF THE INVENTION

Various biosynthetic products are produced in cells via natural metabolic processes and are used in many branches of industry, including the foodstuffs, feedstuffs, cosmetics, feed, food and pharmaceutical industries. These substances, which are summarily referred to as fine chemicals/proteins, comprise, inter alia, organic acids, both proteinogenic and non-proteinogenic amino acids, nucleotides and nucleosides, lipids and fatty acids, diols, carbohydrates, aromatic compounds, vitamins and cofactors, and also proteins and enzymes. They are most conveniently produced on a large scale by growing bacteria strains or other microorganisms which have been developed in order to produce and secrete large quantities of the substance desired in each case. Organisms particularly suitable for this purpose are coryneform bacteria, Gram-positive nonpathogenic bacteria.

It is known that amino acids can be prepared by fermentation of strains of coryneform bacteria, in particular *Corynebacterium glutamicum*. Due to the great importance, continuous work is carried out on improving the production processes. Process improvements may relate to fermentation technique measures such as, for example, stirring and oxygen supply, or to the composition of the nutrient media, such as, for example, the sugar concentration during fermentation, or to the work-up to obtain the product, for example by ion exchange chromatography or else spray drying, or to the intrinsic performance properties of the microorganism itself.

Methods of recombinant DNA technology have likewise been employed for some years to improve *Corynebacterium* strains producing fine chemicals/proteins, by amplifying individual genes and studying the effect on the production of fine chemicals/proteins.

Other ways of developing a process for producing fine chemicals or proteins or of increasing or improving the productivity of an already existing process for preparing fine chemicals or proteins comprise increasing or altering expression of one or more genes and/or influencing translation of an mRNA by way of suitable polynucleotide sequences. In this context, influencing may comprise increasing, reducing or else other parameters of the expression of genes, such as time-related expression patterns.

Various components of bacterial regulatory sequences are known to the skilled worker. A distinction is made between the binding sites of regulators, also known as operators, the binding sites of RNA polymerase holoenzymes, also known as −35 and −10 regions, and the binding site of ribosomal 16S-RNA, also known as ribosomal binding site (RBS) or else Shine-Dalgarno sequence.

The composition of the polynucleotide sequence of the Shine-Dalgarno sequence and the sequence of the bases, but also the distance of a polynucleotide sequence present in the Shine-Dalgarno sequence to the start codon are described in the literature (*E. coli* and *S. typhimurium*, Neidhardt F. C. 1995 ASM Press) as having a substantial influence on the rate of translation initiation.

Nucleic acid sequences having promoter activity can influence the formation of mRNA in different ways. Promoters whose activities are independent of the physiological growth phase of the organism are referred to as constitutive. Other promoters in turn respond to external chemical as well as physical stimuli, such as oxygen, metabolites, heat, pH, etc. Others in turn display a strong dependence of their activity in different growth phases. Examples of promoters which exhibit a particularly pronounced activity during the exponential growth phase of microorganisms, or else exactly in the stationary phase of microbial growth, are described in the literature. Both characteristics of promoters may have a beneficial influence on the productivity for production of fine chemicals and proteins, depending on the metabolic pathway.

Those nucleotide sequences which may be utilized for increasing or attenuating gene expression have already been isolated in *Corynebacterium* species. These regulated promoters may increase or reduce the rate at which a gene is transcribed, as a function of the internal and/or external conditions of the cell. In some cases, the presence of a particular factor, known as inducer, may stimulate the rate of transcription from the promoter. Inducers may influence transcription from the promoter directly or else indirectly. Another class of factors, known as suppressors, is capable of reducing or else inhibiting transcription from the promoter. Like inducers, suppressors may also act directly or indirectly. However, thermally regulated promoters are also known. Thus, a rise of the growth temperature above the normal growth temperature of the cell may increase or else attenuate the level of transcription of such promoters.

A small number of promoters from *C. glutamicum* have been described to date. The promoter of the *C. glutamicum* malate synthase gene was described in DE-A-44 40 118. This promoter was placed upstream of a structural gene coding for a protein. After transformation of such a construct into a coryneform bacterium, the expression of the structural gene downstream of the promoter is regulated. The expression of the structural gene is induced as soon as a corresponding inducer is added to the medium.

Reinscheid et al., Microbiology 145:503 (1999), have described a transcriptional fusion between the pta-ack promoter from *C. glutamicum* and a reporter gene (chloramphenicol acetyltransferase). *C. glutamicum* cells containing such a transcriptional fusion exhibited increased expression of the reporter gene when grown on acetate-containing medium. By comparison, transformed cells growing on glucose showed no increased expression of said reporter gene.

Patek et al., Microbiology 142:1297 (1996), described some *C. glutamicum* DNA sequences which are able to enhance expression of a reporter gene in *C. glutamicum* cells. These sequences were compared to one another in order to define consensus sequences for *C. glutamicum* promoters Further *C. glutamicum* DNA sequences which may be utilized for regulating gene expression have been described in WO 02/40679. These isolated polynucleotides are expression units from *Corynebacterium glutamicum*, which may be utilized either for increasing or else for reducing gene expression. This printed publication furthermore describes recombinant plasmids on which said expression units from *Corynebacterium glutamicum* are associated with heterologous genes. The method described herein, of fusing a *Corynebacterium glutamicum* promoter to a heterologous gene, may be employed, inter alia, for regulating the genes of amino acid biosynthesis.

The older, not previously published patent applications DE-A-103 59 594, DE-A-103 59 595, DE-A-103 59 660 and DE-A-10 2004 035 065 disclosed special single promoters from *C. glutamicum*.

BRIEF DESCRIPTION OF THE INVENTION

The invention was based on the object of making available further regulatory nucleic acid sequences, in particular promoter constructs and/or expression units having advantageous properties, for example increased or altered transcriptional activity and/or translational activity, in comparison with the starting promoter.

The object was achieved according to the invention by providing a multiple promoter-comprising expression unit, comprising, in the 5'-3' direction, a sequence module of the following formula I:

$$5'\text{-}P_1\text{-}(\text{-}A_x\text{-}P_x\text{-})_n\text{-}A_y\text{-}P_y\text{-}3' \qquad (I)$$

where
n is an integer from 0 to 10,
$A_x$ and $A_y$ are identical or different and are a chemical bond or a linker nucleic acid sequence;
$P_1$, $P_x$ and $P_y$ code for identical or different promoter sequences which comprise at least one RNA polymerase-binding region such as, for example, the core region; and at least $P_y$ comprises a ribosome binding-mediating, 3'-terminal sequence section. $P_1$ and individual or all $P_x$ may also have, independently of one another, a sequence section of this kind, which mediates ribosome binding.

According to one embodiment, $P_1$, $P_x$ and $P_y$ are derived from identical or different eukaryotic or, in particular, prokaryotic organisms. Artificial promoters are also usable.

According to a preferred embodiment, $P_1$, $P_x$ and $P_y$ are in each case derived from a contiguous sequence of from 35 to 500 nucleotide residues, preferably 35 to 300 nucleotide residues, more preferably 35 to 210 nucleotide residues, and very particularly preferably 35 to 100 nucleotide residues, which sequence is located 5' upstream of the coding sequence for a protein, for example a protein involved in a biosynthetic pathway of the organism, in the genome of said organism.

According to another embodiment, $P_1$, $P_x$ and $P_y$ of the expression unit are derived from a coryneform bacterium.

According to a preferred embodiment, $P_1$, $P_x$ and $P_y$ of the expression unit are, independently of one another, selected from among promoter sequences for the coding sequence of a protein with high abundance in a eukaryotic or prokaryotic organism, in particular in a coryneform bacterium, such as, for example, in one of the genus *Corynebacterium* or *Brevibacterium*, for example a species or a strain according to the list in table 3.

In addition, individual or all of these promoter sequences may be selected from among promoter sequences for the coding sequence of a protein listed in table 1 and involved in the amino acid biosynthesis of an organism. At least one of the promoters of the expression unit according to the invention should, in this connection, have high abundance as defined herein, however.

According to another preferred embodiment, $P_1$, $P_x$ and $P_y$ of the expression unit are, independently of one another, selected from among the nucleotide sequences depicted in FIG. 1 or, as will be explained later in more detail, are derived from SEQ ID NO:1 (pGRO), SEQ ID NO:2 (pEFTs), SEQ ID NO:3 (pEFTu) and SEQ ID NO:4 (pSOD).

According to another embodiment, $P_1$, $P_x$ and $P_y$ of the expression unit, independently of one another, are selected from among strong, constitutive or regulatable promoters.

In a further aspect, the present invention relates to an expression cassette, comprising, in the 5'-3' direction, a sequence module of the following formula II:

$$5'\text{-}P_1\text{-}(\text{-}A_x\text{-}P_x\text{-})_n\text{-}A_y\text{-}P_y\text{-}G\text{-}3' \qquad (II)$$

where
n, $A_x$, $A_y$, $P_1$, $P_x$ and $P_y$ are as defined above, and
G is at least one coding nucleic acid sequence which is functionally or operatively linked to the 5' upstream regulatory sequence.

According to a preferred embodiment of the expression cassette, G is selected from among
a) nucleic acids encoding a protein of the biosynthetic pathway of proteinogenic and nonproteinogenic amino acids,
b) nucleic acids encoding a protein of the biosynthetic pathway of nucleotides and nucleosides,
c) nucleic acids encoding a protein of the biosynthetic pathway of organic acids,
d) nucleic acids encoding a protein of the biosynthetic pathway of lipids and fatty acids,
e) nucleic acids encoding a protein of the biosynthetic pathway of diols,
f) nucleic acids encoding a protein of the biosynthetic pathway of carbohydrates,
g) nucleic acids encoding a protein of the biosynthetic pathway of aromatic compounds,
h) nucleic acids encoding a protein of the biosynthetic pathway of vitamins,
i) nucleic acids encoding a protein of the biosynthetic pathway of cofactors,
j) nucleic acids encoding a protein of the biosynthetic pathway of enzymes, and
k) nucleic acids encoding a protein of the central metabolism.

According to a particularly preferred embodiment of the expression cassette, G is selected from among nucleic acids coding for proteins of the biosynthetic pathway of amino acids, selected from among aspartate kinase, aspartate semialdehyde dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triosephosphate isomerase, transcriptional regulator LuxR, transcriptional regulator LysR1, transcriptional regulator LysR2, malate-quinone oxidoreductase, glucose-6-phosphate dehydrogenase, 6-phosphogluconate dehydrogenase, transketolase, transaldolase, homoserine O-acetyltransferase, cystathionine gamma-synthase, cystathionine beta-lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase 1, cysteine synthase II, coenzyme B12-dependent methionine synthase, coenzyme B12-independent methionine synthase activity, sulfate adenylyltransferase subunits 1 and 2, phosphoadenosine phosphosulfate reductase, ferredoxin sulfite reductase, ferredoxin NADP reductase, 3-phosphoglycerate dehydrogenase, RXA00655 regulator, RXN2910 regulator, arginyl-tRNA synthetase, phosphoenolpyruvate carboxylase, threonine efflux protein, serine hydroxymethyltransferase, fructose 1,6-bisphosphatase, protein of sulfate reduction RXA077, protein of sulfate reduction RXA248, protein of sulfate reduction RXA247, OpcA protein, 1-phosphofructokinase and 6-phosphofructokinase, tetrahydropicolinate succinylase, succinyl aminoketopimelate aminotransferase, succinyl diaminopimelate desuccinylase, diaminopimelate epimerase, 6-phosphogluconate dehydrogenase, glucose phosphate isomerase, phosphoglycerate mutase, enolase, pyruvate kinase, aspartate transaminase, malate enzyme.

In a further aspect, the present invention relates to a vector which comprises at least one of the abovementioned expression cassettes.

According to yet another aspect, the present invention relates to a genetically modified microorganism which has been transformed with at least one of the above-mentioned vectors or which comprises at least one of the abovementioned expression cassettes, preferably in an integrated form.

According to one embodiment, the generally modified organism is derived from coryneform bacteria.

According to a preferred embodiment, the genetically modified organism is derived from bacteria of the genus *Corynebacterium* or *Brevibacterium*.

According to a further aspect, the present invention relates to a process for preparing a biosynthetic product, which comprises culturing any of the abovementioned, genetically modified microorganisms and isolating the desired product from the culture.

According to one embodiment of the process, the biosynthetic product is selected from among organic acids, proteins, nucleotides and nucleosides, both proteinogenic and nonproteinogenic amino acids, lipids and fatty acids, diols, carbohydrates, aromatic compounds, vitamins and cofactors, enzymes and proteins. Very particularly preferred biosynthetic products are lysine, methionine, threonine and trehalose.

According to a further aspect, the present invention relates to the use of an expression unit of the invention for regulating a product biosynthesis.

DESCRIPTION OF THE FIGURES

FIG. 1 depicts specific sequences for four promoters, which were used for preparing the multiple promoters described in the exemplary embodiments. The promoter sequences for pEFTu (FIG. 1A); for the promoter pGRO (FIG. 1B), for the promoter pEFTs (FIG. 1C) and for the promoter pSOD (FIG. 1D) are shown. Two sequences are indicated for each promoter, the longer of which (top sequence) in each case indicating the complete promoter sequence including the ribosomal binding site (RBS), printed in bold type and in italic. In the case of a 3'-terminal arrangement of the particular promoter in the multiple promoter construct of the invention, preference is given to using in each case the longer nucleotide sequence (including RBS). Promoter sequences 5' upstream of the 3'-terminal promoter unit do not comprise any RBS and were used in the truncated nucleic acid sequence indicated in each case in second position (without RBS). The shorter promoter sequences may also lack, if appropriate, 3'-terminal partial sequences indicated in capital letters and bold type. Potential "−10 regions" are underlined.

DETAILED DESCRIPTION OF THE INVENTION

I. General Definitions

A "biosynthetic product" means for the purposes of the invention those which are produced via natural metabolic processes (biosynthetic pathways) in cells. They are used in many different ways, in particular in the foodstuffs, feedstuffs, cosmetics, feed, food and pharmaceutical industries. These substances which are summarily referred to as fine chemicals/proteins comprise, inter alia, organic acids, both proteinogenic and nonproteinogenic amino acids, nucleotides and nucleosides, lipids and fatty acids, diols, carbohydrates, aromatic compounds, vitamins and cofactors, and also proteins and enzymes.

A "promoter", a "nucleic acid with promoter activity" or a "promoter sequence" means according to the invention a nucleic acid which is functionally linked to a nucleic acid to be transcribed and which regulates transcription of said nucleic acid.

Unless "single promoters" are expressly referred to, the term "promoter" comprises according to the invention and depending on the context also the sequential arrangement of more than one nucleic acid sequence (i.e. "multiple promoters") each of which, when functionally linked to a nucleic acid to be transcribed, would be capable of regulating transcription of the latter.

The term "single promoter" accordingly refers to a single nucleic acid sequence which is capable of regulating transcription of a nucleic acid to be transcribed and which, when functionally linked to a nucleic acid to be transcribed, can transcribe the latter.

In the case of "multiple promoters", at least two identical or different nucleic acid sequences each of which would, when functionally linked to a nucleic acid to be transcribed, be capable of regulating transcription of the latter (single promoters) are sequentially linked in such a way that a transcriptional start from optionally one of said nucleic acid sequences could produce a transcript containing said nucleic acid to be transcribed. In this connection, it is possible for further sequences without promoter function, for example a linker which has, for example, one or more restriction cleavage sites, to be inserted between in each case two single promoters. Optionally, in each case two single promoters may also be linked directly to one another. Said multiple promoters preferably contain only one ribosomal binding site (RBS), in particular in the region of the 3' terminus of the promoter.

Promoter sequences for the coding sequence of a protein with "high abundance" means in particular "strong promoters". If it is intended to employ multiple promoters in order to enhance genes, preference is given to combining in a suitable manner such strong promoters. Strong promoters regulate transcription of genes so as for the latter to be more frequently read by RNA polymerase than the majority of the genes of the organism. In most cases, the presence of a strong promoter results in a large amount of transcript also being present in the cell. When the percentage of said transcript is higher in comparison with the other cellular transcripts, this is referred as an "abundant transcript". In bacteria, the amount of transcript and the amount of the corresponding protein encoded thereby usually correlate, i.e. "abundant transcripts" also result in "abundant proteins" most of the time. A method which allows "strong promoters" to be identified via the abundance of proteins is described below by way of example. Details of the methodical procedure and further references can be found, for example, in Proteomics in Practice—A Laboratory Manual of Proteome Analysis (Authors: R. Westermeier, T. Naven; Publisher: Wiley-VCH Verlag GmbH, 2002). The bacterial cells are disrupted and the proteins of the cell extract are fractionated by means of 2D gel electrophoresis. The proteins are then stained by common methods such as, for example, Coomassie, silver or fluorescent dye staining. Overstaining of the proteins is to be avoided here in order to enable the individual protein spots to be quantified later. Subsequently, the gel is scanned and the image obtained is analyzed with the aid of suitable software (e.g. Melanie, Amersham Biosciences). For this purpose, all detectable spots are identified first and the spot volume is determined. The sum of all spot volumes corresponds, in a first approximation, to the total protein. The spots which have particularly large spot volumes may then be selected with the aid of the image analysis software. For example, spots with volumes occupying more than 0.1% of the total spot volume may be referred to as abundant. Subsequently, spots containing particularly abundant proteins are cut out of the gel. Normally, the protein present in the gel slice is then proteolytically digested (e.g. with trypsin) and the molar mass of the resultant peptides is determined, for example with the aid of MALDI-ToF MS (Matrix assisted laser desorption ionization-Time of Flight Mass Spectrometry). Based on the molar mass of some of the tryptic peptides of the protein, the corresponding protein may then be identified in database searches. This is possible in particular if the genome of the organism to be studied has been sequenced, as is the case for C. glutamicum, E. coli and many other bacteria. The ORF (open reading frame) encoding said protein may then be determined based on the identity of said protein. In bacteria, the promoters regulating said gene are usually located immediately upstream of the start codon. Therefore, the "strong" promoters are frequently also present in a region of approx. 200 nucleotides upstream of the start codon of "abundant" proteins.

"Artificial" promoters for the purposes of the invention comprise in particular those sequences which have no transcriptional activity in situ and which are transcriptionally active in another sequence context, such as, in particular, in the context of an expression unit or expression cassette of the invention.

"Promoter activity" means according to the invention the amount of RNA formed by the promoter in a particular time, i.e. the rate of transcription.

"Specific" promoter activity means according to the invention the amount of RNA formed by the promoter in a particular time, for each promoter.

In the case of a "caused" promoter activity or rate of transcription with respect to a gene, in comparison with the wild type, thus, in comparison with the wild type, the formation of an RNA which has not been present in this form in the wild type is caused.

In the case of an "altered" promoter activity or rate of transcription with respect to a gene, in comparison with the wild type, thus, in comparison with the wild type, the amount of RNA formed in a particular time is altered.

"Altered" in this connection means preferably increased or reduced.

A "functional" or "operative" linkage means in this connection, for example, the sequential arrangement of any of the nucleic acids of the invention which have promoter activity and a nucleic acid sequence to be transcribed and, if appropriate, further regulatory elements such as, for example, nucleic acid sequences which ensure transcription of nucleic acids, as well as a terminator, for example, so as for each of said regulatory elements to be able to fulfill its function in transcription of said nucleic acid sequence. This does not necessarily require a direct linkage in the chemical sense. Genetic control sequences such as, for example, enhancer sequences can exert their function on the target sequence also from more distant positions or even from other DNA molecules. Preference is given to arrangements in which the nucleic acid sequence to be transcribed is positioned behind (i.e. at the 3' end of) the promoter sequence of the invention, so that the two sequences are covalently connected to one another. The distance between the promoter sequence and the nucleic acid sequence to be expressed transgenically is here preferably less than 200 base pairs, particularly preferably less than 100 base pairs, very particularly preferably less than 50 base pairs.

The sequence of a "ribosomal binding site" or "ribosome binding site" (RBS) (or referred to as Shine-Dalgarno sequence) in accordance with the present invention means A/G-rich polynucleotide sequences which are located up to 30 bases upstream of the translation initiation codon.

"Transcription" means according to the invention the process which, starting from a DNA template, produces a complementary RNA molecule. This process involves proteins such as RNA polymerase, "sigma factors" and transcriptional regulatory proteins. The synthesized RNA then serves as template in the translation process which then results in the biosynthetically active protein.

A "core region" of a promoter means according to the invention a contiguous nucleic acid sequence of from about 20 to 80, or 30 to 60, nucleotides, which comprises at least one potential "−10 region". Examples of potential −10 regions are described herein for individual preferred promoter sequences; compare FIG. 1 in particular. "−10 regions" are also referred to as TATA boxes or Pribnow-Schaller sequences. Each promoter used should comprise at least one of these potential −10 regions, for example 1, 2, 3, 4 or 5. The core region is located 5' upstream of the RBS and may be at a distance from the latter of from 1 to 200 or 10 to 150 or 20 to 100 nucleotide residues.

An "expression unit" means according to the invention a nucleic acid having expression activity, which comprises a multiple promoter as defined herein and which, after functional linkage to a nucleic acid or a gene to be expressed, regulates expression, i.e. transcription and translation, of said nucleic acid or said gene. In this connection, therefore, said nucleic acid sequence is also referred to as a "regulatory nucleic acid sequence". In addition to the multiple promoter construct, further regulatory elements such as, for example, enhancers, may be present.

An "expression cassette" means according to the invention an expression unit which is functionally linked to the nucleic acid to be expressed or the gene to be expressed. In contrast to an expression unit, an expression cassette thus comprises not only nucleic acid sequences regulating transcription and translation but also the nucleic acid sequences which are to be expressed as protein as a result of transcription and translation.

"Expression activity" means according to the invention the amount of protein formed by the expression cassette or its expression unit in a particular time, i.e. the rate of expression.

"Specific expression activity" means according to the invention the amount of protein formed by the expression cassette or its expression unit in a particular time, for each expression unit.

In the case of a "caused expression activity" or rate of expression with respect to a gene, in comparison with the wild type, thus, in comparison with the wild type, the formation of an protein which has not been present in this form in the wild type is caused.

In the case of an "altered" expression activity or rate of expression with respect to a gene, in comparison with the wild type, thus, in comparison with the wild type, the amount of protein formed in a particular time is altered. "Altered" in this connection means preferably increased or reduced. This may take place, for example, by increasing or reducing the specific activity of the endogenous expression unit, for example by way of mutation, or by way of stimulation or inhibition. The altered expression activity or rate of expression may furthermore be achieved, for example, by regulating expression of genes in the microorganism by expression units of the invention, the genes being heterologous with respect to the expression units.

The "rate of formation" at which a biosynthetically active protein is produced is a product of the rates of transcription and translation. Both rates may be influenced according to the invention and thus influence the rate of formation of products/fine chemicals in a microorganism.

The term "wild type" means according to the invention the appropriate starting microorganism and need not necessarily correspond to a naturally occurring organism.

Depending on the context, the term "microorganism" may mean the starting microorganism (wild type) or a genetically modified microorganism of the invention or both.

Preferably, and in particular in cases where it is not possible to assign the microorganism or the wild type unambiguously, "wild type" for altering or causing the promoter activity or rate of transcription, for altering or causing the expression activity or rate of expression and for increasing the biosynthetic product content in each case means a "reference organism". In a preferred embodiment, this "reference organism" is *Corynebacterium glutamicum* ATCC 13032 or a microorganism derived from ATCC 13032 by specific or unspecific mutation.

Use is made in particular of "starting microorganisms" which are already capable of producing the desired product (fine chemical/protein).

A "derived" sequence, for example a derived promoter sequence, means according to the invention, if no other information is given, a sequence whose identity with the starting sequence is at least 80% or at least 90%, in particular 91%, 92%, 93%, 94%, 95%, 96%, 97%, 98% and 99%.

"Identity" between two nucleic acids means the identity of the nucleotides over the entire length of the nucleic acid in each case, in particular the identity calculated by comparison with the aid of the Vector NTI Suite 7.1 software from Informax (USA), applying the Clustal method (Higgins D G, Sharp P M. Fast and sensitive multiple sequence alignments on a microcomputer. Comput Appl. Biosci. 1989 April; 5(2): 151-1), setting the following parameters:
Multiple Alignment Parameter:
Gap opening penalty 10
Gap extension penalty 10
Gap separation penalty range 8
Gap separation penalty off
% identity for alignment delay 40
Residue specific gaps off
Hydrophilic residue gap off
Transition weighing 0
Pairwise Alignment Parameter:
FAST algorithm on
K-tuple size 1
Gap penalty 3
Window size 5
Number of best diagonals 5

"To hybridize" means the ability of a poly- or oligonucleotide to bind under stringent conditions to a virtually complementary sequence, while unspecific bonds between non-complementary partners are not formed under these conditions. For this purpose, the sequences should preferably be 90-100% complementary. The property of complementary sequences being able to bind specifically to one another is utilized, for example, in the Northern or Southern Blotting Technique or for primer binding in PCR or RT-PCR.

According to the invention, "hybridization" takes place under stringent conditions. Hybridization conditions of this kind are described, for example, in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6. Stringent hybridization conditions mean in particular:

Incubation at 42° C. overnight in a solution consisting of 50% formamide, 5×SSC (750 mM NaCl, 75 mM trisodium citrate), 50 mM sodium phosphate (pH 7.6), 5×Denhardt's solution, 10% dextrane sulfate and 20 g/ml denatured, sheared salmon sperm DNA, followed by washing the filters with 0.1×SSC at 65° C.

A "functionally equivalent fragment" means for nucleic acid sequences having promoter activity fragments which essentially have the same or an altered, lower or higher specific promoter activity than the starting sequence.

"Essentially identical" means a specific promoter activity which has at least 50%, such as, for example, at least 60%, 70%, 80%, 90%, or at least 95%, of the specific promoter activity of the starting sequence.

II. Expression Units, Expression Cassettes and Components Thereof a) Expression Units The present invention relates inter alia to providing a multiple promoter-comprising expression unit, comprising, in the 5'-3' direction, a sequence module of the following formula I:

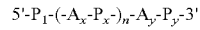

$$5'\text{-}P_1\text{-}(\text{-}A_x\text{-}P_x\text{-})_n\text{-}A_y\text{-}P_y\text{-}3'$$

where
n is an integer from 0 to 10, such as for example 1, 2, 3, 4, 5 or 6;
$A_x$ and $A_y$ are identical or different and are a chemical, in particular covalent bond, or a chemically, in particular covalently, integrated linker nucleic acid sequence;
$P_1$, $P_x$ and $P_y$ code for identical or different promoter sequences which comprise at least one RNA polymerase-binding region such as, for example, a core region; and at least, for example only, $P_y$ comprises a ribosome binding-mediating, 3'-terminal sequence section.

The promoter sequences $P_1$, $P_x$ and $P_y$ may be derived from genes from organisms, which code for proteins involved in a biosynthetic pathway of said organism. The promoter sequences here are located from 20 to 500 nucleotide residues, or from 20 to 300 nucleotide residues, for example from 20 to 210 nucleotide residues, and in particular from 20 to 100 or 35 to 100 nucleotide residues, 5' upstream of the coding sequence of the particular protein in the genome of said organism. Examples of sequences from which promoter sequences $P_1$, $P_x$ and $P_y$ may be derived are the genes listed in Table 1 below.

Nonlimiting examples of special promoter sequences are derived from the nucleic acid sequences according to SEQ ID NO:1, SEQ ID NO:2, SEQ ID NO:3 and SEQ ID NO:4, and FIG. 1, without being limited thereto, however.

In this connection, SEQ ID NO:1 corresponds to the sequence located upstream of the coding region of the GroES Chaperonin (pGRO), SEQ ID NO:2 corresponds to the sequence located upstream of the coding region of protein elongation factor TS (pEFTs), SEQ ID NO:3 corresponds to the sequence located upstream of the coding region of protein elongation factor TU (pEFTu), and SEQ ID NO:4 corresponds to the sequence located upstream of the coding region of superoxide dismutase (pSOD), in each case from *Corynebacterium glutamicum*. SEQ. ID. NO. 1, SEQ ID NO:2, SEQ ID NO:3 and SEQ ID NO:4 correspond to the promoter sequences of the wild type.

A "derived" sequence means according to the invention a sequence which is at least 80% or at least 90%, such as 91%, 92%, 93%, 94%, 95%, 96%, 97%, 98%, and in particular 99%, identical to the starting sequence. This degree of identity applies in particular to the above-defined "core region" of the particular promoter. The degree of identity outside the particular core region may be lower here and may be in the range from 0 to 80%, such as, for example, 10 to 80%, 20 to 70%, 30 to 60% or 40 to 50%.

Usable core regions are located, for example
for pGRO in the range from position 50 to 80 of SEQ ID NO:1;
for pEFTs in the range from position 130 to 170 of SEQ ID NO:2;
for pEFTu in the range from position 30 to 110 of SEQ ID NO:3;
for pSOD in the range from position 50 to 100 of SEQ ID NO:4.

The expression units of the invention contain in particular two or more nucleic acid sequences having promoter activity,
a) preferably derived from identical or different sequences selected from among SEQ. ID. NO. 1, SEQ ID NO:2, SEQ ID NO:3 and SEQ ID NO:4; or other promoter sequences for genes with comparable or higher abundance;
b) with, if appropriate, one or more of said sequences representing a sequence derived by substitution, insertion, inversion or deletion or addition of nucleotides, which sequence is, in particular in the core region, at least 80% identical at the nucleic acid level to a sequence preferably selected from among sequence SEQ ID NO: 1, 2, 3 or 4 or other promoter sequences for genes with comparable or higher abundance,
c) or with, if appropriate, one or more of these nucleic acid sequences present hybridizing under stringent conditions with a sequence which is complementary to one of the nucleic acid sequences according to SEQ ID NO: 1, 2, 3 or 4 and/or to other promoter sequences for genes with comparable or higher abundance,
d) or with, if appropriate, one or more of these nucleic acid sequences present being "functionally equivalent fragments" of the sequences under a), b) or c).

Other natural promoters which are usable as a component of a multiple promoter of the invention can readily be identified, for example, from various organisms whose genomic sequence is known, by comparing the identities of the nucleic acid sequences from databases with the above-described sequences SEQ ID NO: 1, 2, 3 or 4 or according to FIG. 1 or other promoter sequences for genes with comparable or higher abundance.

Further suitable natural promoters can readily be identified from various organisms whose genomic sequence is not known by applying hybridization techniques in a manner known per se, starting from the above-described nucleic acid sequences, in particular starting from the sequence SEQ ID NO: 1, 2, 3 or 4 and/or from promoter sequences for genes with comparable or higher abundance.

Further suitable natural promoters can also be isolated by methods known to the skilled worker, as are described, for example, in Cadenas et al (1991) Gene 98, 117-121; Eikmanns et al, (1991) Gene 102, 93-98.; Patek et al (1996) Microbiology 142, 1297-1309 or Santamaria et al (1987) Gene 56, 199-208. This usually involves using "promoter probe" vectors into which genomic fragments from the genome in question are inserted. The promoter activity of an individual fragment can then be determined in the experimental setup mentioned by measuring the activity of a downstream reporter gene, for example chloramphenicol acetyltransferase.

The invention therefore also comprises the combination of those promoters which are not listed herein by name. This also applies to the combination of already known single promoters, as are described, for example, in Patek et al (2003). J of Biotechnology 104, 311-323; Vasicova et al. (1999) J. Bacteriol 181, 6188-6191).

The invention therefore also relates to nucleic acids having promoter activity for incorporation into a multiple promoter-comprising expression unit of the invention, said nucleic acids having promoter activity comprising a nucleic acid sequence which hybridizes with the nucleic acid sequence SEQ ID NO: 1, 2, 3 or 4 or with promoter sequences for genes with comparable or higher abundance under stringent conditions. This nucleic acid sequence comprises at least 10, preferably more than 12, 15, 30, 50, or more than 150, nucleotides.

Artificial promoter sequences for incorporation into a multiple promoter-comprising expression unit of the invention can readily be prepared starting from the sequence SEQ ID NO: 1, 2, 3 or 4 or according to FIG. 1 and/or promoter sequences for genes with comparable or higher abundance by way of artificial variation and mutation, for example by addition, substitution, insertion, inversion or deletion of one or more, individual or contiguous nucleotide residues. (Patek et al (2003). J of Biotechnology 104, 311-323; Vasicova et al. (1999) J. bacteriol 181, 6188-6191 and references mentioned therein).

Suitable examples of ribosome binding-mediating 3'-terminal sequence sections of a promoter sequence $P_y$ are RBS of pGRO: GGAGGGA; the RBS of pEFTs: AGGAGGA; the RBS of pEFTu: AGGAGGA; and the RBS of pSOD: GGAGGGA (cf. also FIG. 1, attached). The theoretically optimal RBS, i.e. the sequence which is 100% complementary to the anti-Shine-Dalgarno sequence on the *C. glutamicum* 16S rRNA, is: 5' GAAAGGAGG 3'. Other suitable RBS sequence sections can readily be identified, for example, by artificial variation and mutation, for example by substitution, insertion, inversion, addition or deletion of nucleotides, or via homology comparisons with promoter sequences in databases.

Nonlimiting examples of multiple promoter-comprising expression units of the invention are selected from among:
e) sequences coding for
PeftuPsod, from position 18 to 390 in SEQ ID NO: 45;
PsodPeftu, from position 18 to 395 in SEQ ID NO: 52;

PgroPsod, from position 18 to 369 in SEQ ID NO: 55;
PgroPsodPefts, from position 11 to 538 in SEQ ID NO: 59;
PeftuPsodPefts; from position 11 to 559 in SEQ ID NO: 60;
or f) sequences which are derived from sequences according to e) by substitution, insertion, inversion, addition or deletion of nucleotides and which, in comparison with said starting sequence, are at least 80% or at least 90% identical at the nucleic acid level; or g) nucleic acid sequences which hybridize with a sequence complementary to e) under stringent conditions; or h) "functionally equivalent fragments" of the abovementioned sequences e), f) and g).

A "functionally equivalent fragment", in particular according to the embodiments d) and h), means, for expression units, fragments which have essentially the same or a higher specific expression activity as/than the starting sequence.

"Essentially identical" means a specific expression activity which has at least 50%, preferably 60%, more preferably 70%, more preferably 80%, more preferably 90%, particularly preferably 95%, of the specific expression activity of the starting sequence.

"Fragments" means partial sequences of the sequences described by embodiment a) to h). Said fragments preferably have more than 10, but more preferably more than 12, 15, 30, 50, or particularly preferably more than 150, contiguous nucleotides of the starting sequence.

The expression units of the invention may preferably comprise one or more of the following genetic elements: a −10 region; a transcription start, an enhancer region; and an operator region.

These genetic elements are preferably specific for the species *corynebacteria*, especially for *Corynebacterium glutamicum*.

Bacterial promoters normally consist of three RNA polymerase recognition sites, namely the −10 region, the −35 region and the UP element. These promoter elements are highly conserved in *E. coli*, but not in *C. glutamicum*. This applies especially to the -35 region. The latter can therefore be derived from the sequence often only unreliably, if at all. The −10 region, too, is less highly conserved than in organisms comprising AT-rich genomes. Consensus sequences which have previously been described here are TGNGNTA(C/T)AATGG and GNTANAATNG (Patek et al (2003), J. of Biotechnology 104, 311-323; Vasicova et al. (1999) J. Bacteriol 181, 6188-6191).

It is well known that a high variability generally occurs in the consensus sequences of bacteria having a moderate or high GC content (such as, for example, *C. glutamicum*) (Bourn and Babb, 1995., Bashyam et al, 1996). This applies in particular to the −35 region which therefore frequently cannot be predicted. This is described, for example, in Patek et al (2003). J of Biotechnology 104, 325-334.

b) Expression Cassettes

The invention further relates to the multiple promoter-comprising expression units of the invention, functionally linked to a translatable nucleic acid sequence. These constructs which are capable of expressing genes are, for the purposes of the invention, also referred to as expression cassettes.

A "functional linkage" means in this connection, for example, the sequential arrangement of any of the expression units of the invention and a nucleic acid sequence to be expressed transgenically and, if appropriate, further regulatory elements such as a terminator, for example, so as for each of said regulatory elements to be able to fulfill a function in transgenic expression of said nucleic acid sequence. This does not necessarily require a direct linkage in the chemical sense. Genetic control sequences such as, for example, enhancer sequences can exert their function on the target sequence also from more distant positions or even from other DNA molecules. Preference is given to arrangements in which the nucleic acid sequence to be expressed transgenically is positioned behind (i.e. at the 3' end of) the expression unit sequence of the invention, so that the two sequences are covalently connected to one another. The distance between the expression unit sequence and the nucleic acid sequence to be expressed transgenically is here preferably less than 200 base pairs, particularly preferably less than 100 base pairs, very particularly preferably less than 50 base pairs.

The multiple promoter-comprising expression cassettes of the invention make it possible to achieve an expression activity which is different in comparison with the original expression activity and thus to fine-regulate expression of the desired gene.

Regulation of the expression of genes in the microorganism by expression units of the invention is preferably achieved by introducing one or more expression units of the invention, if appropriate with altered specific expression activity, into the genome of the microorganism so that one or more endogenous genes are expressed under the control of the introduced expression units of the invention; or introducing one or more nucleic acid constructs comprising an expression unit of the invention, if appropriate with altered specific expression activity, and, functionally linked, one or more nucleic acids to be expressed, i.e. an expression cassette, into the microorganism.

In the expression cassettes of the invention, the physical position of the expression unit relative to the gene to be expressed is chosen so as for said expression unit to regulate transcription, and preferably also translation, of the gene to be expressed and thus to enable the formation of one or more proteins. "To enable the formation" here includes to constitutively increase said formation, to attenuate or block said formation under specific conditions and/or to increase said formation under specific conditions. The "conditions" here comprise: (1) adding a component to the culture medium, (2) removing a component from the culture medium, (3) replacing a component in the culture medium with a second component, (4) increasing the temperature of the culture medium, (5) reducing the temperature of the culture medium, and (6) regulating the atmospheric conditions such as, for example, oxygen concentration or nitrogen concentration, in which the culture medium is maintained.

c) General Information:

All of the abovementioned nucleic acids having promoter activity and expression units and expression cassettes may furthermore be prepared in a manner known per se by chemical synthesis from the nucleotide building blocks, for example by fragment condensation of individual overlapping complementary nucleic acid building blocks of the double helix. The chemical synthesis of oligonucleotides may be carried out, for example, in a manner known per using the phosphoamidite method (Voet, Voet, $2^{nd}$ edition, Wiley Press New York, pp. 896-897). The assembly of synthetic oligonucleotides and the filling-in of gaps with the aid of the Klenow fragment of DNA polymerase and ligation reactions and also general cloning processes are described in Sambrook et al. (1989), Molecular cloning: A laboratory manual, Cold Spring Harbor Laboratory Press.

The methods and techniques utilized for the present inventions are known to the skilled worker trained in microbiological and recombinant DNA techniques. Methods and techniques for growing bacterial cells, transporting isolated DNA molecules into the host cell and isolating, cloning and sequencing isolated nucleic acid molecules, etc., are examples of such techniques and methods. These methods are described in many items of the standard literature: Davis et al., Basic Methods In Molecular Biology (1986); J. H. Miller, Experiments in Molecular Genetics, Cold Spring Harbor Laboratory Press, Cold Spring Harbor, N.Y. (1972); J. H. Miller, A Short Course in Bacterial Genetics, Cold Spring Harbor Laboratory Press, Cold Spring Harbor, N.Y. (1992); M. Singer and P. Berg, Genes & Genomes, University Science Books, Mill Valley, Calif. (1991); J. Sambrook, E. F. Fritsch and T. Maniatis, Molecular Cloning: A Laboratory Manual, 2$^{nd}$ ed., Cold Spring Harbor Laboratory Press, Cold Spring Harbor, N.Y. (1989); P. B. Kaufmann et al., Handbook of Molecular and Cellular Methods in Biology and Medicine, CRC Press, Boca Raton, Fla. (1995); Methods in Plant Molecular Biology and Biotechnology, B. R. Glick and J. E. Thompson, eds., CRC Press, Boca Raton, Fla. (1993); and P. F. Smith-Keary, Molecular Genetics of *Escherichia coli*, The Guilford Press, New York, N.Y. (1989).

All nucleic acid molecules of the present invention are preferably in the form of an isolated nucleic acid molecule. An "isolated" nucleic acid molecule is removed from other nucleic acid molecules present in the natural source of said nucleic acid and may additionally be essentially free of other cellular material or culture medium, if prepared by recombinant techniques, or free of chemical precursors or other chemicals, if synthesized chemically.

The invention furthermore comprises the nucleic acid molecules complementary to the specifically described nucleotide sequences, or a section thereof.

The nucleotide sequences of the invention also enable probes and primers to be generated which can be used for identifying and/or cloning homologous sequences in other cell types and microorganisms. Probes and primers of this kind usually comprise a nucleotide sequence region which, under stringent conditions, hybridizes to at least about 12, preferably at least about 25, such as, for example, about 40, 50 or 75, continuous nucleotides of a sense strand of a nucleic acid sequence of the invention or of a corresponding antisense strand.

The invention also comprises those nucleic acid sequences which comprise "silent mutations" or which have been altered in comparison with a specifically mentioned sequence according to the codon usage of a special source or host organism, as well as naturally occurring variants, for example splice variants or allelic variants, thereof.

III. Expression Vectors

The invention also relates to expression vectors comprising an above-described expression cassette of the invention.

Vectors are well known to the skilled worker and can be found, for example, in "Cloning Vectors" (Pouwels P. H. et al., eds., Elsevier, Amsterdam-New York-Oxford, 1985). Apart from plasmids, vectors also mean any other vectors known to the skilled worker, such as, for example, phages, transposons, IS elements, plasmids, cosmids, and linear or circular DNA. Said vectors may be replicated autonomously in the host organism or may be replicated chromosomally.

Preferred plasmids are particularly preferably those which are replicated in coryneform bacteria. Numerous known plasmid vectors such as, for example, pZ1 (Menkel et al., Applied and Environmental Microbiology (1989) 64: 549-554), pEKEx1 (Eikmanns et al., Gene 102: 93-98 (1991)) or pHS2-1 (Sonnen et al., Gene 107: 69-74 (1991)) are based on the cryptic plasmids pHM1519, pBL1 or pGA1. Other plasmid vectors such as, for example, pCLiK5MCS (see Example 1) or those based on pCG4 (U.S. Pat. No. 4,489,160) or pNG2 (Serwold-Davis et al., FEMS Microbiology Letters 66, 119-124 (1990)) or pAG1 (U.S. Pat. No. 5,158,891) may be used in the same way.

Furthermore suitable are also those plasmid vectors with the aid of which the process of gene amplification by integration into the chromosome can be applied, as has been described, for example, by Remscheid et al. (Applied and Environmental Microbiology 60, 126-132 (1994)) for the duplication and amplification of the hom-thrB operon. In this method, the complete gene is cloned into a plasmid vector which can replicate in a host (typically *E. coli*) but not in *C. glutamicum*. Examples of suitable vectors are pSUP301 (Simon et al., Bio/Technology 1, 784-791 (1983)), pK18mob or pK19mob (Schäfer et al., Gene 145, 69-73 (1994)), Bernard et al., Journal of Molecular Biology, 234: 534-541 (1993)), pEM1 (Schrumpf et al. 1991, Journal of Bacteriology 173: 4510-4516) or pBGS8 (Spratt et al., 1986, Gene 41: 337-342). The plasmid vector which contains the gene to be amplified is subsequently transferred by transformation into the desired *C. glutamicum* strain. Transformation methods are described, for example, in Thierbach et al. (Applied Microbiology and Biotechnology 29, 356-362 (1988)), Dunican and Shivnan (Biotechnology 7, 1067-1070 (1989)) and Tauch et al. (FEMS Microbiological Letters 123, 343-347 (1994)).

IV. Genes and Proteins Encoded Thereby

The rate of transcription and/or the rate of translation of genes in microorganisms, in comparison with the wild type, may be altered or caused by regulating the transcription of genes in said microorganism by expression units of the invention, said genes being heterologous with respect to said expression units.

This is preferably achieved by
introducing one or more nucleic acids of the invention having promoter activity into the genome of the microorganism so that one or more endogenous genes are transcribed under the control of said introduced nucleic acid having promoter activity, if appropriate having an altered specific promoter activity, or
introducing one or more nucleic acid constructs containing a nucleic acid of the invention having promoter activity and, functionally linked, one or more exogenous or endogenous nucleic acids to be transcribed, into the microorganism.

If one or more genes are introduced into the genome of a microorganism so that one or more introduced genes are transcribed under the control of the nucleic acids of the invention, insertion may take place so as for the gene or the genes to be integrated into coding or noncoding regions. The insertion preferably takes place into noncoding regions.

In this connection, nucleic acid constructs may be inserted chromosomally or extrachromosomally. The nucleic acid constructs are preferably inserted chromosomally. A "chromosomal" integration is the insertion of a DNA fragment into the chromosome of a host cell.

"Endogenous" means genetic information such as, for example, genes, which is already present in the wild-type genome (as defined above).

"Exogenous" means genetic information such as, for example, genes, which is not present in the wild-type genome. If exogenous genetic information, for example the multiple promoter-comprising expression units of the invention, is introduced into the genome of a wild-type strain, thereby generating a genetically modified strain, then this genetic information is endogenous in a comparison of the initially generated genetic strain with its progeny, but exogenous in a comparison with the original wild-type strain which did not comprise said genetic information.

The term "genes" with respect to regulation of transcription by the nucleic acids of the invention having promoter activity means preferably nucleic acids which comprise a region to be transcribed, i.e., for example, a region regulating translation, a coding region and, if appropriate, further regulatory elements such as, for example, a terminator.

The term "genes" with respect to the regulation of expression by the expression units of the invention means preferably nucleic acids which comprise a coding region and, if appropriate, further regulatory elements such as, for example, a terminator.

A "coding region" means a nucleic acid sequence which encodes a protein.

"Heterologous" with respect to nucleic acids having promoter activity and genes means that the genes used are not transcribed in the wild type with regulation of the nucleic acids of the invention having promoter activity, but that a new functional linkage which does not occur in the wild type is produced, and the functional combination of nucleic acid of the invention having promoter activity and specific gene does not occur in the wild type.

"Heterologous" with respect to expression units and genes means that the genes used are not expressed in the wild type with regulation of the expression units of the invention, but that a new functional linkage which does not occur in the wild type is produced, and the functional combination of expression unit of the invention and specific gene does not occur in the wild type.

In a preferred embodiment of the above-described processes of the invention for altering or causing the rate of transcription and/or rate of expression of genes in microorganisms, the genes are selected from the group consisting of nucleic acids encoding a protein of the biosynthetic pathway of fine chemicals, it being possible for said genes to contain further regulatory elements, if appropriate.

In a particularly preferred embodiment of the above-described processes of the invention for altering or causing the rate of transcription and/or the rate of expression of genes in microorganisms, the genes are selected from among:

Nucleic acids encoding a protein of the biosynthetic pathway of proteinogenic and nonproteinogenic amino acids, nucleic acids encoding a protein of the biosynthetic pathway of nucleotides and nucleosides, nucleic acids encoding a protein of the biosynthetic pathway of organic acids, nucleic acids encoding a protein of the biosynthetic pathway of lipids and fatty acids, nucleic acids encoding a protein of the biosynthetic pathway of diols, nucleic acids encoding a protein of the biosynthetic pathway of carbohydrates, nucleic acids encoding a protein of the biosynthetic pathway of aromatic compounds, nucleic acids encoding a protein of the biosynthetic pathway of vitamins, nucleic acids encoding a protein of the biosynthetic pathway of cofactors, and nucleic acids encoding a protein of the biosynthetic pathway of enzymes, nucleic acids encoding a protein of the central metabolism, it being possible for the genes to contain further regulatory elements, if appropriate.

In a particularly preferred embodiment, the proteins are selected from the biosynthetic pathway of amino acids, namely:

aspartate kinase, aspartate semialdehyde dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triosephosphate isomerase, transcriptional regulator LuxR, transcriptional regulator LysR1, transcriptional regulator LysR2, malate-quinone oxidoreductase, glucose-6-phosphate dehydrogenase, 6-phosphogluconate dehydrogenase, transketolase, transaldolase, homoserine O-acetyltransferase, cystathionine gamma-synthase, cystathionine beta-lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase I, cysteine synthase II, coenzyme B12-dependent methionine synthase, coenzyme B12-independent methionine synthase activity, sulfate adenylyltransferase subunits 1 and 2, phosphoadenosine phosphosulfate reductase, ferredoxin sulfite reductase, ferredoxin NADP reductase, 3-phosphoglycerate dehydrogenase, RXA00655 regulator, RXN2910 regulator, arginyl-tRNA synthetase, phosphoenolpyruvate carboxylase, threonine efflux protein, serine hydroxymethyltransferase, fructose 1,6-bisphosphatase, protein of sulfate reduction RXA077, protein of sulfate reduction RXA248, protein of sulfate reduction RXA247, OpcA protein, 1-phosphofructokinase, 6-phosphofructokinase, tetrahydropicolinate succinylase, succinyl aminoketopimelate aminotransferase, succinyl diaminopimelate desuccinylase, diaminopimelate epimerase, 6-phosphogluconate dehydrogenase, glucose-phosphate isomerase, phosphoglycerate mutase, enolase, pyruvate kinase, aspartate transaminase, and malate enzyme.

Preferred proteins and nucleic acids encoding said proteins are protein sequences and, respectively, nucleic acid sequences of microbial origin, preferably from bacteria of the genus *Corynebacterium* or *Brevibacterium*, preferably from coryneform bacteria, particularly preferably from *Corynebacterium glutamicum*.

Examples of particularly preferred protein sequences and of the corresponding nucleic acid sequences encoding said proteins of the biosynthetic pathway of amino acids, the document referring thereto, and the designation thereof in the reference document are listed in Table 1:

TABLE 1

| Protein | Nucleic acid encoding protein | Reference document | SEQ. ID. NO. in reference document |
|---|---|---|---|
| Aspartate kinase | ask or lysC | EP1108790 | DNA: 281 Protein: 3781 |
| Aspartate semialdehyde dehydrogenase | asd | EP1108790 | DNA: 331 Protein: 3831 |
| Dihydrodipicolinate synthetase | dapA | WO 0100843 | DNA: 55 Protein: 56 |
| Dihydrodipicolinate reductase | dapB | WO 0100843 | DNA: 35 Protein: 36 |
| meso-Diaminopimelate D-dehydrogenase | ddh | EP1108790 | DNA: 3494 Protein: 6944 |
| Diaminopimelate decarboxylase | lysA | EP1108790 | DNA: 3451 Prot.: 6951 |
| Lysine exporter | lysE | EP1108790 | DNA: 3455 Prot.: 6955 |
| Tetrahydropicolinate succinylase | dapD | EP1108790 | DNA: 1229 Prot: 4729 |

TABLE 1-continued

| Protein | Nucleic acid encoding protein | Reference document | SEQ. ID. NO. in reference document |
|---|---|---|---|
| Succinyl aminoketopimelate aminotransferase | dapC | WO 0100843 | DNA: 327<br>Prot: 328 |
| Succinyl diaminopimelate desuccinylase | dapE | WO 0100843 | DNA: 31<br>Prot: 32 |
| Diaminopimelate epimerase | dapF | EP1108790 | DNA: 2131<br>Prot: 5632 |
| Arginyl-tRNA synthetase | argS | EP1108790 | DNA: 3450<br>Prot.: 6950 |
| Glucose-6-phosphate dehydrogenase | zwf | WO 0100844 | DNA: 243<br>Prot.: 244 |
| Transketolase | RXA2739 | EP 1108790 | DNA: 1740<br>Prot: 5240 |
| Transaldolase | RXA2738 | WO 0100844 | DNA: 245<br>Prot: 246 |
| OpcA | opcA | WO 0100804 | DNA: 79<br>Prot: 80 |
| 6-Phospho-gluconolactonase | RXA2735 | WO 0100844 | DNA: 1<br>Prot.: 2 |
| 6-Phosphogluconate dehydrogenase | | EP1108790 | DNA: 1605<br>Prot: 5105 |
| Glucosephosphate isomerase | gpi | WO 0100844 | DNA: 41<br>Prot.: 42 |
| Malate-quinone oxidoreductase | mqo | WO 0100844 | DNA: 569<br>Protein: 570 |
| Glyceraldehyde-3-phosphate dehydrogenase | gap | WO 0100844 | DNA: 187<br>Prot.: 188 |
| 3-Phosphoglycerate kinase | pgk | WO 0100844 | DNA: 69<br>Prot.: 70 |
| Triosephosphate isomerase | tpi | WO 0100844 | DNA: 61<br>Prot.: 62 |
| 1-Phosphofructokinase 1 | pfk1 | WO0100844 | DNA: 55<br>Protein: 56 |
| 1-Phosphofructokinase 2 | pfk2 | WO0100844 | DNA: 57<br>Protein: 58 |
| 6-Phosphofructokinase 1 | 6-pfk1 | EP 1108790 | DNA: 1383<br>Protein: 4883 |
| 6-Phosphofructokinase 2 | 6-pfk2 | DE 10112992 | DNA: 1<br>Protein: 2 |
| Fructose-1,6-bisphosphatase 1 | fbr1 | EP1108790 | DNA: 1136<br>Protein: 4636 |
| Pyruvate oxidase | poxB | WO 0100844 | DNA: 85<br>Protein: 86 |
| Phosphoglycerate mutase | | WO 0100844 | DNA: 49<br>Prot.: 50 |
| Enolase | eno | WO 0100844 | DNA: 71<br>Prot.: 72 |
| Pyruvate kinase | pykA | WO 0100844 | DNA: 75<br>Prot.: 76 |
| Pyruvate kinase | pykA | EP1108790 | DNA: 3328<br>Prot.: 6828 |
| Pyruvate carboxylase | pycA | EP1108790 | DNA: 765<br>Prot.: 4265 |
| Aspartate transaminase | | EP1108790 | DNA: 3226<br>Prot: 4726<br>DNA: 3134<br>Prot.: 6634<br>DNA: 2861<br>Prot.: 6361<br>DNA: 911<br>Prot.: 4411 |
| PEP-carboxylase | pck | EP1108790 | DNA: 3470<br>Prot.: 6970 |
| Malate enzyme | malE | EP1108790 | DNA: 3328<br>Prot: 6828 |
| Biotin ligase | birA | EP1108790 | DNA: 786<br>Prot.: 4286 |
| Homoserine kinase | thrB | WO 0100843 | DNA: 173<br>Prot.: 174 |
| Threonine synthase | thrC | WO 0100843 | DNA: 175<br>Prot.: 176 |
| Threonine export carrier | thrE | WO 0251231 | DNA: 41<br>Prot.: 42 |
| Threonine efflux protein | RXA2390 | WO 0100843 | DNA: 7<br>Prot: 8 |
| Threonine dehydratase | ilvA | EP 1108790 | DNA: 2328<br>Prot.: 5828 |
| Homoserine-O-acetyltransferase | metA | EP 1108790 | DNA: 727<br>Prot.: 4227 |
| Cystathionine gamma-synthase | metB | EP 1108790 | DNA: 3491<br>Prot: 6991 |
| Cystathionine beta-lyase | metC | EP 1108790 | DNA: 2535<br>Prot: 6035 |
| Coenzyme B12-dependent methionine synthase | metH | EP 1108790 | DNA: 1663<br>Prot: 5163 |
| O-acetylhomoserine sulfhydrylase | metY | EP 1108790 | DNA: 726<br>Prot: 4226 |
| Methylenetetrahydro-folate reductase | metF | EP 1108790 | DNA: 2379<br>Prot: 5879 |
| D-3-Phosphoglycerate dehydrogenase | serA | EP 1108790 | DNA: 1415<br>Prot: 4915 |
| Phosphoserine phosphatase 1 | serB | WO 0100843 | DNA: 153<br>Prot.: 154 |
| Phosphoserine phosphatase 2 | serB | EP 1108790 | DNA.: 467<br>Prot.: 3967 |
| Phosphoserine phosphatase 3 | serB | EP 1108790 | DNA: 334<br>Prot.: 3834 |
| Phosphoserine aminotransferase | serC | WO 0100843 | DNA: 151<br>Prot.: 152 |
| Serine acetyl transferase | cysE | WO 0100843 | DNA: 243<br>Prot.: 244 |
| Cysteine synthase I | cysK | EP 1108790 | DNA: 2817<br>Prot.: 6317 |
| Cysteine synthase II | CysM | EP 1108790 | DNA: 2338<br>Prot.: 5838 |
| Homoserine dehydrogenase | hom | EP 1108790 | DNA: 3452<br>Prot.: 6952 |
| Coenzyme B12-independent methionine synthase | metE | WO 0100843 | DNA: 755<br>Prot.: 756 |
| Serine hydroxymethyl transferase | glyA | WO 0100843 | DNA: 143<br>Prot.: 144 |
| Protein in sulfate reduction | RXA247 | EP 1108790 | DNA: 3089<br>Prot.: 6589 |
| Protein in sulfate reduction | RXA248 | EP 1108790 | DNA: 3090<br>Prot.: 6590 |
| Sulfate adenylyltransferase subunit 1 | CysN | EP 1108790 | DNA: 3092<br>Prot.: 6592 |
| Sulfate adenylyltransferase subunit 2 | CysD | EP 1108790 | DNA: 3093<br>Prot.: 6593 |
| Phosphoadenosine phosphosulfate reductase | CysH | WO 02729029 | DNA: 7<br>Prot.: 8 |
| Ferredoxin sulfite reductase | RXA073 | WO 0100842 | DNA: 329<br>Prot.: 330 |
| Ferredoxin NADP reductase | RXA076 | WO 0100843 | DNA: 79<br>Prot.: 80 |
| Transcriptional regulator LuxR | luxR | WO 0100842 | DNA: 297<br>Protein: 298 |
| Transcriptional regulator LysR1 | lysR1 | EP 1108790 | DNA: 676<br>Protein: 4176 |
| Transcriptional regulator LysR2 | lysR2 | EP 1108790 | DNA: 3228<br>Protein: 6728 |
| Transcriptional regulator LysR3 | lysR3 | EP 1108790 | DNA: 2200<br>Protein: 5700 |
| RXA00655 regulator | RXA655 | US2003162267.2 | DNA: 1<br>Prot.: 2 |
| RXN02910 regulator | RXN2910 | US2003162267.2 | DNA: 5<br>Prot.: 6 |

Preference is given to selecting the target gene G to be regulated according to the invention from the genes listed above.

Further particularly preferred protein sequences from the biosynthetic pathway of amino acids have in each case the amino acid sequence indicated in Table 1 for this protein, where the respective protein has, in at least one of the amino acid positions indicated in Table 2, column 2 for this amino acid sequence, a different proteinogenic amino acid than the respective amino acid indicated in Table 2, column 3 in the same line. In a further preferred embodiment, the proteins have, in at least one of the amino acid positions indicated in Table 2, column 2 for the amino acid sequence, the amino acid indicated in Table 2, column 4 in the same line. The proteins indicated in Table 2 are mutated proteins of the biosynthetic pathway of amino acids, which have particularly advantageous properties and are therefore particularly suitable for expressing the corresponding nucleic acids through a promoter construct of the invention and for producing amino acids. For example, the mutation T311I leads to the feedback inhibition of ask being switched off.

The corresponding nucleic acids which encode a mutated protein described above from Table 2 can be prepared by conventional methods.

A suitable starting point for preparing the nucleic acid sequences encoding a mutated protein is, for example, the genome of a *Corynebacterium glutamicum* strain which is obtainable from the American Type Culture Collection under the designation ATCC 13032, or the nucleic acid sequences referred to in Table 1. For the back-translation of the amino acid sequence of the mutated proteins into the nucleic acid sequences encoding these proteins, it is advantageous to use the codon usage of the organism into which the nucleic acid sequence is to be introduced or in which the nucleic acid sequence is present. For example, it is advantageous to use the codon usage of *Corynebacterium glutamicum* for *Corynebacterium glutamicum*. The codon usage of the particular organism can be ascertained in a manner known per se from databases or patent applications which describe at least one protein and one gene which encodes this protein from the desired organism.

The information in Table 2 is to be understood in the following way:

In column 1 "identification", an unambiguous designation for each sequence in relation to Table 1 is indicated.

In column 2 "AA-POS", the respective number refers to the amino acid position of the corresponding polypeptide sequence from Table 1. A "26" in the column "AA-POS" accordingly means amino acid position 26 of the correspondingly indicated polypeptide sequence. The numbering of the position starts at +1 at the N terminus.

In column 3 "AA wild type", the respective letter designates the amino acid—represented in one-letter code—at the position indicated in column 2 in the corresponding wild-type strain of the sequence from Table 1.

In column 4 "AA mutant", the respective letter designates the amino acid—represented in one-letter code—at the position indicated in column 2 in the corresponding mutant strain.

In column 5 "function", the physiological function of the corresponding polypeptide sequence is indicated.

For a mutated protein with a particular function (column 5) and a particular initial amino acid sequence (Table 1), columns 2, 3 and 4 describe at least one mutation, and a plurality of mutations for some sequences. This plurality of mutations always refers to the closest initial amino acid sequence above in each case (Table 1). The term "at least one of the amino acid positions" of a particular amino acid sequence preferably means at least one of the mutations described for this amino acid sequence in columns 2, 3 and 4.

One-letter code for proteinogenic amino acids:

| | |
|---|---|
| A | alanine |
| C | cysteine |
| D | aspartate |
| E | glutamate |
| F | phenylalanine |
| G | glycine |
| H | histidine |
| I | isoleucine |
| K | lysine |
| L | leucine |
| M | methionine |
| N | asparagine |
| P | proline |
| Q | glutamine |
| R | arginine |
| S | serine |
| T | threonine |
| V | valine |
| W | tryptophan |
| Y | tyrosine |

TABLE 2

| Column 1 Identification | Column 2 AA position | Column 3 AA wild type | Column 4 AA mutant | Column 5 Function |
|---|---|---|---|---|
| ask | 317 | S | A | aspartate kinase |
| | 311 | T | I | |
| | 279 | A | T | |
| asd | 66 | D | G | aspartate-semialdehyde dehydrogenase |
| | 234 | R | H | |
| | 272 | D | E | |
| | 285 | K | E | |
| | 20 | L | F | |
| dapA | 2 | S | A | dihydrodipicolinate synthetase |
| | 84 | K | N | |
| | 85 | L | V | |
| dapB | 91 | D | A | dihydrodipicolinate reductase |
| | 83 | D | N | |
| ddh | 174 | D | E | meso-diaminopimelate D-dehydrogenase |
| | 235 | F | L | |
| | 237 | S | A | |
| lysA | 265 | A | D | diaminopicolinate decarboxylase |
| | 320 | D | N | |
| | 332 | I | V | |

TABLE 2-continued

| Column 1 Identification | Column 2 AA position | Column 3 AA wild type | Column 4 AA mutant | Column 5 Function |
|---|---|---|---|---|
| argS | 355 | G | D | arginyl-tRNA synthetase |
|  | 156 | A | S |  |
|  | 513 | V | A |  |
|  | 540 | H | R |  |
| zwf | 8 | S | T | glucose-6-phosphate dehydrogenase |
|  | 150 | T | A |  |
|  | 321 | G | S |  |
| gap | 264 | G | S | glyceraldehyde-3-phosphate dehydrogenase |
| pycA | 7 | S | L | pyruvate carboxylase |
|  | 153 | E | D |  |
|  | 182 | A | S |  |
|  | 206 | A | S |  |
|  | 227 | H | R |  |
|  | 455 | A | G |  |
|  | 458 | P | S |  |
|  | 639 | S | T |  |
|  | 1008 | R | H |  |
|  | 1059 | S | P |  |
|  | 1120 | D | E |  |
| pck | 162 | H | Y | PEP carboxylase |
|  | 241 | G | D |  |
|  | 829 | T | R |  |
| thrB | 103 | S | A | homoserine kinase |
|  | 190 | T | A |  |
|  | 133 | A | V |  |
|  | 138 | P | S |  |
| thrC | 69 | G | R | threonine synthase |
|  | 478 | T | I |  |
| RXA330 | 85 | I | M | threonine efflux protein |
|  | 161 | F | I |  |
|  | 195 | G | D |  |
| hom | 104 | V | I | homoserine dehydrogenase |
|  | 116 | T | I |  |
|  | 148 | G | A |  |
|  | 59 | V | A |  |
|  | 270 | T | S |  |
|  | 345 | R | P |  |
|  | 268 | K | N |  |
|  | 61 | D | H |  |
|  | 72 | E | Q |  |
| lysR1 | 80 | R | H | transcriptional regulator LysR1 |
| lysR3 | 142 | R | W | transcriptional regulator LysR3 |
|  | 179 | A | T |  |
| RXA2739 | 75 | N | D | transketolase |
|  | 329 | A | T |  |
|  | 332 | A | T |  |
|  | 556 | V | I |  |
| RXA2738 | 242 | K | M | transaldolase |
| opcA | 107 | Y | H | OpcA |
|  | 219 | K | N |  |
|  | 233 | P | S |  |
|  | 261 | Y | H |  |
|  | 312 | S | F |  |
|  | 65 | G | R | aspartate-1-decarboxylase |
|  | 33 | G | S | 6-phosphogluconolactonase |

Genetically Modified Microorganisms

The expression units of the invention, the above-described genes and the above-described nucleic acid constructs or expression cassettes are introduced into the microorganism, in particular into coryneform bacteria, by methods known to the skilled worker, such as conjugation or electroporation (for example, Liebl et al (1989) FEMS Microbiology Letters 53, 299-303).

Integrated expression cassettes are preferably selected by the SacB method. The SacB method is known to the skilled worker and is described, for example, in Schäfer A, Tauch A, Jäger W. Kalinowski J. Thierbach G. Pühler A.; Small mobilizable multi-purpose cloning vectors derived from the *Escherichia coli* plasmids pK18 and pK19: selection of defined deletions in the chromosome of *Corynebacterium glutamicum*, Gene. 1994 Jul. 22; 145(1):69-73 and Blomfield I C, Vaughn V, Rest R F, Eisenstein B I.; Allelic exchange in *Escherichia coli* using the *Bacillus subtilis* sacB gene and a temperature-sensitive pSC101 replicon; Mol. Microbiol. 1991 June; 5(6):1447-57.

Preference is given to using according to the invention as starting microorganisms those which already produce the desired variable product (fine chemical/protein).

The invention therefore also relates to a genetically modified microorganism which comprises an expression cassette of the invention or a vector comprising the expression cassette of the invention.

The present invention particularly preferably relates to genetically modified microorganisms, in particular coryneform bacteria, which comprise a vector, in particular a shuttle vector or plasmid vector, which carries at least one expression cassette of the invention.

Preferred microorganisms or genetically modified microorganisms are bacteria, algae, fungi or yeasts.

Particularly preferred microorganisms are, in particular, coryneform bacteria.

Preferred coryneform bacteria are bacteria of the genus *Corynebacterium*, in particular of the species *Corynebacterium glutamicum*, *Corynebacterium acetoglutamicum*, *Corynebacterium acetoacidophilum*, *Corynebacterium thermoaminogenes*, *Corynebacterium melassecola* and *Corynebacterium efficiens* or of the genus *Brevibacterium*, in particular of the species *Brevibacterium flavum*, *Brevibacterium lactofermentum* and *Brevibacterium divaricatum*.

Particularly preferred bacteria of the genera *Corynebacterium* and *Brevibacterium* are selected from the group consisting of *Corynebacterium glutamicum* ATCC 13032, *Corynebacterium acetoglutamicum* ATCC 15806, *Corynebacterium acetoacidophilum* ATCC 13870, *Corynebacterium thermoaminogenes* FERM BP-1539, *Corynebacterium melassecola* ATCC 17965, *Corynebacterium efficiens* DSM 44547, *Corynebacterium efficiens* DSM 44548. *Corynebacterium efficiens* DSM 44549, *Brevibacterium flavum* ATCC 14067, *Brevibacterium lactofermentum* ATCC 13869, *Brevibacterium divaricatum* ATCC 14020, *Corynebacterium glutamicum* KFCC10065 and *Corynebacterium glutamicum* ATCC 21608, and also strains derived therefrom, for example by classical mutation and selection or by directed mutation.

The abbreviation KFCC means the Korean Federation of Culture Collection, the abbreviation ATCC means the American type strain culture collection, and the abbreviation DSM (or DSMZ) means the Deutsche Sammlung von Mikroorganismen (Deutsche Sammlung von Mikroorganismen and Zellkulturen).

Further particularly preferred bacteria of the genera *Corynebacterium* and *Brevibacterium* are listed in Table 3:

TABLE 3

| Bacterium | | Deposition number | | | | | | | |
|---|---|---|---|---|---|---|---|---|---|
| Genus | species | ATCC | FERM | NRRL | CECT | NCIMB | CBS | NCTC | DSMZ |
| Brevibacterium | ammoniagenes | 21054 | | | | | | | |
| Brevibacterium | ammoniagenes | 19350 | | | | | | | |
| Brevibacterium | ammoniagenes | 19351 | | | | | | | |
| Brevibacterium | ammoniagenes | 19352 | | | | | | | |
| Brevibacterium | ammoniagenes | 19353 | | | | | | | |
| Brevibacterium | ammoniagenes | 19354 | | | | | | | |
| Brevibacterium | ammoniagenes | 19355 | | | | | | | |
| Brevibacterium | ammoniagenes | 19356 | | | | | | | |
| Brevibacterium | ammoniagenes | 21055 | | | | | | | |
| Brevibacterium | ammoniagenes | 21077 | | | | | | | |
| Brevibacterium | ammoniagenes | 21553 | | | | | | | |
| Brevibacterium | ammoniagenes | 21580 | | | | | | | |
| Brevibacterium | ammoniagenes | 39101 | | | | | | | |
| Brevibacterium | butanicum | 21196 | | | | | | | |
| Brevibacterium | divaricatum | 21792 | P928 | | | | | | |
| Brevibacterium | flavum | 21474 | | | | | | | |
| Brevibacterium | flavum | 21129 | | | | | | | |
| Brevibacterium | flavum | 21518 | | | | | | | |
| Brevibacterium | flavum | | | B11474 | | | | | |
| Brevibacterium | flavum | | | B11472 | | | | | |
| Brevibacterium | flavum | 21127 | | | | | | | |
| Brevibacterium | flavum | 21128 | | | | | | | |
| Brevibacterium | flavum | 21427 | | | | | | | |
| Brevibacterium | flavum | 21475 | | | | | | | |
| Brevibacterium | flavum | 21517 | | | | | | | |
| Brevibacterium | flavum | 21528 | | | | | | | |
| Brevibacterium | flavum | 21529 | | | | | | | |
| Brevibacterium | flavum | | | B11477 | | | | | |
| Brevibacterium | flavum | | | B11478 | | | | | |
| Brevibacterium | flavum | 21127 | | | | | | | |
| Brevibacterium | flavum | | | B11474 | | | | | |
| Brevibacterium | healii | 15527 | | | | | | | |
| Brevibacterium | ketoglutamicum | 21004 | | | | | | | |
| Brevibacterium | ketoglutamicum | 21089 | | | | | | | |
| Brevibacterium | ketosoreductum | 21914 | | | | | | | |
| Brevibacterium | lactofermentum | | | | 70 | | | | |
| Brevibacterium | lactofermentum | | | | 74 | | | | |
| Brevibacterium | lactofermentum | | | | 77 | | | | |
| Brevibacterium | lactofermentum | 21798 | | | | | | | |
| Brevibacterium | lactofermentum | 21799 | | | | | | | |
| Brevibacterium | lactofermentum | 21800 | | | | | | | |
| Brevibacterium | lactofermentum | 21801 | | | | | | | |
| Brevibacterium | lactofermentum | | | B11470 | | | | | |
| Brevibacterium | lactofermentum | | | B11471 | | | | | |
| Brevibacterium | lactofermentum | 21086 | | | | | | | |
| Brevibacterium | lactofermentum | 21420 | | | | | | | |
| Brevibacterium | lactofermentum | 21086 | | | | | | | |
| Brevibacterium | lactofermentum | 31269 | | | | | | | |
| Brevibacterium | linens | 9174 | | | | | | | |
| Brevibacterium | linens | 19391 | | | | | | | |
| Brevibacterium | linens | 8377 | | | | | | | |
| Brevibacterium | paraffinolyticum | | | | | 11160 | | | |

TABLE 3-continued

| Bacterium | | Deposition number | | | | | | | |
|---|---|---|---|---|---|---|---|---|---|
| Genus | species | ATCC | FERM | NRRL | CECT | NCIMB | CBS | NCTC | DSMZ |
| *Brevibacterium* | spec. | | | | | | 717.73 | | |
| *Brevibacterium* | spec. | | | | | | 717.73 | | |
| *Brevibacterium* | spec. | 14604 | | | | | | | |
| *Brevibacterium* | spec. | 21860 | | | | | | | |
| *Brevibacterium* | spec. | 21864 | | | | | | | |
| *Brevibacterium* | spec. | 21865 | | | | | | | |
| *Brevibacterium* | spec. | 21866 | | | | | | | |
| *Brevibacterium* | spec. | 19240 | | | | | | | |
| *Corynebacterium* | acetoacidophilum | 21476 | | | | | | | |
| *Corynebacterium* | acetoacidophilum | 13870 | | | | | | | |
| *Corynebacterium* | acetoglutamicum | | | B11473 | | | | | |
| *Corynebacterium* | acetoglutamicum | | | B11475 | | | | | |
| *Corynebacterium* | acetoglutamicum | 15806 | | | | | | | |
| *Corynebacterium* | acetoglutamicum | 21491 | | | | | | | |
| *Corynebacterium* | acetoglutamicum | 31270 | | | | | | | |
| *Corynebacterium* | acetophilum | | | B3671 | | | | | |
| *Corynebacterium* | ammoniagenes | 6872 | | | | | | 2399 | |
| *Corynebacterium* | ammoniagenes | 15511 | | | | | | | |
| *Corynebacterium* | fujiokense | 21496 | | | | | | | |
| *Corynebacterium* | glutamicum | 14067 | | | | | | | |
| *Corynebacterium* | glutamicum | 39137 | | | | | | | |
| *Corynebacterium* | glutamicum | 21254 | | | | | | | |
| *Corynebacterium* | glutamicum | 21255 | | | | | | | |
| *Corynebacterium* | glutamicum | 31830 | | | | | | | |
| *Corynebacterium* | glutamicum | 13032 | | | | | | | |
| *Corynebacterium* | glutamicum | 14305 | | | | | | | |
| *Corynebacterium* | glutamicum | 15455 | | | | | | | |
| *Corynebacterium* | glutamicum | 13058 | | | | | | | |
| *Corynebacterium* | glutamicum | 13059 | | | | | | | |
| *Corynebacterium* | glutamicum | 13060 | | | | | | | |
| *Corynebacterium* | glutamicum | 21492 | | | | | | | |
| *Corynebacterium* | glutamicum | 21513 | | | | | | | |
| *Corynebacterium* | glutamicum | 21526 | | | | | | | |
| *Corynebacterium* | glutamicum | 21543 | | | | | | | |
| *Corynebacterium* | glutamicum | 13287 | | | | | | | |
| *Corynebacterium* | glutamicum | 21851 | | | | | | | |
| *Corynebacterium* | glutamicum | 21253 | | | | | | | |
| *Corynebacterium* | glutamicum | 21514 | | | | | | | |
| *Corynebacterium* | glutamicum | 21516 | | | | | | | |
| *Corynebacterium* | glutamicum | 21299 | | | | | | | |
| *Corynebacterium* | glutamicum | 21300 | | | | | | | |
| *Corynebacterium* | glutamicum | 39684 | | | | | | | |
| *Corynebacterium* | glutamicum | 21488 | | | | | | | |
| *Corynebacterium* | glutamicum | 21649 | | | | | | | |
| *Corynebacterium* | glutamicum | 21650 | | | | | | | |
| *Corynebacterium* | glutamicum | 19223 | | | | | | | |
| *Corynebacterium* | glutamicum | 13869 | | | | | | | |
| *Corynebacterium* | glutamicum | 21157 | | | | | | | |
| *Corynebacterium* | glutamicum | 21158 | | | | | | | |
| *Corynebacterium* | glutamicum | 21159 | | | | | | | |
| *Corynebacterium* | glutamicum | 21355 | | | | | | | |
| *Corynebacterium* | glutamicum | 31808 | | | | | | | |
| *Corynebacterium* | glutamicum | 21674 | | | | | | | |
| *Corynebacterium* | glutamicum | 21562 | | | | | | | |
| *Corynebacterium* | glutamicum | 21563 | | | | | | | |
| *Corynebacterium* | glutamicum | 21564 | | | | | | | |
| *Corynebacterium* | glutamicum | 21565 | | | | | | | |
| *Corynebacterium* | glutamicum | 21566 | | | | | | | |
| *Corynebacterium* | glutamicum | 21567 | | | | | | | |
| *Corynebacterium* | glutamicum | 21568 | | | | | | | |
| *Corynebacterium* | glutamicum | 21569 | | | | | | | |
| *Corynebacterium* | glutamicum | 21570 | | | | | | | |
| *Corynebacterium* | glutamicum | 21571 | | | | | | | |
| *Corynebacterium* | glutamicum | 21572 | | | | | | | |
| *Corynebacterium* | glutamicum | 21573 | | | | | | | |
| *Corynebacterium* | glutamicum | 21579 | | | | | | | |
| *Corynebacterium* | glutamicum | 19049 | | | | | | | |
| *Corynebacterium* | glutamicum | 19050 | | | | | | | |
| *Corynebacterium* | glutamicum | 19051 | | | | | | | |
| *Corynebacterium* | glutamicum | 19052 | | | | | | | |
| *Corynebacterium* | glutamicum | 19053 | | | | | | | |
| *Corynebacterium* | glutamicum | 19054 | | | | | | | |
| *Corynebacterium* | glutamicum | 19055 | | | | | | | |
| *Corynebacterium* | glutamicum | 19056 | | | | | | | |
| *Corynebacterium* | glutamicum | 19057 | | | | | | | |
| *Corynebacterium* | glutamicum | 19058 | | | | | | | |

TABLE 3-continued

| Bacterium | | Deposition number | | | | | | | |
|---|---|---|---|---|---|---|---|---|---|
| Genus | species | ATCC | FERM | NRRL | CECT | NCIMB | CBS | NCTC | DSMZ |
| Corynebacterium | glutamicum | 19059 | | | | | | | |
| Corynebacterium | glutamicum | 19060 | | | | | | | |
| Corynebacterium | glutamicum | 19185 | | | | | | | |
| Corynebacterium | glutamicum | 13286 | | | | | | | |
| Corynebacterium | glutamicum | 21515 | | | | | | | |
| Corynebacterium | glutamicum | 21527 | | | | | | | |
| Corynebacterium | glutamicum | 21544 | | | | | | | |
| Corynebacterium | glutamicum | 21492 | | | | | | | |
| Corynebacterium | glutamicum | | | B8183 | | | | | |
| Corynebacterium | glutamicum | | | B8182 | | | | | |
| Corynebacterium | glutamicum | | | B12416 | | | | | |
| Corynebacterium | glutamicum | | | B12417 | | | | | |
| Corynebacterium | glutamicum | | | B12418 | | | | | |
| Corynebacterium | glutamicum | | | B11476 | | | | | |
| Corynebacterium | glutamicum | 21608 | | | | | | | |
| Corynebacterium | lilium | | P973 | | | | | | |
| Corynebacterium | nitrilophilus | 21419 | | | | 11594 | | | |
| Corynebacterium | spec. | | P4445 | | | | | | |
| Corynebacterium | spec. | | P4446 | | | | | | |
| Corynebacterium | spec. | 31088 | | | | | | | |
| Corynebacterium | spec. | 31089 | | | | | | | |
| Corynebacterium | spec. | 31090 | | | | | | | |
| Corynebacterium | spec. | 31090 | | | | | | | |
| Corynebacterium | spec. | 31090 | | | | | | | |
| Corynebacterium | spec. | 15954 | | | | | | | 20145 |
| Corynebacterium | spec. | 21857 | | | | | | | |
| Corynebacterium | spec. | 21862 | | | | | | | |
| Corynebacterium | spec. | 21863 | | | | | | | |

The abbreviations have the following meaning:
ATCC: American Type Culture Collection, Rockville, MD, USA
FERM: Fermentation Research Institute, Chiba, Japan
NRRL: ARS Culture Collection, Northern Regional Research Laboratory, Peoria, IL, USA
CECT: Coleccion Espanola de Cultivos Tipo, Valencia, Spain
NCIMB: National Collection of Industrial and Marine Bacteria Ltd., Aberdeen, UK
CBS: Centraalbureau voor Schimmelcultures, Baarn, NL
NCTC: National Collection of Type Cultures, London, UK
DSMZ: Deutsche Sammlung von Mikroorganismen and Zellkulturen, Braunschweig, Germany Particular preference is given here to microorganisms of bacteria of the genus *Corynebacterium*, in particular those which are already capable of producing L-lysine, L-methionine and/or L-threonine. These are in particular coryne bacteria in which, for example, the gene coding for an aspartate kinase (ask gene) is deregulated or feedback inhibition has been eliminated or reduced. For example, such bacteria have a mutation in the ask gene, which results in a reduction or elimination of feedback inhibition, such as, for example, the mutation T311I.

The expression units of the invention enable the metabolic pathways to specific biosynthetic products in the above-described genetically modified microorganisms of the invention to be regulated.

For this purpose, for example, metabolic pathways which result in a specific biosynthetic product are enhanced by causing or increasing the rate of transcription or the rate of expression of genes of this biosynthetic pathway in which the increased amount of protein results in an increased total activity of these proteins of the desired biosynthetic pathway and thus in an enhanced metabolic flux toward the desired biosynthetic product.

Furthermore, metabolic pathways which diverge from a specific biosynthetic product may be attenuated by reducing the rate of transcription or rate of expression of genes of this diverging biosynthetic pathway in which the reduced amount of protein results in a reduced total activity of these proteins of the unwanted biosynthetic pathway and thus additionally in an enhanced metabolic flux toward the desired biosynthetic product.

The genetically modified microorganisms of the invention are capable, for example, of producing biosynthetic products from glucose, sucrose, lactose, fructose, maltose, molasses, starch, cellulose or from glycerol and ethanol.

The invention therefore relates to a process for producing biosynthetic products by culturing genetically modified microorganisms of the invention.

Depending on the desired biosynthetic product, the rate of transcription or rate of expression of various genes must be increased or reduced. It is usually advantageous to alter the rate of transcription or rate of expression of a plurality of genes, i.e. to increase the rate of transcription or rate of expression of a combination of genes and/or to reduce of the rate of transcription or rate of expression of a combination of genes.

In the genetically modified microorganisms of the invention, at least one altered, i.e. increased or reduced, rate of transcription or rate of expression of a gene can be attributed to a nucleic acid of the invention having promoter activity or to an expression unit of the invention.

Further, additionally altered, i.e. additionally increased or additionally reduced, rates of transcription or rates of expression of further genes in the genetically modified microorganism may, but need not, derive from the nucleic acids of the invention having promoter activity or the expression units of the invention.

The invention therefore furthermore relates to a process for producing biosynthetic products by culturing genetically modified microorganisms of the invention.

V. Fields of Application of the Invention

The multiple promoter-comprising expression units, expression cassettes and vectors of the invention can, for example by used particularly advantageously in improved processes for fermentation production of biosynthetic products as described below.

The multiple promoter-comprising expression units of the invention or expression cassettes comprising them have the particular advantage of allowing a modulation of the expression of the functionally linked structural gene.

The expression units of the invention or expression cassettes comprising them may be used for altering, i.e. increasing or reducing, or for causing the rate of expression of genes in microorganisms, in comparison with the wild type. This provides the possibility, in the case of an increase in the rate of expression, of maximizing expression of the gene in question. By choosing a suitable expression unit, however, expression may also be at a strength which is below the maximum obtainable by a different expression unit, but which at the same time delivers the expression product in an amount more compatible for the expressing microorganism. This is particularly advantageous if expression product concentrations which are too high are toxic for the expressing microorganism. By way of selection from among expression units with in each case different strength of expression, the expression units of the invention thus enable expression to be fine-regulated to an optimal value, in particular for long-term expression.

The expression units of the invention or expression cassettes comprising said expression units may also be used for regulating and enhancing the formation of various biosynthetic products such as, for example, fine chemicals, proteins, in particular amino acids, in microorganisms, in particular in *Corynebacterium* species.

The invention therefore relates to the use of a multiple promoter-comprising expression unit of the invention for regulating a product biosynthesis. Here, the gene of a protein involved in the regulation of a product biosynthesis is put under the control of such an expression unit. Said product biosynthesis is influenced depending on the rate of transcription of the selected, multiple promoter-comprising expression unit. Alternatively, the gene of a protein involved in the regulation of a product biosynthesis may be expressed as constituent of an expression cassette of the invention in a microorganism and said product biosynthesis may be regulated by the protein expressed thereby. If the activity of a multiple promoter is weaker than that of the endogenous promoter, a multiple promoter may also be employed in order to attenuate specifically unwanted biosynthetic pathways.

The rate of transcription of a multiple promoter-comprising expression unit of the invention may furthermore be regulated by specific mutation of one or more individual promoters which constitute said multiple promoter. An increased or reduced promoter activity may be achieved by replacing nucleotides in the binding site of the RNA polymerase holoenzyme binding sites (known to the skilled worker also as −10 region and −35 region). An influence may furthermore be exerted by reducing or extending the distance between the RNA polymerase holoenzyme binding sites described by nucleotide deletions or nucleotide insertions; furthermore, by putting binding sites (also known as operators to the skilled worker) for regulatory proteins (known as repressors and activators to the skilled worker) in spatial proximity to the binding sites of the RNA polymerase holoenzyme, so that these regulators, after binding to a promoter sequence, attenuate or enhance binding and transcriptional activity of the RNA polymerase holoenzyme or else subject said binding and transcriptional activity to a new regulatory influence. Translational activity may also be influenced by mutating the ribosome binding-mediating, 3'-terminal sequence section of a single promoter $P_y$ within the multiple promoter-comprising expression unit of the invention.

VI. Biosynthetic Products and Preferred Production Processes

Preferred biosynthetic products prepared according to the invention are fine chemicals.

The term "fine chemical" is familiar to the skilled worker and includes compounds which are produced by an organism and are used in various branches of industry such as, for example but not restricted to, the pharmaceutical industry, the agriculture, cosmetics, food and feed industries. These compounds comprise organic acids such as, for example, lactic acid, succinic acid, tartaric acid, itaconic acid and diaminopimelic acid, and proteinogenic and nonproteinogenic amino acids, purine bases and pyrimidine bases, nucleosides and nucleotides (as described for example in Kuninaka, A. (1996) Nucleotides and related compounds, pp. 561-612, in Biotechnology vol. 6, Rehm et al., editors, VCH: Weinheim and the references present therein), lipids, saturated and unsaturated fatty acids (e.g. arachidonic acid), diols (e.g. propanediol and butanediol), carbohydrates (e.g. hyaluronic acid and trehalose), aromatic compounds (e.g. aromatic amines, vanillin and indigo), vitamins and cofactors (as described in Ullmann's Encyclopedia of Industrial Chemistry, vol. A27, "Vitamins", pp. 443-613 (1996) VCH: Weinheim and the references present therein; and Ong, A. S., Niki, E. and Packer, L. (1995) "Nutrition, Lipids, Health and Disease" Proceedings of the UNESCO/Confederation of Scientific and Technological Associations in Malaysia and the Society for Free Radical Research—Asia, held on Sep. 1-3, 1994 in Penang, Malaysia, AOCS Press (1995)), enzymes and all other chemicals described by Gutcho (1983) in Chemicals by Fermentation, Noyes Data Corporation, ISBN: 0818805086 and the references indicated therein.

Particularly preferred biosynthetic products are selected from the group of organic acids, proteins, nucleotides and nucleosides, both proteinogenic and nonproteinogenic amino acids, lipids and fatty acids, diols, carbohydrates, aromatic compounds, vitamins and cofactors, enzymes and proteins.

Preferred organic acids are lactic acid, succinic acid, tartaric acid, itaconic acid and diaminopimelic acid.

Preferred nucleosides and nucleotides are described for example in Kuninaka, A. (1996) Nucleotides and related compounds, pp. 561-612, in Biotechnology, vol. 6, Rehm et al., editors VCH: Weinheim and references present therein.

Preferred biosynthetic products are additionally lipids, saturated and unsaturated fatty acids such as, for example, arachidonic acid, diols such as, for example, propanediol and butanediol, carbohydrates such as, for example, hyaluronic acid and trehalose, aromatic compounds such as, for example, aromatic amines, vanillin and indigo, vitamins and cofactors as described for example in Ullmann's Encyclopedia of Industrial Chemistry, vol. A27, "Vitamins", pp. 443-613 (1996) VCH: Weinheim and the references present therein; and Ong, A. S., Niki, E. and Packer, L. (1995) "Nutrition, Lipids, Health and Disease" Proceedings of the UNESCO/ Confederation of Scientific and Technological Associations in Malaysia and the Society for Free Radical Research— Asia, held on Sep. 1-3, 1994 in Penang, Malaysia, AOCS Press (1995)), enzymes, polyketides (Cane et al. (1998) Science 282: 63-68) and all other chemicals described by Gutcho (1983) in Chemicals by Fermentation, Noyes Data Corporation, ISBN: 0818805086 and the references indicated therein.

Particularly preferred biosynthetic products are amino acids, particularly preferably essential amino acids, in particular L-glycine, L-alanine, L-leucine, L-methionine, L-phenylalanine, L-tryptophan, L-lysine, L-glutamine, L-glutamic acid, L-serine, L-proline, L-valine, L-isoleucine, L-cysteine, L-tyrosine, L-histidine, L-arginine, L-asparagine, L-aspartic acid and L-threonine, L-homoserine, especially L-lysine, L-methionine and L-threonine. An amino acid such as, for example, lysine, methionine and threonine means hereinafter both in each case the L and the D form of the amino acid, preferably the L form, i.e. for example L-lysine, L-methionine and L-threonine.

The following sections describe the particularly preferred preparations of lysine, methionine and threonine in more detail.

a) Preparation of Lysine

The invention relates in particular to a process for producing lysine by culturing genetically modified microorganisms with increased or caused expression rate of at least one gene compared with the wild type, where
  the expression activity in the microorganism of at least one endogenous gene is regulated by an expression unit of the invention, or
  the expression of at least one gene in the microorganism is caused or altered by introducing into said microorganism an expression cassette of the invention comprising said gene.

The genes are selected here in particular from among nucleic acids encoding an aspartate kinase, nucleic acids encoding an aspartate-semialdehyde dehydrogenase, nucleic acids encoding a diaminopimelate dehydrogenase, nucleic acids encoding a diaminopimelate decarboxylase, nucleic acids encoding a dihydrodipicolinate synthetase, nucleic acids encoding a dihydrodipicolinate reductase, nucleic acids encoding a glyceraldehyde-3-phosphate dehydrogenase, nucleic acids encoding a 3-phosphoglycerate kinase, nucleic acids encoding a pyruvate carboxylase, nucleic acids encoding a triosephosphate isomerase, nucleic acids encoding a transcriptional regulator LuxR, nucleic acids encoding a transcriptional regulator LysR1, nucleic acids encoding a transcriptional regulator LysR2, nucleic acids encoding a malate-quinone oxidoreductase, nucleic acids encoding a glucose-6-phosphate dehydrogenase, nucleic acids encoding a 6-phosphogluconate dehydrogenase, nucleic acids encoding a transketolase, nucleic acids encoding a transaldolase, nucleic acids encoding a lysine exporter, nucleic acids encoding a biotin ligase, nucleic acids encoding an arginyl-tRNA synthetase, nucleic acids encoding a phosphoenolpyruvate carboxylase, nucleic acids encoding a fructose-1,6-bisphosphatase, nucleic acids encoding a protein OpcA, nucleic acids encoding a 1-phosphofructokinase, nucleic acids encoding a 6-phosphofructokinase, nucleic acids encoding a tetrahydropicolinate succinylase, nucleic acids encoding a succinyl aminoketopimelate aminotransferase, nucleic acids encoding a succinyl diaminopimelate desuccinylase, nucleic acids encoding a diaminopimelate epimerase, nucleic acids encoding a 6-phosphogluconate dehydrogenase, nucleic acids encoding a glucose phosphate isomerase, nucleic acids encoding a phosphoglycerate mutase, nucleic acids encoding an enolase, nucleic acids encoding a pyruvate kinase, nucleic acids encoding an aspartate transaminase and nucleic acids encoding a malate enzyme.

A further preferred embodiment of the process described above for preparing lysine comprises the genetically modified microorganisms, compared with the wild type, having additionally an increased activity, of at least one of the activities selected from among
aspartate kinase activity, aspartate semialdehyde dehydrogenase activity, diaminopimelate dehydrogenase activity, diaminopimelate decarboxylase activity, dihydrodipicolinate synthetase activity, dihydrodipicolinate reductase activity, glyceraldehyde-3-phosphate dehydrogenase activity, 3-phosphoglycerate kinase activity, pyruvate carboxylase activity, triosephosphate isomerase activity, activity of the transcriptional regulator LuxR, activity of the transcriptional regulator LysR1, activity of the transcriptional regulator LysR2, malate-quinone oxidoreductase activity, glucose-6-phosphate dehydrogenase activity, 6-phosphogluconate dehydrogenase activity, transketolase activity, transaldolase activity, lysine exporter activity, arginyl-tRNA synthetase activity, phosphoenolpyruvate carboxylase activity, fructose-1,6-bisphosphatase activity, protein OpcA activity, 1-phosphofructokinase activity, 6-phosphofructokinase activity, biotin ligase activity, and tetrahydropicolinate succinylase activity, succinyl aminoketopimelate aminotransferase activity, succinyl diaminopimelate desuccinylase activity, diaminopimelate epimerase activity, 6-phosphogluconate dehydrogenase activity, glucose phosphate isomerase activity, phosphoglycerate mutase activity, enolase activity, pyruvate kinase activity, aspartate transaminase activity and malate enzyme activity.

A further particularly preferred embodiment of the process described above for preparing lysine comprises the genetically modified microorganisms having, compared with the wild type, additionally a reduced activity, of at least one of the activities selected from the group of threonine dehydratase activity, homoserine O-acetyl-transferase activity, O-acetyl-homoserine sulfhydrylase activity, phosphoenolpyruvate carboxykinase activity, pyruvate oxidase activity, homoserine kinase activity, homoserine dehydrogenase activity, threonine exporter activity, threonine efflux protein activity, asparaginase activity, aspartate decarboxylase activity and threonine synthase activity.

b) Preparation of Methionine

The invention further relates to a process for preparing methionine by culturing genetically modified microorganisms with increased or caused expression rate of at least one gene compared with the wild type, where
  the expression activity in the microorganism of at least one endogenous gene is regulated by an expression unit of the invention, or
  the expression of at least one gene in the microorganism is caused or altered by introducing into said microorganism an expression unit of the invention comprising said gene.

The genes are selected here in particular from nucleic acids encoding an aspartate kinase, nucleic acids encoding an aspartate semialdehyde dehydrogenase, nucleic acids encoding a homoserine dehydrogenase, nucleic acids encoding a glyceraldehyde-3-phosphate dehydrogenase, nucleic acids encoding a 3-phosphoglycerate kinase, nucleic acids encoding a pyruvate carboxylase, nucleic acids encoding a triosephosphate isomerase, nucleic acids encoding a homoserine O-acetyltransferase, nucleic acids encoding a cystathionine gamma-synthase, nucleic acids encoding a cystathionine beta-lyase, nucleic acids encoding a serine hydroxymethyltransferase, nucleic acids encoding an O-acetylhomoserine sulfhydrylase, nucleic acids encoding a methylenetetrahydrofolate reductase, nucleic acids encoding a phosphoserine aminotransferase, nucleic acids encoding a phosphoserine phosphatase, nucleic acids encoding a serine acetyltransferase, nucleic acids encoding a cysteine synthase activity I, nucleic acids encoding a cysteine synthase activity II, nucleic acids encoding a coenzyme B12-dependent methionine synthase activity, nucleic acids encoding a coenzyme B12-independent methionine synthase activity, nucleic acids encoding a sulfate adenylyltransferase activity, nucleic acids encoding a phosphoadenosine phosphosulfate reductase activity, nucleic acids encoding a ferredoxin sulfite reductase activity, nucleic acids encoding a ferredoxin NADPH reductase activity, nucleic acids encoding a ferredoxin activity, nucleic acids encoding a protein of sulfate reduction RXA077, nucleic acids encoding a protein of sulfate reduction RXA248, nucleic acids encoding a protein of sulfate reduction RXA247, nucleic acids encoding an RXA0655 regulator and nucleic acids encoding an RXN2910 regulator, nucleic acids encoding a 6-phosphogluconate dehydrogenase, glucose phosphate isomerase, phosphoglycerate mutase, enolase, pyruvate kinase, aspartate transaminase or malate enzyme.

A further preferred embodiment of the process described above for preparing methionine comprises the genetically modified microorganisms having, compared with the wild type, additionally an increased activity of at least one of the activities selected from the group of aspartate kinase activity, aspartate semialdehyde dehydrogenase activity, homoserine dehydrogenase activity, glyceraldehyde-3-phosphate dehydrogenase activity, 3-phosphoglycerate kinase activity, pyruvate carboxylase activity, triosephosphate isomerase activity, homoserine O-acetyltransferase activity, cystathionine gamma-synthase activity, cystathionine beta-lyase activity, serine hydroxymethyltransferase activity, O-acetylhomoserine sulfhydrylase activity, methylenetetrahydrofolate reductase activity, phosphoserine aminotransferase activity, phosphoserine phosphatase activity, serine acetyltransferase activity, cysteine synthase I activity, cysteine synthase II activity, coenzyme B12-dependent methionine synthase activity, coenzyme B12-independent methionine synthase activity, sulfate adenylyltransferase activity, phosphoadenosine phosphosulfate reductase activity, ferredoxin sulfite reductase activity, ferredoxin NADPH reductase activity, ferredoxin activity, activity of a protein of sulfate reduction RXA077, activity of a protein of sulfate reduction RXA248, activity of a protein of sulfate reduction RXA247, activity of an RXA655 regulator and activity of an RXN2910 regulator, activity of a 6-phosphogluconate dehydrogenase, activity of a glucose phosphate isomerase, activity of a phosphoglycerate mutase, activity of an enolase, activity of a pyruvate kinase, activity of an aspartate transaminase and activity of the malate enzyme.

A further particularly preferred embodiment of the method described above for preparing methionine comprises the genetically modified microorganisms having, compared with the wild type, additionally a reduced activity of at least one of the activities selected from the group of homoserine kinase activity, threonine dehydratase activity, threonine synthase activity, meso-diaminopimelate D-dehydrogenase activity, phosphoenolpyruvate carboxykinase activity, pyruvate oxidase activity, dihydrodipicolinate synthase activity, dihydrodipicolinate reductase activity and diaminopicolinate decarboxylase activity.

c) Preparation of Threonine

The invention further relates to a process for preparing threonine by culturing genetically modified microorganisms with increased or caused expression rate of at least one gene compared with the wild type, where the expression activity in the microorganism of at least one endogenous gene is regulated by an expression unit of the invention, or the expression of at least one gene in the microorganism is caused or altered by introducing into said microorganism an expression unit of the invention comprising said gene.

The genes are selected here in particular from nucleic acids encoding an aspartate kinase, nucleic acids encoding an aspartate-semialdehyde dehydrogenase, nucleic acids encoding a glyceraldehyde-3-phosphate dehydrogenase, nucleic acids encoding a 3-phosphoglycerate kinase, nucleic acids encoding a pyruvate carboxylase, nucleic acids encoding a triosephosphate isomerase, nucleic acids encoding a homoserine kinase, nucleic acids encoding a threonine synthase, nucleic acids encoding a threonine exporter carrier, nucleic acids encoding a glucose-6-phosphate dehydrogenase, nucleic acids encoding a transaldolase, nucleic acids encoding a transketolase, nucleic acids encoding a malate-quinone oxidoreductase, nucleic acids encoding a 6-phosphogluconate dehydrogenase, nucleic acids encoding a lysine exporter, nucleic acids encoding a biotin ligase, nucleic acids encoding a phosphoenolpyruvate carboxylase, nucleic acids encoding a threonine efflux protein, nucleic acids encoding a fructose-1,6-bisphosphatase, nucleic acids encoding an OpcA protein, nucleic acids encoding a 1-phosphofructokinase, nucleic acids encoding a 6-phosphofructokinase, and nucleic acids encoding a homoserine dehydrogenase, and nucleic acids encoding a 6-phosphogluconate dehydrogenase, glucose phosphate isomerase, phosphoglycerate mutase, enolase, pyruvate kinase, aspartate transaminase and malate enzyme.

A further preferred embodiment of the process described above for preparing threonine comprises the genetically modified microorganisms having, compared with the wild type, additionally an increased activity of at least one of the activities selected from the group of:

aspartate kinase activity, aspartate-semialdehyde dehydrogenase activity, glyceraldehyde-3-phosphate dehydrogenase activity, 3-phosphoglycerate kinase activity, pyruvate carboxylase activity, triosephosphate isomerase activity, threonine synthase activity, activity of a threonine export carrier, transaldolase activity, transketolase activity, glucose-6-phosphate dehydrogenase activity, malate-quinone oxidoreductase activity, homoserine kinase activity, biotin ligase activity, phosphoenolpyruvate carboxylase activity, threonine efflux protein activity, protein OpcA activity, 1-phosphofructokinase activity, 6-phosphofructokinase activity, fructose-1,6-bisphosphatase activity, 6-phosphogluconate dehydrogenase, homoserine dehydrogenase activity and activity of a 6-phosphogluconate dehydrogenase, activity of a glucose phosphate isomerase, activity of a phosphoglycerate mutase, activity of an enolase, activity of a pyruvate kinase, activity of an aspartate transaminase and activity of the malate enzyme.

A further particularly preferred embodiment of the process described above for preparing threonine comprises the genetically modified microorganisms having, compared with the wild type, additionally a reduced activity of at least one of the activities selected from the group of threonine dehydratase activity, homoserine O-acetyltransferase activity, serine hydroxymethyltransferase activity, O-acetyl-homoserine sulfhydrylase activity, meso-diaminopimelate D-dehydrogenase activity, phosphoenolpyruvate carboxykinase activity, pyruvate oxidase activity, dihydrodipicolinate synthetase activity, dihydrodipicolinate reductase activity, asparaginase activity, aspartate decarboxylase activity, lysine exporter activity, acetolactate synthase activity, ketol-acid reductoisomerase activity, branched chain aminotransferase activity, coenzyme B12-dependent methionine synthase activity, coenzyme B12-independent methionine synthase activity, dihydroxy-acid dehydratase activity and diaminopicolinate decarboxylase activity.

d) Further Information on Preparing Bioproducts According to the Invention

These additional increased or reduced activities of at least one of the activities described above may, but need not, be caused by an expression unit of the invention or an expression cassette of the invention.

The term "activity" of a protein means in the case of enzymes the enzymic activity of the corresponding protein, and in the case of other proteins, for example structural or transport proteins, the physiological activity of the proteins.

The enzymes are ordinarily able to convert a substrate into a product or catalyze this conversion step. Accordingly, the "activity" of an enzyme means the quantity of substrate converted by the enzyme, or the quantity of product formed, in a particular time.

Thus, where an activity is increased compared with the wild type, the quantity of the substrate converted by the enzyme, or the quantity of product formed, in a particular time is increased compared with the wild type.

This increase in the "activity", for example, amounts, for all activities described hereinbefore and hereinafter, to at least 1 to 5%, such as, for example, at least 20%, at least 50%, at least 100%, at least 300%, or at least 500%, or at least 600% of the "activity of the wild type".

Thus, where an activity is reduced compared with the wild type, the quantity of substrate converted by the enzyme, or the quantity of product formed, in a particular time is reduced compared with the wild type.

A reduced activity preferably means the partial or substantially complete suppression or blocking, based on various cell biological mechanisms, of the functionality of this enzyme in a microorganism.

A reduction in the activity comprises a quantitative decrease in an enzyme as far as substantially complete absence of the enzyme (i.e. lack of detectability of the corresponding activity or lack of immunological detectability of the enzyme). The activity in the microorganism is preferably reduced, compared with the wild type, by at least 5%, such as by at least 20%, by at least 50%, or by about 100%. "Reduction" also means in particular the complete absence of the corresponding activity.

The activity of particular enzymes in genetically modified microorganisms and in the wild type, and thus the increase or reduction in the enzymic activity, can be measured by known methods such as, for example, enzyme assays.

An additional increasing of activities can take place in various ways, for example by switching off inhibitory regulatory mechanisms at the expression and protein level or by increasing gene expression of nucleic acids encoding the proteins described above compared with the wild type.

Increasing the gene expression of the nucleic acids encoding the proteins described above compared with the wild type can likewise take place in various ways, for example by inducing the gene by activators or, as described above, by increasing the promoter activity or increasing the expression activity or by introducing one or more gene copies into the microorganism.

Increasing the gene expression of a nucleic acid encoding a protein also means according to the invention manipulation of the expression of the endogenous proteins intrinsic to the microorganism. This can be achieved for example, as described above, by altering the promoter sequences of the genes, introducing an expression unit of the invention for regulatory control of the genes and altering the introduced expression units of the invention. Such an alteration, which results in an increased expression rate of the gene, can take place for example by deletion or insertion of DNA sequences.

It is possible, as described above, to alter the expression of the endogenous proteins by applying exogenous stimuli. This can take place through particular physiological conditions, i.e. through the application of foreign substances.

The skilled worker may have recourse to further different procedures, singly or in combination, to achieve an increase in gene expression. Thus, for example, the copy number of the appropriate genes can be increased, or the promoter and regulatory region or the ribosome binding site located upstream of the structural gene can be mutated. It is additionally possible to increase the expression during fermentative production through inducible promoters. Procedures to prolong the lifespan of the mRNA likewise improve expression. Enzymic activity is likewise enhanced also by preventing degradation of the enzyme protein. The genes or gene constructs may be either present in plasmids with varying copy number or integrated and amplified in the chromosome. It is also possible as an alternative to achieve overexpression of the relevant genes by altering the composition of the media and management of the culture.

The skilled worker can find guidance on this inter alia in Martin et al. (Biotechnology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP-A 0472869, in U.S. Pat. No. 4,601,893, in Schwarzer and Pühler (Biotechnology 9, 84-87 (1991), in Reinscheid et al. (Applied and Environmental Microbiology 60, 126-132 (1994), in LaBarre et al. (Journal of Bacteriology 175, 1001-1007 (1993)), in WO 96/15246, in Malumbres et al. (Gene 134, 15-24 (1993)), in JP-A-10-229891, in Jensen and Hammer (Biotechnology and Bioengineering 58, 191-195 (1998)), in Makrides (Microbiological Reviews 60: 512-538 (1996) and in well-known textbooks of genetics and molecular biology.

It may additionally be advantageous for the production of biosynthetic products, especially L-lysine, L-methionine and L-threonine, besides the expression or enhancement of a gene, to eliminate unwanted side reactions (Nakayama: "Breeding of Amino Acid Producing Microorganisms", in: Overproduction of Microbial Products, Krumphanzl, Sikyta, Vanek (eds.), Academic Press, London, UK, 1982).

In a preferred embodiment, gene expression of a nucleic acid encoding one of the proteins described above is increased by introducing at least one nucleic acid encoding a corresponding protein into the microorganism. The introduction of the nucleic acid can take place chromosomally or extrachromosomally, i.e. through increasing the copy number on the chromosome and/or a copy of the gene on a plasmid which replicates in the host microorganism.

The introduction of the nucleic acid, for example in the form of an expression cassette of the invention comprising the nucleic acid, preferably takes place chromosomally, in particular by the SacB method described above. It is possible in principle to use for this purpose any gene which encodes one of the proteins described above.

In the case of genomic nucleic acid sequences from eukaryotic sources which comprise introns, if the host microorganism is unable or cannot be made able to express the corresponding proteins it is preferred to use nucleic acid sequences which have already been processed, such as the corresponding cDNAs.

Examples of the corresponding genes are listed in Table 1 and 2.

The activities described above in microorganisms are preferably reduced by at least one of the following methods:

- introduction of at least one sense ribonucleic acid sequence for inducing cosuppression or of an expression cassette ensuring expression thereof
- introduction of at least one DNA- or protein-binding factor against a corresponding gene, an RNA or a protein or of an expression cassette ensuring expression thereof
- introduction of at least one viral nucleic acid sequence which causes RNA degradation, or of an expression cassette ensuring expression thereof
- introduction of at least one construct to produce a loss of function, such as, for example, generation of stop codons or shifts in the reading frame, of a gene, for example by producing an insertion, deletion, inversion or mutation in a gene. It is possible and preferred to generate knockout mutants by targeted insertion into the desired target gene through homologous recombination or introduction of sequence-specific nucleases against the target gene.
- introduction of a promoter with reduced promoter activity or of an expression unit with reduced expression activity.
- introduction of an antisense RNA which reduces translation of the sense RNA (mRNA).

The skilled worker is aware that further processes can also be employed within the scope of the present invention for reducing its activity or function. For example, the introduction of a dominant negative variant of a protein or of an expression cassette ensuring expression thereof may also be advantageous.

It is moreover possible for each single one of these processes to bring about a reduction in the quantity of protein, quantity of mRNA and/or activity of a protein. A combined use is also conceivable. Further methods are known to the skilled worker and may comprise impeding or suppressing the processing of the protein, of the transport of the protein or its mRNA, inhibition of ribosome attachment, inhibition of RNA splicing, induction of an RNA-degrading enzyme and/or inhibition of translation elongation or termination.

VII. Cultivation of Microorganisms and Isolation of Products

In the process of the invention for preparing biosynthetic products, the step of culturing the genetically modified microorganisms is preferably followed by an isolation of biosynthetic products from the microorganisms and/or from the fermentation broth. These steps may take place at the same time and/or preferably after the culturing step.

The genetically modified microorganisms of the invention can be cultured to produce biosynthetic products, in particular L-lysine, L-methionine and L-threonine, continuously or discontinuously in a batch process (batch culturing) or in the fed batch or repeated fed batch process. A summary of known culturing methods is to be found in the textbook by Chemiel (Bioprozeβtechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must satisfy in a suitable manner the demands of the respective strains. There are descriptions of culture media for various microorganisms in the handbook "Manual of Methods for General Bacteriology" of the American Society for Bacteriology (Washington D.C., USA, 1981).

These media which can be employed according to the invention usually comprise one or more carbon sources, nitrogen sources, inorganic salts, vitamins and/or trace elements.

Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch or cellulose. Sugars can be put in the media also via complex compounds such as molasses, or other by-products of sugar refining. It may also be advantageous to add mixtures of various carbon sources. Other possible carbon sources are oils and fats such as, for example, soybean oil, sunflower oil, peanut oil and coconut fat, fatty acids such as, for example, palmitic acid, stearic acid or linoleic acid, alcohols such as, for example, glycerol, methanol or ethanol and organic acids such as, for example, acetic acid or lactic acid.

Nitrogen sources are usually organic or inorganic nitrogen compounds or materials containing these compounds. Examples of nitrogen sources comprise ammonia gas or ammonium salts such as ammonium sulfate, ammonium chloride, ammonium phosphate, ammonium carbonate or ammonium nitrate, nitrates, urea, amino acids or complex nitrogen sources such as corn steep liquor, soybean flour, soybean protein, yeast extract, meat extract and others. The nitrogen sources may be used singly or as mixtures.

Inorganic salt compounds which may be present in the media comprise the chloride, phosphoric or sulfate salts of calcium, magnesium, sodium, cobalt, molybdenum, potassium, manganese, zinc, copper and iron.

For preparing fine chemicals, especially methionine, it is possible to use as sulfur source inorganic compounds such as, for example, sulfates, sulfites, dithionites, tetrathionates, thiosulfates, sulfides, but also organic sulfur compounds such as mercaptans and thiols.

It is possible to use as phosphorus source phosphoric acid, potassium dihydrogenphosphate or dipotassium hydrogenphosphate or the corresponding sodium-containing salts.

Chelating agents can be added to the medium in order to keep the metal ions in solution. Particularly suitable chelating agents comprise dihydroxyphenols such as catechol or protocatechuate, or organic acids such as citric acid.

The fermentation media employed according to the invention normally also comprise other growth factors such as vitamins or growth promoters, which include for example biotin, riboflavin, thiamine, folic acid, nicotinic acid, pantothenate and pyridoxine. Growth factors and salts are frequently derived from complex components of the media, such as yeast extract, molasses, corn steep liquor and the like. Suitable precursors may also be added to the culture medium. The exact composition of the compounds in the media depends greatly on the particular experiment and will be decided individually for each specific case. Information on optimization of media is obtainable from the textbook "Applied Microbiol. Physiology, A Practical Approach" (editors P. M. Rhodes, P. F. Stanbury, IRL Press (1997) pp. 53-73, ISBN 0 19 963577 3). Growth media can also be purchased from commercial suppliers, such as Standard 1 (Merck) or BHI (Brain heart infusion, DIFCO) and the like.

All the components of the media are sterilized either by heat (20 min at 1.5 bar and 121° C.) or by sterilizing filtration. The components can be sterilized either together or, if necessary, separately. All the components of the media may be present at the start of culturing or optionally be added continuously or batchwise.

The temperature of the culture is normally between 15° C. and 45° C., preferably at 25° C. to 40° C. and can be kept constant or changed during the experiment. The pH of the medium should be in the range from 5 to 8.5, preferably around 7.0. The pH for the culturing can be controlled during the culturing by adding basic compounds such as sodium hydroxide, potassium hydroxide, ammonia or aqueous ammonia or acidic compounds such as phosphoric acid or sulfuric acid. The development of foam can be controlled by employing antifoams such as, for example, fatty acid polyglycol esters. The stability of plasmids can be maintained by adding to the medium suitable substances with a selective action, such as, for example, antibiotics. Aerobic conditions are maintained by introducing oxygen or oxygen-containing gas mixtures such as, for example, ambient air into the culture. The temperature of the culture is normally 20° C. to 45° C. The culture is continued until formation of the desired product is at a maximum. This aim is normally reached within 10 hours to 160 hours.

The dry matter content of the fermentation broths obtained in this way is normally from 7.5 to 25% by weight.

It is additionally advantageous also to run the fermentation with sugar limitation at least at the end, but in particular over at least 30% of the fermentation time. This means that the concentration of utilizable sugar in the fermentation medium is kept at 0 to 3 g/l, or is reduced, during this time.

Biosynthetic products are isolated from the fermentation broth and/or the microorganisms in a manner known per se in accordance with the physical/chemical properties of the required biosynthetic product and the biosynthetic by-products.

The fermentation broth can then be processed further for example. Depending on the requirement, the biomass can be removed wholly or partly from the fermentation broth by separation methods such as, for example, centrifugation, filtration, decantation or a combination of these methods, or left completely in it.

The fermentation broth can then be thickened or concentrated by known methods such as, for example, with the aid of a rotary evaporator, thin-film evaporator, falling-film evaporator, by reverse osmosis or by nanofiltration. This concentrated fermentation broth can then be worked up by freeze drying, spray drying, spray granulation or by other processes.

However, it is also possible to purify the biosynthetic products, especially L-lysine, L-methionine and L-threonine, further. For this purpose, the product-containing broth is subjected, after removal of the biomass, to a chromatography using a suitable resin, with the desired product or the impurities being retained wholly or partly on the chromatography resin. These chromatographic steps can be repeated if required, using the same or different chromatography resins. The skilled worker is proficient in the selection of suitable chromatography resins and their most effective use. The purified product can be concentrated by filtration or ultrafiltration and be stored at a temperature at which the stability of the product is a maximum.

The biosynthetic products may result in various forms, for example in the form of their salts or esters.

The identity and purity of the isolated compound(s) can be determined by prior art techniques. These comprise high pressure liquid chromatography (HPLC), spectroscopic methods, staining methods, thin-layer chromatography, NIRS, enzyme assay or microbiological assays. These analytical methods are summarized in: Patek et al. (1994) Appl. Environ. Microbiol. 60:133-140; Malakhova et al. (1996) Biotekhnologiya 11 27-32; and Schmidt et al. (1998) Bioprocess Engineer. 19:67-70. Ullmann's Encyclopedia of Industrial Chemistry (1996) vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

The invention is now described in more detail by means of the following nonlimiting examples:

Example 1

Preparation of the Vector pCLiK5MCS

First, the ampicillin resistance and origin of replication of the vector pBR322 were amplified with the aid of the polymerase chain reaction (PCR) using the oligonucleotide primers SEQ ID NO:5 and SEQ ID NO: 6.

```
SEQ ID NO: 5:
5'-CCCGGGATCCGCTAGCGGCGCGCCGGCCGGCCCGGTGTGAAATACCG

CACAG-3'

SEQ ID NO: 6:
5'-TCTAGACTCGAGCGGCCGCGGCCGGCCTTTAAATTGAAGACGAAAGG

GCCTCG-3'
```

Apart from the sequences complementary to pBR322, the SEQ ID NO: 5 oligonucleotide primer comprises, in the 5'-3' direction, the cleavage sites for the restriction endonucleases SmaI, BamHI, NheI and AscI, and the SEQ ID NO: 6 oligonucleotide primer comprises, in the 5'-3' direction, the cleavage sites for the restriction endonucleases XbaI, XhoI, NotI and DraI. The PCR reaction was carried out by a standard method such as Innis et al. (PCR Protocols. A Guide to Methods and Applications, Academic Press (1990)) using Pfu Turbo polymerase (Stratagene, La Jolla, USA). The DNA fragment obtained, whose size is approximately 2.1 kb, was purified using the GFX™ PCR, DNA and Gel Band Purification Kit (Amersham Pharmacia, Freiburg, Germany) according to the manufacturer's information. The blunt ends of the DNA fragment were ligated to one another using the Rapid DNA Ligation Kit (Roche Diagnostics, Mannheim, Germany) according to the manufacturer's information and the ligation mixture was transformed according to standard methods as described in Sambrook et al. (Molecular Cloning. A Laboratory Manual, Cold Spring Harbor, (1989)), in competent E. coli XL-1Blue (Stratagene, La Jolla, USA). Selection for plasmid-harboring cells was achieved by plating out on ampicillin (50 µg/ml)-containing LB Agar (Lennox, 1955, Virology, 1:190).

The plasmid DNA of an individual clone was isolated using the Qiaprep Spin Miniprep Kit (Qiagen, Hilden, Germany) according to the manufacturer's information and checked via restriction digestions. The plasmid obtained in this way is denoted pCLiK1.

Starting from the plasmid pWLT1 (Liebl et al., 1992) as template for a PCR reaction, a kanamycin resistance cassette was amplified using the oligonucleotide primers SEQ ID NO:7 and SEQ ID NO:8.

```
SEQ ID NO: 7:
5'-GAGATCTAGACCCGGGGATCCGCTAGCGGGCTGCTAAAGGAAGCGG

A-3'

SEQ ID NO: 8
5'-GAGAGGCGCGCCGCTAGCGTGGGCGAAGAACTCCAGCA-3'
```

Apart from the sequences complementary to pWLT1, the SEQ ID NO: 7 oligonucleotide primer comprises, in the 5'-3' direction, the cleavage sites for the restriction endonucleases XbaI, SmaI, BamHI, NheI, and the SEQ ID NO:8 oligonucleotide primer comprises, in the 5'-3' direction, the cleavage sites for the restriction endonucleases AscI and NheI. The PCR reaction was carried out by standard method such as Innis et al. (PCR Protocols. A Guide to Methods and Applications, Academic Press (1990)), using Pfu Turbo polymerase (Stratagene, La Jolla, USA). The DNA fragment obtained, whose size is approximately 1.3 kb, was purified using the GFX™ PCR, DNA and Gel Band Purification Kit (Amersham Pharmacia, Freiburg) according to the manufacturer's information. The DNA fragment was cut by the restriction endonucleases XbaI and AscI (New England Biolabs, Beverly, USA) and subsequently purified again using the GFX™ PCR, DNA and Gel Band Purification Kit (Amersham Pharmacia, Freiburg) according to the manufacturer's information. The pCLiK1 vector was likewise cut by the XbaI and AscI restriction endonucleases and dephosphorylated by alkali phosphatase (I (Roche Diagnostics, Mannheim)) according to the manufacturer's information. After electrophoresis in a 0.8% strength agarose gel, the linearized vector (approx. 2.1 kb) was isolated using the GFX™ PCR, DNA and Gel Band Purification Kit (Amersham Pharmacia, Freiburg) according to the manufacturer's information. This vector fragment was ligated with the cut PCR fragment with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1 Blue (Stratagene, La Jolla, USA). Selection for plasmid-harboring cells was achieved by plating out on LB agar containing ampicillin (50 µg/ml) and kanamycin (20 µg/ml) (Lennox, 1955, Virology, 1:190).

The plasmid DNA of an individual clone was isolated using the Qiaprep Spin Miniprep Kit (Qiagen, Hilden, Germany) according to the manufacturer's information and checked via restriction digestions. The plasmid obtained in this way is denoted pCLiK2.

The pCLiK2 vector was cut by the restriction endonuclease DraI (New England Biolabs, Beverly, USA). After electrophoresis in a 0.8% strength agarose gel, an approx. 2.3 kb vector fragment was isolated with the GFX™ PCR, DNA and Gel Band Purification Kit (Amersham Pharmacia, Freiburg) according to the manufacturer's information. This vector fragment was religated with the aid of the Rapid DNA Ligation Kit (Roche Diagnostics, Mannheim) according to the manufacturer's information and the ligation mixture was transformed by standard methods as described in Sambrook et al. (Molecular Cloning. A Laboratory Manual, Cold Spring Harbor, (1989)), into competent *E. coli* XL-1 Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA of an individual clone was isolated using the Qiaprep Spin Miniprep Kit (Qiagen, Hilden, Germany) according to the manufacturer's information and checked via restriction digestions. The plasmid obtained in this way is denoted pCLiK3.

Starting from the plasmid pWLQ2 (Liebl et al., 1992) as template for a PCR reaction, the pHM1519 origin of replication was amplified using the oligonucleotide primers SEQ ID NO:9 and SEQ ID NO:10.

SEQ ID NO: 9:
5'-GAGAGGGCGGCCGCGCAAAGTCCCGCTTCGTGAA-3'

SEQ ID NO: 10:
5'-GAGAGGGCGGCCGCTCAAGTCGGTCAAGCCACGC-3'

Apart from the sequences complementary to pWLQ2, the SEQ ID NO:9 and SEQ ID NO:10 oligonucleotide primers comprise cleavage sites for the NotI restriction endonuclease. The PCR reaction was carried out by standard method such as Innis et al. (PCR Protocols. A Guide to Methods and Applications, Academic Press (1990)), using Pfu Turbo polymerase (Stratagene, La Jolla, USA). The DNA fragment obtained, whose size is approximately 2.7 kb, was purified using the GFX™ PCR, DNA and Gel Band Purification Kit (Amersham Pharmacia, Freiburg) according to the manufacturer's information. The DNA fragment was cut by the restriction endonuclease NotI (New England Biolabs, Beverly, USA) and subsequently purified again using the GFX™ PCR, DNA and Gel Band Purification Kit (Amersham Pharmacia, Freiburg) according to the manufacturer's information. The pCLiK3 vector was likewise cut by the NotI restriction endonuclease and dephosphorylated by alkali phosphatase (I (Roche Diagnostics, Mannheim)) according to the manufacturer's information. After electrophoresis in a 0.8% strength agarose gel, the linearized vector (approx. 2.3 kb) was isolated using the GFX™ PCR, DNA and Gel Band Purification Kit (Amersham Pharmacia, Freiburg) according to the manufacturer's information. This vector fragment was ligated with the cut PCR fragment with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA of an individual clone was isolated using the Qiaprep Spin Miniprep Kit (Qiagen, Hilden, Germany) according to the manufacturer's information and checked via restriction digestions. The plasmid obtained in this way is denoted pCLiK5.

In order to extend pCLiK5 by a "multiple cloning site" (MCS), the two synthetic, essentially complementary oligonucleotides SEQ ID NO:11 and SEQ ID NO:12, which comprise cleavage sites for the restriction endonucleases SwaI, XhoI, AatI, ApaI, Asp718, MluI, NdeI, SpeI, EcoRV, SalI, ClaI, BamHI, XbaI and SmaI were combined by heating them together to 95° C. followed by slow cooling to give a double-stranded DNA fragment.

SEQ ID NO: 11:
5'-TCGAATTTAAATCTCGAGAGGCCTGACGTCGGGCCCGGTACCACGCG

TCATATGACTAGTTCGGACCTAGGGATATCGTCGACATCGATGCTCTTCT

GCGTTAATTAACAATTGGGATCCTCTAGACCCGGGATTTAAAT-3'

SEQ ID NO: 12:
5'-GATCATTTAAATCCCGGGTCTAGAGGATCCCAATTGTTAATTAACGC

AGAAGAGCATCGATGTCGACGATATCCCTAGGTCCGAACTAGTCATATGA

CGCGTGGTACCGGGCCCGACGTCAGGCCTCTCGAGATTTAAAT-3'

The pCLiK5 vector was cut by the restriction endonucleases XhoI and BamHI (New England Biolabs, Beverly, USA) and dephosphorylated by alkali phosphatase (I (Roche Diagnostics, Mannheim)) according to the manufacturer's information. After electrophoresis in a 0.8% strength agarose gel, the linearized vector (approx. 5.0 kb) was isolated using the GFX™ PCR, DNA and Gel Band Purification Kit (Amersham Pharmacia, Freiburg) according to the manufacturer's information. This vector fragment was ligated with the synthetic double-stranded DNA fragment with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent E. coli XL-1 Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA of an individual clone was isolated using the Qiaprep Spin Miniprep Kit (Qiagen, Hilden, Germany) according to the manufacturer's information and checked via restriction digestions. The plasmid obtained in this way is denoted pCLiK5MCS.

Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt, Germany).

The resultant plasmid, pCLiK5MCS, is listed as SEQ ID NO:13.

Example 2

Preparation of the Plasmid PmetA metA

C. glutamicum ATCC 13032 chromosomal DNA was prepared according to Tauch et al. (1995) Plasmid 33:168-179 or Eikmanns et al. (1994) Microbiology 140:1817-1828. Using the oligonucleotide primers SEQ ID NO: 14 and SEQ ID NO: 15, the chromosomal DNA as template and Pfu Turbo polymerase (Stratagene), the metA gene, including the noncoding 5' region, was amplified with the aid of the polymerase chain reaction (PCR) by standard methods as described in Innis et al. (1990) PCR Protocols. A Guide to Methods and Applications, Academic Press.

```
                                    SEQ ID NO: 14
5'-GCGCGGTACCTAGACTCACCCCAGTGCT-3'
and
                                    SEQ ID NO: 15
5'-CTCTACTAGTTTAGATGTAGAACTCGATGT-3'
```

The approx. 1.3 kb DNA fragment obtained was purified using the GFX™ PCR, DNA and Gel Band Purification Kit (Amersham Pharmacia, Freiburg) according to the manufacturer's information. It was subsequently cleaved by the restriction enzymes Asp718 and SpeI (Roche Diagnostics, Mannheim), and the DNA fragment was purified using the GFX™ PCR, DNA and Gel Band Purification Kit.

The vector pClik5MCS SEQ ID NO: 13 was cut by the Asp718 and SpeI restriction enzymes, and a 5 kb fragment was isolated, after electrophoretic fractionation, using the GFX™ PCR, DNA and Gel Band Purification Kit.

The vector fragment was ligated together with the PCR fragment with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent E. coli XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The resultant plasmid, pCLiK5MCS PmetA metA, is listed as SEQ ID NO 16.

Example 3

Preparation of the Plasmid pCLiK5MCS Psod metA

C. glutamicum ATCC 13032 chromosomal DNA was prepared according to Tauch et al. (1995) Plasmid 33:168-179 or Eikmanns et al. (1994) Microbiology 140:1817-1828. Using the oligonucleotide primers SEQ ID NO: 17 and SEQ ID NO: 18, the chromosomal DNA as template and Pfu Turbo polymerase (Stratagene), a DNA fragment of approx. 200 base pairs from the noncoding 5' region (region of the expression unit) of superoxide dismutase (Psod) was amplified with the aid of the polymerase chain reaction (PCR) by standard methods such as Innis et al. (1990) PCR Protocols. A Guide to Methods and Applications, Academic Press.

```
                                    SEQ ID NO: 17
5'-GAGACTCGAGAGCTGCCAATTATTCCGGG-3'
and
                                    SEQ ID NO: 18
5'-CCTGAAGGCGCGAGGGTGGGCATGGGTAAAAAATCCTTTCG-3'
```

The DNA fragment obtained was purified using the GFX™ PCR, DNA and Gel Band Purification Kit (Amersham Pharmacia, Freiburg) according to the manufacturer's information.

Starting from the PmetA metA SEQ ID NO: 16 plasmid as template for a PCR reaction, metA was partially amplified using the oligonucleotide primers SEQ ID NO: 19 and SEQ ID NO: 20.

```
                                    SEQ ID NO: 19
        5'-CCCACCCTCGCGCCTTCAG-3'
        and
                                    SEQ ID NO: 20
        5'-CTGGGTACATTGCGGCCC-3'
```

The DNA fragment obtained of approximately 470 base pairs was purified using the GFX™ PCR, DNA and Gel Band Purification Kit according to the manufacturer's information.

The two fragments obtained above were used together as template in a further PCR reaction. In the course of the PCR reaction, the metA-homologous sequences introduced with the oligonucleotide primer SEQ ID NO: 18 cause the two fragments to attach to one another and to be extended by the polymerase used to give a continuous DNA strand. The standard method was modified in that the oligonucleotide primers used, SEQ ID NO: 17 and SEQ ID NO: 20, were only added to the reaction mixture at the start of the 2nd cycle.

The amplified DNA fragment of approximately 675 base pairs was purified using the GFX™ PCR, DNA and Gel Band Purification Kit according to the manufacturer's information. It was subsequently cleaved by the restriction enzymes XhoI and NcoI (Roche Diagnostics, Mannheim) and fractionated by gel electrophoresis. The approx. 620 base pair DNA fragment was then purified from the agarose, using the GFX™ PCR, DNA and Gel Band Purification Kit (Amersham Pharmacia, Freiburg).

The PmetA metA SEQ ID NO: 16 plasmid was cleaved by the restriction enzymes NcoI and SpeI (Roche Diagnostics, Mannheim). After fractionation by gel electrophoresis, an approx. 0.7 kb metA fragment was purified from the agarose, using the GFX™ PCR, DNA and Gel Band Purification Kit.

The pClik5MCS SEQ ID NO: 13 vector was cut by the restriction enzymes XhoI and SpeI (Roche Diagnostics, Mannheim), and a 5 kb fragment was isolated, after electrophoretic fractionation, using the GFX™ PCR, DNA and Gel Band Purification Kit.

The vector fragment was ligated together with the PCR fragment and the metA fragment with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The plasmid obtained, pCLiK5MCS PSODmetA, is listed as SEQ ID NO: 21.

Example 4

Preparation of the Plasmid pCLiK5MCS P EF-TU metA

*C. glutamicum* ATCC 13032 chromosomal DNA was prepared according to Tauch et al. (1995) Plasmid 33:168-179 or Eikmanns et al. (1994) Microbiology 140:1817-1828. Using the oligonucleotide primers SEQ ID NO: 22 and SEQ ID NO: 23, the chromosomal DNA as template and Pfu Turbo polymerase (Stratagene), a DNA fragment of approx. 200 base pairs from the noncoding 5' region (promoter region) of superoxide dismutase (Psod) was amplified with the aid of the polymerase chain reaction (PCR) by standard methods such as Innis et al. (1990) PCR Protocols. A Guide to Methods and Applications, Academic Press.

```
                                         SEQ ID NO: 22
5'-GAGACTCGAGGGCCGTTACCCTGCGAATG-3'
and
                                         SEQ ID NO: 23
5'-CCTGAAGGCGCGAGGGTGGGCATTGTATGTCCTCCTGGAC-3'
```

The DNA fragment obtained was purified using the GFX™ PCR, DNA and Gel Band Purification Kit (Amersham Pharmacia, Freiburg) according to the manufacturer's information.

Starting from the PmetA metA SEQ ID NO: 16 plasmid as template for a PCR reaction, metA was partially amplified using the oligonucleotide primers SEQ ID NO: 24 and SEQ ID NO: 25.

```
                                         SEQ ID NO: 24
5'-CCCACCCTCGCGCCTTCAG-3'
and
                                         SEQ ID NO: 25
5'-CTGGGTACATTGCGGCCC-3'
```

The DNA fragment obtained of approximately 470 base pairs was purified using the GFX™ PCR, DNA and Gel Band Purification Kit according to the manufacturer's information.

The two fragments obtained above were used together as template in a further PCR reaction. In the course of the PCR reaction, the metA-homologous sequences introduced with the oligonucleotide primer SEQ ID NO: 18 cause the two fragments to attach to one another and to be extended by the polymerase used to give a continuous DNA strand. The standard method was modified in that the oligonucleotide primers used, SEQ ID NO: 22 and SEQ ID NO: 25, were only added to the reaction mixture at the start of the 2nd cycle.

The amplified DNA fragment of approximately 675 base pairs was purified using the GFX™ PCR, DNA and Gel Band Purification Kit according to the manufacturer's information. It was subsequently cleaved by the restriction enzymes XhoI and NcoI (Roche Diagnostics, Mannheim) and fractionated by gel electrophoresis. The approx. 620 base pair DNA fragment was then purified from the agarose, using the GFX™ PCR, DNA and Gel Band Purification Kit (Amersham Pharmacia, Freiburg).

The PmetA metA SEQ ID NO: 16 plasmid was cleaved with the restriction enzymes NcoI and SpeI (Roche Diagnostics, Mannheim). After fractionation by gel electrophoresis, an approx. 0.7 kb metA fragment was purified from the agarose, using the GFX™ PCR, DNA and Gel Band Purification Kit.

The pClik5MCS SEQ ID NO: 13 vector was cut by the restriction enzymes XhoI and SpeI (Roche Diagnostics, Mannheim), and a 5 kb fragment was isolated, after electrophoretic fractionation, using the GFX™ PCR, DNA and Gel Band Purification Kit.

The vector fragment was ligated together with the PCR fragment and the metA fragment with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The plasmid obtained, pCLiK5MCS P_EFTUmetA, is listed as SEQ ID NO: 26.

Example 5

Preparation of the Plasmid pCLiK5MCS Pgro metA

*C. glutamicum* ATCC 13032 chromosomal DNA was prepared according to Tauch et al. (1995) Plasmid 33:168-179 or Eikmanns et al. (1994) Microbiology 140:1817-1828. Using the oligonucleotide primers SEQ ID NO: 27 and SEQ ID NO: 28, the chromosomal DNA as template and Pfu Turbo polymerase (Stratagene), a DNA fragment of approx. 200 base pairs from the noncoding 5' region (promoter region) of GroES gene (Pgro) was amplified with the aid of the polymerase chain reaction (PCR) by standard methods such as Innis et al. (1990) PCR Protocols. A Guide to Methods and Applications, Academic Press.

```
                                           SEQ ID NO: 27
5'-GAGACTCGAGCGGCTTAAAGTTTGGCTGCC-3'

SEQ ID NO: 28
5'-CCTGAAGGCGCGAGGGTGGGCATGATGAATCCCTCCATGAG-3'
```

The DNA fragment obtained was purified using the GFX™ PCR, DNA and Gel Band Purification Kit (Amersham Pharmacia, Freiburg) according to the manufacturer's information.

Starting from the PmetA metA plasmid as template for a PCR reaction, metA was partially amplified using the oligonucleotide primers SEQ ID NO: 29: and SEQ ID NO: 30.

```
                                           SEQ ID NO: 29
        5'-CCCACCCTCGCGCCTTCAG-3'

SEQ ID NO: 30
        5'-CTGGGTACATTGCGGCCC-3'
```

The DNA fragment obtained of approximately 470 base pairs was purified using the GFX™ PCR, DNA and Gel Band Purification Kit according to the manufacturer's information.

The two fragments obtained above were used together as template in a further PCR reaction. In the course of the PCR reaction, the metA-homologous sequences introduced with the oligonucleotide primer SEQ ID NO: 28 cause the two fragments to attach to one another and to be extended by the polymerase used to give a continuous DNA strand. The standard method was modified in that the oligonucleotide primers used, SEQ ID NO: 27 and SEQ ID NO: 30, were only added to the reaction mixture at the start of the 2nd cycle.

The amplified DNA fragment of approximately 675 base pairs was purified using the GFX™ PCR, DNA and Gel Band Purification Kit according to the manufacturer's information. It was subsequently cleaved by the restriction enzymes XhoI and NcoI (Roche Diagnostics, Mannheim) and fractionated by gel electrophoresis. The approx. 620 base pair DNA fragment was then purified from the agarose, using the GFX™ PCR, DNA and Gel Band Purification Kit (Amersham Pharmacia, Freiburg).

The PmetA metA SEQ ID NO: 16 plasmid was cleaved by the restriction enzymes NcoI and SpeI (Roche Diagnostics, Mannheim). After fractionation by gel electrophoresis, an approx. 0.7 kb metA fragment was purified from the agarose, using the GFX™ PCR, DNA and Gel Band Purification Kit.

The pClik5MCS SEQ ID NO: 13 vector was cut by the restriction enzymes XhoI and SpeI (Roche Diagnostics, Mannheim), and a 5 kb fragment was isolated, after electrophoretic fractionation, using the GFX™ PCR, DNA and Gel Band Purification Kit.

The vector fragment was ligated together with the PCR fragment and the metA fragment with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1Blue (Stratagene, La Jolla, USA). Selection for plasmid-harboring cells was achieved by plating out on LB agar containing kanamycin (20 μg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The plasmid obtained, pCLiK5MCS Pgro metA, is listed as SEQ ID NO: 31.

Example 6

Preparation of the Plasmid P EF-TS metA

*C. glutamicum* ATCC 13032 chromosomal DNA was prepared according to Tauch et al. (1995) Plasmid 33:168-179 or Eikmanns et al. (1994) Microbiology 140:1817-1828. Using the oligonucleotide primers BK 1849 (SEQ ID NO: 32) and BK 1862 (SEQ ID NO: 33), the chromosomal DNA as template and Pfu Turbo polymerase (Stratagene), the MetaA gene which codes for homoserine O-acetyltransferase was amplified with the aid of the polymerase chain reaction (PCR) by standard methods as described in Innis et al. (1990) PCR Protocols. A Guide to Methods and Applications, Academic Press.

```
BK 1849
                                           (SEQ ID NO: 32)
    5'-GTGTGTCGACTTAGATGTAGAACTCGATGTAG-3'
    and BK 1862
                                           (SEQ ID NO: 33)
    5'-ATGCCCACCCTCGCGCC-3'
```

The approx. 1134 bp DNA fragment obtained was purified using the GFX™ PCR, DNA and Gel Band Purification Kit (Amersham Pharmacia, Freiburg) according to the manufacturer's information.

Using the oligonucleotide primers Haf 26 (SEQ ID NO: 34) and Haf 27 (SEQ ID NO: 35), the chromosomal DNA as template and Pfu Turbo polymerase (Stratagene), a DNA fragment of approx. 200 base pairs from the noncoding 5' region (region of the expression unit) of the gene coding for elongation factor TS was amplified with the aid of the polymerase chain reaction (PCR) by standard methods as described in Innis et al. (1990) PCR Protocols. A Guide to Methods and Applications, Academic Press.

```
Haf 26
                                           (SEQ ID NO: 34)
    5'-GAGAGGATCCCCCCCACGACAATGGAAC-3'
    and Haf 27
                                           (SEQ ID NO: 35)
    5'-CCTGAAGGCGCGAGGGTGGGCATTACGGGGCGATCCTCCTTATG-3'
```

The approx. 195 bp DNA fragment obtained was purified using the GFX™ PCR, DNA and Gel Band Purification Kit (Amersham Pharmacia, Freiburg) according to the manufacturer's information.

The Haf 27 and BK 1862 primers comprise an overlapping sequence and their 5' ends are homologous to one another.

The PCR products obtained above were used as template for another PCR which made use of the primers BK 1849 (SEQ ID NO: 32) and Haf 26 (SEQ ID NO: 34).

Using this approach, a DNA fragment was amplified which corresponded to the expected size of 1329 bp. This P EF-TS/metA fusion was then cloned via the BamHI and SalI restriction cleavage sites into pClik 5a MCS (SEQ ID NO: 13) vector.

The vector fragment was ligated together with the PCR fragment with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The resulting plasmid was referred to as pClik 5a MCS P EF-TS metA (SEQ ID NO: 36).

Example 7

Preparation of the Plasmid P EF-Tu pSOD metA (H473)

*C. glutamicum* ATCC 13032 chromosomal DNA was prepared according to Tauch et al. (1995) Plasmid 33:168-179 or Eikmanns et al. (1994) Microbiology 140:1817-1828. Using the oligonucleotide primers BK 1753 (SEQ ID NO: 37) and BK 1754 (SEQ ID NO: 38), the chromosomal DNA as template and Pfu Turbo polymerase (Stratagene), the GroEL terminator was amplified with the aid of the polymerase chain reaction (PCR) by standard methods as described in Innis et al. (1990) PCR Protocols. A Guide to Methods and Applications, Academic Press.

```
BK 1753
                                        (SEQ ID NO: 37)
GGATCTAGAGTTCTGTGAAAAACACCGTG

BK 1754
                                        (SEQ ID NO: 38)
GCGACTAGTGCCCCACAAATAAAAAACAC
```

The approx. 77 bp DNA fragment obtained was purified using the GFX™ PCR, DNA and Gel Band Purification Kit (Amersham Pharmacia, Freiburg) according to the manufacturer's information, cut by the Xba I and Bcu I restriction enzymes and purified once more.

The pClik5MCS (SEQ ID NO: 13) vector was linearized by the XbaI restriction enzyme and purified using the GFX™ PCR, DNA and Gel Band Purification Kit (Amersham Pharmacia, Freiburg) according to the manufacturer's information.

The linearized vector was ligated together with the PCR fragment with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The resulting plasmid was referred to as H247 (SEQ ID NO: 39).

This plasmid was treated with the BcuI and SalI restriction enzymes and purified using the GFX™ PCR, DNA and Gel Band Purification Kit (Amersham Pharmacia, Freiburg) according to the manufacturer's information.

A PCR using the oligonucleotides BK 1848 (SEQ ID NO: 40) and BK 1849 (SEQ ID NO: 41), the pClik5MCS Psod metA (SEQ ID NO: 21) plasmid as template and Pfu Turbo polymerase (Stratagene) was carried out by standard methods as described in Innis et al. (1990) PCR Protocols. A Guide to Methods and Applications, Academic Press. The amplified fragment had an expected length of approx. 1350 bp and was purified using the GFX™ PCR, DNA and Gel Band Purification Kit (Amersham Pharmacia, Freiburg) according to the manufacturer's information, cut by the BcuI and SalI restriction enzymes and purified once more.

This fragment was ligated with the H247 plasmid (BcuI and SalI cleavage sites) with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, beschrieben (1989)), into competent *E. coli* XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The resulting plasmid was referred to as pG A4 (H344) and is listed under SEQ ID NO: 42.

```
                                        SEQ ID NO: 40
  (BK 1848) GAGAACTAGTAGCTGCCAATTATTCCGGG

SEQ ID NO: 41
  (BK 1849) GTGTGTCGACTTAGATGTAGAACTCGATGTAG
```

The pG A4 (SEQ ID NO: 42) plasmid was cut by the XhoI and BcuI restriction enzymes and purified using the GFX™ PCR, DNA and Gel Band Purification Kit (Amersham Pharmacia, Freiburg) according to the manufacturer's information.

Construction of H473:

*C. glutamicum* ATCC 13032 chromosomal DNA was prepared according to Tauch et al. (1995) Plasmid 33:168-179 or Eikmanns et al. (1994) Microbiology 140:1817-1828. Using the oligonucleotides primers BK 1695 (SEQ ID NO: 43) and Haf16 (SEQ ID NO: 44), the chromosomal DNA as template and Pfu Turbo polymerase (Stratagene), a DNA fragment of approx. 182 base pairs from the noncoding 5' region (region of the expression unit) of the EF Tu gene (Peftu) was amplified with the aid of the polymerase chain reaction (PCR) by standard methods as described in Innis et al. (1990) PCR Protocols. A Guide to Methods and Applications, Academic Press.

```
                                      SEQ ID NO: 43
(BK1695) GAGACTCGAGGGCCGTTACCCTGCGAATG

SEQ ID NO: 44
(Haf16)  GAGAACTAGTGTGGCTACGACTTTCGCAGC
```

The approx. 200 bp DNA fragment obtained was purified using the GFX™ PCR, DNA and Gel Band Purification Kit (Amersham Pharmacia, Freiburg) according to the manufacturer's information, cut by the Xho I and Bcu I restriction enzymes and purified once more.

This fragment was ligated with the pG A4 (H344) plasmid (XhoI and BcuI cleavage sites) with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor (1989)), into competent E. coli XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid obtained was referred to as pClik5MCS PeftuPsod metA (H473). It is listed under SEQ ID NO: 45. It comprises (from 5' to 3') a Peftu promoter, a Psod expression unit and, immediately downstream thereof, the metA open reading frame.

Example 8

Preparation of the plasmid PsodPeftu metA (H505)

C. glutamicum ATCC 13032 chromosomal DNA was prepared according to Tauch et al. (1995) Plasmid 33:168-179 or Eikmanns et al. (1994) Microbiology 140:1817-1828. Using the oligonucleotide primers SEQ ID NO: 46 (Haf64) and SEQ ID NO: 47 (Haf65), the chromosomal DNA as template and Pfu Turbo polymerase (Stratagene), a DNA fragment of approx. 200 base pairs from the noncoding 5' region (region of the expression unit) of the EF Tu gene (Peftu) was amplified with the aid of the polymerase chain reaction (PCR) by standard methods as described in Innis et al. (1990) PCR Protocols. A Guide to Methods and Applications, Academic Press.

```
                                      SEQ ID NO: 46
(Haf64) GAGAACTAGTGGCCGTTACCCTGCGAATG

SEQ ID NO: 47
(Haf65) GCGCGAGGGTGGGCATTGTATGTCCTCCTGGACTTC
```

The approx. 200 bp DNA fragment obtained was purified using the GFX™ PCR, DNA and Gel Band Purification Kit (Amersham Pharmacia, Freiburg) according to the manufacturer's information.

In a second PCR, using the oligonucleotide primers BK1862 (SEQ ID NO: 48) and BK1849 (SEQ ID NO: 49) and the H344 (SEQ ID NO: 42) plasmid as template, the metA open reading frame was amplified by standard methods as described in Innis et al. (1990) PCR Protocols. A Guide to Methods and Applications, Academic Press. The approx. 1140 bp fragment obtained was purified using the GFX™ PCR, DNA and Gel Band Purification Kit (Amersham Pharmacia, Freiburg) according to the manufacturer's information.

```
                                      SEQ ID NO: 48
(BK1862) ATGCCCACCCTCGCGCC

SEQ ID NO: 49
(BK1849) GTGTGTCGACTTAGATGTAGAACTCGATGTAG
```

The two fragments obtained above were used together as template in a further PCR reaction. In the course of the PCR reaction, the metA-homologous sequences introduced with the oligonucleotide primer Haf 65 SEQ ID NO: 47 cause the two fragments to attach to one another and to be extended by the polymerase used to give a continuous DNA strand. The standard method was modified in that the oligonucleotide primers used, Haf 64 and BK 1849 SEQ ID NO: 46 and SEQ ID NO: 49 were only added to the reaction mixture at the start of the 2nd cycle.

The amplified DNA fragment of approximately 1350 base pairs was purified using the GFX™ PCR, DNA and Gel Band Purification Kit according to the manufacturer's information. It was subsequently cleaved by the restriction enzymes BcuI and SalI (Roche Diagnostics, Mannheim) and fractionated by gel electrophoresis. The approx. 1340 base pair DNA fragment was then purified from the agarose, using the GFX™ PCR, DNA and Gel Band Purification Kit (Amersham Pharmacia, Freiburg). This fragment comprises the Peftu expression unit fused to the metA ORF (=Peftu-metA fragment).

Using the oligonucleotide primers BK 1697 (SEQ ID NO: 50) and Haf17 (SEQ ID NO: 51), the chromosomal DNA as template and Pfu Turbo polymerase (Stratagene), a DNA fragment (total length: 193 bp, 173 thereof being pSOD) from the noncoding 5' region (region of the expression unit) of the SOD gene (Psod) amplified with the aid of the polymerase chain reaction (PCR) by standard methods as described in Innis et al. (1990) PCR Protocols. A Guide to Methods and Applications, Academic Press.

```
                                      SEQ ID NO: 50
(BK1697) GAGACTCGAGAGCTGCCAATTATTCCGGG

SEQ ID NO: 51
(Haf17)  GAGAACTAGTTAGGTTTCCGCACCGAGC
```

The amplified DNA fragment was purified using the GFX™ PCR, DNA and Gel Band Purification Kit according to the manufacturer's information. It was subsequently cleaved by the restriction enzymes XhoI and BcuI (Roche Diagnostics, Mannheim) and fractionated by gel electrophoresis. The approx. 180 base pair DNA fragment was then purified from the agarose, using the GFX™ PCR, DNA and Gel Band Purification Kit (Amersham Pharmacia, Freiburg) (=Psod fragment).

The (H344) pG A4 SEQ ID NO: 42 plasmid was cleaved by the restriction enzymes XhoI and SalI (Roche Diagnostics, Mannheim) and fractionated by gel electrophoresis. The linearized vector was then purified from the agarose, using the GFX™ PCR, DNA and Gel Band Purification Kit (Amersham Pharmacia, Freiburg).

The linearized vector was ligated with the two fragments (Peftu-metA fragment and Psod fragment) with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The resultant plasmid, pClik5MCS PsodPeftu metA, is listed as SEQ ID NO: 52.

Example 9

Preparation of the Plasmid pClik5MCS Pgro Psod metA (H472)

*C. glutamicum* ATCC 13032 chromosomal DNA was prepared according to Tauch et al. (1995) Plasmid 33:168-179 or Eikmanns et al. (1994) Microbiology 140:1817-1828. Using the oligonucleotide primers SEQ ID NO: 53 (BK1701) and SEQ ID NO: 54 (Haf18), the chromosomal DNA as template and Pfu Turbo polymerase (Stratagene), an approx. 175 nucleotide DNA fragment was and amplified with the aid of the polymerase chain reaction (PCR) by standard methods as described in Innis et al. (1990) PCR Protocols. A Guide to Methods and Applications, Academic Press. It comprises 155 base pairs from the noncoding 5' region (region of the expression unit) of the GRO EL gene (Pgro) and one restriction cleavage site each on the 5' and 3' ends (XhoI and BcuI, respectively).

```
                                     SEQ ID NO: 53
(BK1701) GAGACTCGAGCGGCTTAAAGTTTGGCTGCC

SEQ ID NO: 54
(Haf018) GAGAACTAGTATTTTGTGTGTGCCGGTTGTG
```

The approx. 175 bp DNA fragment obtained was purified using the GFX™ PCR, DNA and Gel Band Purification Kit (Amersham Pharmacia, Freiburg) according to the manufacturer's information. It was subsequently cleaved by the restriction enzymes XhoI and BcuI (Roche Diagnostics, Mannheim), and the DNA fragment was purified using the GFX™ PCR, DNA and Gel Band Purification Kit.

The H344 (SEQ ID NO: 42) plasmid was cut by the XhoI and BcuI restriction enzymes, and an approx. 6.4 kb fragment was isolated, after electrophoretic fractionation, using the GFX™ PCR, DNA and Gel Band Purification Kit.

The PCR product and the cut-open H344 plasmid were ligated with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1 Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467.

The sequencing reactions were fractionated and evaluated by means of ABI Prism 377 (PE Applied Biosystems, Weiterstadt).

The resulting plasmid comprises a Pgro promoter immediately followed by a Psod expression unit and the metA ORF.

It is listed as pCLiK5MCS PgroPsod metA (H472) under SEQ ID NO: 55.

Example 10

Preparation of the Plasmid PgroPsod Pefts metA (H501)

A PCR using the oligonucleotide primers BK1782 (SEQ ID NO: 56) and Haf63 (SEQ ID NO: 57) and the pClik5MCS Pgro Psod metA (SEQ ID NO: 55 (H472)) plasmid as template was carried out by standard methods as described in Innis et al. (1990) PCR Protocols. A Guide to Methods and Applications, Academic Press. The amplified fragment comprises approx. 474 base pairs and a Pgro-Psod cassette with an Acc65I cleavage site at the 3' end. The DNA fragment obtained was purified using the GFX™ PCR, DNA and Gel Band Purification Kit (Amersham Pharmacia, Freiburg) according to the manufacturer's information. It was subsequently cleaved by the XhoI and Acc65I restriction enzymes, and the DNA fragment (333 base pairs) was purified using the GFX™ PCR, DNA and Gel Band Purification Kit.

```
                                     SEQ ID NO: 56
(BK1782) TCGAGAGATTGGATTCTTAC

SEQ ID NO: 57
(Haf 63) TCTCGGTACCCCGCACCGAGCATATACATC
```

The H479 (SEQ ID NO: 58) plasmid comprises the Pefts expression unit fused to the metA ORF. It was cut (directly upstream of Pefts) by the XhoI and Acc65I restriction enzymes, and an approx. 6.4 kb fragment was isolated, after electrophoretic fractionation, using the GFX™ PCR, DNA and Gel Band Purification Kit.

It was then ligated with the PCR fragment (Pgro-Psod cassette) with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The resulting plasmid comprises the 3 promoters, Pgro, Psod and P EF-Ts, fused to the metA ORF.

It is listed as pCLiK5MCS Pgro Psod Pefts metA (H501) under SEQ ID NO: 59.

Example 11

Preparation of the Plasmid Peftu Psod Pefts metA (H502)

A PCR using the oligonucleotide primers BK1782 (SEQ ID NO: 56) and Haf63 (SEQ ID NO: 57) and the pClik5MCS Peftu Psod (SEQ ID NO: 45 (H473)) plasmid as template was carried out by standard methods as described in Innis et al. (1990) PCR Protocols. A Guide to Methods and Applications, Academic Press. The amplified fragment comprises approx. 495 base pairs and a Peftu-Psod cassette with an Acc65I cleavage site at the 3' end. The DNA fragment obtained was purified using the GFX™ PCR, DNA and Gel Band Purification Kit (Amersham Pharmacia, Freiburg) according to the manufacturer's information. It was subsequently cleaved by the XhoI and Acc65I restriction enzymes, and the DNA fragment (354 base pairs) was purified using the GFX™ PCR, DNA and Gel Band Purification Kit.

```
                                            SEQ ID NO: 56
(BK1782) TCGAGAGATTGGATTCTTAC

SEQ ID NO: 57
(Haf 63) TCTCGGTACCCCGCACCGAGCATATACATC
```

The H479 (SEQ ID NO: 58) plasmid comprises the Pefts expression unit fused to the metA ORF. It was cut (directly upstream of Pefts) by the XhoI and Acc65I restriction enzymes, and an approx. 6.4 kb fragment was isolated, after electrophoretic fractionation, using the GFX™ PCR, DNA and Gel Band Purification Kit.

It was then ligated with the PCR fragment (Peftu-Psod cassette) with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent E. coli XL-1 Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The resulting plasmid comprises the 3 regulatory sequences, Peftu, Psod and P EF-Ts, fused to the metA ORF. It is listed as pCLiK5MCS Peftu Psod Pefts metA (H501) under SEQ ID NO: 60.

Example 12

Measurement of metA Activities

The Corynebacterium glutamicum strain ATCC13032 was transformed in each case with the plasmids pClik5 MCS, pClik MCS Psod metA, pClik MCS Peftu metA, pClik5 MCS Pefts metA, pClik5 MCS Peftu Psod metA, pClik5 MCS Psod Peftu metA, pClik5 MCS Pgro Psod meta, pClik5 MCS Pgro Psod Pefts metA, pClik5 MCS Peftu Psod Pefts metA according to the method described (Liebl, et al. (1989) FEMS Microbiology Letters 53:299-303). The transformation mixture was plated on CM plates which additionally contained 20 mg/l kanamycin in order to achieve selection for plasmid-containing cells. Kan-resistant clones obtained were picked and thinned out.

C. glutamicum strains comprising any of said plasmid constructs were grown in MMA Medium ((40 g/l sucrose, 20 g/l $(NH_4)_2SO_4$, 1 g/l $KH_2PO_4$, 1 g/l $K_2HPO_4$, 0.25 g/MgSO$_4$× 7H$_2$O, 54 g of Aces, 1 ml of CaCl$_2$ (10 g/l), 1 ml of protocat- echuate (300 mg/10 ml), 1 ml of trace element solution (10 g/l FeSO$_4$x/H$_2$O, 10 g/l MnSO$_4$×H$_2$O, 2 g/l ZnSO$_4$×7H$_2$O, 0.2 g/l CuSO$_4$, 0.02 g/l NiCl$_2$×6H$_2$O), 100 µg/l vitamin B$_{12}$, 0.3 mg/l thiamine, 1 mM leucine, 1 mg/l pyridoxal HCl, 1 ml of biotin (100 mg/l), pH 7.0) at 30° C. overnight. The cells were removed by centrifugation at 4° C. and washed twice with cold Tris-HCl buffer (0.1%, pH 8.0). After another centrifugation, the cells were taken up in cold Tris-HCl buffer (0.1%, pH 8.0) and the OD$_{600}$ was adjusted to 160. The cells were disrupted by transferring 1 ml of this cell suspension to 2-ml Hybaid Ribolyser tubes and lysed three times for in each case 30 s in a Hybaid Ribolyser, with rotation set to 6.0. The lysate was clarified by centrifugation in an Eppendorf centrifuge at 15 000 rpm and 4° C. for 30 minutes, and the supernatant was transferred to a new Eppendorf cup. The protein content was determined according to Bradford, M. M. (1976) Anal. Biochem. 72:248-254.

The enzymatic activity of MetA was carried out as follows. The 1-ml reaction mixtures contained 100 mM potassium phosphate buffer (pH 7.5), 5 mM MgCl$_2$, 100 µM acetyl-CoA, 5 mM L-homoserine, 500 µM DTNB (Ellman's Reagent) and cell extract. The assay was started by adding the relevant protein lysate and incubated at room temperature. Kinetics were then recorded at 412 nm for 10 min.

The results are depicted in Table 1a.

TABLE 1a

| Strain | Internal construct name | Specific activity |
|---|---|---|
| ATCC 13032 pClik5MCS | H356 (metZ) | 3.1 |
| ATCC 13032 pCLiK5MCS Psod metA | H144 | 1308.7 |
| ATCC 13032 pCLiK5MCS Peftu metA | H146 | 1233.0 |
| ATCC 13032 pCLiK5MCS Pefts metA | H479 | 2339.0 |
| ATCC 13032 pCLiK5MCS Peftu Psod metA | H473 | 2308.1 |
| ATCC 13032 pCLiK5MCS Psod Peftu metA | H505 | 2061.9 |
| ATCC 13032 pCLiK5MCS Pgro Psod metA | H472 | 1501.6 |
| ATCC 13032 pCLiK5MCS Pgro Psod Pefts metA | H501 | 1773.4 |
| ATCC 13032 pCLiK5MCS Peftu Psod Pefts metA | H502 | 2262.2 |

It was possible to modulate the MetA activity by using the various combinations of promoters/expression units.

Example 13

Construction of the Plasmid pCIS lysC

In order to generate a lysine-producing strain, an allelic substitution of the lysC wild-type gene was carried out in Corynebacterium glutamicum ATCC13032. This involved a nucleotide substitution in the lysC gene so that the amino acid Thr at position 311 was replaced by an Ile in the resulting protein. Starting from the chromosomal DNA of ATCC13032 as template for a PCR reaction, lysC was amplified with the aid of the Pfu-Turbo PCR Systems (Stratagene USA) using the oligonucleotide primers SEQ ID NO: 61 and SEQ ID NO: 62, according to the manufacturer's information.

```
                                            SEQ ID NO: 61
5'-GAGAGAGAGACGCGTCCCAGTGGCTGAGACGCATC-3'

SEQ ID NO: 62
5'-CTCTCTCTGTCGACGAATTCAATCTTACGGCCTG-3'
```

C. glutamicum ATCC 13032 chromosomal DNA was prepared according to Tauch et al. (1995) Plasmid 33:168-179 or Eikmanns et al. (1994) Microbiology 140:1817-1828. The amplified fragment is flanked by a SalI restriction cut on its 5' end and by a MluI restriction cut on its 3' end. Prior to cloning, the amplified fragment was digested by these two restriction enzymes and purified using the GFX™ PCR, DNA and Gel Band Purification Kit (Amersham Pharmacia, Freiburg).

The polynucleotide obtained was cloned via the SalI and MluI restriction cuts into pCLIK5 MCS integrative SacB, referred to as pCIS hereinbelow (SEQ ID NO: 63), and transformed into *E. coli* XL-1 blue. Selection for plasmid-harboring cells was achieved by plating out on LB agar containing kanamycin (20 µg/ml) (Lennox, 1955, Virology, 1:190). The plasmid was isolated and the expected nucleotide sequence was confirmed by sequencing. The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt). The plasmid obtained, pCIS lysC, is listed as SEQ ID NO: 64.

Example 14

Mutagenesis of the *C. glutamicum* lysC Gene

Directed mutagenesis of the *C. glutamicum* lysC gene was carried out using the Quick-Change Kit (Stratagene/USA) according to the manufacturer's information. The mutagenesis was carried out in the pCIS lysC, SEQ ID NO:64, plasmid. To replace thr 311 with 311ile with the aid of the Quick-Change method (Stratagene), the following oligonucleotide primers were synthesized:

```
                                               SEQ ID NO: 65
5'-CGGCACCACCGACATCATCTTCACCTGCCCTCGTTCCG-3'

SEQ ID NO: 66
5'-CGGAACGAGGGCAGGTGAAGATGATGTCGGTGGTGCCG-3'
```

The use of these oligonucleotide primers in the Quick-Change reaction results in a substitution of the nucleotide in position 932 (from C to T) in the lysC gene SEQ ID NO: 67. The resulting amino acid substitution, Thr311Ile, in the lysC gene was confirmed by a sequencing reaction, after transformation into *E. coli* XL1-blue and plasmid preparation. The plasmid was denoted pCIS lysC thr311 ile and is listed as SEQ ID NO: 68.

The pCIS lysC thr311ile plasmid was transformed into *C. glutamicum* ATCC13032 by means of electroporation as described in Liebl, et al. (1989) FEMS Microbiology Letters 53:299-303. Modifications of the protocol are described in DE 10046870. The chromosomal arrangement of the lysC locus of individual transformants was checked by standard methods through Southern blot and hybridization, as described in Sambrook et al. (1989), Molecular Cloning. A Laboratory Manual, Cold Spring Harbor. This ensured that the transformants have integrated the transformed plasmid at the lysC locus by way of homologous recombination. After growing such colonies in media which do not contain any antibiotic overnight, the cells are plated out on a sucrose CM-agar medium (10% sucrose, 10 g/l glucose; 2.5 g/l NaCl; 2 g/l urea, 10 g/l Bacto Peptone (Difco); 10 g/l yeast extract, 22.0 g/L Agar (Difco)) and incubated at 30° C. for 24 hours.

Since the sacB gene present in the pCIS lysC thr311ile vector converts sucrose into a toxic product, only those colonies can grow in which the sacB gene has been deleted by a second homologous recombination step between the wild-type lysC gene and the mutated lysC thr311ile gene. It is possible, during homologous recombination, for either the wild-type gene or the mutated gene to be deleted together with the sacB gene. If the sacB gene is removed together with the wild-type gene, the result is a mutated transformant.

Growing colonies are picked and tested for a kanamycin-sensitive phenotype. Clones with deleted sacB gene must, at the same time, display kanamycin-sensitive growth behavior. Such Kan-sensitive clones were tested in a shaker flask for their lysine productivity (see Example 19). The untreated *C. glutamicum* ATCC13032 was grown for comparison. Clones having increased lysine production, compared with the control, were selected, chromosomal DNA was recovered and the corresponding region of the lysC gene was amplified by a PCR reaction and sequenced. A clone of this kind, which has the property of increased lysine synthesis and a detected mutation in lysC at position 932, was denoted ATCC13032 lysC$^{fbr}$.

Example 15

Preparation of the Plasmid pCIS Peftu ddh

*C. glutamicum* ATCC 13032 chromosomal DNA was prepared according to Tauch et al. (1995) Plasmid 33:168-179 or Eikmanns et al. (1994) Microbiology 140:1817-1828.

Using the oligonucleotide primers SEQ ID NO: 69 (Old38) and SEQ ID NO: 70 (Old 39), the chromosomal DNA as template and Pfu Turbo polymerase (Stratagene), a DNA fragment of approx. 200 base pairs from the noncoding 5' region (region of the expression unit) of the EFTu gene (Peftu) was amplified with the aid of the polymerase chain reaction (PCR) by standard methods as described in Innis et al. (1990) PCR Protocols. A Guide to Methods and Applications, Academic Press.

```
                                               SEQ ID NO: 69
(Old38)  ACATCCATGGTGGCCGTTACCCTGCGAAT

SEQ ID NO: 70
(Old39)  TGTATGTCCTCCTGGACTTC
```

The approx. 200 bp DNA fragment obtained was purified using the GFX™ PCR, DNA and Gel Band Purification Kit (Amersham Pharmacia, Freiburg) according to the manufacturer's information.

In a second PCR, using the oligonucleotide primers Old40 (SEQ ID NO: 71) and SEQ ID NO: 72 (Old 37) and *C. glutamicum* ATCC 13032 chromosomal DNA as template, the ddh open reading frame was amplified by standard methods as described in Innis et al. (1990) PCR Protocols. A Guide to Methods and Applications, Academic Press. The approx. 1017 bp fragment obtained was purified using the GFX™ PCR, DNA and Gel Band Purification Kit (Amersham Pharmacia, Freiburg) according to the manufacturer's information.

```
                                               (SEQ ID NO: 71)
Old40  GAAGTCCAGGAGGACATACAATGACCAACATCCGCGTAGC (SEQ ID NO: 72)
Old37  GAAACCACACTGTTTCCTTGC
```

The two fragments obtained above were used together as template in a further PCR reaction. In the course of the PCR reaction, the Peftu-homologous sequences introduced with the oligonucleotide primer Old40 SEQ ID NO: 71 cause the two fragments to attach to one another and to be extended by the polymerase used to give a continuous DNA strand. The standard method was modified in that the oligonucleotide primers used, Old37 and Old 38 (SEQ ID NO: 72 and SEQ ID NO: 69), were only added to the reaction mixture at the start of the 2nd cycle.

The amplified DNA fragment of approximately 1207 base pairs was purified using the GFX™ PCR, DNA and Gel Band Purification Kit according to the manufacturer's information. It was subsequently cleaved by the restriction enzymes NcoI and XhoII (Roche Diagnostics, Mannheim) and fractionated by gel electrophoresis. The approx. 1174 base pair DNA fragment was then purified from the agarose, using the GFX™ PCR, DNA and Gel Band Purification Kit (Amersham Pharmacia, Freiburg). This fragment comprises the Peftu expression unit fused to the ddh ORF (=Peftu-ddh fragment).

Using the oligonucleotide primers Old 32 (SEQ ID NO: 73) and Old 33 (SEQ ID NO: 74), the chromosomal DNA as template and Pfu Turbo polymerase (Stratagene), a DNA fragment from the noncoding 5' region of the ddh gene was amplified with the aid of the polymerase chain reaction (PCR) by standard methods as described in Innis et al. (1990) PCR Protocols. A Guide to Methods and Applications, Academic Press.

```
                                        SEQ ID 73
(Old32) ATCAACGCGTCGACACCACATCATCAATCAC

SEQ ID 74
(Old33) ATCACCATGGGTTCTTGTAATCCTCCAAATTG
```

The amplified DNA fragment was purified using the GFX™ PCR, DNA and Gel Band Purification Kit according to the manufacturer's information. It was subsequently cleaved by the restriction enzymes MluI and NcoI (Roche Diagnostics, Mannheim) and fractionated by gel electrophoresis. The approx. 720 base pair DNA fragment was then purified from the agarose, using the GFX™ PCR, DNA and Gel Band Purification Kit (Amersham Pharmacia, Freiburg) (=5' ddh fragment).

The pCIS (SEQ ID NO: 63) plasmid was cleaved by the restriction enzymes MluI and XhoI (Roche Diagnostics, Mannheim) and fractionated by gel electrophoresis. The linearized vector was then purified from the agarose, using the GFX™ PCR, DNA and Gel Band Purification Kit (Amersham Pharmacia, Freiburg).

The linearized vector was ligated with the two fragments (Peftu-ddh fragment and 5' ddh fragment) with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1Blue (Stratagene, La Jolla, USA). Selection for plasmid-harboring cells was achieved by plating out on LB agar containing kanamycin (20 μg/ml) (Lennox, 1955, Virology, 1:190).

The plasmid DNA was prepared by methods and with materials from Quiagen. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt).

The resultant plasmid, pCIS Peftu ddh, is listed as SEQ ID NO: 75.

Example 16

Preparation of pCIS PeftuPsod Ddh

*C. glutamicum* ATCC 13032 chromosomal DNA was prepared according to Tauch et al. (1995) Plasmid 33:168-179 or Eikmanns et al. (1994) Microbiology 140:1817-1828. Using the oligonucleotide primers SEQ ID NO: 76 and SEQ ID NO: 77, the chromosomal DNA as template and Pfu Turbo polymerase (Stratagene), a DNA fragment of approx. 677 base pairs from the 5' region of the ddh gene was amplified with the aid of the polymerase chain reaction (PCR) by standard methods such as Innis et al. (1990) PCR Protocols. A Guide to Methods and Applications, Academic Press (5' ddh fragment).

```
                                        SEQ ID NO: 76
(CK461) CCTGACGTCGCAATATAGGCAGCTGAATC

SEQ ID NO: 77
(CK466) GCCCAATTGGTTCTTGTAATCCTCCAAAA
```

The DNA fragment obtained was purified using the GFX™ PCR, DNA and Gel Band Purification Kit (Amersham Pharmacia, Freiburg) according to the manufacturer's information. It was subsequently cleaved by the restriction enzymes AatII and MunI (Roche Diagnostics, Mannheim) and fractionated by gel electrophoresis. The approx. 661 base pair DNA fragment was then purified from the agarose, using the GFX™ PCR, DNA and Gel Band Purification Kit (Amersham Pharmacia, Freiburg). The resultant fragment comprises the 5' region of the ddh ORF.

Starting from the P EF-Tu pSOD metA (H473) (SEQ ID 45) plasmid as template for a PCR reaction, a PeftuPsod cassette was amplified using the oligonucleotide primers SEQ ID NO: 78 and SEQ ID NO: 79.

```
                                        SEQ ID NO: 78
(CK426) CGCCAATTGTCGAGGGCCGTTACCCT

SEQ ID NO: 79
(CK463) GCTACGCGGATGTTGGTCATGGGTAAAAAATCCTTTCGTA
```

The DNA fragment obtained of approximately 378 base pairs was purified using the GFX™ PCR, DNA and Gel Band Purification Kit according to the manufacturer's information.

The ddh ORF was amplified in a subsequent PCR. For this purpose, *C. glutamicum* ATCC 13032 chromosomal DNA was prepared according to Tauch et al. (1995) Plasmid 33:168-179 or Eikmanns et al. (1994) Microbiology 140: 1817-1828. Using the oligonucleotide primers SEQ ID NO: 80 (CK464) and SEQ ID NO: 81 (CK467), the chromosomal DNA as template and Pfu Turbo polymerase (Stratagene), a DNA fragment of approx. 992 base pairs (ddh ORF) was amplified with the aid of the polymerase chain reaction (PCR) according to standard methods such as Innis et al. (1990) PCR Protocols. A Guide to Methods and Applications, Academic Press. The amplified DNA fragment was purified using the GFX™ PCR, DNA and Gel Band Purification Kit according to the manufacturer's information.

SEQ ID NO: 80
(CK464)  TACGAAAGGATTTTTTACCCATGACCAACATCCGCGTAGC

SEQ ID NO: 81
(CK467)  AGACCCGGGTTAGACGTCGCGTGCGATCA

The two fragments obtained above (PeftuPsod cassette and ddh ORF) were used together as template in a further PCR reaction. In the course of the PCR reaction, the Psod-homologous sequences introduced with the oligonucleotide primer SEQ ID NO: 80 (CK464) cause the two fragments to attach to one another and to be extended by the polymerase used to give a continuous DNA strand. The standard method was modified in that the oligonucleotide primers used, SEQ ID NO: 79 (CK426) and SEQ ID NO: 81 (CK467), were only added to the reaction mixture at the start of the 2nd cycle.

The amplified DNA fragment of approximately 1359 base pairs was purified using the GFX™ PCR, DNA and Gel Band Purification Kit according to the manufacturer's information.

It was subsequently cleaved by the restriction enzymes MunI and SmaI (Roche Diagnostics, Mannheim) and fractionated by gel electrophoresis. The approx. 1359 base pair DNA fragment was then purified from the agarose, using the GFX™ PCR, DNA and Gel Band Purification Kit (Amersham Pharmacia, Freiburg).

The resultant fragment comprises (from 5' to 3') a Peftu promoter, a Psod expression unit and, immediately downstream thereof, the ddh open reading frame (PeftuPsod ddh).

The pCIS vector was cut by the AatII and SmaI restriction endonucleases and dephosphorylated by alkali phosphatase (Roche Diagnostics, Mannheim) according to the manufacturer's information. After electrophoresis in a 0.8% strength agarose gel, the linearized vector (approx. 4.2 kb) was isolated using the GFX™ PCR, DNA and Gel Band Purification Kit (Amersham Pharmacia, Freiburg) according to the manufacturer's information. This vector fragment was ligated with the two cut PCR fragments (5'ddh and PeftuPsod ddh) with the aid of the Rapid DNA Ligation Kit (Roche Diagnostics, Mannheim) according to the manufacturer's information, and the ligation mixture was transformed by standard methods as described in Sambrook et al. (Molecular Cloning. A Laboratory Manual, Cold Spring Harbor, (1989)), into competent *E. coli* XL-1Blue (Stratagene, La Jolla, USA). Selection for plasmid-harboring cells was achieved by plating out on LB agar containing kanamycin (20 µg/ml) (Lennox, 1955, Virology, 1:190).

The plasmid DNA of individual clones was isolated using the Qiaprep Spin Miniprep Kit (Qiagen, Hilden, Germany) according to the manufacturer's information and checked via restriction digestions. Two correct plasmids were sequenced. Sequencing reactions were carried out according to Sanger et al. (1977) Proceedings of the National Academy of Sciences USA 74:5463-5467. The sequencing reactions were fractionated and evaluated by means of ABI Prism 377 (PE Applied Biosystems, Weiterstadt). The resultant plasmid, pClik Peftu Psod ddh, is suitable for integrating the PeftuPsodcassette chromosomally upstream of the ddh ORF with the aid of two successive recombination events.

The pCIS PeftuPsod ddh plasmid is listed as SEQ ID NO: 82.

Example 17

Generation of the Strains ATCC13032 lysC$^{fbr}$ Peftu ddh and ATCC13032 lysC$^{fbr}$ PeftuPsod ddh Cells of the *E. coli* strain Mn522 (Stratagene, Amsterdam, The Netherlands) were transformed with either of the plasmids pCIS Peftu ddh and pCIS PeftuPsod ddh and with the plasmid pTc15AcglM according to Liebl, et al. (1989) FEMS Microbiology Letters 53:299-303. The pTc15AcglM plasmid enables DNA to be methylated according to the *Corynebacterium glutamicum* methylation pattern (DE 10046870). This methylation increases the stability of the pCIS Peftu ddh and pCIS PeftuPsod ddh plasmids in *C. glutamicum* cells. The plasmid DNA was subsequently isolated from the Mn522 cells by standard methods and introduced with the aid of electroporation into the above-described *Corynebacterium glutamicum* strain ATCC 13032 ask (fbr). Said electroporation and the subsequent selection on CM plates containing kanamycin (25 µg/ml) produced a plurality of transconjugants. In order to select for the second recombination event which should excise the vector, said transconjugants were grown in CM medium without kanamycin overnight and subsequently plated out on CM plates containing 10% sucrose for selection. The sacB gene present on the pCIS vector codes for the enzyme levan sucrase and, with growth on sucrose, leads to the synthesis of levan. Since levan is toxic for *C. glutamicum*, only *C. glutamicum* cells which have lost the integration plasmid due to the second recombination step grow on sucrose-containing medium (Jäger et al., Journal of Bacteriology 174 (1992) 5462-5466). 100 sucrose-resistant clones were checked for their kanamycin sensitivity. In a plurality of the clones tested, a sensitivity to kanamycin was also detected, in addition to resistance to sucrose, which is expected with the desired excision of the vector sequences. The polymerase chain reaction (PCR) was used in order to check whether the desired integration of the Peftu or PeftuPsod expression unit had also occurred. To this end, the particular clones were removed from the agar plate using a toothpick and suspended in 100 µl of $H_2O$ and boiled at 95° C. for 10 min. 10 µl of the solution obtained were in each case used as template in the PCR. The primers used were oligonucleotides which are homologous to the expression unit to be introduced and the ddh gene. The PCR conditions were chosen as follows: initial denaturation: 5 min at 95° C.; denaturation: 30 at 95° C.; hybridization: 30 s at 55° C.; amplification: 2 min at 72° C.; 30 cycles: final extension: 5 min at 72° C. In the reaction mixture containing the DNA of the starting strain, the choice of oligonucleotides did not produce any PCR product. A band was expected only for clones in which the Peftu or PeftuPsod expression units had been integrated immediately 5' of the ddh gene as a result of the 2nd recombination. The successful integration by the clones tested positive here was moreover also confirmed through Southern blot analysis (by standard methods as described, for example, in Sambrook et al. (Molecular Cloning. A Laboratory Manual, Cold Spring Harbor, (1989)). 2 different hydrolyses with restriction enzymes were carried out here for each strain to be generated, which hydrolyses would allow the starting strain (ATCC13032 ask (fbr)) and the desired strain to be distinguished unambiguously. The fact that the strains obtained do not have any kanamycin genes in the chromosome was moreover confirmed with the aid of a probe which is homologous to the kanamycin resistance gene.

Thus the following strains were generated:
ATCC13032 lysC$^{fbr}$ Peftu ddh
ATCC13032 lysC$^{fbr}$ PeftuPsod ddh All of these strains comprise a feedback-deregulated ask gene and therefore produce lysine. They differ from one another only by the regulatory unit controlling transcription of the ddh gene.

Example 18

Effect of ddh Enhancement by a Double Promoter on Lysine Production

In order to study the effect of enhancement of the ddh gene with the aid of a double promoter, the following strains were tested for lysine production:
ATCC13032 lysCfbr
ATCC13032 lysCfbr Peftu ddh
ATCC13032 lysCfbr Peftu Psod ddh For this purpose, the strains were grown on CM plates (10.0 g/L D-glucose, 2.5 g/L NaCl, 2.0 g/L urea, 10.0 g/L Bacto Peptone (Difco), 5.0 g/L Yeast Extract (Difco), 5.0 g/L Beef Extract (Difco), 22.0 g/L Agar (Difco), autoclaved (20 min, 121° C.)) at 30° C. for 3 days. The cells were then scraped off the plate and resuspended in saline. For the main culture, 10 ml of medium 1 and 0.5 g of autoclaved $CaCO_3$ (Riedel de Haen) were inoculated with the cell suspension to an $OD_{600}$ of 1.5 in a 100 ml Erlenmeyer flask and incubated on an Infors AJ118 (Infors, Bottmingen, Switzerland) at 220 rpm for 40 h. This was followed by determining the concentration of the lysine secreted into the medium.

Medium I:

| | |
|---|---|
| 40 g/l | Sucrose |
| 60 g/l | Molasses (based on 100% sugar content) |
| 10 g/l | $(NH_4)_2SO_4$ |
| 0.4 g/l | $MgSO_4*7H_2O$ |
| 0.6 g/l | $KH_2PO_4$ |
| 0.3 mg/l | Thiamine*HCl |
| 1 mg/l | Biotin (from a 1 mg/ml stock solution which has been sterilized by filtration and adjusted to pH 8.0 with $NH_4OH$) |
| 2 mg/l | $FeSO_4$ |
| 2 mg/l | $MnSO_4$ adjusted to pH 7.8 with $NH_4OH$, autoclaved (121° C., 20 min). |

Additionally, vitamin B12 (hydroxycobalamine, Sigma Chemicals) is added from a stock solution (200 µg/ml, sterilized by filtration) to a final concentration of 100 µg/l.

The amino acid concentration was determined by means of high pressure liquid chromatography according to Agilent on an Agilent 1100 Series LC System HPLC. A guard column derivatization with ortho-phthalaldehyde allows quantification of the amino acids formed, and the amino acid mixture is fractionated on a Hypersil AA column (Agilent).

The result of the study is depicted in the table below.

| Strain | Relative lysine concentration (%) |
|---|---|
| ATCC13032 lys$C^{fbr}$ | 100 |
| ATCC13032 lys$C^{fbr}$ Peftu ddh | 102.9 |
| ATCC13032 lys$C^{fbr}$ PeftuPsod ddh | 106.9 |

The invention claimed is:

1. A multiple promoter-comprising recombinant expression unit, comprising, in the 5'-3' direction, a sequence module of the following formula I:

$$5'\text{-}P_1\text{-}(\text{-}A_x\text{-}P_x\text{-})n\text{-}A_y\text{-}P_y\text{-}3' \quad (I)$$

wherein
n is an integer from 0 to 10,
$A_x$ and $A_y$ are identical or different and are a chemical bond or a linker nucleic acid sequence;
and wherein each of $P_1$, $P_x$ and $P_y$ is selected from the group consisting of SEQ ID NO: 1, SEQ ID NO: 2, SEQ ID NO: 3 and SEQ ID NO: 4; and wherein at least one of the $P_1$, $P_x$ and $P_y$ is different from the other sequences.

2. An expression cassette, comprising, in the 5'-3' direction, a sequence module of the following formula II:

$$5'\text{-}P_1\text{-}(\text{-}A_x\text{-}P_x\text{-})n\text{-}A_y\text{-}P_y\text{-}G\text{-}3' \quad (II)$$

wherein
n is an integer from 0 to 10,
$A_x$ and $A_y$ are identical or different and are a chemical bond or a linker nucleic acid sequence;
and wherein each of $P_1$, $P_x$ and $P_y$ is selected from the group consisting of SEQ ID NO: 1, SEQ ID NO: 2, SEQ ID NO: 3 and SEQ ID NO: 4; and wherein at least one of the $P_1$, $P_x$ and $P_y$ is different from the other sequences; and G is at least one coding nucleic acid sequence which is functionally linked to the 5' upstream regulatory sequence.

3. The expression cassette of claim 2, wherein G is selected from the group consisting of
a. a nucleic acid encoding a protein of the biosynthetic pathway of proteinogenic and nonproteinogenic amino acids,
b. a nucleic acid encoding a protein of the biosynthetic pathway of nucleotides and nucleosides,
c. a nucleic acid encoding a protein of the biosynthetic pathway of organic acids,
d. a nucleic acid encoding a protein of the biosynthetic pathway of lipids and fatty acids,
e. a nucleic acid encoding a protein of the biosynthetic pathway of diols,
f. a nucleic acid encoding a protein of the biosynthetic pathway of carbohydrates,
g. a nucleic acid encoding a protein of the biosynthetic pathway of aromatic compounds,
h. a nucleic acid encoding a protein of the biosynthetic pathway of vitamins,
i. a nucleic acid encoding a protein of the biosynthetic pathway of cofactors,
j. a nucleic acid encoding a protein of the biosynthetic pathway of enzymes, and
k. a nucleic acid encoding a protein of the central metabolism.

4. The expression cassette of claim 3, wherein the protein of the biosynthetic pathway of proteinogenic and nonproteinogenic amino acids of part a) is selected from the group consisting of aspartate kinase, aspartate semialdehyde dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triosephosphate isomerase, transcriptional regulator LuxR, transcriptional regulator LysR1, transcriptional regulator LysR2, malate-quinone oxidoreductase, glucose-6-phosphate dehydrogenase, 6-phosphogluconate dehydrogenase, transketolase, transaldolase, homoserine O-acetyltransferase, cystathionine gamma synthase, cystathionine beta lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase I, cysteine synthase II, coenzyme B12-dependent methionine synthase, coenzyme B12-independent methionine synthase activity, sulfate adenylyltransferase subunits 1 and 2, phosphoadenosine phosphosulfate reductase, ferredoxin sulfite reductase, ferredoxin NADP reductase, 3-phosphoglycerate dehydrogenase, RXA00655 regulator, RXN2910 regulator, arginyl-t-RNA synthetase, phosphoenolpyruvate carboxylase, threonine efflux protein, serine hydroxymethyltransferase, fructose 1,6-bisphosphatase, protein of sulfate reduction RXA077, protein of sulfate reduction RXA248, protein of sulfate reduction RXA247, OpcA protein, 1-phosphofructokinase, 6-phosphofructokinase, tetrahydropicolinate succinylase, succinyl aminoketopimelate aminotransferase, succinyl diaminopimelate desuccinylase, diaminopimelate epimerase, 6-phosphogluconate dehydrogenase, glucose phosphate isomerase, phosphoglycerate mutase, enolase, pyruvate kinase, aspartate transaminase, and malate enzyme.

5. A vector, comprising at least one expression cassette of claim 2.

6. A genetically modified microorganism transformed with at least one vector of claim 5.

7. A genetically modified microorganism comprising at least one expression cassette of claim 2.

8. The genetically modified microorganism of claim 6 or 7, obtained from coryneform bacteria.

9. The genetically modified microorganism of claim 6 or 7, obtained from bacteria of the genus *Corynebacterium* or *Brevibacterium*.

10. The genetically modified microorganism of claim 6 or 7, comprising at least one expression cassette in an integrated form.

11. A method for preparing a biosynthetic product, comprising culturing the genetically modified microorganism of claim 6 or 7 and isolating the product from the culture.

12. The method of claim 11, wherein the biosynthetic product is selected from the group consisting of organic acids, proteins, nucleotides and nucleosides, both proteinogenic and nonproteinogenic amino acids, lipids and fatty acids, diols, carbohydrates, aromatic compounds, vitamins and cofactors, enzymes and proteins.

13. A method for regulating product biosynthesis in a cell, comprising transfecting the cell with the expression cassette of claim 2, and culturing said cell.

* * * * *

SEQUENCE LISTING

```
<160> NUMBER OF SEQ ID NOS: 84

<210> SEQ ID NO 1
<211> LENGTH: 177
<212> TYPE: DNA
<213> ORGANISM: Corynebacterium glutamicum
<220> FEATURE:
<221> NAME/KEY: misc_feature
<223> OTHER INFORMATION: pGRO
<220> FEATURE:
<221> NAME/KEY: misc_feature
<222> LOCATION: (1)..(177)
<223> OTHER INFORMATION: promoter sequence if no further downstream
      promoter occurs
<220> FEATURE:
<221> NAME/KEY: misc_feature
<222> LOCATION: (1)..(155)
<223> OTHER INFORMATION: promoter sequence if a further promoter is
      attached downstream
<220> FEATURE:
<221> NAME/KEY: misc_feature
<222> LOCATION: (70)..(75)
<223> OTHER INFORMATION: putative -10 region
<220> FEATURE:
<221> NAME/KEY: misc_feature
<222> LOCATION: (165)..(172)
<223> OTHER INFORMATION: putative ribosome binding sequence

<400> SEQUENCE: 1
cggcttaaag tttggctgcc atgtgaattt ttagcaccct caacagttga gtgctggcac      60
tctcgggggt agagtgccaa ataggttgtt tgacacacag ttgttcaccc gcgacgacgg     120
ctgtgctgga aacccacaac cggcacacac aaaattttc tcatggaggg attcatc         177

<210> SEQ ID NO 2
```

```
<211> LENGTH: 195
<212> TYPE: DNA
<213> ORGANISM: Corynebacterium glutamicum
<220> FEATURE:
<221> NAME/KEY: misc_feature
<223> OTHER INFORMATION: pEFTS
<220> FEATURE:
<221> NAME/KEY: misc_feature
<222> LOCATION: (1)..(195)
<223> OTHER INFORMATION: promoter sequence if no further downstream
      promoter occurs
<220> FEATURE:
<221> NAME/KEY: misc_feature
<222> LOCATION: (1)..(178)
<223> OTHER INFORMATION: promoter sequence if a further promoter is
      attached downstream
<220> FEATURE:
<221> NAME/KEY: misc_feature
<222> LOCATION: (147)..(152)
<223> OTHER INFORMATION: putative -10 region
<220> FEATURE:
<221> NAME/KEY: misc_feature
<222> LOCATION: (162)..(167)
<223> OTHER INFORMATION: putative -10 region
<220> FEATURE:
<221> NAME/KEY: misc_feature
<222> LOCATION: (179)..(185)
<223> OTHER INFORMATION: putative ribosome binding sequence

<400> SEQUENCE: 2
cccccacgac aatggaactt tgacttttaa aatttcatcg ccgtgggggc ttttgggca      60 gccagcccgc cgtgtcgcaa cgtaatcgac tgaataccctg tacgatcact ttttagacgg   120
gcgggtaggg ctactgtgcc ctaacctaag cttgtaaagc attaattatc catacataag    180
gaggatcgcc ccgta                                                    195

<210> SEQ ID NO 3
<211> LENGTH: 199
<212> TYPE: DNA
<213> ORGANISM: Corynebacterium glutamicum
<220> FEATURE:
<221> NAME/KEY: misc_feature
<223> OTHER INFORMATION: pEFTU
<220> FEATURE:
<221> NAME/KEY: misc_feature
<222> LOCATION: (1)..(199)
<223> OTHER INFORMATION: promoter sequence if no further downstream
      promoter occurs
<220> FEATURE:
<221> NAME/KEY: misc_feature
<222> LOCATION: (1)..(176)
<223> OTHER INFORMATION: promoter sequence if a further promoter is
      attached downstream
<220> FEATURE:
<221> NAME/KEY: misc_feature
<222> LOCATION: (36)..(41)
<223> OTHER INFORMATION: putative -10 region
<220> FEATURE:
<221> NAME/KEY: misc_feature
<222> LOCATION: (63)..(68)
<223> OTHER INFORMATION: putative -10 region
<220> FEATURE:
<221> NAME/KEY: misc_feature
<222> LOCATION: (92)..(97)
<223> OTHER INFORMATION: putative -10 region
<220> FEATURE:
<221> NAME/KEY: misc_feature
<222> LOCATION: (187)..(193)
<223> OTHER INFORMATION: putative ribosome binding sequence

<400> SEQUENCE: 3
ggccgttacc ctgcgaatgt ccacagggta gctggtagtt tgaaaatcaa cgccgttgcc    60
cttaggattc agtaactggc acattttgta atgcgctaga tctgtgtgct cagtcttcca   120
```

```
ggctgcttat cacagtgaaa gcaaaaccaa ttcgtggctg cgaaagtcgt agccaccacg    180
aagtccagga ggacataca                                                 199

<210> SEQ ID NO 4
<211> LENGTH: 191
<212> TYPE: DNA
<213> ORGANISM: Corynebacterium glutamicum
<220> FEATURE:
<221> NAME/KEY: misc_feature
<223> OTHER INFORMATION: pSOD
<220> FEATURE:
<221> NAME/KEY: misc_feature
<222> LOCATION: (1)..(191)
<223> OTHER INFORMATION: promoter sequence if no further downstream
      promoter occurs
<220> FEATURE:
<221> NAME/KEY: misc_feature
<222> LOCATION: (1)..(173)
<223> OTHER INFORMATION: promoter sequence if a further promoter is
      attached downstream
<220> FEATURE:
<221> NAME/KEY: misc_feature
<222> LOCATION: (65)..(70)
<223> OTHER INFORMATION: putative -10 region
<220> FEATURE:
<221> NAME/KEY: misc_feature
<222> LOCATION: (86)..(92)
<223> OTHER INFORMATION: putative -10 region
<220> FEATURE:
<221> NAME/KEY: misc_feature
<222> LOCATION: (175)..(181)
<223> OTHER INFORMATION: putative ribosome binding sequence

<400> SEQUENCE: 4
agctgccaat tattccgggc ttgtgacccg ctacccgata aataggtcgg ctgaaaaatt    60
tcgttgcaat atcaacaaaa aggcctatca ttgggaggtg tcgcaccaag tacttttgcg   120
aagcgccatc tgacggattt tcaaaagatg tatatgctcg gtgcggaaac ctacgaaagg   180
attttttacc c                                                         191

<210> SEQ ID NO 5
<211> LENGTH: 52
<212> TYPE: DNA
<213> ORGANISM: Artificial Sequence
<220> FEATURE:
<223> OTHER INFORMATION: Primer

<400> SEQUENCE: 5
cccgggatcc gctagcggcg cgccggccgg cccggtgtga ataccgcac ag            52

<210> SEQ ID NO 6
<211> LENGTH: 53
<212> TYPE: DNA
<213> ORGANISM: Artificial Sequence
<220> FEATURE:
<223> OTHER INFORMATION: Primer

<400> SEQUENCE: 6
tctagactcg agcggccgcg gccggccttt aaattgaaga cgaaagggcc tcg          53

<210> SEQ ID NO 7
<211> LENGTH: 47
<212> TYPE: DNA
<213> ORGANISM: Artificial Sequence
<220> FEATURE:
<223> OTHER INFORMATION: Primer

<400> SEQUENCE: 7
gagatctaga cccggggatc cgctagcggg ctgctaaagg aagcgga                 47
```

```
<210> SEQ ID NO 8
<211> LENGTH: 38
<212> TYPE: DNA
<213> ORGANISM: Artificial Sequence
<220> FEATURE:
<223> OTHER INFORMATION: Primer

<400> SEQUENCE: 8
gagaggcgcg ccgctagcgt gggcgaagaa ctccagca                    38

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
gagagggcgg ccgcgcaaag tcccgcttcg tgaa                        34

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
gagagggcgg ccgctcaagt cggtcaagcc acgc                        34

<210> SEQ ID NO 11
<211> LENGTH: 140
<212> TYPE: DNA
<213> ORGANISM: Artificial Sequence
<220> FEATURE:
<223> OTHER INFORMATION: Oligonucleotide

<400> SEQUENCE: 11
tcgaatttaa atctcgagag gcctgacgtc gggcccggta ccacgcgtca tatgactagt    60
tcggacctag ggatatcgtc gacatcgatg ctcttctgcg ttaattaaca attgggatcc   120
tctagacccg ggatttaaat                                               140

<210> SEQ ID NO 12
<211> LENGTH: 140
<212> TYPE: DNA
<213> ORGANISM: Artificial Sequence
<220> FEATURE:
<223> OTHER INFORMATION: Oligonucleotide

<400> SEQUENCE: 12
gatcatttaa atcccgggtc tagaggatcc caattgttaa ttaacgcaga agagcatcga    60
tgtcgacgat atccctaggt ccgaactagt catatgacgc gtggtaccgg gcccgacgtc   120
aggcctctcg agatttaaat                                               140

<210> SEQ ID NO 13
<211> LENGTH: 4323
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: Plasmid pCLiK5MCS
<220> FEATURE:
```

```
<221> NAME/KEY: misc_feature
<222> LOCATION: (457)..(1248)
<223> OTHER INFORMATION: KanR
<220> FEATURE:
<221> NAME/KEY: misc_feature
<222> LOCATION: (3840)..(4302)
<223> OTHER INFORMATION: PsacB (complementary)
<220> FEATURE:
<221> NAME/KEY: misc_feature
<222> LOCATION: (2418)..(3839)
<223> OTHER INFORMATION: SacB (complementary)
<220> FEATURE:
<221> NAME/KEY: misc_feature
<222> LOCATION: (1515)..(2375)
<223> OTHER INFORMATION: Ori-Ec (pMB) (complementary)

<400> SEQUENCE: 13
```

| | | | | | |
|---|---|---|---|---|---|
| tcgagaggcc | tgacgtcggg | cccggtacca | cgcgtcatat | gactagttcg | gacctaggga | 60 |
| tatcgtcgac | atcgatgctc | ttctgcgtta | attaacaatt | gggatcctct | agacccggga | 120 |
| tttaaatcgc | tagcgggctg | ctaaaggaag | cggaacacgt | agaaagccag | tccgcagaaa | 180 |
| cggtgctgac | cccggatgaa | tgtcagctac | tgggctatct | ggacaaggga | aaacgcaagc | 240 |
| gcaaagagaa | agcaggtagc | ttgcagtggg | cttacatggc | gatagctaga | ctgggcggtt | 300 |
| ttatggacag | caagcgaacc | ggaattgcca | gctggggcgc | cctctggtaa | ggttgggaag | 360 |
| ccctgcaaag | taaactggat | ggctttcttg | ccgccaagga | tctgatgcg | caggggatca | 420 |
| agatctgatc | aagagacagg | atgaggatcg | tttcgcatga | ttgaacaaga | tggattgcac | 480 |
| gcaggttctc | cggccgcttg | ggtggagagg | ctattcggct | atgactgggc | acaacagaca | 540 |
| atcggctgct | ctgatgccgc | cgtgttccgg | ctgtcagcgc | agggggcgccc | ggttcttttt | 600 |
| gtcaagaccg | acctgtccgg | tgccctgaat | gaactgcagg | acgaggcagc | gcggctatcg | 660 |
| tggctggcca | cgacgggcgt | tccttgcgca | gctgtgctcg | acgttgtcac | tgaagcggga | 720 |
| agggactggc | tgctattggg | cgaagtgccg | gggcaggatc | tcctgtcatc | tcaccttgct | 780 |
| cctgccgaga | aagtatccat | catggctgat | gcaatgcggc | ggctgcatac | gcttgatccg | 840 |
| gctacctgcc | cattcgacca | ccaagcgaaa | catcgcatcg | agcgagcacg | tactcggatg | 900 |
| gaagccggtc | ttgtcgatca | ggatgatctg | gacgaagagc | atcaggggct | cgcgccagcc | 960 |
| gaactgttcg | ccaggctcaa | ggcgcgcatg | cccgacggcg | aggatctcgt | cgtgacccat | 1020 |
| ggcgatgcct | gcttgccgaa | tatcatggtg | gaaaatggcc | gcttttctgg | attcatcgac | 1080 |
| tgtggccggc | tgggtgtggc | ggaccgctat | caggacatag | cgttggctac | ccgtgatatt | 1140 |
| gctgaagagc | ttggcggcga | atgggctgac | cgcttcctcg | tgctttacgg | tatcgccgct | 1200 |
| cccgattcgc | agcgcatcgc | cttctatcgc | cttcttgacg | agttcttctg | agcgggactc | 1260 |
| tggggttcga | aatgaccgac | caagcgacgc | ccaacctgcc | atcacgagat | ttcgattcca | 1320 |
| ccgccgcctt | ctatgaaagg | ttgggcttcg | gaatcgtttt | ccgggacgcc | ggctggatga | 1380 |
| tcctccagcg | cggggatctc | atgctggagt | tcttcgccca | cgctagcggc | gcgccggccg | 1440 |
| gcccggtgtg | aaataccgca | cagatgcgta | aggagaaaat | accgcatcag | gcgctcttcc | 1500 |
| gcttcctcgc | tcactgactc | gctgcgctcg | gtcgttcggc | tgcggcgagc | ggtatcagct | 1560 |
| cactcaaagg | cggtaatacg | gttatccaca | gaatcagggg | ataacgcagg | aaagaacatg | 1620 |
| tgagcaaaag | gccagcaaaa | ggccaggaac | cgtaaaaagg | ccgcgttgct | ggcgtttttc | 1680 |
| cataggctcc | gcccccctga | cgagcatcac | aaaaatcgac | gctcaagtca | gaggtggcga | 1740 |
| aacccgacag | gactataaag | ataccaggcg | tttccccctg | gaagctccct | cgtgcgctct | 1800 |
| cctgttccga | ccctgccgct | taccggatac | ctgtccgcct | ttctcccttc | gggaagcgtg | 1860 |

```
gcgctttctc atagctcacg ctgtaggtat ctcagttcgg tgtaggtcgt tcgctccaag    1920
ctgggctgtg tgcacgaacc ccccgttcag cccgaccgct gcgccttatc cggtaactat    1980
cgtcttgagt ccaacccggt aagacacgac ttatcgccac tggcagcagc cactggtaac    2040
aggattagca gagcgaggta tgtaggcggt gctacagagt tcttgaagtg gtggcctaac    2100
tacggctaca ctagaaggac agtatttggt atctgcgctc tgctgaagcc agttaccttc    2160
ggaaaaagag ttggtagctc ttgatccggc aaacaaacca ccgctggtag cggtggtttt    2220
tttgtttgca agcagcagat tacgcgcaga aaaaaggat ctcaagaaga tcctttgatc    2280
ttttctacgg ggtctgacgc tcagtggaac gaaaactcac gttaagggat tttggtcatg    2340
agattatcaa aaaggatctt cacctagatc cttttaaagg ccggccgcgg ccgccatcgg    2400 catttttcttt tgcgttttta tttgttaact gttaattgtc cttgttcaag gatgctgtct    2460
ttgacaacag atgttttctt gcctttgatg ttcagcagga agctcggcgc aaacgttgat    2520 tgttgtctg cgtagaatcc tctgtttgtc atatagcttg taatcacgac attgtttcct    2580
ttcgcttgag gtacagcgaa gtgtgagtaa gtaaaggtta catcgttagg atcaagatcc    2640 attttttaaca caaggccagt tttgttcagc ggcttgtatg ggccagttaa gaattagaa    2700 acataaccaa gcatgtaaat atcgttagac gtaatgccgt caatcgtcat ttttgatccg    2760
cgggagtcag tgaacaggta ccatttgccg ttcattttaa agacgttcgc gcgttcaatt    2820
tcatctgtta ctgtgttaga tgcaatcagc ggtttcatca cttttttcag tgtgtaatca    2880
tcgtttagct caatcatacc gagagcgccg tttgctaact cagccgtgcg ttttttatcg    2940
ctttgcagaa gttttttgact tcttgacgg aagaatgatg tgcttttgcc atagtatgct    3000
ttgttaaata aagattcttc gccttggtag ccatcttcag ttccagtgtt tgcttcaaat    3060
actaagtatt tgtggccttt atcttctacg tagtgaggat ctctcagcgt atggttgtcg    3120
cctgagctgt agttgccttc atcgatgaac tgctgtacat tttgatacgt ttttccgtca    3180
ccgtcaaaga ttgatttata atcctctaca ccgttgatgt tcaaagagct gtctgatgct    3240
gatacgttaa cttgtgcagt tgtcagtgtt tgtttgccgt aatgtttacc ggagaaatca    3300
gtgtagaata aacggatttt tccgtcagat gtaaatgtgg ctgaacctga ccattcttgt    3360
gtttggtctt ttaggataga atcatttgca tcgaatttgt cgctgtcttt aaagacgcgg    3420
ccagcgtttt tccagctgtc aatagaagtt tcgccgactt tttgatagaa catgtaaatc    3480
gatgtgtcat ccgcattttt aggatctccg gctaatgcaa agacgatgtg gtagccgtga    3540
tagtttgcga cagtgccgtc agcgttttgt aatggccagc tgtcccaaac gtccaggcct    3600
tttgcagaag agatatttt aattgtggac gaatcaaatt cagaaacttg atattttttca    3660 ttttttttgct gttcagggat ttgcagcata tcatggcgtg taatatggga aatgccgtat    3720
gtttccttat atggcttttg gttcgtttct ttcgcaaacg cttgagttgc gcctcctgcc    3780
agcagtgcgg tagtaaaggt taatactgtt gcttgttttg caaactttt gatgttcatc    3840 gttcatgtct cctttttat gtactgtgtt agcggtctgc ttcttccagc cctcctgttt    3900
gaagatggca agttagttac gcacaataaa aaaagaccta aatatgtaa ggggtgacgc    3960 caaagtatac actttgccct ttacacattt taggtcttgc ctgctttatc agtaacaaac    4020
ccgcgcgatt tacttttcga cctcattcta ttagactctc gtttggattg caactggtct    4080
attttcctct tttgtttgat agaaaatcat aaaaggattt gcagactacg ggcctaaaga    4140
actaaaaaat ctatctgttt cttttcattc tctgtatttt ttatagtttc tgttgcatgg    4200
gcataaagtt gccttttttaa tcacaattca gaaaatatca taatatctca tttcactaaa    4260
```

```
taatagtgaa cggcaggtat atgtgatggg ttaaaaagga tcggcggccg ctcgatttaa    4320
atc                                                                  4323
```

```
<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
gcgcggtacc tagactcacc ccagtgct                                         28

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
ctctactagt ttagatgtag aactcgatgt                                       30

<210> SEQ ID NO 16
<211> LENGTH: 6349
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: pCLiK5MCS PmetA metA
<220> FEATURE:
<221> NAME/KEY: misc_feature
<222> LOCATION: (1727)..(2518)
<223> OTHER INFORMATION: KanR
<220> FEATURE:
<221> NAME/KEY: misc_feature
<222> LOCATION: (4799)..(5920)
<223> OTHER INFORMATION: Rep Protein
<220> FEATURE:
<221> NAME/KEY: misc_feature
<222> LOCATION: (3791)..(4465)
<223> OTHER INFORMATION: Ori-Ec (pMB) (complementary)
<220> FEATURE:
<221> NAME/KEY: misc_feature
<222> LOCATION: (2785)..(3645)
<223> OTHER INFORMATION: Orf1
<220> FEATURE:
<221> NAME/KEY: misc_feature
<222> LOCATION: (42)..(177)
<223> OTHER INFORMATION: PmetA
<220> FEATURE:
<221> NAME/KEY: misc_feature
<222> LOCATION: (178)..(1311)
<223> OTHER INFORMATION: metA

<400> SEQUENCE: 16
tcgatttaaa tctcgagagg cctgacgtcg ggcccggtac ctagactcac cccagtgctt      60
aaagcgctgg ttttttcttt ttcagactcg tgagaatgca aactagacta gacagagctg    120
tccatataca ctggacgaag ttttagtctt gtccacccag aacaggcggt tatttttcatg   180 cccacccctcg cgccttcagg tcaacttgaa atccaagcga tcggtgatgt ctccaccgaa   240
gccggagcaa tcattacaaa cgctgaaatc gcctatcacc gctggggtga ataccgcgta   300
gataaagaag gacgcagcaa tgtcgttctc atcgaacacg ccctcactgg agattccaac   360
gcagccgatt ggtgggctga cttgctcggt cccggcaaag ccatcaacac tgatatttac   420
tgcgtgatct gtaccaacgt catcggtggt tgcaacggtt ccaccggacc tggctccatg   480
```

```
catccagatg gaaatttctg gggtaatcgc ttccccgcca cgtccattcg tgatcaggta      540
aacgccgaaa aacaattcct cgacgcactc ggcatcacca cggtcgccgc agtacttggt      600
ggttccatgg gtggtgcccg cacccctagag tgggccgcaa tgtacccaga aactgttggc    660
gcagctgctg ttcttgcagt ttctgcacgc gccagcgcct ggcaaatcgg cattcaatcc     720
gcccaaatta aggcgattga aaacgaccac cactggcacg aaggcaacta ctacgaatcc     780
ggctgcaacc cagccaccgg actcggcgcc gcccgacgca tcgcccacct cacctaccgt     840
ggcgaactag aaatcgacga acgcttcggc accaaagccc aaaagaacga aacccactc      900 ggtccctacc gcaagcccga ccagcgcttc gccgtggaat cctacttgga ctaccaagca     960
gacaagctag tacagcgttt cgacgccggc tcctacgtct tgctcaccga cgccctcaac    1020
cgccacgaca ttggtcgcga ccgcggaggc ctcaacaagg cactcgaatc catcaaagtt    1080
ccagtccttg tcgcaggcgt agataccgat attttgtacc cctaccacca gcaagaacac    1140
ctctccagaa acctgggaaa tctactggca atggcaaaaa tcgtatcccc tgtcggccac    1200
gatgctttcc tcaccgaaag ccgccaaatg gatcgcatcg tgaggaactt cttcagcctc    1260
atctccccag acgaagacaa cccttcgacc tacatcgagt tctacatcta aactagttcg    1320
gacctaggga tatcgtcgac atcgatgctc ttctgcgtta attaacaatt gggatcctct    1380
agacccggga tttaaatcgc tagcgggctg ctaaaggaag cggaacacgt agaaagccag    1440
tccgcagaaa cggtgctgac cccggatgaa tgtcagctac tgggctatct ggacaaggga    1500
aaacgcaagc gcaaagagaa agcaggtagc ttgcagtggg cttacatggc gatagctaga    1560
ctgggcggtt ttatggacag caagcgaacc ggaattgcca gctggggcgc cctctggtaa    1620
ggttgggaag ccctgcaaag taaactggat ggctttcttg ccgccaagga tctgatggcg    1680
caggggatca agatctgatc aagagacagg atgaggatcg tttcgcatga ttgaacaaga    1740
tggattgcac gcaggttctc cggccgcttg ggtggagagg ctattcggct atgactgggc    1800
acaacagaca atcggctgct ctgatgccgc cgtgttccgg ctgtcagcgc aggggcgccc    1860 ggttctttttt gtcaagaccg acctgtccgg tgccctgaat gaactgcagg acgaggcagc    1920
gcggctatcg tggctggcca cgacgggcgt tccttgcgca gctgtgctcg acgttgtcac    1980
tgaagcggga agggactggc tgctattggg cgaagtgccg gggcaggatc tcctgtcatc    2040
tcaccttgct cctgccgaga agtatccat catggctgat gcaatgcggc ggctgcatac    2100
gcttgatccg gctacctgcc cattcgacca ccaagcgaaa catcgcatcg agcgagcacg    2160
tactcggatg gaagccggtc ttgtcgatca ggatgatctg gacgaagagc atcagggct    2220 cgcgccagcc gaactgttcg ccaggctcaa ggcgcgcatg cccgacgcg aggatctcgt    2280 cgtgacccat ggcgatgcct gcttgccgaa tatcatggtg gaaaatggcc gcttttctgg    2340
attcatcgac tgtggccggc tgggtgtggc ggaccgctat caggacatag cgttggctac    2400
ccgtgatatt gctgaagagc ttggcggcga atgggctgac cgcttcctcg tgctttacgg    2460
tatcgccgct cccgattcgc agcgcatcgc cttctatcgc cttcttgacg agttcttctg    2520
agcgggactc tggggttcga aatgaccgac caagcgacgc ccaacctgcc atcacgagat    2580
ttcgattcca ccgccgcctt ctatgaaagg ttgggcttcg aatcgttttt ccgggacgcc    2640
ggctggatga tcctccagcg cggggatctc atgctggagt tcttcgccca cgctagcggc    2700
gcgccggccg gcccggtgtg aaataccgca cagatgcgta aggagaaaat accgcatcag    2760
gcgctcttcc gcttcctcgc tcactgactc gctgcgctcg tcgttcggc tgcggcgagc    2820 ggtatcagct cactcaaagg cggtaatacg gttatccaca gaatcagggg ataacgcagg    2880
```

```
aaagaacatg tgagcaaaag gccagcaaaa ggccaggaac cgtaaaaagg ccgcgttgct    2940
ggcgtttttc cataggctcc gccccctga cgagcatcac aaaaatcgac gctcaagtca    3000
gaggtggcga aacccgacag gactataaag ataccaggcg tttccccctg gaagctccct    3060
cgtgcgctct cctgttccga ccctgccgct taccggatac ctgtccgcct ttctcccttc    3120
gggaagcgtg gcgctttctc atagctcacg ctgtaggtat ctcagttcgg tgtaggtcgt    3180
tcgctccaag ctgggctgtg tgcacgaacc ccccgttcag cccgaccgct gcgccttatc    3240
cggtaactat cgtcttgagt ccaacccggt aagacacgac ttatcgccac tggcagcagc    3300
cactggtaac aggattagca gagcgaggta tgtaggcggt gctacagagt tcttgaagtg    3360
gtggcctaac tacggctaca ctagaaggac agtatttggt atctgcgctc tgctgaagcc    3420
agttaccttc ggaaaaagag ttggtagctc ttgatccggc aaacaaacca ccgctggtag    3480
cggtggtttt tttgtttgca agcagcagat tacgcgcaga aaaaaggat ctcaagaaga    3540 tcctttgatc ttttctacgg ggtctgacgc tcagtggaac gaaaactcac gttaagggat    3600
tttggtcatg agattatcaa aaaggatctt cacctagatc cttttaaagg ccggccgcgg    3660
ccgcgcaaag tcccgcttcg tgaaaatttt cgtgccgcgt gattttccgc caaaaacttt    3720
aacgaacgtt cgttataatg gtgtcatgac cttcacgacg aagtactaaa attggcccga    3780
atcatcagct atggatctct ctgatgtcgc gctggagtcc gacgcgctcg atgctgccgt    3840
cgatttaaaa acggtgatcg gatttttccg agctctcgat acgacggacg cgccagcatc    3900
acgagactgg gccagtgccg cgagcgacct agaaactctc gtggcggatc ttgaggagct    3960
ggctgacgag ctgcgtgctc ggccagcgcc aggaggacgc acagtagtgg aggatgcaat    4020
cagttgcgcc tactgcggtg gcctgattcc tccccggcct gacccgcgag acggcgcgc    4080 aaaatattgc tcagatgcgt gtcgtgccgc agccagccgc gagcgcgcca caaacgcca    4140 cgccgaggag ctgaggcgg ctaggtcgca aatggcgctg gaagtgcgtc ccccgagcga    4200
aattttggcc atggtcgtca cagagctgga agcggcagcg agaattatcg cgatcgtggc    4260
ggtgcccgca ggcatgacaa acatcgtaaa tgccgcgttt cgtgtgccgt ggccgcccag    4320
gacgtgtcag cgccgccacc acctgcaccg aatcggcagc agcgtcgcgc gtcgaaaaag    4380
cgcacaggcg gcaagaagcg ataagctgca cgaatacctg aaaaatgttg aacgccccgt    4440
gagcggtaac tcacagggcg tcggctaacc cccagtccaa acctgggaga aagcgctcaa    4500
aaatgactct agcggattca cgagacattg acacaccggc ctggaaattt tccgctgatc    4560
tgttcgacac ccatcccgag ctcgcgctgc gatcacgtgg ctggacagc gaagaccgcc    4620 gcgaattcct cgctcacctg ggcagagaaa atttccaggg cagcaagacc cgcgacttcg    4680
ccagcgcttg gatcaaagac ccggacacgg agaaacacag ccgaagttat accgagttgg    4740
ttcaaaatcg cttgcccggt gccagtatgt tgctctgacg cacgcgcagc acgcagccgt    4800
gcttgtcctg gacattgatg tgccgagcca ccaggccggc gggaaaatcg agcacgtaaa    4860
ccccgaggtc tacgcgattt tggagcgctg ggcacgcctg gaaaaagcgc cagcttggat    4920
cggcgtgaat ccactgagcg ggaaatgcca gctcatctgg ctcattgatc cggtgtatgc    4980
cgcagcaggc atgagcagcc cgaatatgcg cctgctggct gcaacgaccg aggaaatgac    5040
ccgcgttttc ggcgctgacc aggcttttc acataggctg agccgtggcc actgcactct    5100
ccgacgatcc cagccgtacc gctggcatgc ccagcacaat cgcgtggatc gcctagctga    5160
tcttatggag gttgctcgca tgatctcagg cacagaaaaa cctaaaaaac gctatgagca    5220 ggagtttttct agcggacggg cacgtatcga agcggcaaga aaagccactg cggaagcaaa    5280
```

-continued

```
agcacttgcc acgcttgaag caagcctgcc gagcgccgct gaagcgtctg gagagctgat    5340
cgacggcgtc cgtgtcctct ggactgctcc agggcgtgcc gcccgtgatg agacggcttt    5400
tcgccacgct ttgactgtgg gataccagtt aaaagcggct ggtgagcgcc taaaagacac    5460
caagggtcat cgagcctacg agcgtgccta caccgtcgct caggcggtcg gaggaggccg    5520
tgagcctgat ctgccgccgg actgtgaccg ccagacggat tggccgcgac gtgtgcgcgg    5580
ctacgtcgct aaaggccagc cagtcgtccc tgctcgtcag acagagacgc agagccagcc    5640
gaggcgaaaa gctctggcca ctatgggaag acgtggcggt aaaaaggccg cagaacgctg    5700
gaaagaccca acagtgagt acgcccgagc acagcgagaa aaactagcta agtccagtca     5760
acgacaagct aggaaagcta aaggaaatcg cttgaccatt gcaggttggt ttatgactgt    5820
tgagggagag actggctcgt ggccgacaat caatgaagct atgtctgaat ttagcgtgtc    5880
acgtcagacc gtgaatagag cacttaaggt ctgcgggcat tgaacttcca cgaggacgcc    5940
gaaagcttcc cagtaaatgt gccatctcgt aggcagaaaa cggttccccc gtagggtctc    6000
tctcttggcc tcctttctag gtcgggctga ttgctcttga agctctctag ggggctcac    6060 accataggca gataacgttc cccaccggct cgcctcgtaa gcgcacaagg actgctccca    6120
aagatcttca aagccactgc cgcgactgcc ttcgcgaagc cttgccccgc ggaaatttcc    6180
tccaccgagt tcgtgcacac ccctatgcca agcttctttc accctaaatt cgagagattg    6240
gattcttacc gtggaaattc ttcgcaaaaa tcgtcccctg atcgcccttg cgacgttggc    6300
gtcggtgccg ctggttgcgc ttggcttgac cgacttgatc agcggccgc                6349
```

```
<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
gagactcgag agctgccaat tattccggg                                      29

<210> SEQ ID NO 18
<211> LENGTH: 41
<212> TYPE: DNA
<213> ORGANISM: Artificial Sequence
<220> FEATURE:
<223> OTHER INFORMATION: Primer

<400> SEQUENCE: 18
cctgaaggcg cgagggtggg catgggtaaa aaatcctttc g                        41

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
cccaccctcg cgccttcag                                                 19

<210> SEQ ID NO 20
<211> LENGTH: 18
<212> TYPE: DNA
<213> ORGANISM: Artificial Sequence
<220> FEATURE:
<223> OTHER INFORMATION: Primer
```

<400> SEQUENCE: 20
ctgggtacat tgcggccc                                                      18

<210> SEQ ID NO 21
<211> LENGTH: 6386
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: pCLiK5MCS PSODmetA
<220> FEATURE:
<221> NAME/KEY: misc_feature
<222> LOCATION: (1752)..(2543)
<223> OTHER INFORMATION: KanR
<220> FEATURE:
<221> NAME/KEY: misc_feature
<222> LOCATION: (4824)..(5945)
<223> OTHER INFORMATION: Rep Protein
<220> FEATURE:
<221> NAME/KEY: misc_feature
<222> LOCATION: (2810)..(3670)
<223> OTHER INFORMATION: Ori-Ec (pMB) (complementary)
<220> FEATURE:
<221> NAME/KEY: misc_feature
<222> LOCATION: (3816)..(4490)
<223> OTHER INFORMATION: orf1
<220> FEATURE:
<221> NAME/KEY: misc_feature
<222> LOCATION: (6)..(196)
<223> OTHER INFORMATION: Psod
<220> FEATURE:
<221> NAME/KEY: misc_feature
<222> LOCATION: (197)..(1330)
<223> OTHER INFORMATION: metA

<400> SEQUENCE: 21

| | | | | | |
|---|---|---|---|---|---|
| tcgagagctg | ccaattattc | cgggcttgtg | acccgctacc | cgataaatag | gtcggctgaa | 60 |
| aaatttcgtt | gcaatatcaa | caaaaaggcc | tatcattggg | aggtgtcgca | ccaagtactt | 120 |
| ttgcgaagcg | ccatctgacg | gattttcaaa | agatgtatat | gctcggtgcg | gaaacctacg | 180 |
| aaaggatttt | tacccatgcc | caccctcgc | gccttcaggt | caacttgaaa | tccaagcgat | 240 |
| cggtgatgtc | tccaccgaag | ccggagcaat | cattacaaac | gctgaaatcg | cctatcaccg | 300 |
| ctggggtgaa | taccgcgtag | ataaagaagg | acgcagcaat | gtcgttctca | tcgaacacgc | 360 |
| cctcactgga | gattccaacg | cagccgattg | gtgggctgac | ttgctcggtc | ccggcaaagc | 420 |
| catcaacact | gatatttact | gcgtgatctg | taccaacgtc | atcggtggtt | gcaacggttc | 480 |
| caccggacct | ggctccatgc | atccagatgg | aaatttctgg | ggtaatcgct | tccccgccac | 540 |
| gtccattcgt | gatcaggtaa | acgccgaaaa | acaattcctc | gacgcactcg | gcatcaccac | 600 |
| ggtcgccgca | gtacttggtg | gttccatggg | tggtgcccgc | accctagagt | gggccgcaat | 660 |
| gtacccagaa | actgttggcg | cagctgctgt | tcttgcagtt | tctgcacgcg | ccagcgcctg | 720 |
| gcaaatcggc | attcaatccg | cccaaattaa | ggcgattgaa | aacgaccacc | actggcacga | 780 |
| aggcaactac | tacgaatccg | gctgcaaccc | agccaccgga | ctcggcgccg | cccgacgcat | 840 |
| cgcccacctc | acctaccgtg | gcgaactaga | atcgacgaa | cgcttcggca | ccaaagccca | 900 |
| aaagaacgaa | aacccactcg | gtccctaccg | caagcccgac | cagcgcttcg | ccgtggaatc | 960 |
| ctacttggac | taccaagcag | acaagctagt | acagcgtttc | gacgccggct | cctacgtctt | 1020 |
| gctcaccgac | gccctcaacc | gccacgacat | tggtcgcgac | cgcggaggcc | tcaacaaggc | 1080 |
| actcgaatcc | atcaaagttc | cagtccttgt | cgcaggcgta | gataccgata | ttttgtaccc | 1140 |

```
ctaccaccag caagaacacc tctccagaaa cctgggaaat ctactggcaa tggcaaaaat    1200
cgtatcccct gtcggccacg atgctttcct caccgaaagc cgccaaatgg atcgcatcgt    1260
gaggaacttc ttcagcctca tctccccaga cgaagacaac ccttcgacct acatcgagtt    1320
ctacatctaa catatgacta gttcggacct agggatatcg tcgacatcga tgctcttctg    1380
cgttaattaa caattgggat cctctagacc cgggatttaa atcgctagcg ggctgctaaa    1440
ggaagcggaa cacgtagaaa gccagtccgc agaaacggtg ctgaccccgg atgaatgtca    1500
gctactgggc tatctggaca agggaaaacg caagcgcaaa gagaaagcag gtagcttgca    1560
gtgggcttac atggcgatag ctagactggg cggttttatg gacagcaagc gaaccggaat    1620
tgccagctgg ggcgccctct ggtaaggttg gaagccctg caaagtaaac tggatggctt    1680
tcttgccgcc aaggatctga tggcgcaggg atcaagatc tgatcaagag acaggatgag    1740
gatcgtttcg catgattgaa caagatggat tgcacgcagg ttctccggcc gcttgggtgg    1800
agaggctatt cggctatgac tgggcacaac agacaatcgg ctgctctgat gccgccgtgt    1860
tccggctgtc agcgcagggg cgcccggttc tttttgtcaa gaccgacctg tccggtgccc    1920
tgaatgaact gcaggacgag gcagcgcggc tatcgtggct ggccacgacg ggcgttcctt    1980
gcgcagctgt gctcgacgtt gtcactgaag cgggaaggga ctggctgcta ttgggcgaag    2040
tgccggggca ggatctcctg tcatctcacc ttgctcctgc cgagaaagta tccatcatgg    2100
ctgatgcaat gcggcggctg catacgcttg atccggctac ctgcccattc gaccaccaag    2160
cgaaacatcg catcgagcga gcacgtactc ggatggaagc cggtcttgtc gatcaggatg    2220
atctggacga agagcatcag gggctcgcgc cagccgaact gttcgccagg ctcaaggcgc    2280
gcatgcccga cggcgaggat ctcgtcgtga cccatggcga tgcctgcttg ccgaatatca    2340
tggtggaaaa tggccgcttt tctggattca tcgactgtgg ccggctgggt gtggcggacc    2400
gctatcagga catagcgttg ctacccgtg atattgctga agagcttggc ggcgaatggg    2460
ctgaccgctt cctcgtgctt tacggtatcg ccgctcccga ttcgcagcgc atcgccttct    2520
atcgccttct tgacgagttc ttctgagcgg gactctgggg ttcgaaatga ccgaccaagc    2580
gacgcccaac ctgccatcac gagatttcga ttccaccgcc gccttctatg aaaggttggg    2640
cttcggaatc gttttccggg acgccggctg gatgatcctc cagcgcgggg atctcatgct    2700
ggagttcttc gcccacgcta gcggcgcgcc ggccggcccg gtgtgaaata ccgcacagat    2760
gcgtaaggag aaaataccgc atcaggcgct cttccgcttc ctcgctcact gactcgctgc    2820
gctcggtcgt tcggctgcgg cgagcggtat cagctcactc aaaggcggta atacggttat    2880
ccacagaatc aggggataac gcaggaaaga acatgtgagc aaaaggccag caaaaggcca    2940
ggaaccgtaa aaaggccgcg ttgctggcgt ttttccatag gctccgcccc cctgacgagc    3000
atcacaaaaa tcgacgctca agtcagaggt ggcgaaaccc gacaggacta taaagatacc    3060
aggcgtttcc ccctggaagc tccctcgtgc gctctcctgt tccgaccctg ccgcttaccg    3120
gatacctgtc cgcctttctc ccttcgggaa gcgtggcgct ttctcatagc tcacgctgta    3180
ggtatctcag ttcggtgtag tcgttcgct ccaagctggg ctgtgtgcac gaaccccccg    3240
ttcagcccga ccgctgcgcc ttatccggta actatcgtct tgagtccaac ccggtaagac    3300
acgacttatc gccactggca gcagccactg gtaacaggat tagcagagcg aggtatgtag    3360
gcggtgctac agagttcttg aagtggtggc ctaactacgg ctacactaga aggacagtat    3420
ttggtatctg cgctctgctg aagccagtta ccttcggaaa aagagttggt agctcttgat    3480
ccggcaaaca aaccaccgct ggtagcggtg gtttttttgt ttgcaagcag cagattacgc    3540
```

```
gcagaaaaaa aggatctcaa gaagatcctt tgatcttttc tacggggtct gacgctcagt    3600
ggaacgaaaa ctcacgttaa gggattttgg tcatgagatt atcaaaaagg atcttcacct    3660
agatcctttt aaaggccggc cgcggccgcg caaagtcccg cttcgtgaaa attttcgtgc    3720
cgcgtgattt tccgccaaaa actttaacga acgttcgtta taatggtgtc atgaccttca    3780
cgacgaagta ctaaaattgg cccgaatcat cagctatgga tctctctgat gtcgcgctgg    3840
agtccgacgc gctcgatgct gccgtcgatt taaaaacggt gatcggattt ttccgagctc    3900
tcgatacgac ggacgcgcca gcatcacgag actgggccag tgccgcgagc gacctagaaa    3960
ctctcgtggc ggatcttgag gagctggctg acgagctgcg tgctcggcca cgcgcaggag    4020
gacgcacagt agtggaggat gcaatcagtt gcgcctactg cggtggcctg attcctcccc    4080
ggcctgaccc gcgaggacgg cgcgcaaaat attgctcaga tgcgtgtcgt gccgcagcca    4140
gccgcgagcg cgccaacaaa cgccacgccg aggagctgga ggcggctagg tcgcaaatgg    4200
cgctggaagt gcgtcccccg agcgaaattt tggccatggt cgtcacagag ctggaagcgg    4260
cagcgagaat tatcgcgatc gtggcggtgc ccgcaggcat gacaaacatc gtaaatgccg    4320
cgtttcgtgt gccgtggccg cccaggacgt gtcagcgccg ccaccacctg caccgaatcg    4380
gcagcagcgt cgcgcgtcga aaaagcgcac aggcggcaag aagcgataag ctgcacgaat    4440
acctgaaaaa tgttgaacgc cccgtgagcg gtaactcaca gggcgtcggc taaccccag    4500 tccaaacctg ggagaaagcg ctcaaaaatg actctagcgg attcacgaga cattgacaca    4560
ccggcctgga aattttccgc tgatctgttc gacacccatc ccgagctcgc gctgcgatca    4620
cgtggctgga cgagcgaaga ccgccgcgaa ttcctcgctc acctgggcag agaaaatttc    4680
cagggcagca agaccccgcga cttcgccagc gcttggatca aagacccgga cacggagaaa    4740
cacagccgaa gttataccga gttggttcaa aatcgcttgc ccggtgccag tatgttgctc    4800
tgacgcacgc gcagcacgca gccgtgcttg tcctggacat tgatgtgccg agccaccagg    4860
ccggcgggaa aatcgagcac gtaaaccccg aggtctacgc gattttggag cgctgggcac    4920
gcctggaaaa agcgccagct tggatcggcg tgaatccact gagcgggaaa tgccagctca    4980
tctggctcat tgatccggtg tatgccgcag caggcatgag cagcccgaat atgcgcctgc    5040
tggctgcaac gaccgaggaa atgacccgcg ttttcggcgc tgaccaggct ttttcacata    5100
ggctgagccg tggccactgc actctccgac gatcccagcc gtaccgctgg catgcccagc    5160
acaatcgcgt ggatcgccta gctgatctta tggaggttgc tcgcatgatc tcaggcacag    5220
aaaaacctaa aaaacgctat gagcaggagt tttctagcgg acgggcacgt atcgaagcgg    5280
caagaaaagc cactgcggaa gcaaagcac ttgccacgct tgaagcaagc ctgccgagcg    5340
ccgctgaagc gtctggagag ctgatcgacg gcgtccgtgt cctctggact gctccagggc    5400
gtgccgcccg tgatgagacg gcttttcgcc acgctttgac tgtgggatac cagttaaaag    5460
cggctggtga gcgcctaaaa gacaccaagg gtcatcgagc ctacgagcgt gcctacaccg    5520
tcgctcaggc ggtcggagga ggccgtgagc ctgatctgcc gccggactgt gaccgccaga    5580
cggattggcc gcgacgtgtg cgcggctacg tcgctaaagg ccagccagtc gtccctgctc    5640
gtcagacaga gacgcagagc cagccgaggc gaaaagctct ggccactatg ggaagacgtg    5700
gcggtaaaaa ggccgcagaa cgctggaaag acccaaacag tgagtacgcc cgagcacagc    5760
gagaaaaact agctaagtcc agtcaacgac aagctaggaa agctaaagga aatcgcttga    5820
ccattgcagg ttggttatg actgttgagg gagagactgg ctcgtggccg acaatcaatg    5880
aagctatgtc tgaatttagc gtgtcacgtc agaccgtgaa tagagcactt aaggtctgcg    5940
```

```
ggcattgaac ttccacgagg acgccgaaag cttcccagta aatgtgccat ctcgtaggca    6000
gaaaacggtt cccccgtagg gtctctctct tggcctcctt tctaggtcgg gctgattgct    6060
cttgaagctc tctaggggg ctcacaccat aggcagataa cgttcccac cggctcgcct     6120 cgtaagcgca caaggactgc tcccaaagat cttcaaagcc actgccgcga ctgccttcgc    6180
gaagccttgc cccgcggaaa tttcctccac cgagttcgtg cacacccta tgccaagctt    6240 cttcaccct aaattcgaga gattggattc ttaccgtgga aattcttcgc aaaaatcgtc    6300
ccctgatcgc ccttgcgacg ttggcgtcgg tgccgctggt tgcgcttggc ttgaccgact    6360
tgatcagcgg ccgctcgatt taaatc                                        6386
```

```
<210> SEQ ID NO 22
<211> LENGTH: 29
<212> TYPE: DNA
<213> ORGANISM: Artificial Sequence
<220> FEATURE:
<223> OTHER INFORMATION: Primer

<400> SEQUENCE: 22
gagactcgag ggccgttacc ctgcgaatg                                       29

<210> SEQ ID NO 23
<211> LENGTH: 40
<212> TYPE: DNA
<213> ORGANISM: Artificial Sequence
<220> FEATURE:
<223> OTHER INFORMATION: Primer

<400> SEQUENCE: 23
cctgaaggcg cgagggtggg cattgtatgt cctcctggac                           40

<210> SEQ ID NO 24
<211> LENGTH: 19
<212> TYPE: DNA
<213> ORGANISM: Artificial Sequence
<220> FEATURE:
<223> OTHER INFORMATION: Primer

<400> SEQUENCE: 24
cccaccctcg cgccttcag                                                  19

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
ctgggtacat tgcggccc                                                   18

<210> SEQ ID NO 26
<211> LENGTH: 6394
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: pCLiK5MCS P EFTUmetA
<220> FEATURE:
<221> NAME/KEY: misc_feature
<222> LOCATION: (1772)..(2563)
<223> OTHER INFORMATION: KanR
<220> FEATURE:
<221> NAME/KEY: misc_feature
```

```
<222> LOCATION: (4844)..(6965)
<223> OTHER INFORMATION: Rep Protein
<220> FEATURE:
<221> NAME/KEY: misc_feature
<222> LOCATION: (2830)..(3690)
<223> OTHER INFORMATION: Ori-Ec (pMB) (complementary)
<220> FEATURE:
<221> NAME/KEY: misc_feature
<222> LOCATION: (3836)..(4510)
<223> OTHER INFORMATION: Orf1
<220> FEATURE:
<221> NAME/KEY: misc_feature
<222> LOCATION: (18)..(216)
<223> OTHER INFORMATION: Peftu
<220> FEATURE:
<221> NAME/KEY: misc_feature
<222> LOCATION: (217)..(1350)
<223> OTHER INFORMATION: metA

<400> SEQUENCE: 26
tcgatttaaa tctcgagggc cgttaccctg cgaatgtcca cagggtagct ggtagtttga      60
aaatcaacgc cgttgccctt aggattcagt aactggcaca ttttgtaatg cgctagatct     120
gtgtgctcag tcttccaggc tgcttatcac agtgaaagca aaaccaattc gtggctgcga     180
aagtcgtagc caccacgaag tccaggagga catacaatgc ccaccctcgc gccttcaggt     240
caacttgaaa tccaagcgat cggtgatgtc tccaccgaag ccggagcaat cattacaaac     300
gctgaaatcg cctatcaccg ctggggtgaa taccgcgtag ataaagaagg acgcagcaat     360
gtcgttctca tcgaacacgc cctcactgga gattccaacg cagccgattg gtgggctgac     420
ttgctcggtc ccggcaaagc catcaacact gatatttact gcgtgatctg taccaacgtc     480
atcggtggtt gcaacggttc caccggacct ggctccatgc atccagatgg aaatttctgg     540
ggtaatcgct tccccgccac gtccattcgt gatcaggtaa acgccgaaaa acaattcctc     600
gacgcactcg gcatcaccac ggtcgccgca gtacttggtg gttccatggg tggtgcccgc     660
accctagagt gggccgcaat gtacccagaa actgttggcg cagctgctgt tcttgcagtt     720
tctgcacgcg ccagcgcctg gcaaatcggc attcaatccg cccaaattaa ggcgattgaa     780
aacgaccacc actggcacga aggcaactac tacgaatccg gctgcaaccc agccaccgga     840
ctcggcgccg cccgacgcat cgcccacctc acctaccgtg gcgaactaga aatcgacgaa     900
cgcttcggca ccaaagccca aaagaacgaa aacccactcg gtccctaccg caagcccgac     960
cagcgcttcg ccgtggaatc ctacttggac taccaagcag acaagctagt acagcgtttc    1020
gacgccggct cctacgtctt gctcaccgac gccctcaacc gccacgacat tggtcgcgac    1080
cgcggaggcc tcaacaaggc actcgaatcc atcaaagttc cagtccttgt cgcaggcgta    1140
gataccgata ttttgtaccc ctaccaccag caagaacacc tctccagaaa cctgggaaat    1200
ctactggcaa tggcaaaaat cgtatcccct gtcggccacg atgctttcct caccgaaagc    1260
cgccaaatgg atcgcatcgt gaggaacttc ttcagcctca tctccccaga cgaagacaac    1320
ccttcgacct acatcgagtt ctacatctaa catatgacta gttcggacct agggatatcg    1380
tcgacatcga tgctcttctg cgttaattaa caattgggat cctctagacc cgggatttaa    1440
atcgctagcg ggctgctaaa ggaagcggaa cacgtagaaa gccagtccgc agaaacggtg    1500
ctgaccccgg atgaatgtca gctactgggc tatctggaca agggaaaacg caagcgcaaa    1560
gagaaagcag gtagcttgca gtgggcttac atggcgatag ctagactggg cggttttatg    1620
gacagcaagc gaaccggaat tgccagctgg ggcgccctct ggtaaggttg ggaagccctg    1680
caaagtaaac tggatggctt tcttgccgcc aaggatctga tggcgcaggg gatcaagatc    1740
tgatcaagag acaggatgag gatcgtttcg catgattgaa caagatggat tgcacgcagg    1800
```

```
ttctccggcc gcttgggtgg agaggctatt cggctatgac tgggcacaac agacaatcgg    1860
ctgctctgat gccgccgtgt tccggctgtc agcgcagggg cgcccggttc tttttgtcaa    1920
gaccgacctg tccggtgccc tgaatgaact gcaggacgag gcagcgcggc tatcgtggct    1980
ggccacgacg ggcgttcctt gcgcagctgt gctcgacgtt gtcactgaag cgggaaggga    2040
ctggctgcta ttgggcgaag tgccggggca ggatctcctg tcatctcacc ttgctcctgc    2100
cgagaaagta tccatcatgg ctgatgcaat gcggcggctg catacgcttg atccggctac    2160
ctgcccattc gaccaccaag cgaaacatcg catcgagcga gcacgtactc ggatggaagc    2220
cggtcttgtc gatcaggatg atctggacga agagcatcag gggctcgcgc cagccgaact    2280
gttcgccagg ctcaaggcgc gcatgcccga cggcgaggat ctcgtcgtga cccatggcga    2340
tgcctgcttg ccgaatatca tggtggaaaa tggccgcttt tctggattca tcgactgtgg    2400
ccggctgggt gtggcggacc gctatcagga catagcgttg gctacccgtg atattgctga    2460
agagcttggc ggcgaatggg ctgaccgctt cctcgtgctt tacggtatcg ccgctcccga    2520
ttcgcagcgc atcgccttct atcgccttct tgacgagttc ttctgagcgg gactctgggg    2580
ttcgaaatga ccgaccaagc gacgcccaac ctgccatcac gagatttcga ttccaccgcc    2640
gccttctatg aaaggttggg cttcggaatc gttttccggg acgccggctg atgatcctc    2700 cagcgcgggg atctcatgct ggagttcttc gcccacgcta gcggcgcgcc ggccggcccg    2760
gtgtgaaata ccgcacagat gcgtaaggag aaaataccgc atcaggcgct cttccgcttc    2820
ctcgctcact gactcgctgc gctcggtcgt tcggctgcgg cgagcggtat cagctcactc    2880
aaaggcggta atacggttat ccacagaatc aggggataac gcaggaaaga acatgtgagc    2940
aaaaggccag caaaaggcca ggaaccgtaa aaaggccgcg ttgctggcgt ttttccatag    3000
gctccgcccc cctgacgagc atcacaaaaa tcgacgctca agtcagaggt ggcgaaaccc    3060
gacaggacta taaagatacc aggcgtttcc ccctggaagc tccctcgtgc gctctcctgt    3120
tccgaccctg ccgcttaccg gatacctgtc cgcctttctc ccttcgggaa gcgtggcgct    3180
ttctcatagc tcacgctgta ggtatctcag ttcggtgtag gtcgttcgct ccaagctggg    3240
ctgtgtgcac gaaccccccg ttcagcccga ccgctgcgcc ttatccggta actatcgtct    3300
tgagtccaac ccggtaagac acgacttatc gccactggca gcagccactg gtaacaggat    3360
tagcagagcg aggtatgtag gcggtgctac agagttcttg aagtggtggc ctaactacgg    3420
ctacactaga aggacagtat ttggtatctg cgctctgctg aagccagtta ccttcggaaa    3480
aagagttggt agctcttgat ccggcaaaca aaccaccgct ggtagcggtg gtttttttgt    3540
ttgcaagcag cagattacgc gcagaaaaaa aggatctcaa gaagatcctt tgatcttttc    3600
tacggggtct gacgctcagt ggaacgaaaa ctcacgttaa gggattttgg tcatgagatt    3660
atcaaaaagg atcttcacct agatcctttt aaaggccggc cgcggccgcg caaagtcccg    3720
cttcgtgaaa attttcgtgc cgcgtgattt tccgccaaaa actttaacga acgttcgtta    3780
taatggtgtc atgaccttca cgacgaagta ctaaaattgg cccgaatcat cagctatgga    3840
tctctctgat gtcgcgctgg agtccgacgc gctcgatgct gccgtcgatt taaaaacggt    3900
gatcggattt ttccgagctc tcgatacgac ggacgcgcca gcatcacgag actgggccag    3960
tgccgcgagc gacctagaaa ctctcgtggc ggatcttgag gagctggctg acgagctgcg    4020
tgctcggcca gcgccaggag gacgcacagt agtggaggat gcaatcagtt gcgcctactg    4080
cggtggccta attcctcccc ggcctgaccc gcgaggacgg cgcgcaaaat attgctcaga    4140
tgcgtgtcgt gccgcagcca gccgcgagcg cgccaacaaa cgccacgccg aggagctgga    4200
```

-continued

```
ggcggctagg tcgcaaatgg cgctggaagt gcgtccccg agcgaaattt tggccatggt     4260
cgtcacagag ctggaagcgg cagcgagaat tatcgcgatc gtggcggtgc ccgcaggcat     4320
gacaaacatc gtaaatgccg cgtttcgtgt gccgtggccg cccaggacgt gtcagcgccg     4380
ccaccacctg caccgaatcg gcagcagcgt cgcgcgtcga aaaagcgcac aggcggcaag     4440
aagcgataag ctgcacgaat acctgaaaaa tgttgaacgc cccgtgagcg gtaactcaca     4500
gggcgtcggc taaccccag tccaaacctg ggagaaagcg ctcaaaaatg actctagcgg     4560
attcacgaga cattgacaca ccggcctgga aattttccgc tgatctgttc gacacccatc     4620
ccgagctcgc gctgcgatca cgtggctgga cgagcgaaga ccgccgcgaa ttcctcgctc     4680
acctgggcag agaaaatttc cagggcagca agacccgcga cttcgccagc gcttggatca     4740
aagacccgga cacggagaaa cacagccgaa gttataccga gttggttcaa aatcgcttgc     4800
ccggtgccag tatgttgctc tgacgcacgc gcagcacgca gccgtgcttg tcctggacat     4860
tgatgtgccg agccaccagg ccggcgggaa atcgagcac gtaaaccccg aggtctacgc     4920
gattttggag cgctgggcac gcctggaaaa agcgccagct tggatcggcg tgaatccact     4980
gagcgggaaa tgccagctca tctggctcat tgatccggtg tatgccgcag caggcatgag     5040
cagcccgaat atgcgcctgc tggctgcaac gaccgaggaa atgacccgcg ttttcggcgc     5100
tgaccaggct ttttcacata ggctgagccg tggccactgc actctccgac gatcccagcc     5160
gtaccgctgg catgcccagc acaatcgcgt ggatcgccta gctgatctta tggaggttgc     5220
tcgcatgatc tcaggcacag aaaaacctaa aaaacgctat gagcaggagt tttctagcgg     5280
acgggcacgt atcgaagcgg caagaaaagc cactgcggaa gcaaaagcac ttgccacgct     5340
tgaagcaagc ctgccgagcg ccgctgaagc gtctggagag ctgatcgacg gcgtccgtgt     5400
cctctggact gctccagggc gtgccgcccg tgatgagacg gcttttcgcc acgctttgac     5460
tgtgggatac cagttaaaag cggctggtga gcgcctaaaa gacaccaagg gtcatcgagc     5520
ctacgagcgt gcctacaccg tcgctcaggc ggtcggagga ggccgtgagc ctgatctgcc     5580
gccggactgt gaccgccaga cggattggcc gcgacgtgtg cgcggctacg tcgctaaagg     5640
ccagccagtc gtccctgctc gtcagacaga gacgcagagc cagccgaggc gaaaagctct     5700
ggccactatg gaagacgtg gcggtaaaaa ggccgcagaa cgctggaaag acccaaacag     5760
tgagtacgcc cgagcacagc gagaaaaact agctaagtcc agtcaacgac aagctaggaa     5820
agctaaagga aatcgcttga ccattgcagg ttggtttatg actgttgagg gagagactgg     5880
ctcgtggccg acaatcaatg aagctatgtc tgaatttagc gtgtcacgtc agaccgtgaa     5940
tagagcactt aaggtctgcg ggcattgaac ttccacgagg acgccgaaag cttcccagta     6000
aatgtgccat ctcgtaggca gaaaacggtt ccccgtagg gtctctctct tggcctcctt     6060
tctaggtcgg gctgattgct cttgaagctc tctagggggg ctcacaccat aggcagataa     6120
cgttccccac cggctcgcct cgtaagcgca caaggactgc tcccaaagat cttcaaagcc     6180
actgccgcga ctgccttcgc gaagccttgc cccgcgaaa tttcctccac cgagttcgtg     6240 cacacccta tgccaagctt cttttcaccct aaattcgaga gattggattc ttaccgtgga     6300
aattcttcgc aaaaatcgtc ccctgatcgc ccttgcgacg ttggcgtcgg tgccgctggt     6360
tgcgcttggc ttgaccgact tgatcagcgg ccgc                                  6394
```

<210> SEQ ID NO 27
<211> LENGTH: 30
<212> TYPE: DNA
<213> ORGANISM: Artificial Sequence

```
<220> FEATURE:
<223> OTHER INFORMATION: Primer

<400> SEQUENCE: 27
gagactcgag cggcttaaag tttggctgcc                              30

<210> SEQ ID NO 28
<211> LENGTH: 41
<212> TYPE: DNA
<213> ORGANISM: Artificial Sequence
<220> FEATURE:
<223> OTHER INFORMATION: Primer

<400> SEQUENCE: 28
cctgaaggcg cgagggtggg catgatgaat ccctccatga g                 41

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
cccaccctcg cgccttcag                                          19

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30
ctgggtacat tgcggccc                                           18

<210> SEQ ID NO 31
<211> LENGTH: 6372
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: pCLiK5MCS PGroESmetA
<220> FEATURE:
<221> NAME/KEY: misc_feature
<222> LOCATION: (1735)..(2526)
<223> OTHER INFORMATION: KanR
<220> FEATURE:
<221> NAME/KEY: misc_feature
<222> LOCATION: (4807)..(5928)
<223> OTHER INFORMATION: Rep Protein
<220> FEATURE:
<221> NAME/KEY: misc_feature
<222> LOCATION: (2793)..(3653)
<223> OTHER INFORMATION: Ori-EC (pMB) (complementary)
<220> FEATURE:
<221> NAME/KEY: misc_feature
<222> LOCATION: (3799)..(4473)
<223> OTHER INFORMATION: Orf1
<220> FEATURE:
<221> NAME/KEY: misc_feature
<222> LOCATION: (3)..(179)
<223> OTHER INFORMATION: Pgro
<220> FEATURE:
<221> NAME/KEY: misc_feature
<222> LOCATION: (180)..(1313)
<223> OTHER INFORMATION: metA

<400> SEQUENCE: 31
```

```
agcggcttaa agtttggctg ccatgtgaat ttttagcacc ctcaacagtt gagtgctggc    60
actctcgggg gtagagtgcc aaataggttg tttgacacac agttgttcac ccgcgacgac   120
ggctgtgctg gaaacccaca accggcacac acaaaatttt tctcatggag ggattcatca   180
tgcccaccct cgcgccttca ggtcaacttg aaatccaagc gatcggtgat gtctccaccg   240
aagccggagc aatcattaca aacgctgaaa tcgcctatca ccgctggggt gaataccgcg   300
tagataaaga aggacgcagc aatgtcgttc tcatcgaaca cgccctcact ggagattcca   360
acgcagccga ttggtgggct gacttgctcg gtcccggcaa agccatcaac actgatattt   420
actgcgtgat ctgtaccaac gtcatcggtg gttgcaacgg ttccaccgga cctggctcca   480
tgcatccaga tggaaatttc tggggtaatc gcttccccgc cacgtccatt cgtgatcagg   540
taaacgccga aaacaattc ctcgacgcac tcggcatcac cacggtcgcc gcagtacttg   600
gtggttccat gggtggtgcc cgcacccctag agtgggccgc aatgtaccca gaaactgttg   660
gcgcagctgc tgttcttgca gtttctgcac gcgccagcc ctggcaaatc ggcattcaat   720
ccgcccaaat taaggcgatt gaaaacgacc accactggca cgaaggcaac tactacgaat   780
ccggctgcaa cccagccacc ggactcggcg ccgcccgacg catcgcccac ctcacctacc   840
gtggcgaact agaaatcgac gaacgcttcg gcaccaaagc ccaaaagaac gaaaacccac   900
tcggtcccta ccgcaagccc gaccagcgct tcgccgtgga atcctacttg gactaccaag   960
cagacaagct agtacagcgt tcgacgccg gctcctacgt cttgctcacc gacgccctca  1020
accgccacga cattggtcgc gaccgcgag gcctcaacaa ggcactcgaa tccatcaaag  1080
ttccagtcct tgtcgcaggc gtagataccg atattttgta cccctaccac cagcaagaac  1140
acctctccag aaacctggga aatctactgg caatggcaaa aatcgtatcc cctgtcggcc  1200
acgatgcttt cctcaccgaa agccgccaaa tggatcgcat cgtgaggaac ttcttcagcc  1260
tcatctcccc agacgaagac aacccttcga cctacatcga gttctacatc taacatatga  1320
ctagttcgga cctagggata tcgtcgacat cgatgctctt ctgcgttaat taacaattgg  1380
gatcctctag acccgggatt taaatcgcta gcgggctgct aaaggaagcg gaacacgtag  1440
aaagccagtc cgcagaaacg gtgctgaccc cggatgaatg tcagctactg ggctatctgg  1500
acaagggaaa acgcaagcgc aaagagaaag caggtagctt gcagtgggct tacatggcga  1560
tagctagact gggcggtttt atggacagca agcgaaccgg aattgccagc tggggcgccc  1620
tctggtaagg ttgggaagcc ctgcaaagta aactggatgg ctttcttgcc gccaaggatc  1680
tgatggcgca ggggatcaag atctgatcaa gagacaggat gaggatcgtt tcgcatgatt  1740
gaacaagatg gattgcacgc aggttctccg gccgcttggg tggagaggct attcggctat  1800
gactgggcac aacagacaat cggctgctct gatgccgccg tgttccggct gtcagcgcag  1860
gggcgcccgg ttcttttttgt caagaccgac ctgtccggtg ccctgaatga actgcaggac  1920
gaggcagcgc ggctatcgtg gctggccacg acgggcgttc cttgcgcagc tgtgctcgac  1980
gttgtcactg aagcgggaag ggactggctg ctattgggcg aagtgccggg gcaggatctc  2040
ctgtcatctc accttgctcc tgccgagaaa gtatccatca tggctgatgc aatgcggcgg  2100
ctgcatacgc ttgatccggc tacctgccca ttcgaccacc aagcgaaaca tcgcatcgag  2160
cgagcacgta ctcggatgga agccggtctt gtcgatcagg atgatctgga cgaagagcat  2220
caggggctcg cgccagccga actgttcgcc aggctcaagg cgcgcatgcc cgacggcgag  2280
gatctcgtcg tgacccatgg cgatgcctgc ttgccgaata tcatggtgga aaatggccgc  2340
ttttctggat tcatcgactg tggccggctg ggtgtggcgg accgctatca ggacatagcg  2400
```

```
ttggctaccc gtgatattgc tgaagagctt ggcggcgaat gggctgaccg cttcctcgtg    2460
ctttacggta tcgccgctcc cgattcgcag cgcatcgcct tctatcgcct tcttgacgag    2520
ttcttctgag cgggactctg gggttcgaaa tgaccgacca agcgacgccc aacctgccat    2580
cacgagattt cgattccacc gccgccttct atgaaaggtt gggcttcgga atcgttttcc    2640
gggacgccgg ctggatgatc tccagcgcg gggatctcat gctggagttc ttcgcccacg    2700
ctagcggcgc gccggccggc ccggtgtgaa ataccgcaca gatgcgtaag gagaaaatac    2760
cgcatcaggc gctcttccgc ttcctcgctc actgactcgc tgcgctcggt cgttcggctg    2820
cggcgagcgg tatcagctca ctcaaaggcg gtaatacggt tatccacaga atcaggggat    2880
aacgcaggaa agaacatgtg agcaaaaggc cagcaaaagg ccaggaaccg taaaaaggcc    2940
gcgttgctgg cgttttttcca taggctccgc cccctgacg agcatcacaa aaatcgacgc    3000
tcaagtcaga ggtggcgaaa cccgacagga ctataaagat accaggcgtt tccccctgga    3060
agctccctcg tgcgctctcc tgttccgacc ctgccgctta ccggatacct gtccgccttt    3120
ctcccttcgg gaagcgtggc gctttctcat agctcacgct gtaggtatct cagttcggtg    3180
taggtcgttc gctccaagct gggctgtgtg cacgaacccc ccgttcagcc cgaccgctgc    3240
gccttatccg gtaactatcg tcttgagtcc aacccggtaa gacacgactt atcgccactg    3300
gcagcagcca ctggtaacag gattagcaga gcgaggtatg taggcggtgc tacagagttc    3360
ttgaagtggt ggcctaacta cggctacact agaaggacag tatttggtat ctgcgctctg    3420
ctgaagccag ttaccttcgg aaaaagagtt ggtagctctt gatccggcaa acaaaccacc    3480
gctggtagcg gtggtttttt tgtttgcaag cagcagatta cgcgcagaaa aaaggatct    3540 caagaagatc ctttgatctt ttctacgggg tctgacgctc agtggaacga aaactcacgt    3600
taagggattt tggtcatgag attatcaaaa aggatcttca cctagatcct tttaaaggcc    3660
ggccgcggcc gcgcaaagtc ccgcttcgtg aaaattttcg tgccgcgtga ttttccgcca    3720
aaaactttaa cgaacgttcg ttataatggt gtcatgacct tcacgacgaa gtactaaaat    3780
tgccccgaat catcagctat ggatctctct gatgtcgcgc tggagtccga cgcgctcgat    3840
gctgccgtcg atttaaaaac ggtgatcgga ttttccgag ctctcgatac gacggacgcg    3900
ccagcatcac gagactgggc cagtgccgcg agcgacctag aaactctcgt ggcggatctt    3960
gaggagctgg ctgacgagct gcgtgctcgg ccagcgccag gaggacgcac agtagtggag    4020
gatgcaatca gttgcgccta ctgcggtggc ctgattcctc cccggcctga cccgcgagga    4080
cggcgcgcaa atattgctc agatgcgtgt cgtgccgcag ccagccgcga gcgcgccaac    4140
aaacgccacg ccgaggagct ggaggcggct aggtcgcaaa tggcgctgga agtgcgtccc    4200
ccgagcgaaa ttttggccat ggtcgtcaca gagctggaag cggcagcgag aattatcgcg    4260
atcgtggcgg tgcccgcagg catgacaaac atcgtaaatg ccgcgtttcg tgtgccgtgg    4320
ccgcccagga cgtgtcagcg ccgccaccac ctgcaccgaa tcggcagcag cgtcgcgcgt    4380
cgaaaaagcg cacaggcggc aagaagcgat aagctgcacg aatacctgaa aaatgttgaa    4440
cgccccgtga gcgtaactc acagggcgtc ggctaacccc cagtccaaac ctgggagaaa    4500
gcgctcaaaa atgactctag cggattcacg agacattgac acaccggcct ggaaattttc    4560
cgctgatctg ttcgacaccc atcccgagct cgcgctgcga tcacgtggct ggacgagcga    4620
agaccgccgc gaattcctcg ctcacctggg cagagaaaat ttccagggca gcaagacccg    4680
cgacttcgcc agcgcttgga tcaaagaccc ggacacggag aaacacagcc gaagttatac    4740
cgagttggtt caaaatcgct tgcccggtgc cagtatgttg ctctgacgca cgcgcagcac    4800
```

-continued

```
gcagccgtgc ttgtcctgga cattgatgtg ccgagccacc aggccggcgg gaaaatcgag    4860
cacgtaaacc ccgaggtcta cgcgattttg gagcgctggg cacgcctgga aaaagcgcca    4920
gcttggatcg gcgtgaatcc actgagcggg aaatgccagc tcatctggct cattgatccg    4980
gtgtatgccg cagcaggcat gagcagcccg aatatgcgcc tgctggctgc aacgaccgag    5040
gaaatgaccc gcgttttcgg cgctgaccag gcttttttcac ataggctgag ccgtggccac    5100
tgcactctcc gacgatccca gccgtaccgc tggcatgccc agcacaatcg cgtggatcgc    5160
ctagctgatc ttatggaggt tgctcgcatg atctcaggca cagaaaaacc taaaaaacgc    5220
tatgagcagg agtttttctag cggacgggca cgtatcgaag cggcaagaaa agccactgcg    5280
gaagcaaaag cacttgccac gcttgaagca agcctgccga gcgccgctga agcgtctgga    5340
gagctgatcg acggcgtccg tgtcctctgg actgctccag ggcgtgccgc ccgtgatgag    5400
acggcttttc gccacgcttt gactgtggga taccagttaa aagcggctgg tgagcgccta    5460
aaagacacca aggtcatcg agcctacgag cgtgcctaca ccgtcgctca ggcggtcgga    5520
ggaggccgtg agcctgatct gccgccggac tgtgaccgcc agacggattg gccgcgacgt    5580
gtgcgcggct acgtcgctaa aggccagcca gtcgtccctg ctcgtcagac agagacgcag    5640
agccagccga ggcgaaaagc tctggccact atgggaagac gtggcggtaa aaaggccgca    5700
gaacgctgga aagacccaaa cagtgagtac gcccgagcac agcgagaaaa actagctaag    5760
tccagtcaac gacaagctag gaaagctaaa ggaaatcgct tgaccattgc aggttggttt    5820
atgactgttg agggagagac tggctcgtgg ccgacaatca atgaagctat gtctgaattt    5880
agcgtgtcac gtcagaccgt gaatagagca cttaaggtct gcgggcattg aacttccacg    5940
aggacgccga aagcttccca gtaaatgtgc catctcgtag gcagaaaacg gttccccgt     6000 agggtctctc tcttggcctc ctttctaggt cgggctgatt gctcttgaag ctctctaggg    6060
gggctcacac cataggcaga taacgttccc caccggctcg cctcgtaagc gcacaaggac    6120
tgctcccaaa gatcttcaaa gccactgccg cgactgcctt cgcgaagcct tgccccgcgg    6180
aaatttcctc caccgagttc gtgcacaccc ctatgccaag cttctttcac cctaaattcg    6240
agagattgga ttcttaccgt ggaaattctt cgcaaaaatc gtcccctgat cgcccttgcg    6300
acgttggcgt cggtgccgct ggttgcgctt ggcttgaccg acttgatcag cggccgctcg    6360
atttaaatct cg                                                       6372
```

<210> SEQ ID NO 32
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK 1849

<400> SEQUENCE: 32

```
gtgtgtcgac ttagatgtag aactcgatgt ag                                  32
```

<210> SEQ ID NO 33
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK 1862

<400> SEQUENCE: 33
atgcccaccc tcgcgcc                                                     17

<210> SEQ ID NO 34
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Haf 26

<400> SEQUENCE: 34
gagaggatcc cccccacgac aatggaac                                         28

<210> SEQ ID NO 35
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Haf 27)

<400> SEQUENCE: 35
cctgaaggcg cgagggtggg cattacgggg cgatcctcct tatg                       44

<210> SEQ ID NO 36
<211> LENGTH: 6389
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: pCLiK5MCS P EF-TS metA
<220> FEATURE:
<221> NAME/KEY: misc_feature
<222> LOCATION: (1767)..(2558)
<223> OTHER INFORMATION: KanR
<220> FEATURE:
<221> NAME/KEY: misc_feature
<222> LOCATION: (4839)..(5960)
<223> OTHER INFORMATION: Rep Protein
<220> FEATURE:
<221> NAME/KEY: misc_feature
<222> LOCATION: (2825)..(3685)
<223> OTHER INFORMATION: Ori-Ec (pMB) (complementary)
<220> FEATURE:
<221> NAME/KEY: misc_feature
<222> LOCATION: (3831)..(4505)
<223> OTHER INFORMATION: Orf1
<220> FEATURE:
<221> NAME/KEY: misc_feature
<222> LOCATION: (1217)..(1411)
<223> OTHER INFORMATION: P EF-TS (complementary)
<220> FEATURE:
<221> NAME/KEY: misc_feature
<222> LOCATION: (83)..(1216)
<223> OTHER INFORMATION: metA (complementary)

<400> SEQUENCE: 36
tcgatttaaa tctcgagagg cctgacgtcg ggcccggtac cacgcgtcat atgactagtt      60
cggacctagg gatatcgtcg acttagatgt agaactcgat gtaggtcgaa gggttgtctt    120
cgtctgggga gatgaggctg aagaagttcc tcacgatgcg atccatttgg cggctttcgg    180
tgaggaaagc atcgtggccg acaggggata cgattttttgc cattgccagt agatttccca   240
ggtttctgga gaggtgttct tgctggtggt aggggtacaa aatatcggta tctacgcctg   300

```
cgacaaggac tggaactttg atggattcga gtgccttgtt gaggcctccg cggtcgcgac    360
caatgtcgtg gcggttgagg gcgtcggtga gcaagacgta ggagccggcg tcgaaacgct    420
gtactagctt gtctgcttgg tagtccaagt aggattccac ggcgaagcgc tggtcgggct    480
tgcggtaggg accgagtggg ttttcgttct tttgggcttt ggtgccgaag cgttcgtcga    540
tttctagttc gccacggtag gtgaggtggg cgatgcgtcg ggcggcgccg agtccggtgg    600
ctgggttgca gccggattcg tagtagttgc cttcgtgcca gtggtggtcg ttttcaatcg    660
ccttaatttg ggcggattga atgccgattt gccaggcgct ggcgcgtgca gaaactgcaa    720
gaacagcagc tgcgccaaca gtttctgggt acattgcggc ccactctagg gtgcgggcac    780
cacccatgga accaccaagt actgcggcga ccgtggtgat gccgagtgcg tcgaggaatt    840 gttttcggc gtttacctga tcacgaatgg acgtggcggg gaagcgatta ccccagaaat    900
ttccatctgg atgcatggag ccaggtccgg tggaaccgtt gcaaccaccg atgacgttgg    960
tacagatcac gcagtaaata tcagtgttga tggctttgcc gggaccgagc aagtcagccc   1020
accaatcggc tgcgttggaa tctccagtga gggcgtgttc gatgagaacg acattgctgc   1080
gtccttcttt atctacgcgg tattcacccc agcggtgata ggcgatttca gcgtttgtaa   1140
tgattgctcc ggcttcggtg gagacatcac cgatcgcttg gatttcaagt tgacctgaag   1200
gcgcgagggt gggcattacg gggcgatcct cctatgtat ggataattaa tgctttacaa    1260
gcttaggtta gggcacagta gccctacccg cccgtctaaa aagtgatcgt acaggtattc   1320
agtcgattac gttgcgacac ggcgggctgg ctgcccaaaa agcccccacg gcgatgaaat   1380
tttaaaagtc aaagttccat tgtcgtgggg gggatcctct agacccggga tttaaatcgc   1440
tagcgggctg ctaaaggaag cggaacacgt agaaagccag tccgcagaaa cggtgctgac   1500
cccggatgaa tgtcagctac tgggctatct ggacaaggga aaacgcaagc gcaaagagaa   1560
agcaggtagc ttgcagtggg cttacatggc gatagctaga ctgggcggtt ttatggacag   1620
caagcgaacc ggaattgcca gctggggcgc cctctggtaa ggttgggaag ccctgcaaag   1680
taaactggat ggctttcttg ccgccaagga tctgatggcg caggggatca agatctgatc   1740
aagagacagg atgaggatcg tttcgcatga ttgaacaaga tggattgcac gcaggttctc   1800
cggccgcttg ggtggagagg ctattcggct atgactgggc acaacagaca atcggctgct   1860
ctgatgccgc cgtgttccgg ctgtcagcgc agggggcgcc cggttcttttt gtcaagaccg   1920 acctgtccgg tgccctgaat gaactgcagg acgaggcagc gcggctatcg tggctggcca   1980
cgacgggcgt tccttgcgca gctgtgctcg acgttgtcac tgaagcggga agggactggc   2040
tgctattggg cgaagtgccg gggcaggatc tcctgtcatc tcaccttgct cctgccgaga   2100
aagtatccat catggctgat gcaatgcggc ggctgcatac gcttgatccg gctacctgcc   2160
cattcgacca ccaagcgaaa catcgcatcg agcgagcacg tactcggatg aagccggtc   2220 tgtcgatca ggatgatctg gacgaagagc atcaggggct cgcgccagcc gaactgttcg    2280
ccaggctcaa ggcgcgcatg cccgacggcg aggatctcgt cgtgacccat ggcgatgcct   2340
gcttgccgaa tatcatggtg gaaaatggcc gcttttctgg attcatcgac tgtggccggc   2400
tgggtgtggc ggaccgctat caggacatag cgttggctac ccgtgatatt gctgaagagc   2460
ttggcggcga atgggctgac cgcttcctcg tgctttacgg tatcgccgct cccgattcgc   2520
agcgcatcgc cttctatcgc cttcttgacg agttcttctg agcgggactc tggggttcga   2580
aatgaccgac caagcgacgc ccaacctgcc atcacgagat ttcgattcca ccgccgcctt   2640
ctatgaaagg ttgggcttcg gaatcgtttt ccgggacgcc ggctggatga tcctccagcg   2700
```

```
cggggatctc atgctggagt tcttcgccca cgctagcggc gcgccggccg gcccggtgtg    2760
aaataccgca cagatgcgta aggagaaaat accgcatcag gcgctcttcc gcttcctcgc    2820
tcactgactc gctgcgctcg gtcgttcggc tgcggcgagc ggtatcagct cactcaaagg    2880
cggtaatacg gttatccaca gaatcagggg ataacgcagg aaagaacatg tgagcaaaag    2940
gccagcaaaa ggccaggaac cgtaaaaagg ccgcgttgct ggcgtttttc cataggctcc    3000
gcccccctga cgagcatcac aaaaatcgac gctcaagtca gaggtggcga aacccgacag    3060
gactataaag ataccaggcg tttccccctg gaagctccct cgtgcgctct cctgttccga    3120
ccctgccgct taccggatac ctgtccgcct ttctcccttc gggaagcgtg gcgctttctc    3180
atagctcacg ctgtaggtat ctcagttcgg tgtaggtcgt tcgctccaag ctgggctgtg    3240
tgcacgaacc ccccgttcag cccgaccgct gcgccttatc cggtaactat cgtcttgagt    3300
ccaacccggt aagacacgac ttatcgccac tggcagcagc cactggtaac aggattagca    3360
gagcgaggta tgtaggcggt gctacagagt tcttgaagtg gtggcctaac tacggctaca    3420
ctagaaggac agtatttggt atctgcgctc tgctgaagcc agttaccttc ggaaaaagag    3480
ttggtagctc ttgatccggc aaacaaacca ccgctggtag cggtggtttt tttgtttgca    3540
agcagcagat tacgcgcaga aaaaaaggat ctcaagaaga tcctttgatc ttttctacgg    3600
ggtctgacgc tcagtggaac gaaaactcac gttaagggat tttggtcatg agattatcaa    3660
aaaggatctt cacctagatc cttttaaagg ccggccgcgg ccgcgcaaag tcccgcttcg    3720
tgaaaatttt cgtgccgcgt gattttccgc caaaactttt aacgaacgtt cgttataatg    3780
gtgtcatgac cttcacgacg aagtactaaa attggcccga atcatcagct atggatctct    3840
ctgatgtcgc gctggagtcc gacgcgctcg atgctgccgt cgatttaaaa acggtgatcg    3900 gattttttccg agctctcgat acgacggacg cgccagcatc acgagactgg gccagtgccg    3960
cgagcgacct agaaactctc gtggcggatc ttgaggagct ggctgacgag ctgcgtgctc    4020
ggccagcgcc aggaggacgc acagtagtgg aggatgcaat cagttgcgcc tactgcggtg    4080
gcctgattcc tccccggcct gacccgcgag gacggcgcgc aaaatattgc tcagatgcgt    4140
gtcgtgccgc agccagccgc gagcgcgcca acaaacgcca cgccgaggag ctggaggcgg    4200
ctaggtcgca aatggcgctg gaagtgcgtc ccccgagcga aattttggcc atggtcgtca    4260
cagagctgga agcggcagcg agaattatcg cgatcgtggc ggtgcccgca ggcatgacaa    4320
acatcgtaaa tgccgcgttt cgtgtgccgt ggccgcccag gacgtgtcag cgccgccacc    4380
acctgcaccg aatcggcagc agcgtcgcgc gtcgaaaaag cgcacaggcg gcaagaagcg    4440
ataagctgca cgaatacctg aaaaatgttg aacgccccgt gagcggtaac tcacagggcg    4500
tcggctaacc cccagtccaa acctgggaga aagcgctcaa aaatgactct agcggattca    4560
cgagacattg acacaccggc ctggaaattt tccgctgatc tgttcgacac ccatcccgag    4620
ctcgcgctgc gatcacgtgg ctggacgagc gaagaccgcc gcgaattcct cgctcacctg    4680
ggcagagaaa atttccaggg cagcaagacc cgcgacttcg ccagcgcttg gatcaaagac    4740
ccggacacgg agaaacacag ccgaagttat accgagttgg ttcaaaatcg cttgcccggt    4800
gccagtatgt tgctctgacg cacgcgcagc acgcagccgt gcttgtcctg gacattgatg    4860
tgccgagcca ccaggccggc gggaaaatcg agcacgtaaa ccccgaggtc tacgcgattt    4920
tggagcgctg ggcacgcctg gaaaagcgc cagcttggat cggcgtgaat ccactgagcg    4980
ggaaatgcca gctcatctgg ctcattgatc cggtgtatgc cgcagcaggc atgagcagcg    5040
cgaatatgcg cctgctggct gcaacgaccg aggaaatgac ccgcgttttc ggcgctgacc    5100
```

-continued

```
aggcttttc  acataggctg  agccgtggcc  actgcactct  ccgacgatcc  cagccgtacc   5160
gctggcatgc  ccagcacaat  cgcgtggatc  gcctagctga  tcttatggag  gttgctcgca   5220
tgatctcagg  cacagaaaaa  cctaaaaaac  gctatgagca  ggagttttct  agcggacggg   5280
cacgtatcga  agcggcaaga  aaagccactg  cggaagcaaa  agcacttgcc  acgcttgaag   5340
caagcctgcc  gagcgccgct  gaagcgtctg  gagagctgat  cgacggcgtc  cgtgtcctct   5400
ggactgctcc  agggcgtgcc  gcccgtgatg  agacggcttt  tcgccacgct  ttgactgtgg   5460
gataccagtt  aaaagcggct  ggtgagcgcc  taaaagacac  caagggtcat  cgagcctacg   5520
agcgtgccta  caccgtcgct  caggcggtcg  gaggaggccg  tgagcctgat  ctgccgccgg   5580
actgtgaccg  ccagacggat  tggccgcgac  gtgtgcgcgg  ctacgtcgct  aaaggccagc   5640
cagtcgtccc  tgctcgtcag  acagagacgc  agagccagcc  gaggcgaaaa  gctctggcca   5700
ctatgggaag  acgtggcggt  aaaaaggccg  cagaacgctg  gaaagaccca  aacagtgagt   5760
acgcccgagc  acagcgagaa  aaactagcta  agtccagtca  acgacaagct  aggaaagcta   5820
aaggaaatcg  cttgaccatt  gcaggttggt  ttatgactgt  tgagggagag  actggctcgt   5880
ggccgacaat  caatgaagct  atgtctgaat  ttagcgtgtc  acgtcagacc  gtgaatagag   5940
cacttaaggt  ctgcgggcat  tgaacttcca  cgaggacgcc  gaaagcttcc  cagtaaatgt   6000
gccatctcgt  aggcagaaaa  cggttccccc  gtagggtctc  tctcttggcc  tcctttctag   6060
gtcgggctga  ttgctcttga  agctctctag  ggggctcac   accataggca  gataacgttc   6120
cccaccggct  cgcctcgtaa  gcgcacaagg  actgctccca  aagatcttca  aagccactgc   6180
cgcgactgcc  ttcgcgaagc  cttgccccgc  ggaaatttcc  tccaccgagt  tcgtgcacac   6240
ccctatgcca  agcttctttc  accctaaatt  cgagagattg  gattcttacc  gtggaaattc   6300
ttcgcaaaaa  tcgtcccctg  atcgcccttg  cgacgttggc  gtcggtgccg  ctggttgcgc   6360
ttggcttgac  cgacttgatc  agcggccgc                                       6389
```

<210> SEQ ID NO 37
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK 1753

<400> SEQUENCE: 37
ggatctagag ttctgtgaaa aacaccgtg                                          29

<210> SEQ ID NO 38
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK 1754

<400> SEQUENCE: 38
gcgactagtg ccccacaaat aaaaaacac                                          29

<210> SEQ ID NO 39
<211> LENGTH: 5156
<212> TYPE: DNA
<213> ORGANISM: Artificial Sequence

```
<220> FEATURE:
<223> OTHER INFORMATION: Plasmid
<220> FEATURE:
<221> NAME/KEY: misc_feature
<223> OTHER INFORMATION: H247

<400> SEQUENCE: 39
tcgatttaaa tctcgagagg cctgacgtcg ggcccggtac cacgcgtcat atgactagtt      60
cggacctagg gatatcgtcg acatcgatgc tcttctgcgt taattaacaa ttgggatcct     120
ctagagttct gtgaaaaaca ccgtggggca gtttctgctt cgcggtgttt tttatttgtg     180
gggcactaga cccgggattt aaatcgctag cgggctgcta aaggaagcgg aacacgtaga     240
aagccagtcc gcagaaacgg tgctgacccc ggatgaatgt cagctactgg gctatctgga     300
caagggaaaa cgcaagcgca aagagaaagc aggtagcttg cagtgggctt acatggcgat     360
agctagactg gcggttttta tggacagcaa gcgaaccgga attgccagct ggggcgccct     420
ctggtaaggt tgggaagccc tgcaaagtaa actggatggc tttcttgccg ccaaggatct     480
gatggcgcag gggatcaaga tctgatcaag agacaggatg aggatcgttt cgcatgattg     540
aacaagatgg attgcacgca ggttctccgg ccgcttgggt ggagaggcta ttcggctatg     600
actgggcaca acagacaatc ggctgctctg atgccgccgt gttccggctg tcagcgcagg     660
ggcgcccggt tctttttgtc aagaccgacc tgtccggtgc cctgaatgaa ctgcaggacg     720
aggcagcgcg gctatcgtgg ctggccacga cgggcgttcc ttgcgcagct gtgctcgacg     780
ttgtcactga gcgggaagg gactggctgc tattgggcga agtgccgggg caggatctcc     840
tgtcatctca ccttgctcct gccgagaaag tatccatcat ggctgatgca atgcggcggc     900
tgcatacgct tgatccggct acctgcccat tcgaccacca agcgaaacat cgcatcgagc     960
gagcacgtac tcggatggaa gccggtcttg tcgatcagga tgatctggac gaagagcatc    1020
aggggctcgc gccagccgaa ctgttcgcca ggctcaaggc gcgcatgccc gacggcgagg    1080
atctcgtcgt gacccatggc gatgcctgct tgccgaatat catggtggaa aatggccgct    1140
tttctggatt catcgactgt ggccggctgg gtgtggcgga ccgctatcag gacatagcgt    1200
tggctacccg tgatattgct gaagagcttg gcggcgaatg ggctgaccgc ttcctcgtgc    1260
tttacggtat cgccgctccc gattcgcagc gcatcgcctt ctatcgcctt cttgacgagt    1320
tcttctgagc gggactctgg ggttcgaaat gaccgaccaa gcgacgccca acctgccatc    1380
acgagatttc gattccaccg ccgccttcta tgaaaggttg gcttcggaa tcgttttccg    1440
ggacgccggc tggatgatcc tccagcgcgg ggatctcatg ctggagttct cgcccacgc    1500
tagcggcgcg ccggccggcc cggtgtgaaa taccgcacag atgcgtaagg agaaaatacc    1560
gcatcaggcg ctcttccgct tcctcgctca ctgactcgct gcgctcggtc gttcggctgc    1620
ggcgagcggt atcagctcac tcaaaggcgg taatacggtt atccacagaa tcaggggata    1680
acgcaggaaa gaacatgtga gcaaaaggcc agcaaaggc caggaaccgt aaaaaggccg    1740
cgttgctggc gtttttccat aggctccgcc cccctgacga gcatcacaaa aatcgacgct    1800
caagtcagag gtggcgaaac ccgacaggac tataaagata ccaggcgttt ccccctggaa    1860
gctccctcgt gcgctctcct gttccgaccc tgccgcttac cggatacctg tccgcctttc    1920
tcccttcggg aagcgtggcg ctttctcata gctcacgctg taggtatctc agttcggtgt    1980
aggtcgttcg ctccaagctg ggctgtgtgc acgaacccc cgttcagccc gaccgctgcg    2040
ccttatccgg taactatcgt cttgagtcca acccggtaag acacgactta tcgccactgg    2100
cagcagccac tggtaacagg attagcagag cgaggtatgt aggcggtgct acagagttct    2160
```

```
tgaagtggtg gcctaactac ggctacacta gaaggacagt atttggtatc tgcgctctgc    2220
tgaagccagt taccttcgga aaaagagttg gtagctcttg atccggcaaa caaaccaccg    2280
ctggtagcgg tggttttttt gtttgcaagc agcagattac gcgcagaaaa aaaggatctc    2340
aagaagatcc tttgatcttt tctacggggt ctgacgctca gtggaacgaa aactcacgtt    2400
aagggatttt ggtcatgaga ttatcaaaaa ggatcttcac ctagatcctt ttaaaggccg    2460
gccgcggccg cgcaaagtcc cgcttcgtga aaattttcgt gccgcgtgat tttccgccaa    2520
aaactttaac gaacgttcgt tataatggtg tcatgacctt cacgacgaag tactaaaatt    2580
ggcccgaatc atcagctatg gatctctctg atgtcgcgct ggagtccgac gcgctcgatg    2640
ctgccgtcga tttaaaaacg gtgatcggat ttttccgagc tctcgatacg acggacgcgc    2700
cagcatcacg agactgggcc agtgccgcga gcgacctaga aactctcgtg gcggatcttg    2760
aggagctggc tgacgagctg cgtgctcggc cagcgccagg aggacgcaca gtagtggagg    2820
atgcaatcag ttgcgcctac tgcggtggcc tgattcctcc ccggcctgac ccgcgaggac    2880
ggcgcgcaaa atattgctca gatgcgtgtc gtgccgcagc cagccgcgag cgcgccaaca    2940
aacgccacgc cgaggagctg gaggcggcta ggtcgcaaat ggcgctggaa gtgcgtcccc    3000
cgagcgaaat tttggccatg gtcgtcacag agctggaagc ggcagcgaga attatcgcga    3060
tcgtggcggt gccgcaggc atgacaaaca tcgtaaatgc cgcgtttcgt gtgccgtggc    3120
cgcccaggac gtgtcagcgc cgccaccacc tgcaccgaat cggcagcagc gtcgcgcgtc    3180
gaaaaagcgc acaggcggca agaagcgata agctgcacga atacctgaaa aatgttgaac    3240
gccccgtgag cggtaactca cagggcgtcg gctaaccccc agtccaaacc tgggagaaag    3300
cgctcaaaaa tgactctagc ggattcacga gacattgaca caccggcctg gaaattttcc    3360
gctgatctgt tcgacaccca tcccgagctc gcgctgcgat cacgtggctg gacgagcgaa    3420
gaccgccgcg aattcctcgc tcacctgggc agagaaaatt tccagggcag caagacccgc    3480
gacttcgcca gcgcttggat caaagacccg gacacggaga aacacagccg aagttatacc    3540
gagttggttc aaaatcgctt gcccggtgcc agtatgttgc tctgacgcac gcgcagcacg    3600
cagccgtgct tgtcctggac attgatgtgc cgagccacca ggccggcggg aaaatcgagc    3660
acgtaaaccc cgaggtctac gcgattttgg agcgctgggc acgcctggaa aaagcgccag    3720
cttggatcgg cgtgaatcca ctgagcggga atgccagct catctggctc attgatccgg    3780
tgtatgccgc agcaggcatg agcagcccga atatgcgcct gctggctgca acgaccgagg    3840
aaatgacccg cgtttcggc gctgaccagg cttttcaca taggctgagc cgtgccact    3900 gcactctccg acgatcccag ccgtaccgct ggcatgccca gcacaatcgc gtggatcgcc    3960
tagctgatct tatggaggtt gctcgcatga tctcaggcac agaaaaacct aaaaaacgct    4020
atgagcagga gttttctagc ggacgggcac gtatcgaagc ggcaagaaaa gccactgcgg    4080
aagcaaaagc acttgccacg cttgaagcaa gcctgccgag cgccgctgaa gcgtctggag    4140
agctgatcga cggcgtccgt gtcctctgga ctgctccagg gcgtgccgcc cgtgatgaga    4200
cggcttttcg ccacgctttg actgtgggat accagttaaa agcggctggt gagcgcctaa    4260
aagacaccaa gggtcatcga gcctacgagc gtgcctacac cgtcgctcag gcggtcggag    4320
gaggccgtga gcctgatctg ccgccggact gtgaccgcca gacggattgg ccgcgacgtg    4380
tgcgcggcta cgtcgctaaa ggccagccag tcgtccctgc tcgtcagaca gagacgcaga    4440
gccagccgag gcgaaaagct ctggcccacta tgggaagacg tggcggtaaa aaggccgcag    4500
aacgctggaa agacccaaac agtgagtacg cccgagcaca gcgagaaaaa ctagctaagt    4560
```

```
ccagtcaacg acaagctagg aaagctaaag gaaatcgctt gaccattgca ggttggttta    4620
tgactgttga gggagagact ggctcgtggc cgacaatcaa tgaagctatg tctgaattta    4680
gcgtgtcacg tcagaccgtg aatagagcac ttaaggtctg cgggcattga acttccacga    4740
ggacgccgaa agcttcccag taaatgtgcc atctcgtagg cagaaaacgg ttcccccgta    4800
gggtctctct cttggcctcc tttctaggtc gggctgattg ctcttgaagc tctctagggg    4860
ggctcacacc ataggcagat aacgttcccc accggctcgc ctcgtaagcg cacaaggact    4920
gctcccaaag atcttcaaag ccactgccgc gactgccttc gcgaagcctt gccccgcgga    4980
aatttcctcc accgagttcg tgcacacccc tatgccaagc ttctttcacc ctaaattcga    5040
gagattggat tcttaccgtg gaaattcttc gcaaaaatcg tcccctgatc gcccttgcga    5100
cgttggcgtc ggtgccgctg gttgcgcttg gcttgaccga cttgatcagc ggccgc       5156
```

<210> SEQ ID NO 40
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK 1848

<400> SEQUENCE: 40

```
gagaactagt agctgccaat tattccggg                                         29
```

<210> SEQ ID NO 41
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK 1849

<400> SEQUENCE: 41

```
gtgtgtcgac ttagatgtag aactcgatgt ag                                     32
```

<210> SEQ ID NO 42
<211> LENGTH: 6464
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: internal designation: pG A4 (H344)

<400> SEQUENCE: 42

```
tcgatttaaa tctcgagagg cctgacgtcg ggcccggtac cacgcgtcat atgactagta      60
gctgccaatt attccgggct tgtgacccgc tacccgataa ataggtcggc tgaaaaattt    120
cgttgcaata tcaacaaaaa ggcctatcat tgggaggtgt cgcaccaagt acttttgcga    180
agcgccatct gacggatttt caaaagatgt atatgctcgg tgcggaaacc tacgaaagga    240
ttttttaccc atgccacccc tcgcgccttc aggtcaactt gaaatccaag cgatcggtga    300
tgtctccacc gaagccggag caatcattac aaacgctgaa atcgcctatc accgctgggg    360
tgaataccgc gtagataaag aaggacgcag caatgtcgtt ctcatcgaac acgccctcac    420
tggagattcc aacgcagccg attggtgggc tgacttgctc ggtcccggca aagccatcaa    480
cactgatatt tactgcgtga tctgtaccaa cgtcatcggt ggttgcaacg gttccaccgg    540
```

-continued

```
acctggctcc atgcatccag atggaaattt ctggggtaat cgcttccccg ccacgtccat      600
tcgtgatcag gtaaacgccg aaaaacaatt cctcgacgca ctcggcatca ccacggtcgc      660
cgcagtactt ggtggttcca tgggtggtgc ccgcaccta gagtgggccg caatgtaccc       720
agaaactgtt ggcgcagctg ctgttcttgc agtttctgca cgcgccagcg cctggcaaat      780
cggcattcaa tccgcccaaa ttaaggcgat tgaaaacgac caccactggc acgaaggcaa      840
ctactacgaa tccggctgca acccagccac cggactcggc gccgcccgac gcatcgccca      900
cctcacctac cgtggcgaac tagaaatcga cgaacgcttc ggcaccaaag cccaaaagaa      960
cgaaaaccca ctcggtccct accgcaagcc cgaccagcgc ttcgccgtgg aatcctactt     1020
ggactaccaa gcagacaagc tagtacagcg tttcgacgcc ggctcctacg tcttgctcac     1080
cgacgccctc aaccgccacg acattggtcg cgaccgcgga ggcctcaaca aggcactcga     1140
atccatcaaa gttccagtcc ttgtcgcagg cgtagatacc gatattttgt acccctacca     1200
ccagcaagaa cacctctcca gaaacctggg aaatctactg gcaatggcaa aaatcgtatc     1260
ccctgtcggc cacgatgctt cctcaccga aagccgccaa atggatcgca tcgtgaggaa      1320
cttcttcagc ctcatctccc cagacgaaga caacccttcg acctacatcg agttctacat     1380
ctaagtcgac atcgatgctc ttctgcgtta attaacaatt gggatcctct agagttctgt     1440
gaaaaacacc gtgggcagt ttctgcttcg cggtgttttt tatttgtggg gcactagacc      1500
cgggatttaa atcgctagcg ggctgctaaa ggaagcggaa cacgtagaaa gccagtccgc     1560
agaaacggtg ctgaccccgg atgaatgtca gctactgggc tatctggaca agggaaaacg     1620
caagcgcaaa gagaaagcag gtagcttgca gtgggcttac atggcgatag ctagactggg     1680 cggtttatatg gacagcaagc gaaccggaat tgccagctgg ggcgccctct ggtaaggttg     1740
ggaagccctg caaagtaaac tggatggctt tcttgccgcc aaggatctga tggcgcaggg     1800
gatcaagatc tgatcaagag acaggatgag gatcgtttcg catgattgaa caagatggat     1860
tgcacgcagg ttctccggcc gcttgggtgg agaggctatt cggctatgac tgggcacaac     1920
agacaatcgg ctgctctgat gccgccgtgt tccggctgtc agcgcagggg cgcccggttc     1980
tttttgtcaa gaccgacctg tccggtgccc tgaatgaact gcaggacgag gcagcgcggc     2040
tatcgtggct ggccacgacg ggcgttcctt gcgcagctgt gctcgacgtt gtcactgaag     2100
cgggaaggga ctggctgcta ttgggcgaag tgccggggca ggatctcctg tcatctcacc     2160
ttgctcctgc cgagaaagta tccatcatgg ctgatgcaat gcggcggctg catacgcttg     2220
atccggctac ctgcccattc gaccaccaag cgaaacatcg catcgagcga gcacgtactc     2280
ggatggaagc cggtcttgtc gatcaggatg atctggacga agagcatcag gggctcgcgc     2340
cagccgaact gttcgccagg ctcaaggcgc gcatgcccga cggcgaggat ctcgtcgtga     2400
cccatggcga tgcctgcttg ccgaatatca tggtggaaaa tggccgcttt tctggattca     2460
tcgactgtgg ccggctgggt gtggcggacc gctatcagga catagcgttg gctacccgtg     2520
atattgctga agagcttggc ggcgaatggg ctgaccgctt cctcgtgctt tacggtatcg     2580
ccgctcccga ttcgcagcgc atcgccttct atcgccttct tgacgagttc ttctgagcgg     2640
gactctgggg ttcgaaatga ccgaccaagc gacgcccaac ctgccatcac gagatttcga     2700
ttccaccgcc gccttctatg aaaggttggg cttcggaatc gttttccggg acgccggctg     2760
gatgatcctc cagcgcgggg atctcatgct ggagttcttc gcccacgcta gcggcgcgcc     2820
ggccggcccg gtgtgaaata ccgcacagat gcgtaaggag aaaataccgc atcaggcgct     2880
cttccgcttc ctcgctcact gactcgctgc gctcggtcgt tcggctgcgg cgagcggtat     2940
```

```
cagctcactc aaaggcggta atacggttat ccacagaatc aggggataac gcaggaaaga    3000
acatgtgagc aaaaggccag caaaaggcca ggaaccgtaa aaaggccgcg ttgctggcgt    3060
ttttccatag gctccgcccc cctgacgagc atcacaaaaa tcgacgctca agtcagaggt    3120
ggcgaaaccc gacaggacta taaagatacc aggcgtttcc ccctggaagc tccctcgtgc    3180
gctctcctgt tccgaccctg ccgcttaccg gatacctgtc cgcctttctc ccttcgggaa    3240
gcgtggcgct ttctcatagc tcacgctgta ggtatctcag ttcggtgtag gtcgttcgct    3300
ccaagctggg ctgtgtgcac gaaccccccg ttcagcccga ccgctgcgcc ttatccggta    3360
actatcgtct tgagtccaac ccggtaagac acgacttatc gccactggca gcagccactg    3420
gtaacaggat tagcagagcg aggtatgtag gcggtgctac agagttcttg aagtggtggc    3480
ctaactacgg ctacactaga aggacagtat ttggtatctg cgctctgctg aagccagtta    3540
ccttcggaaa aagagttggt agctcttgat ccggcaaaca aaccaccgct ggtagcggtg    3600
gtttttttgt ttgcaagcag cagattacgc gcagaaaaaa aggatctcaa gaagatcctt    3660
tgatcttttc tacggggtct gacgctcagt ggaacgaaaa ctcacgttaa gggattttgg    3720
tcatgagatt atcaaaaagg atcttcacct agatcctttt aaaggccggc cgcggccgcg    3780
caaagtcccg cttcgtgaaa attttcgtgc cgcgtgattt tccgccaaaa actttaacga    3840
acgttcgtta taatggtgtc atgaccttca cgacgaagta ctaaaattgg cccgaatcat    3900
cagctatgga tctctctgat gtcgcgctgg agtccgacgc gctcgatgct gccgtcgatt    3960
taaaaacggt gatcggattt ttccgagctc tcgatacgac ggacgcgcca gcatcacgag    4020
actgggccag tgccgcgagc gacctagaaa ctctcgtggc ggatcttgag gagctggctg    4080
acgagctgcg tgctcggcca gcgccaggag gacgcacagt agtggaggat gcaatcagtt    4140
gcgcctactg cggtggcctg attcctcccc ggcctgaccc gcgaggacgg cgcgcaaaat    4200
attgctcaga tgcgtgtcgt gccgcagcca gccgcgagcg cgccaacaaa cgccacgccg    4260
aggagctgga ggcggctagg tcgcaaatgg cgctggaagt gcgtcccccg agcgaaattt    4320
tggccatggt cgtcacagag ctggaagcgg cagcgagaat tatcgcgatc gtggcggtgc    4380
ccgcaggcat gacaaacatc gtaaatgccg cgtttcgtgt gccgtggccg cccaggacgt    4440
gtcagcgccg ccaccacctg caccgaatcg gcagcagcgt cgcgcgtcga aaaagcgcac    4500
aggcggcaag aagcgataag ctgcacgaat acctgaaaaa tgttgaacgc cccgtgagcg    4560
gtaactcaca gggcgtcggc taaccccccag tccaaacctg ggagaaagcg ctcaaaaatg    4620
actctagcgg attcacgaga cattgacaca ccggcctgga aattttccgc tgatctgttc    4680
gacacccatc ccgagctcgc gctgcgatca cgtggctgga cgagcgaaga ccgccgcgaa    4740
ttcctcgctc acctgggcag agaaaatttc cagggcagca agacccgcga cttcgccagc    4800
gcttggatca aagacccgga cacggagaaa cacagccgaa gttataccga gttggttcaa    4860
aatcgcttgc ccggtgccag tatgttgctc tgacgcacgc gcagcacgca gccgtgcttg    4920
tcctggacat tgatgtgccg agccaccagg ccggcgggaa aatcgagcac gtaaaccccg    4980
aggtctacgc gattttggag cgctgggcac gcctggaaaa agcgccagct tggatcggcg    5040
tgaatccact gagcgggaaa tgccagctca tctggctcat tgatccggtg tatgccgcag    5100
caggcatgag cagcccgaat atgcgcctgc tggctgcaac gaccgaggaa atgacccgcg    5160
ttttcggcgc tgaccaggct ttttcacata ggctgagccg tggccactgc actctccgac    5220
gatcccagcc gtaccgctgg catgcccagc acaatcgcgt ggatcgccta gctgatctta    5280
tggaggttgc tcgcatgatc tcaggcacag aaaaacctaa aaaacgctat gagcaggagt    5340
```

-continued

```
tttctagcgg acgggcacgt atcgaagcgg caagaaaagc cactgcggaa gcaaaagcac    5400
ttgccacgct tgaagcaagc ctgccgagcg ccgctgaagc gtctggagag ctgatcgacg    5460
gcgtccgtgt cctctggact gctccagggc gtgccgcccg tgatgagacg gcttttcgcc    5520
acgctttgac tgtgggatac cagttaaaag cggctggtga gcgcctaaaa gacaccaagg    5580
gtcatcgagc ctacgagcgt gcctacaccg tcgctcaggc ggtcggagga ggccgtgagc    5640
ctgatctgcc gccggactgt gaccgccaga cggattggcc gcgacgtgtg cgcggctacg    5700
tcgctaaagg ccagccagtc gtccctgctc gtcagacaga gacgcagagc cagccgaggc    5760
gaaaagctct ggccactatg ggaagacgtg gcggtaaaaa ggccgcagaa cgctggaaag    5820
acccaaacag tgagtacgcc cgagcacagc gagaaaaact agctaagtcc agtcaacgac    5880
aagctaggaa agctaaagga aatcgcttga ccattgcagg ttggtttatg actgttgagg    5940
gagagactgg ctcgtggccg acaatcaatg aagctatgtc tgaatttagc gtgtcacgtc    6000
agaccgtgaa tagagcactt aaggtctgcg ggcattgaac ttccacgagg acgccgaaag    6060
cttcccagta aatgtgccat tcgtaggca gaaaacggtt ccccgtagg gtctctctct    6120 tggcctcctt tctaggtcgg gctgattgct cttgaagctc tctaggggg ctcacaccat    6180 aggcagataa cgttccccac cggctcgcct cgtaagcgca caaggactgc tcccaaagat    6240
cttcaaagcc actgccgcga ctgccttcgc gaagccttgc cccgcggaaa tttcctccac    6300
cgagttcgtg cacacccta tgccaagctt ctttcaccct aaattcgaga gattggattc    6360
ttaccgtgga aattcttcgc aaaaatcgtc ccctgatcgc ccttgcgacg ttggcgtcgg    6420
tgccgctggt tgcgcttggc ttgaccgact tgatcagcgg ccgc                    6464
```

<210> SEQ ID NO 43
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK 1695

<400> SEQUENCE: 43
gagactcgag ggccgttacc ctgcgaatg                                      29

<210> SEQ ID NO 44
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Haf16

<400> SEQUENCE: 44
gagaactagt gtggctacga ctttcgcagc                                     30

<210> SEQ ID NO 45
<211> LENGTH: 6604
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: internal designation: pCliK5MCS PeftuPsod metA
      (H473)

<400> SEQUENCE: 45

```
tcgatttaaa tctcgagggc cgttaccctg cgaatgtcca cagggtagct ggtagtttga      60
aaatcaacgc cgttgccctt aggattcagt aactggcaca ttttgtaatg cgctagatct     120
gtgtgctcag tcttccaggc tgcttatcac agtgaaagca aaaccaattc gtggctgcga     180
aagtcgtagc cacactagta gctgccaatt attccgggct tgtgacccgc tacccgataa     240
ataggtcggc tgaaaaattt cgttgcaata tcaacaaaaa ggcctatcat tgggaggtgt     300
cgcaccaagt acttttgcga agcgccatct gacggatttt caaaagatgt atatgctcgg     360
tgcggaaacc tacgaaagga ttttttaccc atgcccaccc tcgcgccttc aggtcaactt     420
gaaatccaag cgatcggtga tgtctccacc gaagccggag caatcattac aaacgctgaa     480
atcgcctatc accgctgggg tgaataccgc gtagataaag aaggacgcag caatgtcgtt     540
ctcatcgaac acgccctcac tggagattcc aacgcagccg attggtgggc tgacttgctc     600
ggtcccggca aagccatcaa cactgatatt tactgcgtga tctgtaccaa cgtcatcggt     660
ggttgcaacg gttccaccgg acctggctcc atgcatccag atggaaattt ctggggtaat     720
cgcttccccg ccacgtccat tcgtgatcag gtaaacgccg aaaaacaatt cctcgacgca     780
ctcggcatca ccacggtcgc cgcagtactt ggtggttcca tgggtggtgc ccgcacccta     840
gagtgggcca caatgtaccc agaaactgtt ggcgcagctg ctgttcttgc agtttctgca     900
cgcgccagcg cctggcaaat cggcattcaa tccgcccaaa ttaaggcgat tgaaaacgac     960
caccactggc acgaaggcaa ctactacgaa tccggctgca acccagccac cggactcggc    1020
gccgcccgac gcatcgccca cctcacctac cgtggcgaac tagaaatcga cgaacgcttc    1080
ggcaccaaag cccaaaagaa cgaaaaccca ctcggtccct accgcaagcc cgaccagcgc    1140
ttcgccgtgg aatcctactt ggactaccaa gcagacaagc tagtacagcg tttcgacgcc    1200
ggctcctacg tcttgctcac cgacgccctc aaccgccacg acattggtcg cgaccgcgga    1260
ggcctcaaca aggcactcga atccatcaaa gttccagtcc ttgtcgcagg cgtagatacc    1320
gatattttgt accctacca ccagcaagaa cacctctcca gaaacctggg aaatctactg    1380
gcaatggcaa aaatcgtatc ccctgtcggc cacgatgctt tcctcaccga aagccgccaa    1440
atggatcgca tcgtgaggaa cttcttcagc ctcatctccc cagacgaaga caaccctctcg    1500
acctacatcg agttctacat ctaagtcgac atcgatgctc ttctgcgtta attaacaatt    1560
gggatcctct agagttctgt gaaaaacacc gtggggcagt ttctgcttcg cggtgttttt    1620
tatttgtggg gcactagacc cgggatttaa atcgctagcg ggctgctaaa ggaagcggaa    1680
cacgtagaaa gccagtccgc agaaacggtg ctgaccccgg atgaatgtca gctactgggc    1740
tatctggaca agggaaaacg caagcgcaaa gagaaagcag gtagcttgca gtgggcttac    1800
atggcgatag ctagactggg cggttttatg gacagcaagc gaaccggaat tgccagctgg    1860
ggcgccctct ggtaaggttg ggaagccctg caaagtaaac tggatggctt tcttgccgcc    1920
aaggatctga tggcgcaggg gatcaagatc tgatcaagag acaggatgag gatcgtttcg    1980
catgattgaa caagatggat tgcacgcagg ttctccggcc gcttgggtgg agaggctatt    2040
cggctatgac tgggcacaac agacaatcgg ctgctctgat gccgccgtgt tccggctgtc    2100
agcgcagggg cgcccggttc tttttgtcaa gaccgacctg tccggtgccc tgaatgaact    2160
gcaggacgag gcagcgcggc tatcgtggct ggccacgacg ggcgttcctt gcgcagctgt    2220
gctcgacgtt gtcactgaag cgggaaggga ctggctgcta ttgggcgaag tgccggggca    2280
ggatctcctg tcatctcacc ttgctcctgc cgagaaagta tccatcatgg ctgatgcaat    2340
```

```
gcggcggctg catacgcttg atccggctac ctgcccattc gaccaccaag cgaaacatcg    2400
catcgagcga gcacgtactc ggatggaagc cggtcttgtc gatcaggatg atctggacga    2460
agagcatcag gggctcgcgc cagccgaact gttcgccagg ctcaaggcgc gcatgcccga    2520
cggcgaggat ctcgtcgtga cccatggcga tgcctgcttg ccgaatatca tggtggaaaa    2580
tggccgcttt tctggattca tcgactgtgg ccggctgggt gtggcggacc gctatcagga    2640
catagcgttg gctacccgtg atattgctga agagcttggc ggcgaatggg ctgaccgctt    2700
cctcgtgctt tacggtatcg ccgctcccga ttcgcagcgc atcgccttct atcgccttct    2760
tgacgagttc ttctgagcgg gactctgggg ttcgaaatga ccgaccaagc gacgcccaac    2820
ctgccatcac gagatttcga ttccaccgcc gccttctatg aaaggttggg cttcggaatc    2880
gttttccggg acgccggctg gatgatcctc cagcgcgggg atctcatgct ggagttcttc    2940
gcccacgcta gcggcgcgcc ggccggcccg gtgtgaaata ccgcacagat gcgtaaggag    3000
aaaataccgc atcaggcgct cttccgcttc ctcgctcact gactcgctgc gctcggtcgt    3060
tcggctgcgg cgagcggtat cagctcactc aaaggcggta atacggttat ccacagaatc    3120 agggggataac gcaggaaaga acatgtgagc aaaaggccag caaaaggcca ggaaccgtaa    3180
aaaggccgcg ttgctggcgt ttttccatag gctccgcccc cctgacgagc atcacaaaaa    3240
tcgacgctca agtcagaggt ggcgaaaccc gacaggacta taaagatacc aggcgtttcc    3300
ccctggaagc tccctcgtgc gctctcctgt tccgaccctg ccgcttaccg gatacctgtc    3360
cgcctttctc ccttcgggaa gcgtggcgct ttctcatagc tcacgctgta ggtatctcag    3420
ttcggtgtag gtcgttcgct ccaagctggg ctgtgtgcac gaaccccccg ttcagcccga    3480
ccgctgcgcc ttatccggta actatcgtct tgagtccaac ccggtaagac acgacttatc    3540
gccactggca gcagccactg gtaacaggat tagcagagcg aggtatgtag gcggtgctac    3600
agagttcttg aagtggtggc ctaactacgg ctacactaga aggacagtat ttggtatctg    3660
cgctctgctg aagccagtta ccttcggaaa aagagttggt agctcttgat ccggcaaaca    3720
aaccaccgct ggtagcggtg gtttttttgt ttgcaagcag cagattacgc gcagaaaaaa    3780
aggatctcaa gaagatcctt tgatcttttc tacggggtct gacgctcagt ggaacgaaaa    3840
ctcacgttaa gggattttgg tcatgagatt atcaaaaagg atcttcacct agatcctttt    3900
aaaggccggc cgcggccgcg caaagtcccg cttcgtgaaa attttcgtgc cgcgtgattt    3960
tccgccaaaa actttaacga acgttcgtta taatggtgtc atgaccttca cgacgaagta    4020
ctaaaattgg cccgaatcat cagctatgga tctctctgat gtcgcgctgg agtccgacgc    4080
gctcgatgct gccgtcgatt taaaaacggt gatcggattt ttccgagctc tcgatacgac    4140
ggacgcgcca gcatcacgag actgggccag tgccgcgagc gacctagaaa ctctcgtggc    4200
ggatcttgag gagctggctg acgagctgcg tgctcggcca gcgccaggag gacgcacagt    4260
agtggaggat gcaatcagtt gcgcctactg cggtggcctg attcctcccc ggcctgaccc    4320
gcgaggacgg cgcgcaaaat attgctcaga tgcgtgtcgt gccgcagcca gccgcgagcg    4380
cgccaacaaa cgccacgccg aggagctgga ggcggctagg tcgcaaatgg cgctggaagt    4440
gcgtcccccg agcgaaattt tggccatggt cgtcacagag ctggaagcgg cagcgagaat    4500
tatcgcgatc gtggcggtgc ccgcaggcat gacaaacatc gtaaatgccg cgtttcgtgt    4560
gccgtggccc cccaggacgt gtcagcgccg ccaccacctg caccgaatcg gcagcagcgt    4620
cgcgcgtcga aaaagcgcac aggcggcaag aagcgataag ctgcacgaat acctgaaaaa    4680
tgttgaacgc cccgtgagcg gtaactcaca gggcgtcggc taaccccag tccaaacctg     4740
```

```
ggagaaagcg ctcaaaaatg actctagcgg attcacgaga cattgacaca ccggcctgga    4800
aattttccgc tgatctgttc gacacccatc ccgagctcgc gctgcgatca cgtggctgga    4860
cgagcgaaga ccgccgcgaa ttcctcgctc acctgggcag agaaaatttc cagggcagca    4920 agaccogcga cttcgccagc gcttggatca aagacccgga cacggagaaa cacagccgaa    4980
gttataccga gttggttcaa aatcgcttgc ccggtgccag tatgttgctc tgacgcacgc    5040
gcagcacgca gccgtgcttg tcctggacat tgatgtgccg agccaccagg ccggcgggaa    5100
aatcgagcac gtaaaccccg aggtctacgc gattttggag cgctgggcac gcctggaaaa    5160
agcgccagct tggatcggcg tgaatccact gagcgggaaa tgccagctca tctggctcat    5220
tgatccggtg tatgccgcag caggcatgag cagcccgaat atgcgcctgc tggctgcaac    5280
gaccgaggaa atgacccgcg ttttcggcgc tgaccaggct ttttcacata ggctgagccg    5340
tggccactgc actctccgac gatcccagcc gtaccgctgg catgcccagc acaatcgcgt    5400
ggatcgccta gctgatctta tggaggttgc tcgcatgatc tcaggcacag aaaaacctaa    5460
aaaacgctat gagcaggagt tttctagcgg acgggcacgt atcgaagcgg caagaaaagc    5520
cactgcggaa gcaaaagcac ttgccacgct tgaagcaagc ctgccgagcg ccgctgaagc    5580
gtctggagag ctgatcgacg gcgtccgtgt cctctggact gctccagggc gtgccgcccg    5640
tgatgagacg gcttttcgcc acgctttgac tgtgggatac cagttaaaag cggctggtga    5700
gcgcctaaaa gacaccaagg gtcatcgagc ctacgagcgt gcctacaccg tcgctcaggc    5760
ggtcggagga ggccgtgagc ctgatctgcc gccggactgt gaccgccaga cggattggcc    5820
gcgacgtgtg cgcggctacg tcgctaaagg ccagccagtc gtccctgctc gtcagacaga    5880
gacgcagagc cagccgaggc gaaaagctct ggccactatg gaagacgtg gcggtaaaaa    5940 ggccgcagaa cgctggaaag acccaaacag tgagtacgcc cgagcacagc gagaaaaact    6000
agctaagtcc agtcaacgac aagctaggaa agctaaagga aatcgcttga ccattgcagg    6060
ttggtttatg actgttgagg gagagactgg ctcgtggccg acaatcaatg aagctatgtc    6120
tgaatttagc gtgtcacgtc agaccgtgaa tagagcactt aaggtctgcg ggcattgaac    6180
ttccacgagg acgccgaaag cttcccagta aatgtgccat ctcgtaggca gaaaacggtt    6240
cccccgtagg gtctctctct tggcctcctt tctaggtcgg gctgattgct cttgaagctc    6300
tctagggggg ctcacaccat aggcagataa cgttccccac cggctcgcct cgtaagcgca    6360
caaggactgc tcccaaagat cttcaaagcc actgccgcga ctgccttcgc gaagccttgc    6420
cccgcggaaa tttcctccac cgagttcgtg cacaccccta tgccaagctt ctttcaccct    6480
aaattcgaga gattggattc ttaccgtgga aattcttcgc aaaaatcgtc ccctgatcgc    6540
ccttgcgacg ttggcgtcgg tgccgctggt tgcgcttggc ttgaccgact tgatcagcgg    6600
ccgc                                                                 6604
```

<210> SEQ ID NO 46
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Haf64

<400> SEQUENCE: 46
gagaactagt ggccgttacc ctgcgaatg                                        29

```
<210> SEQ ID NO 47
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Haf65

<400> SEQUENCE: 47
gcgcgagggt gggcattgta tgtcctcctg gacttc                              36

<210> SEQ ID NO 48
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK1862)

<400> SEQUENCE: 48
atgcccaccc tcgcgcc                                                   17

<210> SEQ ID NO 49
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK1849)

<400> SEQUENCE: 49
gtgtgtcgac ttagatgtag aactcgatgt ag                                  32

<210> SEQ ID NO 50
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK 1697

<400> SEQUENCE: 50
gagactcgag agctgccaat tattccggg                                      29

<210> SEQ ID NO 51
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Haf17)

<400> SEQUENCE: 51
gagaactagt taggtttccg caccgagc                                       28

<210> SEQ ID NO 52
<211> LENGTH: 6609
<212> TYPE: DNA
<213> ORGANISM: Artificial Sequence
```

```
<220> FEATURE:
<223> OTHER INFORMATION: Plasmid
<220> FEATURE:
<221> NAME/KEY: misc_feature
<223> OTHER INFORMATION: internal designation: pCLiK5MCS Psod Peft metA
      (H505)

<400> SEQUENCE: 52
tcgatttaaa tctcgagagc tgccaattat tccgggcttg tgacccgcta cccgataaat      60
aggtcggctg aaaaatttcg ttgcaatatc aacaaaaagg cctatcattg ggaggtgtcg     120
caccaagtac ttttgcgaag cgccatctga cggattttca aaagatgtat atgctcggtg     180
cggaaaccta actagtggcc gttaccctgc gaatgtccac agggtagctg gtagtttgaa     240
aatcaacgcc gttgcccttta ggattcagta actggcacat tttgtaatgc gctagatctg     300
tgtgctcagt cttccaggct gcttatcaca gtgaaagcaa aaccaattcg tggctgcgaa     360
agtcgtagcc accacgaagt ccaggaggac atacaatgcc caccctcgcg ccttcaggtc     420
aacttgaaat ccaagcgatc ggtgatgtct ccaccgaagc cggagcaatc attacaaacg     480
ctgaaatcgc ctatcaccgc tggggtgaat accgcgtaga taagaagga cgcagcaatg     540 tcgttctcat cgaacacgcc ctcactggag attccaacgc agccgattgg tgggctgact     600
tgctcggtcc cggcaaagcc atcaacactg atatttactg cgtgatctgt accaacgtca     660
tcggtggttg caacggttcc accggacctg gctccatgca tccagatgga aatttctggg     720
gtaatcgctt ccccgccacg tccattcgtg atcaggtaaa cgccgaaaaa caattcctcg     780
acgcactcgg catcaccacg gtcgccgcag tacttggtgg ttccatgggt ggtgcccgca     840
ccctagagtg ggccgcaatg tacccagaaa ctgttggcgc agctgctgtt cttgcagttt     900
ctgcacgcgc cagcgcctgg caaatcggca ttcaatccgc ccaaattaag gcgattgaaa     960
acgaccacca ctggcacgaa ggcaactact acgaatccgg ctgcaaccca gccaccggac    1020
tcggcgccgc ccgacgcatc gcccacctca cctaccgtgg cgaactagaa atcgacgaac    1080
gcttcggcac caaagcccaa aagaacgaaa acccactcgg tccctaccgc aagcccgacc    1140
agcgcttcgc cgtggaatcc tacttggact accaagcaga caagctagta cagcgtttcg    1200
acgccggctc ctacgtcttg ctcaccgacg ccctcaaccg ccacgacatt ggtcgcgacc    1260
gcggaggcct caacaaggca ctcgaatcca tcaaagttcc agtccttgtc gcaggcgtag    1320
ataccgatat tttgtacccc taccaccagc aagaacacct ctccagaaac ctgggaaatc    1380
tactggcaat ggcaaaaatc gtatcccctg tcggccacga tgctttcctc accgaaagcc    1440
gccaaatgga tcgcatcgtg aggaacttct tcagcctcat ctccccagac gaagacaacc    1500
cttcgaccta catcgagttc tacatctaag tcgacatcga tgctcttctg cgttaattaa    1560
caattgggat cctctagagt tctgtgaaaa acaccgtggg gcagtttctg cttcgcggtg    1620
ttttttattt gtggggcact agacccggga tttaaatcgc tagcgggctg ctaaaggaag    1680
cggaacacgt agaaagccag tccgcagaaa cggtgctgac cccggatgaa tgtcagctac    1740
tgggctatct ggacaaggga aaacgcaagc gcaaagagaa agcaggtagc ttgcagtggg    1800
cttacatggc gatagctaga ctgggcggtt ttatggacag caagcgaacc ggaattgcca    1860 gctgggcgc cctctggtaa ggttgggaag ccctgcaaag taaactggat ggctttcttg    1920
ccgccaagga tctgatggcg caggggatca agatctgatc aagagacagg atgaggatcg    1980
tttcgcatga ttgaacaaga tggattgcac gcaggttctc cggccgcttg ggtggagagg    2040
ctattcggct atgactgggc acaacagaca atcggctgct ctgatgccgc cgtgttccgg    2100
ctgtcagcgc aggggcgccc ggttcttttt gtcaagaccg acctgtccgg tgccctgaat    2160
```

```
gaactgcagg acgaggcagc gcggctatcg tggctggcca cgacgggcgt tccttgcgca   2220
gctgtgctcg acgttgtcac tgaagcggga agggactggc tgctattggg cgaagtgccg   2280
gggcaggatc tcctgtcatc tcaccttgct cctgccgaga agtatccat catggctgat    2340 gcaatgcggc ggctgcatac gcttgatccg gctacctgcc cattcgacca ccaagcgaaa   2400
catcgcatcg agcgagcacg tactcggatg gaagccggtc ttgtcgatca ggatgatctg   2460
gacgaagagc atcaggggct cgcgccagcc gaactgttcg ccaggctcaa ggcgcgcatg   2520
cccgacggcg aggatctcgt cgtgacccat ggcgatgcct gcttgccgaa tatcatggtg   2580
gaaaatggcc gcttttctgg attcatcgac tgtggccggc tgggtgtggc ggaccgctat   2640
caggacatag cgttggctac ccgtgatatt gctgaagagc ttggcggcga atgggctgac   2700
cgcttcctcg tgctttacgg tatcgccgct cccgattcgc agcgcatcgc cttctatcgc   2760
cttcttgacg agttcttctg agcgggactc tggggttcga aatgaccgac caagcgacgc   2820
ccaacctgcc atcacgagat ttcgattcca ccgccgcctt ctatgaaagg ttgggcttcg   2880
gaatcgtttt ccgggacgcc ggctggatga tcctccagcg cggggatctc atgctggagt   2940
tcttcgccca cgctagcggc gcgccggccg gcccggtgtg aaataccgca cagatgcgta   3000
aggagaaaat accgcatcag gcgctcttcc gcttcctcgc tcactgactc gctgcgctcg   3060
gtcgttcggc tgcggcgagc ggtatcagct cactcaaagg cggtaatacg gttatccaca   3120
gaatcagggg ataacgcagg aaagaacatg tgagcaaaag gccagcaaaa ggccaggaac   3180
cgtaaaaagg ccgcgttgct ggcgtttttc cataggctcc gcccccctga cgagcatcac   3240
aaaaatcgac gctcaagtca gaggtggcga aacccgacag gactataaag ataccaggcg   3300
tttccccctg gaagctccct cgtgcgctct cctgttccga ccctgccgct taccggatac   3360
ctgtccgcct ttctcccttc gggaagcgtg gcgctttctc atagctcacg ctgtaggtat   3420
ctcagttcgg tgtaggtcgt tcgctccaag ctgggctgtg tgcacgaacc ccccgttcag   3480
cccgaccgct gcgccttatc cggtaactat cgtcttgagt ccaacccggt aagacacgac   3540
ttatcgccac tggcagcagc cactggtaac aggattagca gagcgaggta tgtaggcggt   3600
gctacagagt tcttgaagtg gtggcctaac tacggctaca ctagaaggac agtatttggt   3660
atctgcgctc tgctgaagcc agttaccttc ggaaaaagag ttggtagctc ttgatccggc   3720
aaacaaacca ccgctggtag cggtggtttt tttgtttgca agcagcagat tacgcgcaga   3780
aaaaaaggat ctcaagaaga tcctttgatc ttttctacgg ggtctgacgc tcagtggaac   3840
gaaaactcac gttaagggat tttggtcatg agattatcaa aaaggatctt cacctagatc   3900
cttttaaagg ccgccgcgg ccgcgcaaag tcccgcttcg tgaaattttt cgtgccgcgt   3960
gattttccgc caaaaacttt aacgaacgtt cgttataatg gtgtcatgac cttcacgacg   4020
aagtactaaa attggcccga atcatcagct atggatctct ctgatgtcgc gctggagtcc   4080
gacgcgctcg atgctgccgt cgatttaaaa acggtgatcg gattttttccg agctctcgat   4140 acgacggacg cgccagcatc acgagactgg gccagtgccg cgagcgacct agaaactctc   4200
gtggcggatc ttgaggagct ggctgacgag ctgcgtgctc ggccagcgcc aggaggacgc   4260
acagtagtgg aggatgcaat cagttgcgcc tactgcggtg gcctgattcc tccccggcct   4320
gacccgcgag gacggcgcgc aaaatattgc tcagatgcgt gtcgtgccgc agccagccgc   4380
gagcgcgcca acaaacgcca cgccgaggag ctggaggcgg ctaggtcgca aatggcgctg   4440
gaagtgcgtc ccccgagcga aattttggcc atggtcgtca cagagctgga agcggcagcg   4500
agaattatcg cgatcgtggc ggtgcccgca ggcatgacaa acatcgtaaa tgccgcgttt   4560
```

-continued

```
cgtgtgccgt ggccgccag  gacgtgtcag cgccgccacc acctgcaccg aatcggcagc    4620
agcgtcgcgc gtcgaaaaag cgcacaggcg gcaagaagcg ataagctgca cgaatacctg    4680
aaaaatgttg aacgcccgt  gagcggtaac tcacagggcg tcggctaacc cccagtccaa    4740
acctgggaga aagcgctcaa aaatgactct agcggattca cgagacattg acacaccggc    4800
ctggaaattt tccgctgatc tgttcgacac ccatcccgag ctcgcgctgc gatcacgtgg    4860
ctggacgagc gaagaccgcc gcgaattcct cgctcacctg gcagagaaa  atttccaggg    4920 cagcaagacc cgcgacttcg ccagcgcttg gatcaaagac ccggacacgg agaaacacag    4980
ccgaagttat accgagttgg ttcaaaatcg cttgcccggt gccagtatgt tgctctgacg    5040
cacgcgcagc acgcagccgt gcttgtcctg gacattgatg tgccgagcca ccaggccggc    5100
gggaaaatcg agcacgtaaa ccccgaggtc tacgcgattt tggagcgctg ggcacgcctg    5160
gaaaaagcgc cagcttggat cggcgtgaat ccactgagcg ggaaatgcca gctcatctgg    5220
ctcattgatc cggtgtatgc cgcagcaggc atgagcagcc gaatatgcg  cctgctggct    5280 gcaacgaccg aggaaatgac ccgcgttttc ggcgctgacc aggctttttc acataggctg    5340
agccgtggcc actgcactct ccgacgatcc cagccgtacc gctggcatgc ccagcacaat    5400
cgcgtggatc gcctagctga tcttatggag gttgctcgca tgatctcagg cacagaaaaa    5460
cctaaaaaac gctatgagca ggagttttct agcggacggg cacgtatcga agcggcaaga    5520
aaagccactg cggaagcaaa agcacttgcc acgcttgaag caagcctgcc gagcgccgct    5580
gaagcgtctg gagagctgat cgacggcgtc cgtgtcctct ggactgctcc agggcgtgcc    5640
gcccgtgatg agacggcttt tcgccacgct ttgactgtgg gataccagtt aaaagcggct    5700
ggtgagcgcc taaagacac  caagggtcat cgagcctacg agcgtgccta caccgtcgct    5760
caggcggtcg gaggaggccg tgagcctgat ctgccgccgg actgtgaccg ccagacggat    5820
tggccgcgac gtgtgcgcgg ctacgtcgct aaaggccagc cagtcgtccc tgctcgtcag    5880
acagagacgc agagccagcc gaggcgaaaa gctctggcca ctatgggaag acgtggcggt    5940
aaaaaggccg cagaacgctg gaaagaccca aacagtgagt acgcccgagc acagcgagaa    6000
aaactagcta agtccagtca acgacaagct aggaaagcta aaggaaatcg cttgaccatt    6060
gcaggttggt ttatgactgt tgagggagag actggctcgt ggccgacaat caatgaagct    6120
atgtctgaat ttagcgtgtc acgtcagacc gtgaatagag cacttaaggt ctgcgggcat    6180
tgaacttcca cgaggacgcc gaaagcttcc cagtaaatgt gccatctcgt aggcagaaaa    6240
cggttccccc gtagggtctc tctcttggcc tcctttctag gtcgggctga ttgctcttga    6300
agctctctag gggggctcac accataggca gataacgttc cccaccggct cgcctcgtaa    6360
gcgcacaagg actgctccca aagatcttca aagccactgc cgcgactgcc ttcgcgaagc    6420
cttgccccgc ggaaatttcc tccaccgagt tcgtgcacac ccctatgcca agcttctttc    6480
accctaaatt cgagagattg gattcttacc gtggaaattc ttcgcaaaaa tcgtcccctg    6540
atcgcccttg cgacgttggc gtcggtgccg ctggttgcgc ttggcttgac cgacttgatc    6600
agcggccgc                                                            6609
```

<210> SEQ ID NO 53
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature

```
<223> OTHER INFORMATION: internal designation: BK1701

<400> SEQUENCE: 53
gagactcgag cggcttaaag tttggctgcc                                    30

<210> SEQ ID NO 54
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Haf018

<400> SEQUENCE: 54
gagaactagt attttgtgtg tgccggttgt g                                  31

<210> SEQ ID NO 55
<211> LENGTH: 6583
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: internal designation: pCLiK5MCS PgroPsod metA
      (H472)

<400> SEQUENCE: 55
tcgatttaaa tctcgagcgg cttaaagttt ggctgccatg tgaatttta gcaccctcaa     60 cagttgagtg ctggcactct cgggggtaga gtgccaaata ggttgtttga cacacagttg   120
ttcacccgcg acgacggctg tgctggaaac ccacaaccgg cacacacaaa atactagtag   180
ctgccaatta ttccgggctt gtgacccgct acccgataaa taggtcggct gaaaaatttc   240
gttgcaatat caacaaaaag gcctatcatt gggaggtgtc gcaccaagta cttttgcgaa   300
gcgccatctg acggattttc aaaagatgta tatgctcggt gcggaaacct acgaaaggat   360 tttttacccca tgcccaccct cgcgccttca ggtcaacttg aaatccaagc gatcggtgat   420
gtctccaccg aagccggagc aatcattaca aacgctgaaa tcgcctatca ccgctggggt   480
gaataccgcg tagataaaga aggacgcagc aatgtcgttc tcatcgaaca cgccctcact   540
ggagattcca acgcagccga ttggtgggct gacttgctcg gtcccggcaa agccatcaac   600
actgatattt actgcgtgat ctgtaccaac gtcatcggtg gttgcaacgg ttccaccgga   660
cctggctcca tgcatccaga tggaaatttc tgggggtaatc gcttccccgc cacgtccatt   720
cgtgatcagg taaacgccga aaaacaattc ctcgacgcac tcggcatcac cacggtcgcc   780
gcagtacttg gtggttccat gggtggtgcc cgcacccttag agtgggccgc aatgtaccca   840
gaaactgttg gcgcagctgc tgttcttgca gtttctgcac gcgccagcgc ctggcaaatc   900
ggcattcaat ccgcccaaat taaggcgatt gaaaacgacc accactggca cgaaggcaac   960
tactacgaat ccggctgcaa cccagccacc ggactcggcg ccgcccgacg catcgcccac  1020
ctcacctacc gtggcgaact agaaatcgac gaacgcttcg gcaccaaagc ccaaaagaac  1080
gaaaacccac tcggtcccta ccgcaagccc gaccagcgct tcgccgtgga atcctacttg  1140
gactaccaag cagacaagct agtacagcgt ttcgacgccg gctcctacgt cttgctcacc  1200
gacgccctca accgccacga cattggtcgc gaccgcggag gcctcaacaa ggcactcgaa  1260
tccatcaaag ttccagtcct tgtcgcaggc gtagataccg atattttgta ccccttaccac  1320 cagcaagaac acctctccag aaacctggga aatctactgg caatggcaaa aatcgtatcc  1380
```

```
cctgtcggcc acgatgcttt cctcaccgaa agccgccaaa tggatcgcat cgtgaggaac   1440
ttcttcagcc tcatctcccc agacgaagac aacccttcga cctacatcga gttctacatc   1500
taagtcgaca tcgatgctct tctgcgttaa ttaacaattg ggatcctcta gagttctgtg   1560
aaaaacaccg tggggcagtt tctgcttcgc ggtgtttttt atttgtgggg cactagaccc   1620
gggatttaaa tcgctagcgg gctgctaaag gaagcggaac acgtagaaag ccagtccgca   1680
gaaacggtgc tgaccccgga tgaatgtcag ctactgggct atctggacaa gggaaaacgc   1740
aagcgcaaag agaaagcagg tagcttgcag tgggcttaca tggcgatagc tagactgggc   1800
ggttttatgg acagcaagcg aaccggaatt gccagctggg gcgccctctg gtaaggttgg   1860
gaagccctgc aaagtaaact ggatggcttt cttgccgcca aggatctgat ggcgcagggg   1920
atcaagatct gatcaagaga caggatgagg atcgtttcgc atgattgaac aagatggatt   1980
gcacgcaggt tctccggccg cttgggtgga gaggctattc ggctatgact gggcacaaca   2040
gacaatcggc tgctctgatg ccgccgtgtt ccggctgtca gcgcagggc gcccggttct   2100 ttttgtcaag accgacctgt ccggtgccct gaatgaactg caggacgagg cagcgcggct   2160
atcgtggctg gccacgacgg gcgttccttg cgcagctgtg ctcgacgttg tcactgaagc   2220
gggaagggac tggctgctat tgggcgaagt gccggggcag gatctcctgt catctcacct   2280
tgctcctgcc gagaaagtat ccatcatggc tgatgcaatg cggcggctgc atacgcttga   2340
tccggctacc tgcccattcg accaccaagc gaaacatcgc atcgagcgag cacgtactcg   2400
gatgaagccg gtcttgtcg atcaggatga tctggacgaa gagcatcagg gctcgcgcc   2460 agccgaactg ttcgccaggc tcaaggcgcg catgcccgac ggcgaggatc tcgtcgtgac   2520
ccatggcgat gcctgcttgc cgaatatcat ggtggaaaat ggccgctttt ctggattcat   2580
cgactgtggc cggctgggtg tggcggaccg ctatcaggac atagcgttgg ctacccgtga   2640
tattgctgaa gagcttggcg gcgaatgggc tgaccgcttc ctcgtgcttt acggtatcgc   2700
cgctcccgat tcgcagcgca tcgccttcta tcgccttctt gacgagttct tctgagcggg   2760
actctggggt tcgaaatgac cgaccaagcg acgcccaacc tgccatcacg agatttcgat   2820
tccaccgccg ccttctatga aaggttgggc ttcggaatcg ttttccggga cgccggctgg   2880
atgatcctcc agcgcgggga tctcatgctg gagttcttcg cccacgctag cggcgcgccg   2940
gccggcccgg tgtgaaatac cgcacagatg cgtaaggaga aaataccgca tcaggcgctc   3000
ttccgcttcc tcgctcactg actcgctgcg ctcggtcgtt cggctgcggc gagcggtatc   3060
agctcactca aaggcggtaa tacggttatc cacagaatca ggggataacg caggaaagaa   3120
catgtgagca aaaggccagc aaaaggccag gaaccgtaaa aaggccgcgt tgctggcgtt   3180
tttccatagg ctccgccccc ctgacgagca tcacaaaaat cgacgctcaa gtcagaggtg   3240
gcgaaacccg acaggactat aaagatacca ggcgtttccc cctggaagct ccctcgtgcg   3300
ctctcctgtt ccgaccctgc cgcttaccgg atacctgtcc gcctttctcc cttcgggaag   3360
cgtggcgctt tctcatagct cacgctgtag gtatctcagt tcggtgtagg tcgttcgctc   3420
caagctgggc tgtgtgcacg aaccccccgt tcagcccgac cgctgcgcct tatccggtaa   3480
ctatcgtctt gagtccaacc cggtaagaca cgacttatcg ccactggcag cagccactgg   3540
taacaggatt agcagagcga ggtatgtagg cggtgctaca gagttcttga agtggtggcc   3600
taactacggc tacactagaa ggacagtatt tggtatctgc gctctgctga agccagttac   3660
cttcggaaaa agagttggta gctcttgatc cggcaaacaa accaccgctg gtagcggtgg   3720
tttttttgtt tgcaagcagc agattacgcg cagaaaaaaa ggatctcaag aagatccttt   3780
```

```
gatcttttct acggggtctg acgctcagtg gaacgaaaac tcacgttaag ggattttggt    3840
catgagatta tcaaaaagga tcttcaccta gatccttta aaggccggcc gcggccgcgc    3900
aaagtcccgc ttcgtgaaaa ttttcgtgcc gcgtgatttt ccgccaaaaa ctttaacgaa    3960
cgttcgttat aatggtgtca tgaccttcac gacgaagtac taaaattggc ccgaatcatc    4020
agctatggat ctctctgatg tcgcgctgga gtccgacgcg ctcgatgctg ccgtcgattt    4080
aaaaacggtg atcggatttt tccgagctct cgatacgacg gacgcgccag catcacgaga    4140
ctgggccagt gccgcgagcg acctagaaac tctcgtggcg gatcttgagg agctggctga    4200
cgagctgcgt gctcggccag cgccaggagg acgcacagta gtggaggatg caatcagttg    4260
cgcctactgc ggtggcctga ttcctccccg gcctgacccg cgaggacggc gcgcaaaata    4320
ttgctcagat gcgtgtcgtg ccgcagccag ccgcgagcgc gccaacaaac gccacgccga    4380
ggagctggag gcggctaggt cgcaaatggc gctggaagtg cgtcccccga gcgaaatttt    4440
ggccatggtc gtcacagagc tggaagcggc agcgagaatt atcgcgatcg tggcggtgcc    4500
cgcaggcatg acaaacatcg taaatgccgc gtttcgtgtg ccgtggccgc ccaggacgtg    4560
tcagcgccgc caccacctgc accgaatcgg cagcagcgtc gcgcgtcgaa aaagcgcaca    4620
ggcggcaaga agcgataagc tgcacgaata cctgaaaaat gttgaacgcc ccgtgagcgg    4680
taactcacag ggcgtcggct aaccccagt ccaaacctgg gagaaagcgc tcaaaaatga    4740
ctctagcgga ttcacgagac attgacacac cggcctggaa attttccgct gatctgttcg    4800
acacccatcc cgagctcgcg ctgcgatcac gtggctggac gagcgaagac cgccgcgaat    4860
tcctcgctca cctgggcaga gaaaatttcc agggcagcaa gacccgcgac ttcgccagcg    4920
cttggatcaa agaccgggac acggagaaac acagccgaag ttataccgag ttggttcaaa    4980
atcgcttgcc cggtgccagt atgttgctct gacgcacgcg cagcacgcag ccgtgcttgt    5040
cctggacatt gatgtgccga gccaccaggc cggcgggaaa atcgagcacg taaaccccga    5100
ggtctacgcg atttggagc gctgggcacg cctggaaaaa gcgccagctt ggatcggcgt    5160
gaatccactg agcgggaaat gccagctcat ctggctcatt gatccggtgt atgccgcagc    5220
aggcatgagc agcccgaata tgcgcctgct ggctgcaacg accgaggaaa tgacccgcgt    5280
tttcggcgct gaccaggctt tttcacatag gctgagccgt ggccactgca ctctccgacg    5340
atcccagccg taccgctggc atgcccagca caatcgcgtg gatcgcctag ctgatcttat    5400
ggaggttgct cgcatgatct caggcacaga aaaacctaaa aaacgctatg agcaggagtt    5460
ttctagcgga cgggcacgta tcgaagcggc aagaaaagcc actgcggaag caaaagcact    5520
tgccacgctt gaagcaagcc tgccgagcgc cgctgaagcg tctggagagc tgatcgacgg    5580
cgtccgtgtc ctctggactg ctccagggcg tgccgcccgt gatgagacgg cttttcgcca    5640
cgctttgact gtgggatacc agttaaaagc ggctggtgag cgcctaaaag acaccaaggg    5700
tcatcgagcc tacgagcgtg cctacaccgt cgctcaggcg gtcggaggag gccgtgagcc    5760
tgatctgccg ccggactgtg accgccgac ggattggccg cgacgtgtgc gcggctacgt    5820
cgctaaaggc cagccagtcg tccctgctcg tcagacagag acgcagagcc agccgaggcg    5880
aaaagctctg gccactatgg gaagacgtgg cggtaaaaag gccgcagaac gctggaaaga    5940
cccaaacagt gagtacgccc gagcacagcg agaaaaacta gctaagtcca gtcaacgaca    6000
agctaggaaa gctaaaggaa atcgcttgac cattgcaggt tggtttatga ctgttgaggg    6060
agagactggc tcgtggccga caatcaatga agctatgtct gaatttagcg tgtcacgtca    6120
gaccgtgaat agagcactta aggtctgcgg gcattgaact tccacgagga cgccgaaagc    6180
```

```
ttcccagtaa atgtgccatc tcgtaggcag aaaacggttc ccccgtaggg tctctctctt      6240
ggcctccttt ctaggtcggg ctgattgctc ttgaagctct ctaggggggc tcacaccata      6300
ggcagataac gttccccacc ggctcgcctc gtaagcgcac aaggactgct cccaaagatc      6360
ttcaaagcca ctgccgcgac tgccttcgcg aagccttgcc ccgcggaaat tcctccacc       6420 gagttcgtgc acacccctat gccaagcttc tttcaccctc aattcgagag attggattct      6480
taccgtggaa attcttcgca aaatcgtccc cctgatcgcc cttgcgacgt tggcgtcggt      6540
gccgctggtt gcgcttggct tgaccgactt gatcagcggc cgc                        6583

<210> SEQ ID NO 56
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: BK1782

<400> SEQUENCE: 56
tcgagagatt ggattcttac                                                  20

<210> SEQ ID NO 57
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Haf63

<400> SEQUENCE: 57
tctcggtacc ccgcaccgag catatacatc                                       30

<210> SEQ ID NO 58
<211> LENGTH: 6450
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: internal designation: H479 (pCliK5MCS PEF-Ts
      metA)

<400> SEQUENCE: 58
aaatctcgag cttggtctat agtggctagg tacccccca cgacaatgga actttgactt        60
ttaaaatttc atcgccgtgg gggcttttg ggcagccagc ccgccgtgtc gcaacgtaat       120
cgactgaata cctgtacgat cacttttag acgggcgggt agggctactg tgccctaacc      180
taagcttgta aagcattaat tatccataca taaggaggat cgccccgtaa tgcccaccct     240
cgcgccttca ggtcaacttg aaatccaagc gatcggtgat gtctccaccg aagccggagc    300
aatcattaca aacgctgaaa tcgcctatca ccgctggggt gaataccgcg tagataaaga   360
aggacgcagc aatgtcgttc tcatcgaaca cgccctcact ggagattcca acgcagccga    420
ttggtgggct gacttgctcg gtcccggcaa agccatcaac actgatattt actgcgtgat   480
ctgtaccaac gtcatcggtg gttgcaacgg ttccaccgga cctggctcca tgcatccaga   540
tggaaatttc tggggtaatc gcttcccgc cacgtccatt cgtgatcagg taaacgccga    600
aaaacaattc ctcgacgcac tcggcatcac cacggtcgcc gcagtacttg gtggttccat    660
```

```
gggtggtgcc cgcaccctag agtgggccgc aatgtaccca gaaactgttg gcgcagctgc    720
tgttcttgca gtttctgcac gcgccagcgc ctggcaaatc ggcattcaat ccgcccaaat    780
taaggcgatt gaaaacgacc accactggca cgaaggcaac tactacgaat ccggctgcaa    840
cccagccacc ggactcggcg ccgcccgacg catcgcccac ctcacctacc gtggcgaact    900
agaaatcgac gaacgcttcg gcaccaaagc ccaaaagaac gaaaacccac tcggtcccta    960
ccgcaagccc gaccagcgct tcgccgtgga atcctacttg gactaccaag cagacaagct   1020
agtacagcgt ttcgacgccg gctcctacgt cttgctcacc gacgccctca accgccacga   1080
cattggtcgc gaccgcggag gcctcaacaa ggcactcgaa tccatcaaag ttccagtcct   1140
tgtcgcaggc gtagataccg atattttgta cccctaccac cagcaagaac acctctccag   1200
aaacctggga atctactgg caatggcaaa aatcgtatcc cctgtcggcc acgatgcttt   1260
cctcaccgaa agccgccaaa tggatcgcat cgtgaggaac ttcttcagcc tcatctcccc   1320
agacgaagac aacccttcga cctacatcga gttctacatc taagtcgaca tcgatgctct   1380
tctgcgttaa ttaacaattg ggatcctcta gagttctgtg aaaaacaccg tggggcagtt   1440
tctgcttcgc ggtgttttt atttgtgggg cactagaccc gggatttaaa tcgctagcgg   1500
gctgctaaag gaagcggaac acgtagaaag ccagtccgca gaaacggtgc tgaccccgga   1560
tgaatgtcag ctactgggct atctggacaa gggaaaacgc aagcgcaaag agaaagcagg   1620
tagcttgcag tgggcttaca tggcgatagc tagactgggc ggttttatgg acagcaagcg   1680
aaccggaatt gccagctggg gcgccctctg gtaaggttgg gaagccctgc aaagtaaact   1740
ggatggcttt cttgccgcca aggatctgat ggcgcagggg atcaagatct gatcaagaga   1800
caggatgagg atcgtttcgc atgattgaac aagatggatt gcacgcaggt tctccggccg   1860
cttgggtgga gaggctattc ggctatgact gggcacaaca gacaatcggc tgctctgatg   1920
ccgccgtgtt ccgcctgtca gcgcagggc gcccggttct ttttgtcaag accgacctgt   1980
ccggtgccct gaatgaactg caggacgagg cagcgcggct atcgtggctg gccacgacgg   2040
gcgttccttg cgcagctgtg ctcgacgttg tcactgaagc gggaagggac tggctgctat   2100
tgggcgaagt gccggggcag gatctcctgt catctcacct tgctcctgcc gagaaagtat   2160
ccatcatggc tgatgcaatg cggcggctgc atacgcttga tccggctacc tgcccattcg   2220
accaccaagc gaaacatcgc atcgagcgag cacgtactcg gatggaagcc ggtcttgtcg   2280
atcaggatga tctggacgaa gagcatcagg ggctcgcgcc agccgaactg ttcgccaggc   2340
tcaaggcgcg catgcccgac ggcgaggatc tcgtcgtgac ccatggcgat gcctgcttgc   2400
cgaatatcat ggtggaaaat ggccgctttt ctggattcat cgactgtggc cggctgggtg   2460
tggcggaccg ctatcaggac atagcgttgg ctacccgtga tattgctgaa gagcttggcg   2520
gcgaatgggc tgaccgcttc ctcgtgcttt acggtatcgc cgctcccgat tcgcagcgca   2580
tcgccttcta tcgccttctt gacgagttct tctgagcggg actctgggt tcgaaatgac   2640 cgaccaagcg acgcccaacc tgccatcacg agatttcgat tccaccgccg ccttctatga   2700
aaggttgggc ttcggaatcg ttttccggga cgccggctgg atgatcctcc agcgcgggga   2760
tctcatgctg gagttcttcg cccacgctag cggcgcgccg gccggccggg tgtgaaatac   2820
cgcacagatg cgtaaggaga aaataccgca tcaggcgctc ttccgcttcc tcgctcactg   2880
actcgctgcg ctcggtcgtt cggctgcggc gagcggtatc agctcactca aaggcggtaa   2940
tacggttatc cacagaatca ggggataacg caggaaagaa catgtgagca aaaggccagc   3000
aaaaggccag gaaccgtaaa aaggccgcgt tgctggcgtt tttccatagg ctccgcccc   3060
```

```
ctgacgagca tcacaaaaat cgacgctcaa gtcagaggtg gcgaaacccg acaggactat     3120
aaagatacca ggcgtttccc cctggaagct ccctcgtgcg ctctcctgtt ccgaccctgc     3180
cgcttaccgg atacctgtcc gcctttctcc cttcgggaag cgtggcgctt tctcatagct     3240
cacgctgtag gtatctcagt tcggtgtagg tcgttcgctc caagctgggc tgtgtgcacg     3300
aaccccccgt tcagcccgac cgctgcgcct tatccggtaa ctatcgtctt gagtccaacc     3360
cggtaagaca cgacttatcg ccactggcag cagccactgg taacaggatt agcagagcga     3420
ggtatgtagg cggtgctaca gagttcttga agtggtggcc taactacggc tacactagaa     3480
ggacagtatt tggtatctgc gctctgctga agccagttac cttcggaaaa agagttggta     3540
gctcttgatc cggcaaacaa accaccgctg gtagcggtgg ttttttttgtt tgcaagcagc     3600 agattacgcg cagaaaaaaa ggatctcaag aagatccttt gatcttttct acggggtctg     3660
acgctcagtg gaacgaaaac tcacgttaag ggattttggt catgagatta tcaaaaagga     3720
tcttcaccta gatcctttta aaggccggcc gcggccgcgc aaagtcccgc ttcgtgaaaa     3780
ttttcgtgcc gcgtgatttt ccgccaaaaa ctttaacgaa cgttcgttat aatggtgtca     3840
tgaccttcac gacgaagtac taaaattggc ccgaatcatc agctatggat ctctctgatg     3900
tcgcgctgga gtccgacgcg ctcgatgctg ccgtcgattt aaaaacggtg atcggatttt     3960
tccgagctct cgatacgacg gacgcgccag catcacgaga ctgggccagt gccgcgagcg     4020
acctagaaac tctcgtggcg gatcttgagg agctggctga cgagctgcgt gctcggccag     4080
cgccaggagg acgcacagta gtggaggatg caatcagttg cgcctactgc ggtggcctga     4140
ttcctccccg gcctgacccg cgaggacggc gcgcaaaata ttgctcagat gcgtgtcgtg     4200
ccgcagccag ccgcgagcgc gccaacaaac gccacgccga ggagctggag gcggctaggt     4260
cgcaaatggc gctggaagtg cgtcccccga gcgaaatttt ggccatggtc gtcacagagc     4320
tggaagcgga agcgagaatt atcgcgatcg tggcggtgcc cgcaggcatg acaaacatcg     4380
taaatgccgc gtttcgtgtg ccgtggccgc ccaggacgtg tcagcgccgc caccacctgc     4440
accgaatcgg cagcagcgtc gcgcgtcgaa aaagcgcaca ggcggcaaga agcgataagc     4500
tgcacgaata cctgaaaaat gttgaacgcc ccgtgagcgg taactcacag ggcgtcggct     4560 aaccccccagt ccaaacctgg gagaaagcgc tcaaaaatga ctctagcgga ttcacgagac     4620
attgacacac cggcctggaa atttttccgct gatctgttcg acacccatcc cgagctcgcg     4680
ctgcgatcac gtggctggac gagcgaagac cgccgcgaat tcctcgctca cctgggcaga     4740
gaaaatttcc agggcagcaa gacccgcgac ttcgccagcg cttggatcaa agacccggac     4800
acggagaaac acagccgaag ttataccgag ttggttcaaa atcgcttgcc cggtgccagt     4860
atgttgctct gacgcacgcg cagcacgcag ccgtgcttgt cctggacatt gatgtgccga     4920
gccaccaggc cggcgggaaa atcgagcacg taaaccccga ggtctacgcg attttggagc     4980
gctgggcacg cctggaaaaa gcgccagctt ggatcggcgt gaatccactg agcgggaaat     5040
gccagctcat ctggctcatt gatccggtgt atgccgcagc aggcatgagc agcccgaata     5100
tgcgcctgct ggctgcaacg accgaggaaa tgacccgcgt tttcggcgct gaccaggctt     5160
tttcacatag gctgagccgt ggccactgca ctctccgacg atcccagccg taccgctggc     5220
atgcccagca caatcgcgtg gatcgcctag ctgatcttat ggaggttgct cgcatgatct     5280
caggcacaga aaaacctaaa aaacgctatg agcaggagtt ttctagcgga cgggcacgta     5340
tcgaagcgga aagaaaagcc actgcggaag caaaagcact tgccacgctt gaagcaagcc     5400
tgccgagcgc cgctgaagcg tctggagagc tgatcgacgg cgtccgtgtc ctctggactg     5460
```

```
ctccagggcg tgccgcccgt gatgagacgg cttttcgcca cgctttgact gtgggatacc   5520
agttaaaagc ggctggtgag cgcctaaaag acaccaaggg tcatcgagcc tacgagcgtg   5580
cctacaccgt cgctcaggcg gtcggaggag gccgtgagcc tgatctgccg ccggactgtg   5640
accgccagac ggattggccg cgacgtgtgc gcggctacgt cgctaaaggc cagccagtcg   5700
tccctgctcg tcagacagag acgcagagcc agccgaggcg aaaagctctg gccactatgg   5760
gaagacgtgg cggtaaaaag gccgcagaac gctggaaaga cccaaacagt gagtacgccc   5820
gagcacagcg agaaaaacta gctaagtcca gtcaacgaca agctaggaaa gctaaaggaa   5880
atcgcttgac cattgcaggt tggtttatga ctgttgaggg agagactggc tcgtggccga   5940
caatcaatga agctatgtct gaatttagcg tgtcacgtca gaccgtgaat agagcactta   6000
aggtctgcgg gcattgaact tccacgagga cgccgaaagc ttcccagtaa atgtgccatc   6060
tcgtaggcag aaaacggttc ccccgtaggg tctctctctt ggcctccttt ctaggtcggg   6120
ctgattgctc ttgaagctct ctagggggc tcacaccata ggcagataac gttccccacc   6180
ggctcgcctc gtaagcgcac aaggactgct cccaaagatc ttcaaagcca ctgccgcgac   6240
tgccttcgcg aagccttgcc ccgcggaaat tcctccacc gagttcgtgc acaccctat   6300 gccaagcttc tttcacccta aattcgagag attggattct taccgtggaa attcttcgca   6360
aaaatcgtcc cctgatcgcc cttgcgacgt tggcgtcggt gccgctggtt gcgcttggct   6420
tgaccgactt gatcagcggc cgctcgattt                                    6450
```

<210> SEQ ID NO 59
<211> LENGTH: 6759
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: internal designation: H501 (pCliK5MCS Pgro Psod
      Pefts metA)

<400> SEQUENCE: 59

```
aaatctcgag cggcttaaag tttggctgcc atgtgaattt ttagcaccct caacagttga     60
gtgctggcac tctcggggt agagtgccaa ataggttgtt tgacacacag ttgttcaccc    120
gcgacgacgg ctgtgctgga aacccacaac cggcacacac aaaatactag tagctgccaa    180
ttattccggg cttgtgaccc gctacccgat aaataggtcg gctgaaaaat ttcgttgcaa    240
tatcaacaaa aaggcctatc attgggaggt gtcgcaccaa gtacttttgc gaagcgccat    300
ctgacggatt tcaaaagat gtatatgctc ggtgcgggt acccccccac gacaatggaa     360
ctttgacttt taaaatttca tcgccgtggg ggcttttgg gcagccagcc cgccgtgtcg    420
caacgtaatc gactgaatac ctgtacgatc acttttaga cgggcgggta gggctactgt    480
gccctaacct aagcttgtaa agcattaatt atccatacat aaggaggatc gccccgtaat    540 gcccacccte gcgccttcag gtcaacttga atccaagcg atcggtgatg tctccaccga    600
agccggagca atcattacaa acgctgaaat cgcctatcac cgctggggtg aataccgcgt    660
agataaagaa ggacgcagca atgtcgttct catcgaacac gccctcactg gagattccaa    720
cgcagccgat tggtgggctg acttgctcgg tcccggcaaa gccatcaaca ctgatatta    780 ctgcgtgatc tgtaccaacg tcatcggtgg ttgcaacggt tccaccggac ctggctccat    840
gcatccagat ggaaatttct ggggtaatcg cttcccgcc acgtccattc gtgatcaggt    900
aaacgccgaa aacaattcc tcgacgcact cggcatcacc acggtcgccg cagtacttgg    960
```

```
tggttccatg ggtggtgccc gcaccctaga gtgggccgca atgtacccag aaactgttgg   1020
cgcagctgct gttcttgcag tttctgcacg cgccagcgcc tggcaaatcg gcattcaatc   1080
cgcccaaatt aaggcgattg aaaacgacca ccactggcac gaaggcaact actacgaatc   1140
cggctgcaac ccagccaccg gactcggcgc cgcccgacgc atcgcccacc tcacctaccg   1200
tggcgaacta gaaatcgacg aacgcttcgg caccaaagcc caaaagaacg aaaacccact   1260
cggtccctac cgcaagcccg accagcgctt cgccgtggaa tcctacttgg actaccaagc   1320
agacaagcta gtacagcgtt tcgacgccgg ctcctacgtc ttgctcaccg acgccctcaa   1380
ccgccacgac attggtcgcg accgcggagg cctcaacaag gcactcgaat ccatcaaagt   1440
tccagtcctt gtcgcaggcg tagataccga tattttgtac ccctaccacc agcaagaaca   1500
cctctccaga aacctgggaa atctactggc aatggcaaaa atcgtatccc ctgtcggcca   1560
cgatgctttc ctcaccgaaa gccgccaaat ggatcgcatc gtgaggaact tcttcagcct   1620
catctcccca gacgaagaca acccttcgac ctacatcgag ttctacatct aagtcgacat   1680
cgatgctctt ctgcgttaat taacaattgg gatcctctag agttctgtga aaaacaccgt   1740
ggggcagttt ctgcttcgcg tgttttttta tttgtggggc actagacccg ggatttaaat   1800
cgctagcggg ctgctaaagg aagcggaaca cgtagaaagc cagtccgcag aaacggtgct   1860
gaccccggat gaatgtcagc tactgggcta tctggacaag ggaaaacgca agcgcaaaga   1920
gaaagcaggt agcttgcagt gggcttacat ggcgatagct agactgggcg gttttatgga   1980
cagcaagcga accggaattg ccagctgggg cgccctctgg taaggttggg aagccctgca   2040
aagtaaactg gatggctttc ttgccgccaa ggatctgatg gcgcagggga tcaagatctg   2100
atcaagagac aggatgagga tcgtttcgca tgattgaaca agatggattg cacgcaggtt   2160
ctccggccgc ttgggtggag aggctattcg gctatgactg ggcacaacag acaatcggct   2220
gctctgatgc cgccgtgttc cggctgtcag cgcaggggcg cccggttctt tttgtcaaga   2280
ccgacctgtc cggtgccctg aatgaactgc aggacgaggc agcgcggcta tcgtggctgg   2340
ccacgacggg cgttccttgc gcagctgtgc tcgacgttgt cactgaagcg ggaagggact   2400
ggctgctatt gggcgaagtg ccggggcagg atctcctgtc atctcacctt gctcctgccg   2460
agaaagtatc catcatggct gatgcaatgc ggcggctgca tacgcttgat ccggctacct   2520
gcccattcga ccaccaagcg aaacatcgca tcgagcgagc acgtactcgg atggaagccg   2580
gtcttgtcga tcaggatgat ctggacgaag agcatcaggg gctcgcgcca gccgaactgt   2640
tcgccaggct caaggcgcgc atgcccgacg gcgaggatct cgtcgtgacc catggcgatg   2700
cctgcttgcc gaatatcatg gtggaaaatg gccgcttttc tggattcatc gactgtggcc   2760
ggctgggtgt ggcggaccgc tatcaggaca tagcgttggc tacccgtgat attgctgaag   2820
agcttggcgg cgaatgggct gaccgcttcc tcgtgcttta cggtatcgcc gctcccgatt   2880
cgcagcgcat cgccttctat cgccttcttg acgagttctt ctgagcggga ctctggggtt   2940
cgaaatgacc gaccaagcga cgcccaacct gccatcacga gatttcgatt ccaccgccgc   3000
cttctatgaa aggttgggct tcggaatcgt tttccgggac gccggctgga tgatcctcca   3060
gcgcggggat ctcatgctgg agttcttcgc ccacgctagc ggcgcgccgg ccggcccggt   3120
gtgaaatacc gcacagatgc gtaaggagaa aataccgcat caggcgctct ccgcttcct   3180
cgctcactga ctcgctgcgc tcggtcgttc ggctgcggcg agcggtatca gctcactcaa   3240
aggcggtaat acgttatcc acagaatcag gggataacgc aggaaagaac atgtgagcaa   3300
aaggccagca aaaggccagg aaccgtaaaa aggccgcgtt gctggcgttt ttccataggc   3360
```

```
tccgccccce tgacgagcat cacaaaaatc gacgctcaag tcagaggtgg cgaaacccga    3420
caggactata aagataccag gcgtttcccc ctggaagctc cctcgtgcgc tctcctgttc    3480
cgaccctgcc gcttaccgga tacctgtccg cctttctccc ttcgggaagc gtggcgcttt    3540
ctcatagctc acgctgtagg tatctcagtt cggtgtaggt cgttcgctcc aagctgggct    3600
gtgtgcacga accccccgtt cagcccgacc gctgcgcctt atccggtaac tatcgtcttg    3660
agtccaaccc ggtaagacac gacttatcgc cactggcagc agccactggt aacaggatta    3720
gcagagcgag gtatgtaggc ggtgctacag agttcttgaa gtggtggcct aactacggct    3780
acactagaag gacagtattt ggtatctgcg ctctgctgaa gccagttacc ttcggaaaaa    3840
gagttggtag ctcttgatcc ggcaaacaaa ccaccgctgg tagcggtggt ttttttgttt    3900
gcaagcagca gattacgcgc agaaaaaaag gatctcaaga agatcctttg atcttttcta    3960
cggggtctga cgctcagtgg aacgaaaact cacgttaagg gattttggtc atgagattat    4020 caaaaggat cttcacctag atcctttta aggccggccg cggccgcgca aagtcccgct    4080
tcgtgaaaat tttcgtgccg cgtgattttc cgccaaaaac tttaacgaac gttcgttata    4140
atggtgtcat gaccttcacg acgaagtact aaaattggcc cgaatcatca gctatggatc    4200
tctctgatgt cgcgctggag tccgacgcgc tcgatgctgc cgtcgattta aaaacggtga    4260
tcggattttt ccgagctctc gatacgacgg acgcgccagc atcacgagac tgggccagtg    4320
ccgcgagcga cctagaaact ctcgtggcgg atcttgagga gctggctgac gagctgcgtg    4380
ctcggccagc gccaggagga cgcacagtag tggaggatgc aatcagttgc gcctactgcg    4440
gtggcctgat tcctccccgg cctgacccgc gaggacggcg cgcaaaatat tgctcagatg    4500
cgtgtcgtgc cgcagccagc cgcgagcgcg ccaacaaacg ccacgccgag gagctggagg    4560
cggctaggtc gcaaatggcg ctggaagtgc gtccccgag cgaaattttg gccatggtcg    4620
tcacagagct ggaagcggca gcgagaatta tcgcgatcgt ggcggtgccc gcaggcatga    4680
caaacatcgt aaatgccgcg tttcgtgtgc cgtggccgcc caggacgtgt cagcgccgcc    4740
accacctgca ccgaatcggc agcagcgtcg cgcgtcgaaa aagcgcacag gcggcaagaa    4800
gcgataagct gcacgaatac ctgaaaaatg ttgaacgccc cgtgagcggt aactcacagg    4860
gcgtcggcta accccagtc caaacctggg agaaagcgct caaaaatgac tctagcggat    4920
tcacgagaca ttgacacacc ggcctggaaa ttttccgctg atctgttcga cacccatccc    4980
gagctcgcgc tgcgatcacg tggctggacg agcgaagacc gccgcgaatt cctcgctcac    5040
ctgggcagag aaaatttcca gggcagcaag acccgcgact tcgccagcgc ttggatcaaa    5100
gacccggaca cggagaaaca cagccgaagt tataccgagt tggttcaaaa tcgcttgccc    5160
ggtgccagta tgttgctctg acgcacgcgc agcacgcagc cgtgcttgtc ctggacattg    5220
atgtgccgag ccaccaggcc ggcgggaaaa tcgagcacgt aaaccccgag gtctacgcga    5280
ttttggagcg ctgggcacgc ctggaaaaag cgccagcttg gatcggcgtg aatccactga    5340
gcgggaaatg ccagctcatc tggctcattg atccggtgta tgccgcagca ggcatgagca    5400
gcccgaatat gcgcctgctg gctgcaacga ccgaggaaat gacccgcgtt ttcggcgctg    5460
accaggcttt ttcacatagg ctgagccgtg gccactgcac tctccgacga tcccagccgt    5520
accgctggca tgcccagcac aatcgcgtgg atcgcctagc tgatcttatg gaggttgctc    5580
gcatgatctc aggcacagaa aaacctaaaa aacgctatga gcaggagttt tctagcggac    5640
gggcacgtat cgaagcggca agaaaagcca ctgcggaagc aaaagcactt gccacgcttg    5700
aagcaagcct gccgagcgcc gctgaagcgt ctggagagct gatcgacggc gtccgtgtcc    5760
```

```
tctggactgc tccagggcgt gccgcccgtg atgagacggc ttttcgccac gctttgactg    5820
tgggatacca gttaaaagcg gctggtgagc gcctaaaaga caccaagggt catcgagcct    5880
acgagcgtgc ctacaccgtc gctcaggcgg tcggaggagg ccgtgagcct gatctgccgc    5940
cggactgtga ccgccagacg gattggccgc gacgtgtgcg cggctacgtc gctaaaggcc    6000
agccagtcgt ccctgctcgt cagacagaga cgcagagcca gccgaggcga aaagctctgg    6060
ccactatggg aagacgtggc ggtaaaaagg ccgcagaacg ctggaaagac ccaaacagtg    6120
agtacgcccg agcacagcga gaaaaactag ctaagtccag tcaacgacaa gctaggaaag    6180
ctaaaggaaa tcgcttgacc attgcaggtt ggtttatgac tgttgaggga gagactggct    6240
cgtggccgac aatcaatgaa gctatgtctg aatttagcgt gtcacgtcag accgtgaata    6300
gagcacttaa ggtctgcggg cattgaactt ccacgaggac gccgaaagct tcccagtaaa    6360
tgtgccatct cgtaggcaga aaacggttcc cccgtagggt ctctctcttg gcctcctttc    6420
taggtcgggc tgattgctct tgaagctctc tagggggggct cacaccatag gcagataacg    6480
ttccccaccg gctcgcctcg taagcgcaca aggactgctc ccaaagatct tcaaagccac    6540
tgccgcgact gccttcgcga agccttgccc cgcggaaatt tcctccaccg agttcgtgca    6600 caccctatg ccaagcttct ttcaccctaa attcgagaga ttggattctt accgtggaaa    6660
ttcttcgcaa aaatcgtccc ctgatcgccc ttgcgacgtt ggcgtcggtg ccgctggttg    6720
cgcttggctt gaccgacttg atcagcggcc gctcgattt                          6759

<210> SEQ ID NO 60
<211> LENGTH: 6780
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: internal designation: H502 (pCliK5MCS Peftu
      Psod Pefts metA)

<400> SEQUENCE: 60
aaatctcgag ggccgttacc ctgcgaatgt ccacagggta gctggtagtt tgaaaatcaa      60
cgccgttgcc cttaggattc agtaactggc acattttgta atgcgctaga tctgtgtgct     120
cagtcttcca ggctgcttat cacagtgaaa gcaaaaccaa ttcgtggctg cgaaagtcgt     180
agccacacta gtagctgcca attattccgg gcttgtgacc cgctacccga taaataggtc     240
ggctgaaaaa tttcgttgca atatcaacaa aaaggcctat cattgggagg tgtcgcacca     300 agtactttg cgaagcgcca tctgacggat tttcaaaaga tgtatatgct cggtgcgggg     360 tacccccca cgacaatgga actttgactt ttaaaatttc atcgccgtgg gggcttttg      420 ggcagccagc ccgccgtgtc gcaacgtaat cgactgaata cctgtacgat cactttttag    480
acgggcgggt agggctactg tgccctaacc taagcttgta aagcattaat tatccataca    540
taaggaggat cgccccgtaa tgcccaccct cgcgccttca ggtcaacttg aaatccaagc    600
gatcggtgat gtctccaccg aagccggagc aatcattaca aacgctgaaa tcgcctatca    660
ccgctggggt gaataccgcg tagataaaga aggacgcagc aatgtcgttc tcatcgaaca    720
cgccctcact ggagattcca acgcagccga ttggtgggct gacttgctcg gtcccggcaa    780
agccatcaac actgatattt actgcgtgat ctgtaccaac gtcatcggtg gttgcaacgg    840
ttccaccgga cctggctcca tgcatccaga tggaaatttc tggggtaatc gcttccccgc    900
cacgtccatt cgtgatcagg taaacgccga aaaacaattc ctcgacgcac tcggcatcac    960
```

-continued

```
cacggtcgcc gcagtacttg gtggttccat gggtggtgcc cgcaccctag agtgggccgc    1020
aatgtaccca gaaactgttg gcgcagctgc tgttcttgca gtttctgcac gcgccagcgc    1080
ctggcaaatc ggcattcaat ccgcccaaat taaggcgatt gaaaacgacc accactggca    1140
cgaaggcaac tactacgaat ccggctgcaa cccagccacc ggactcggcg ccgcccgacg    1200
catcgcccac ctcacctacc gtggcgaact agaaatcgac gaacgcttcg gcaccaaagc    1260
ccaaaagaac gaaaacccac tcggtcccta ccgcaagccc gaccagcgct cgccgtgga    1320 atcctacttg gactaccaag cagacaagct agtacagcgt ttcgacgccg gctcctacgt    1380
cttgctcacc gacgccctca accgccacga cattggtcgc gaccgcggag gcctcaacaa    1440
ggcactcgaa tccatcaaag ttccagtcct tgtcgcaggc gtagataccg atattttgta    1500
cccctaccac cagcaagaac acctctccag aaacctggga aatctactgg caatggcaaa    1560
aatcgtatcc cctgtcggcc acgatgcttt cctcaccgaa agccgccaaa tggatcgcat    1620
cgtgaggaac ttcttcagcc tcatctcccc agacgaagac aacccttcga cctacatcga    1680
gttctacatc taagtcgaca tcgatgctct tctgcgttaa ttaacaattg ggatcctcta    1740
gagttctgtg aaaaacaccg tggggcagtt tctgcttcgc ggtgtttttt atttgtgggg    1800
cactagaccc gggatttaaa tcgctagcgg gctgctaaag aagcggaac acgtagaaag    1860 ccagtccgca gaaacggtgc tgaccccgga tgaatgtcag ctactgggct atctggacaa    1920
gggaaaacgc aagcgcaaag agaaagcagg tagcttgcag tgggcttaca tggcgatagc    1980
tagactgggg ggttttatgg acagcaagcg aaccggaatt gccagctggg gcgccctctg    2040
gtaaggttgg gaagccctgc aaagtaaact ggatggcttt cttgccgcca aggatctgat    2100
ggcgcagggg atcaagatct gatcaagaga caggatgagg atcgtttcgc atgattgaac    2160
aagatggatt gcacgcaggt tctccggccg cttgggtgga gaggctattc ggctatgact    2220
gggcacaaca gacaatcggc tgctctgatg ccgccgtgtt ccggctgtca gcgcaggggc    2280
gcccggttct ttttgtcaag accgacctgt ccggtgccct gaatgaactg caggacgagg    2340
cagcgcggct atcgtggctg gccacgacgg gcgttccttg cgcagctgtg ctcgacgttg    2400
tcactgaagc gggaagggac tggctgctat tgggcgaagt gccggggcag gatctcctgt    2460
catctcacct tgctcctgcc gagaaagtat ccatcatggc tgatgcaatg cggcggctgc    2520
atacgcttga tccggctacc tgcccattcg accaccaagc gaaacatcgc atcgagcgag    2580
cacgtactcg gatggaagcc ggtcttgtcg atcaggatga tctggacgaa gagcatcagg    2640
ggctcgcgcc agccgaactg ttcgccaggc tcaaggcgcg catgcccgac ggcgaggatc    2700
tcgtcgtgac ccatggcgat gcctgcttgc cgaatatcat ggtggaaaat ggccgctttt    2760
ctggattcat cgactgtggc cggctgggtg tggcggaccg ctatcaggac atagcgttgg    2820
ctacccgtga tattgctgaa gagcttggcg gcgaatgggc tgaccgcttc ctcgtgcttt    2880
acggtatcgc cgctcccgat tcgcagcgca tcgccttcta tcgccttctt gacgagttct    2940
tctgagcggg actctggggt tcgaaatgac cgaccaagcg acgcccaacc tgccatcacg    3000
agatttcgat tccaccgccg ccttctatga aaggttgggc ttcggaatcg ttttccggga    3060
cgccggctgg atgatcctcc agcgcgggga tctcatgctg gagttcttcg cccacgctag    3120
cggcgcgccg gccggcccgg tgtgaaatac cgcacagatg cgtaaggaga aaataccgca    3180
tcaggcgctc ttccgcttcc tcgctcactg actcgctgcg ctcggtcgtt cggctgcggc    3240
gagcggtatc agctcactca aaggcggtaa tacggttatc cacagaatca ggggataacg    3300
caggaaagaa catgtgagca aaaggccagc aaaaggccag gaaccgtaaa aaggccgcgt    3360
```

```
tgctggcgtt tttccatagg ctccgccccc ctgacgagca tcacaaaaat cgacgctcaa   3420
gtcagaggtg gcgaaacccg acaggactat aaagatacca ggcgtttccc cctggaagct   3480
ccctcgtgcg ctctcctgtt ccgaccctgc cgcttaccgg atacctgtcc gcctttctcc   3540
cttcgggaag cgtggcgctt tctcatagct cacgctgtag gtatctcagt tcggtgtagg   3600
tcgttcgctc caagctgggc tgtgtgcacg aaccccccgt tcagcccgac cgctgcgcct   3660
tatccggtaa ctatcgtctt gagtccaacc cggtaagaca cgacttatcg ccactggcag   3720
cagccactgg taacaggatt agcagagcga ggtatgtagg cggtgctaca gagttcttga   3780
agtggtggcc taactacggc tacactagaa ggacagtatt tggtatctgc gctctgctga   3840
agccagttac cttcggaaaa agagttggta gctcttgatc cggcaaacaa accaccgctg   3900
gtagcggtgg ttttttttgtt tgcaagcagc agattacgcg cagaaaaaaa ggatctcaag   3960
aagatccttt gatcttttct acggggtctg acgctcagtg gaacgaaaac tcacgttaag   4020
ggattttggt catgagatta tcaaaaagga tcttcaccta gatccttttta aaggccggcc   4080 gcggccgcgc aaagtcccgc ttcgtgaaaa ttttcgtgcc gcgtgatttt ccgccaaaaa   4140
ctttaacgaa cgttcgttat aatggtgtca tgaccttcac gacgaagtac taaaattggc   4200
ccgaatcatc agctatggat ctctctgatg tcgcgctgga gtccgacgcg ctcgatgctg   4260
ccgtcgattt aaaaacggtg atcggatttt tccgagctct cgatacgacg gacgcgccag   4320
catcacgaga ctgggccagt gccgcgagcg acctagaaac tctcgtggcg gatcttgagg   4380
agctggctga cgagctgcgt gctcggccag cgccaggagg acgcacagta gtggaggatg   4440
caatcagttg cgcctactgc ggtggcctga ttcctccccg gcctgacccg cgaggacggc   4500
gcgcaaaata ttgctcagat gcgtgtcgtg ccgcagccag ccgcgagcgc gccaacaaac   4560
gccacgccga ggagctggag gcggctaggt cgcaaatggc gctggaagtg cgtccccga   4620 gcgaaatttt ggccatggtc gtcacagagc tggaagcggc agcgagaatt atcgcgatcg   4680
tggcggtgcc cgcaggcatg acaaacatcg taaatgccgc gtttcgtgtg ccgtggccgc   4740
ccaggacgtg tcagcgccgc caccacctgc accgaatcgg cagcagcgtc gcgcgtcgaa   4800
aaagcgcaca ggcggcaaga agcgataagc tgcacgaata cctgaaaaat gttgaacgcc   4860
ccgtgagcgg taactcacag ggcgtcggct aaccccccagt ccaaacctgg gagaaagcgc   4920
tcaaaaatga ctctagcgga ttcacagagac attgacacac cggcctggaa attttccgct   4980
gatctgttcg acacccatcc cgagctcgcg ctgcgatcac gtggctggac gagcgaagac   5040
cgccgcgaat tcctcgctca cctgggcaga gaaaatttcc agggcagcaa gacccgcgac   5100
ttcgccagcg cttggatcaa agacccggac acggagaaac acagccgaag ttataccgag   5160
ttggttcaaa atcgcttgcc cggtgccagt atgttgctct gacgcacgcg cagcacgcag   5220
ccgtgcttgt cctggacatt gatgtgccga gccaccaggc cggcgggaaa atcgagcacg   5280
taaaccccga ggtctacgcg atttttggagc gctgggcacg cctggaaaaa gcgccagctt   5340
ggatcggcgt gaatccactg agcgggaaat gccagctcat ctggctcatt gatccggtgt   5400
atgccgcagc aggcatgagc agcccgaata tgcgcctgct ggctgcaacg accgaggaaa   5460
tgacccgcgt tttcggcgct gaccaggctt tttcacatag gctgagccgt ggccactgca   5520
ctctccgacg atcccagccg taccgctggc atgcccagca caatcgcgtg gatcgcctag   5580
ctgatcttat ggaggttgct cgcatgatct caggcacaga aaaacctaaa aaacgctatg   5640
agcaggagtt ttctagcgga cgggcacgta tcgaagcgga aagaaaagcc actgcgaag    5700 caaaagcact tgccacgctt gaagcaagcc tgccgagcgc cgctgaagcg tctggagagc   5760
```

-continued

```
tgatcgacgg cgtccgtgtc ctctggactg ctccagggcg tgccgcccgt gatgagacgg    5820
cttttcgcca cgctttgact gtgggatacc agttaaaagc ggctggtgag cgcctaaaag    5880
acaccaaggg tcatcgagcc tacgagcgtg cctacaccgt cgctcaggcg gtcggaggag    5940
gccgtgagcc tgatctgccg ccggactgtg accgccagac ggattggccg cgacgtgtgc    6000
gcggctacgt cgctaaaggc cagccagtcg tccctgctcg tcagacagag acgcagagcc    6060
agccgaggcg aaaagctctg gccactatgg gaagacgtgg cggtaaaaag gccgcagaac    6120
gctggaaaga cccaaacagt gagtacgccc gagcacagcg agaaaaacta gctaagtcca    6180
gtcaacgaca agctaggaaa gctaaaggaa atcgcttgac cattgcaggt tggtttatga    6240
ctgttgaggg agagactggc tcgtggccga caatcaatga agctatgtct gaatttagcg    6300
tgtcacgtca gaccgtgaat agagcactta aggtctgcgg gcattgaact tccacgagga    6360
cgccgaaagc ttcccagtaa atgtgccatc tcgtaggcag aaaacggttc ccccgtaggg    6420
tctctctctt ggcctccttt ctaggtcggg ctgattgctc ttgaagctct ctaggggggc    6480
tcacaccata ggcagataac gttccccacc ggctcgcctc gtaagcgcac aaggactgct    6540
cccaaagatc ttcaaagcca ctgccgcgac tgccttcgcg aagccttgcc ccgcggaaat    6600
ttcctccacc gagttcgtgc acaccccttat gccaagcttc tttcacccta aattcgagag    6660
attggattct taccgtggaa attcttcgca aaaatcgtcc cctgatcgcc cttgcgacgt    6720
tggcgtcggt gccgctggtt gcgcttggct tgaccgactt gatcagcggc cgctcgattt    6780
```

<210> SEQ ID NO 61
<211> LENGTH: 35
<212> TYPE: DNA
<213> ORGANISM: Artificial Sequence
<220> FEATURE:
<223> OTHER INFORMATION: Primer

<400> SEQUENCE: 61

```
gagagagaga cgcgtcccag tggctgagac gcatc                                35
```

<210> SEQ ID NO 62
<211> LENGTH: 34
<212> TYPE: DNA
<213> ORGANISM: Artificial Sequence
<220> FEATURE:
<223> OTHER INFORMATION: Primer

<400> SEQUENCE: 62

```
ctctctctgt cgacgaattc aatcttacgg cctg                                 34
```

<210> SEQ ID NO 63
<211> LENGTH: 4323
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: internal designation: pCLiK5 MCS integrativ
      SacB (also referred to as pCIS)
<220> FEATURE:
<221> NAME/KEY: misc_feature
<222> LOCATION: (457)..(1248)
<223> OTHER INFORMATION: KanR
<220> FEATURE:
<221> NAME/KEY: misc_feature
<222> LOCATION: (3840)..(4302)
<223> OTHER INFORMATION: PsacB (complementary)
<220> FEATURE:
<221> NAME/KEY: misc_feature
<222> LOCATION: (2418)..(3839)
<223> OTHER INFORMATION: SacB (complementary)
<220> FEATURE:
<221> NAME/KEY: misc_feature
<222> LOCATION: (1515)..(2375)
<223> OTHER INFORMATION: Ori-Ec (pMB) (complementary)

<400> SEQUENCE: 63

```
tcgagaggcc tgacgtcggg cccggtacca cgcgtcatat gactagttcg gacctaggga      60
tatcgtcgac atcgatgctc ttctgcgtta attaacaatt gggatcctct agacccggga     120
tttaaatcgc tagcgggctg ctaaaggaag cggaacacgt agaaagccag tccgcagaaa     180
cggtgctgac cccggatgaa tgtcagctac tgggctatct ggacaaggga aaacgcaagc     240
gcaaagagaa agcaggtagc ttgcagtggg cttacatggc gatagctaga ctgggcggtt     300
ttatggacag caagcgaacc ggaattgcca gctggggcgc cctctggtaa ggttgggaag     360
ccctgcaaag taaactggat ggctttcttg ccgccaagga tctgatggcg caggggatca     420
agatctgatc aagagacagg atgaggatcg tttcgcatga ttgaacaaga tggattgcac     480
gcaggttctc cggccgcttg ggtggagagg ctattcggct atgactgggc acaacagaca     540
atcggctgct ctgatgccgc cgtgttccgg ctgtcagcgc aggggcgccc ggttcttttt     600
gtcaagaccg acctgtccgg tgccctgaat gaactgcagg acgaggcagc gcggctatcg     660
tggctggcca cgacgggcgt tccttgcgca gctgtgctcg acgttgtcac tgaagcggga     720
agggactggc tgctattggg cgaagtgccg gggcaggatc tcctgtcatc tcaccttgct     780
cctgccgaga aagtatccat catggctgat gcaatgcggc ggctgcatac gcttgatccg     840
gctacctgcc cattcgacca ccaagcgaaa catcgcatcg agcgagcacg tactcggatg     900
gaagccggtc ttgtcgatca ggatgatctg gacgaagagc atcaggggct cgcgccagcc     960
gaactgttcg ccaggctcaa ggcgcgcatg cccgacggcg aggatctcgt cgtgacccat    1020
ggcgatgcct gcttgccgaa tatcatggtg gaaaatggcc gcttttctgg attcatcgac    1080
tgtggccggc tgggtgtggc ggaccgctat caggacatag cgttggctac ccgtgatatt    1140
gctgaagagc ttggcggcga atgggctgac cgcttcctcg tgctttacgg tatcgccgct    1200
cccgattcgc agcgcatcgc cttctatcgc cttcttgacg agttcttctg agcgggactc    1260
tggggttcga aatgaccgac caagcgacgc ccaacctgcc atcacgagat ttcgattcca    1320
ccgccgcctt ctatgaaagg ttgggcttcg gaatcgtttt ccgggacgcc ggctggatga    1380
tcctccagcg cggggatctc atgctggagt tcttcgccca cgctagcggc gcgcggccg    1440
gcccggtgtg aaataccgca cagatgcgta aggagaaaat accgcatcag gcgctcttcc    1500
gcttcctcgc tcactgactc gctgcgctcg gtcgttcggc tgcggcgagc ggtatcagct    1560
cactcaaagg cggtaatacg gttatccaca gaatcagggg ataacgcagg aaagaacatg    1620
tgagcaaaag gccagcaaaa ggccaggaac cgtaaaaagg ccgcgttgct ggcgtttttc    1680
cataggctcc gccccctga cgagcatcac aaaaatcgac gctcaagtca gaggtggcga    1740
aacccgacag gactataaag ataccaggcg tttccccctg gaagctccct cgtgcgctct    1800
cctgttccga ccctgccgct taccggatac ctgtccgcct ttctcccttc gggaagcgtg    1860
gcgctttctc atagctcacg ctgtaggtat ctcagttcgg tgtaggtcgt tcgctccaag    1920
ctgggctgtg tgcacgaacc ccccgttcag cccgaccgct gcgccttatc cggtaactat    1980
cgtcttgagt ccaacccggt aagacacgac ttatcgccac tggcagcagc cactggtaac    2040
aggattagca gagcgaggta tgtaggcggt gctacagagt tcttgaagtg gtggcctaac    2100
tacggctaca ctagaaggac agtatttggt atctgcgctc tgctgaagcc agttaccttc    2160
```

```
ggaaaaagag ttggtagctc ttgatccggc aaacaaacca ccgctggtag cggtggtttt    2220
tttgtttgca agcagcagat tacgcgcaga aaaaaggat ctcaagaaga tcctttgatc    2280
ttttctacgg ggtctgacgc tcagtggaac gaaaactcac gttaagggat tttggtcatg    2340
agattatcaa aaaggatctt cacctagatc cttttaaagg ccggccgcgg ccgccatcgg    2400
cattttcttt tgcgttttta tttgttaact gttaattgtc cttgttcaag gatgctgtct    2460
ttgacaacag atgttttctt gcctttgatg ttcagcagga agctcggcgc aaacgttgat    2520
tgtttgtctg cgtagaatcc tctgtttgtc atatagcttg taatcacgac attgtttcct    2580
ttcgcttgag gtacagcgaa gtgtgagtaa gtaaggtta catcgttagg atcaagatcc    2640 attttaaca aaggccagt tttgttcagc ggcttgtatg ggccagttaa agaattagaa    2700
acataaccaa gcatgtaaat atcgttagac gtaatgccgt caatcgtcat ttttgatccg    2760
cgggagtcag tgaacaggta ccatttgccg ttcattttaa agacgttcgc gcgttcaatt    2820
tcatctgtta ctgtgttaga tgcaatcagc ggtttcatca ctttttttcag tgtgtaatca    2880 tcgtttagct caatcatacc gagagcgccg tttgctaact cagccgtgcg tttttttatcg    2940 cttttgcagaa gttttttgact ttcttgacgg aagaatgatg tgcttttgcc atagtatgct    3000
ttgttaaata aagattcttc gccttggtag ccatcttcag ttccagtgtt tgcttcaaat    3060
actaagtatt tgtggccttt atcttctacg tagtgaggat ctctcagcgt atggttgtcg    3120
cctgagctgt agttgccttc atcgatgaac tgctgtacat tttgatacgt ttttccgtca    3180
ccgtcaaaga ttgattttata atcctctaca ccgttgatgt tcaaagagct gtctgatgct    3240
gatacgttaa cttgtgcagt tgtcagtgtt tgtttgccgt aatgtttacc ggagaaatca    3300
gtgtagaata aacggatttt tccgtcagat gtaaatgtgg ctgaacctga ccattcttgt    3360
gtttggtctt ttaggataga atcatttgca tcgaatttgt cgctgtcttt aaagacgcgg    3420
ccagcgtttt tccagctgtc aatagaagtt tcgccgactt tttgatagaa catgtaaatc    3480
gatgtgtcat ccgcattttt aggatctccg gctaatgcaa agacgatgtg gtagccgtga    3540
tagtttgcga cagtgccgtc agcgttttgt aatggccagc tgtcccaaac gtccaggcct    3600
tttgcagaag agatatttttt aattgtggac gaatcaaatt cagaaacttg atattttca    3660 ttttttgct gttcagggat ttgcagcata tcatggcgtg taatatggga aatgccgtat    3720
gtttccttat atggcttttg gttcgtttct ttcgcaaacg cttgagttgc gcctcctgcc    3780
agcagtgcgg tagtaaaggt taatactgtt gcttgttttg caaacttttt gatgttcatc    3840
gttcatgtct ccttttttat gtactgtgtt agcggtctgc ttcttccagc cctcctgttt    3900
gaagatggca agttagttac gcacaataaa aaaagaccta aaatatgtaa ggggtgacgc    3960
caaagtatac actttgccct ttacacattt taggtcttgc ctgctttatc agtaacaaac    4020
ccgcgcgatt tacttttcga cctcattcta ttagactctc gtttggattg caactggtct    4080
attttcctct tttgtttgat agaaaatcat aaaaggattt gcagactacg ggcctaaaga    4140
actaaaaaat ctatctgttt cttttcattc tctgtatttt ttatagtttc tgttgcatgg    4200
gcataaagtt gcctttttaa tcacaattca gaaaatatca taatatctca tttcactaaa    4260
taatagtgaa cggcaggtat atgtgatggg ttaaaaagga tcggcggccg ctcgatttaa    4320
atc                                                                  4323
```

<210> SEQ ID NO 64
<211> LENGTH: 5860
<212> TYPE: DNA
<213> ORGANISM: Artificial Sequence

```
<220> FEATURE:
<223> OTHER INFORMATION: Plasmid
<220> FEATURE:
<221> NAME/KEY: misc_feature
<222> LOCATION: (155)..(1420)
<223> OTHER INFORMATION: lysC
<220> FEATURE:
<221> NAME/KEY: misc_feature
<222> LOCATION: (3935)..(5356)
<223> OTHER INFORMATION: sacB (Bacillus subtilis)
<220> FEATURE:
<221> NAME/KEY: misc_feature
<222> LOCATION: (5357)..(5819)
<223> OTHER INFORMATION: Promotor sacB complement
<220> FEATURE:
<221> NAME/KEY: misc_feature
<222> LOCATION: (1974)..(2765)
<223> OTHER INFORMATION: kanR
<220> FEATURE:
<221> NAME/KEY: misc_feature
<222> LOCATION: (3032)..(3892)
<223> OTHER INFORMATION: Ori-EC  complement
<220> FEATURE:
<221> NAME/KEY: misc_feature
<222> LOCATION: (3913)..(3934)
<223> OTHER INFORMATION: sacB downstream region (complement)

<400> SEQUENCE: 64
cccggtacca cgcgtcccag tggctgagac gcatccgcta aagccccagg aaccctgtgc      60
agaaagaaaa cactcctctg ctaggtagaa cacagtttat aaaggtagag ttgagcgggt     120
aactgtcagc acgtagatcg aaaggtgcac aaaggtggcc ctggtcgtac agaaatatgg     180
cggttcctcg cttgagagtg cggaacgcat tagaaacgtc gctgaacgga tcgttgccac     240
caagaaggct ggaaatgatg tcgtggttgt ctgctccgca atgggagaca ccacggatga     300
acttctagaa cttgcagcgg cagtgaatcc cgttccgcca gctcgtgaaa tggatatgct     360
cctgactgct ggtgagcgta tttctaacgc tctcgtcgcc atggctattg agtcccttgg     420
cgcagaagcc caatctttca cgggctctca ggctggtgtg ctcaccaccg agcgccacgg     480
aaacgcacgc attgttgatg tcactccagg tcgtgtgcgt gaagcactcg atgagggcaa     540
gatctgcatt gttgctggtt tccagggtgt taataaagaa accgcgatgt caccacgtt      600 gggtcgtggt ggttctgaca ccactgcagt tgcgttggca gctgctttga acgctgatgt     660
gtgtgagatt tactcggacg ttgacggtgt gtataccgct gacccgcgca tcgttcctaa     720
tgcacagaag ctggaaaagc tcagcttcga agaaatgctg gaacttgctg ctgttggctc     780
caagattttg gtgctgcgca gtgttgaata cgctcgtgca ttcaatgtgc acttcgcgt      840 acgctcgtct tatagtaatg atcccggcac tttgattgcc ggctctatgg aggatattcc     900
tgtggaagaa gcagtcctta ccggtgtcgc aaccgacaag tccgaagcca agtaaccgt      960 tctgggtatt tccgataagc caggcgaggc tgcgaaggtt ttccgtgcgt tggctgatgc    1020
agaaatcaac attgacatgg ttctgcagaa cgtctcttct gtagaagacg gcaccaccga    1080
catcaccttc acctgccctc gttccgacgg ccgccgcgcg atggagatct tgaagaagct    1140
tcaggttcag ggcaactgga ccaatgtgct ttacgacgac caggtcggca agtctccct     1200 cgtgggtgct ggcatgaagt ctcacccagg tgttaccgca gagttcatgg aagctctgcg    1260
cgatgtcaac gtgaacatcg aattgatttc cacctctgag attcgtattt ccgtgctgat    1320
ccgtgaagat gatctggatg ctgctgcacg tgcattgcat gagcagttcc agctgggcgg    1380
cgaagacgaa gccgtcgttt atgcaggcac cggacgctaa agttttaaag gagtagtttt    1440
acaatgacca ccatcgcagt tgttggtgca accggccagg tcggccaggt tatgcgcacc    1500
cttttggaag agcgcaattt cccagctgac actgttcgtt tctttgcttc cccacgttcc    1560
```

```
gcaggccgta agattgaatt cgtcgacatc gatgctcttc tgcgttaatt aacaattggg    1620
atcctctaga cccgggattt aaatcgctag cgggctgcta aaggaagcgg aacacgtaga    1680
aagccagtcc gcagaaacgg tgctgacccc ggatgaatgt cagctactgg gctatctgga    1740
caagggaaaa cgcaagcgca aagagaaagc aggtagcttg cagtgggctt acatggcgat    1800
agctagactg ggcggtttta tggacagcaa gcgaaccgga attgccagct ggggcgccct    1860
ctggtaaggt tgggaagccc tgcaaagtaa actggatggc tttcttgccg ccaaggatct    1920
gatggcgcag gggatcaaga tctgatcaag agacaggatg aggatcgttt cgcatgattg    1980
aacaagatgg attgcacgca ggttctccgg ccgcttgggt ggagaggcta ttcggctatg    2040
actgggcaca acagacaatc ggctgctctg atgccgccgt gttccggctg tcagcgcagg    2100
ggcgcccggt tctttttgtc aagaccgacc tgtccggtgc cctgaatgaa ctgcaggacg    2160
aggcagcgcg gctatcgtgg ctggccacga cgggcgttcc ttgcgcagct gtgctcgacg    2220
ttgtcactga agcgggaagg gactggctgc tattgggcga agtgccgggg caggatctcc    2280
tgtcatctca ccttgctcct gccgagaaag tatccatcat ggctgatgca atgcggcggc    2340
tgcatacgct tgatccggct acctgcccat tcgaccacca agcgaaacat cgcatcgagc    2400
gagcacgtac tcggatggaa gccggtcttg tcgatcagga tgatctggac gaagagcatc    2460
aggggctcgc gccagccgaa ctgttcgcca ggctcaaggc gcgcatgccc gacggcgagg    2520
atctcgtcgt gacccatggc gatgcctgct tgccgaatat catggtggaa aatggccgct    2580
tttctggatt catcgactgt ggccggctgg gtgtggcgga ccgctatcag gacatagcgt    2640
tggctacccg tgatattgct gaagagcttg gcggcgaatg ggctgaccgc ttcctcgtgc    2700
tttacggtat cgccgctccc gattcgcagc gcatcgcctt ctatcgcctt cttgacgagt    2760
tcttctgagc gggactctgg ggttcgaaat gaccgaccaa gcgacgccca acctgccatc    2820
acgagatttc gattccaccg ccgccttcta tgaaaggttg gcttcggaa tcgttttccg    2880 ggacgccggc tggatgatcc tccagcgcgg ggatctcatg ctggagttct cgcccacgc    2940 tagcggcgcg ccgccggcc cggtgtgaaa taccgcacag atgcgtaagg agaaaatacc    3000
gcatcaggcg ctcttccgct tcctcgctca ctgactcgct gcgctcggtc gttcggctgc    3060
ggcgagcggt atcagctcac tcaaaggcgg taatacggtt atccacagaa tcaggggata    3120
acgcaggaaa gaacatgtga gcaaaaggcc agcaaaaggc caggaaccgt aaaaaggccg    3180
cgttgctggc gtttttccat aggctccgcc cccctgacga gcatcacaaa aatcgacgct    3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta gaaggacagt atttggtatc tgcgctctgc    3660
tgaagccagt taccttcgga aaaagagttg gtagctcttg atccggcaaa caaaccaccg    3720
ctggtagcgg tggttttttt gtttgcaagc agcagattac gcgcagaaaa aaggatctc    3780 aagaagatcc tttgatcttt tctacggggt ctgacgctca gtggaacgaa aactcacgtt    3840
aagggatttt ggtcatgaga ttatcaaaaa ggatcttcac ctagatcctt ttaaaggccg    3900
gccgcggccg ccatcggcat tttcttttgc gttttatt gttaactgtt aattgtcctt    3960
```

```
gttcaaggat gctgtctttg acaacagatg ttttcttgcc tttgatgttc agcaggaagc  4020
tcggcgcaaa cgttgattgt ttgtctgcgt agaatcctct gtttgtcata tagcttgtaa  4080
tcacgacatt gtttcctttc gcttgaggta cagcgaagtg tgagtaagta aaggttacat  4140
cgttaggatc aagatccatt tttaacacaa ggccagtttt gttcagcggc ttgtatgggc  4200
cagttaaaga attagaaaca taaccaagca tgtaaatatc gttagacgta atgccgtcaa  4260
tcgtcatttt tgatccgcgg gagtcagtga acaggtacca tttgccgttc attttaaaga  4320
cgttcgcgcg ttcaatttca tctgttactg tgttagatgc aatcagcggt ttcatcactt  4380
ttttcagtgt gtaatcatcg tttagctcaa tcataccgag agcgccgttt gctaactcag  4440
ccgtgcgttt tttatcgctt tgcagaagtt tttgactttc ttgacggaag aatgatgtgc  4500
ttttgccata gtatgctttg ttaaataaag attcttcgcc ttggtagcca tcttcagttc  4560
cagtgtttgc ttcaaatact aagtatttgt ggcctttatc ttctacgtag tgaggatctc  4620
tcagcgtatg gttgtcgcct gagctgtagt tgccttcatc gatgaactgc tgtacatttt  4680
gatacgtttt tccgtcaccg tcaaagattg atttataatc ctctacaccg ttgatgttca  4740
aagagctgtc tgatgctgat acgttaactt gtgcagttgt cagtgtttgt ttgccgtaat  4800
gtttaccgga gaaatcagtg tagaataaac ggattttttcc gtcagatgta aatgtggctg  4860
aacctgacca ttcttgtgtt tggtctttta ggatagaatc atttgcatcg aatttgtcgc  4920
tgtctttaaa gacgcggcca gcgttttttcc agctgtcaat agaagtttcg ccgactttt  4980 gatagaacat gtaaatcgat gtgtcatccg cattttttagg atctccggct aatgcaaaga  5040
cgatgtggta gccgtgatag tttgcgacag tgccgtcagc gttttgtaat ggccagctgt  5100
cccaaacgtc caggccttt gcagaagaga tattttttaat tgtggacgaa tcaaattcag  5160
aaacttgata tttttcattt ttttgctgtt cagggatttg cagcatatca tggcgtgtaa  5220
tatgggaaat gccgtatgtt tccttatatg gcttttggtt cgtttctttc gcaaacgctt  5280
gagttgcgcc tcctgccagc agtgcggtag taaaggttaa tactgttgct tgttttgcaa  5340 acttttttgat gttcatcgtt catgtctcct tttttatgta ctgtgttagc ggtctgcttc  5400
ttccagccct cctgtttgaa gatggcaagt tagttacgca caataaaaaa agacctaaaa  5460
tatgtaaggg gtgacgccaa agtatacact ttgcccttta cacattttag gtcttgcctg  5520
ctttatcagt aacaaacccg cgcgatttac ttttcgacct cattctatta gactctcgtt  5580
tggattgcaa ctggtctatt ttcctctttt gtttgataga aaatcataaa aggatttgca  5640
gactacgggc ctaaagaact aaaaaatcta tctgtttctt ttcattctct gtatttttta  5700
tagtttctgt tgcatgggca taaagttgcc tttttaatca caattcagaa aatatcataa  5760
tatctcattt cactaaataa tagtgaacgg caggtatatg tgatgggtta aaaaggatcg  5820
gcggccgctc gatttaaatc tcgagaggcc tgacgtcggg  5860
```

<210> SEQ ID NO 65
<211> LENGTH: 38
<212> TYPE: DNA
<213> ORGANISM: Artificial Sequence
<220> FEATURE:
<223> OTHER INFORMATION: Primer

<400> SEQUENCE: 65
cggcaccacc gacatcatct tcacctgccc tcgttccg                            38

<210> SEQ ID NO 66
<211> LENGTH: 38

<212> TYPE: DNA
<213> ORGANISM: Artificial Sequence
<220> FEATURE:
<223> OTHER INFORMATION: Primer

<400> SEQUENCE: 66
cggaacgagg gcaggtgaag atgatgtcgg tggtgccg                38

<210> SEQ ID NO 67
<211> LENGTH: 1263
<212> TYPE: DNA
<213> ORGANISM: Corynebacterium glutamicum
<220> FEATURE:
<221> NAME/KEY: misc_feature
<223> OTHER INFORMATION: lysC gene

<400> SEQUENCE: 67
gtggccctgg tcgtacagaa atatggcggt tcctcgcttg agagtgcgga acgcattaga     60
aacgtcgctg aacggatcgt tgccaccaag aaggctggaa atgatgtcgt ggttgtctgc    120
tccgcaatgg agacaccac ggatgaactt ctagaacttg cagcggcagt gaatcccgtt    180
ccgccagctc gtgaaatgga tatgctcctg actgctggtg agcgtatttc taacgctctc    240
gtcgccatgg ctattgagtc ccttggcgca gaagcccaat cttttacggg ctctcaggct    300
ggtgtgctca ccaccgagcg ccacggaaac gcacgcattg ttgatgtcac tccaggtcgt    360
gtgcgtgaag cactcgatga gggcaagatc tgcattgttg ctggtttcca gggtgttaat    420
aaagaaaccc gcgatgtcac cacgttgggt cgtggtggtt ctgacaccac tgcagttgcg    480
ttggcagctg cttttgaacg ctgatgtgtgt gagatttact cggacgttga cggtgtgtat    540
accgctgacc cgcgcatcgt tcctaatgca cagaagctgg aaaagctcag cttcgaagaa    600
atgctggaac ttgctgctgt tggctccaag attttggtgc tgcgcagtgt tgaatacgct    660
cgtgcattca atgtgccact tcgcgtacgc tcgtcttata gtaatgatcc cggcacttg     720 attgccggct ctatggagga tattcctgtg gaagaagcag tccttaccgg tgtcgcaacc    780
gacaagtccg aagccaaagt aaccgttctg ggtatttccg ataagccagg cgaggctgcg    840
aaggttttcc gtgcgttggc tgatgcagaa atcaacattg acatggttct gcagaacgtc    900
tcttctgtag aagacggcac caccgacatc accttcacct gccctcgttc cgacggccgc    960
cgcgcgatgg agatcttgaa gaagcttcag gttcagggca actggaccaa tgtgctttac    1020
gacgaccagg tcggcaaagt ctccctcgtg ggtgctggca tgaagtctca cccaggtgtt    1080
accgcagagt tcatggaagc tctgcgcgat gtcaacgtga acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgc                                                                  1263

<210> SEQ ID NO 68
<211> LENGTH: 5860
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: internal designation: pCIS sysC thr311ile
<220> FEATURE:
<221> NAME/KEY: misc_feature
<222> LOCATION: (155)..(1420)
<223> OTHER INFORMATION: lysC
<220> FEATURE:
<221> NAME/KEY: misc_feature

```
<222> LOCATION: (3935)..(5356)
<223> OTHER INFORMATION: sacB (Bacillus subtilis) complement
<220> FEATURE:
<221> NAME/KEY: misc_feature
<222> LOCATION: (5357)..(5819)
<223> OTHER INFORMATION: Promotor sacB complement
<220> FEATURE:
<221> NAME/KEY: misc_feature
<222> LOCATION: (1974)..(2765)
<223> OTHER INFORMATION: kanR
<220> FEATURE:
<221> NAME/KEY: misc_feature
<222> LOCATION: (3032)..(3892)
<223> OTHER INFORMATION: ori-EC complement

<400> SEQUENCE: 68
cccggtacca cgcgtcccag tggctgagac gcatccgcta aagccccagg aaccctgtgc      60
agaaagaaaa cactcctctg gctaggtaga cacagtttat aaaggtagag ttgagcgggt     120
aactgtcagc acgtagatcg aaaggtgcac aaaggtggcc ctggtcgtac agaaatatgg     180
cggttcctcg cttgagagtg cggaacgcat agaaacgtc gctgaacgga tcgttgccac      240
caagaaggct ggaaatgatg tcgtggttgt ctgctccgca atgggagaca ccacggatga     300
acttctagaa cttgcagcgg cagtgaatcc cgttccgcca gctcgtgaaa tggatatgct     360
cctgactgct ggtgagcgta tttctaacgc tctcgtcgcc atggctattg agtcccttgg     420
cgcagaagcc caatctttca cgggctctca ggctggtgtg ctcaccaccg agcgccacgg     480
aaacgcacgc attgttgatg tcactccagg tcgtgtgcgt gaagcactcg atgagggcaa     540
gatctgcatt gttgctggtt ccagggtgt taataaagaa acccgcgatg tcaccacgtt      600
gggtcgtggt ggttctgaca ccactgcagt tgcgttggca gctgctttga cgctgatgt      660
gtgtgagatt tactcggacg ttgacggtgt gtataccgct gacccgcgca tcgttcctaa     720
tgcacagaag ctggaaaagc tcagcttcga agaaatgctg gaacttgctg ctgttggctc     780
caagattttg gtgctgcgca gtgttgaata cgctcgtgca ttcaatgtgc cacttcgcgt     840
acgctcgtct tatagtaatg atcccggcac tttgattgcc ggctctatgg aggatattcc     900
tgtggaagaa gcagtcctta ccggtgtcgc aaccgacaag tccgaagcca agtaaccgt      960
tctgggtatt tccgataagc caggcgaggc tgcgaaggtt ttccgtgcgt tggctgatgc    1020
agaaatcaac attgacatgg ttctgcagaa cgtctcttct gtagaagacg gcaccaccga    1080
catcatcttc acctgccctc gttccgacgg ccgccgcgcg atggagatct tgaagaagct    1140
tcaggttcag ggcaactgga ccaatgtgct ttacgacgac caggtcggca aagtctccct    1200
cgtgggtgct ggcatgaagt ctcacccagg tgttaccgca gagttcatgg aagctctgcg    1260
cgatgtcaac gtgaacatcg aattgatttc cacctctgag attcgtattt ccgtgctgat    1320
ccgtgaagat gatctggatg ctgctgcacg tgcattgcat gagcagttcc agctgggcgg    1380
cgaagacgaa gccgtcgttt atgcaggcac cggacgctaa agttttaaag gagtagtttt    1440
acaatgacca ccatcgcagt tgttggtgca accggccagg tcggccaggt tatgcgcacc    1500
cttttggaag agcgcaattt cccagctgac actgttcgtt tctttgcttc cccacgttcc    1560
gcaggccgta agattgaatt cgtcgacatc gatgctcttc tgcgttaatt aacaattggg    1620
atcctctaga cccgggattt aaatcgctag cgggctgcta aggaagcgg aacacgtaga     1680
aagccagtcc gcagaaacgg tgctgacccc ggatgaatgt cagctactgg gctatctgga    1740
caagggaaaa cgcaagcgca aagagaaagc aggtagcttg cagtgggctt acatggcgat    1800
agctagactg ggcggtttta tggacagcaa gcgaaccgga attgccagct ggggcgccct    1860
ctggtaaggt tgggaagccc tgcaaagtaa actggatggc tttcttgccg ccaaggatct    1920
```

```
gatggcgcag gggatcaaga tctgatcaag agacaggatg aggatcgttt cgcatgattg    1980
aacaagatgg attgcacgca ggttctccgg ccgcttgggt ggagaggcta ttcggctatg    2040
actgggcaca acagacaatc ggctgctctg atgccgccgt gttccggctg tcagcgcagg    2100
ggcgcccggt tctttttgtc aagaccgacc tgtccggtgc cctgaatgaa ctgcaggacg    2160
aggcagcgcg gctatcgtgg ctggccacga cgggcgttcc ttgcgcagct gtgctcgacg    2220
ttgtcactga agcgggaagg gactggctgc tattgggcga agtgccgggg caggatctcc    2280
tgtcatctca ccttgctcct gccgagaaag tatccatcat ggctgatgca atgcggcggc    2340
tgcatacgct tgatccggct acctgcccat tcgaccacca agcgaaacat cgcatcgagc    2400
gagcacgtac tcggatggaa gccggtcttg tcgatcagga tgatctggac gaagagcatc    2460
aggggctcgc gccagccgaa ctgttcgcca ggctcaaggc gcgcatgccc gacggcgagg    2520
atctcgtcgt gacccatggc gatgcctgct tgccgaatat catggtggaa aatggccgct    2580
tttctggatt catcgactgt ggccggctgg gtgtggcgga ccgctatcag gacatagcgt    2640
tggctacccg tgatattgct gaagagcttg gcggcgaatg ggctgaccgc ttcctcgtgc    2700
tttacggtat cgccgctccc gattcgcagc gcatcgcctt ctatcgcctt cttgacgagt    2760
tcttctgagc gggactctgg ggttcgaaat gaccgaccaa gcgacgccca acctgccatc    2820
acgagatttc gattccaccg ccgccttcta tgaaaggttg gcttcggaa tcgttttccg    2880 ggacgccggc tggatgatcc tccagcgcgg ggatctcatg ctggagttct cgcccacgc    2940 tagcggcgcg ccgccggcc cggtgtgaaa taccgcacag atgcgtaagg agaaaatacc    3000
gcatcaggcg ctcttccgct tcctcgctca ctgactcgct gcgctcggtc gttcggctgc    3060
ggcgagcggt atcagctcac tcaaaggcgg taatacggtt atccacagaa tcaggggata    3120
acgcaggaaa gaacatgtga gcaaaaggcc agcaaaaggc caggaaccgt aaaaaggccg    3180
cgttgctggc gttttccat aggctccgcc cccctgacga gcatcacaaa aatcgacgct    3240
caagtcagag gtggcgaaac ccgacaggac tataaagata ccaggcgttt cccctggaa    3300 gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta aaggacagt atttggtatc tgcgctctgc    3660
tgaagccagt taccttcgga aaagagttg gtagctcttg atccggcaaa caaaccaccg    3720
ctggtagcgg tggttttttt gtttgcaagc agcagattac gcgcagaaaa aaaggatctc    3780
aagaagatcc tttgatcttt tctacggggt ctgacgctca gtggaacgaa aactcacgtt    3840
aagggatttt ggtcatgaga ttatcaaaaa ggatcttcac ctagatcctt ttaaaggccg    3900 gccgcgccg ccatcggcat tttcttttgc gtttttattt gttaactgtt aattgtcctt    3960
gttcaaggat gctgtctttg acaacagatg ttttcttgcc tttgatgttc agcaggaagc    4020
tcggcgcaaa cgttgattgt tgtctgcgt agaatcctct gtttgtcata tagcttgtaa    4080
tcacgacatt gtttcctttc gcttgaggta cagcgaagtg tgagtaagta aaggttacat    4140
cgttaggatc aagatccatt tttaacacaa ggccagtttt gttcagcggc ttgtatgggc    4200
cagttaaaga attagaaaca taaccaagca tgtaaatatc gttagacgta atgccgtcaa    4260
tcgtcatttt tgatccgcgg gagtcagtga acaggtacca tttgccgttc attttaaaga    4320
```

```
cgttcgcgcg ttcaatttca tctgttactg tgttagatgc aatcagcggt ttcatcactt    4380 tttcagtgt gtaatcatcg tttagctcaa tcataccgag agcgccgttt gctaactcag    4440
ccgtgcgttt tttatcgctt tgcagaagtt tttgactttc ttgacggaag aatgatgtgc    4500
ttttgccata gtatgctttg ttaaataaag attcttcgcc ttggtagcca tcttcagttc    4560
cagtgtttgc ttcaaatact aagtatttgt ggcctttatc ttctacgtag tgaggatctc    4620
tcagcgtatg gttgtcgcct gagctgtagt tgccttcatc gatgaactgc tgtacatttt    4680
gatacgtttt tccgtcaccg tcaaagattg atttataatc ctctacaccg ttgatgttca    4740
aagagctgtc tgatgctgat acgttaactt gtgcagttgt cagtgtttgt ttgccgtaat    4800
gtttaccgga gaaatcagtg tagaataaac ggatttttcc gtcagatgta aatgtggctg    4860
aacctgacca ttcttgtgtt tggtctttta ggatagaatc atttgcatcg aatttgtcgc    4920
tgtctttaaa gacgcggcca gcgttttttcc agctgtcaat agaagtttcg ccgacttttt    4980
gatagaacat gtaaatcgat gtgtcatccg cattttagg atctccggct aatgcaaaga    5040
cgatgtggta gccgtgatag tttgcgacag tgccgtcagc gttttgtaat ggccagctgt    5100
cccaaacgtc caggcctttt gcagaagaga tattttaat tgtggacgaa tcaaattcag    5160
aaacttgata tttttcattt tttgctgtt cagggatttg cagcatatca tggcgtgtaa    5220
tatgggaaat gccgtatgtt tccttatatg gcttttggtt cgtttctttc gcaaacgctt    5280
gagttgcgcc tcctgccagc agtgcggtag taaaggttaa tactgttgct tgttttgcaa    5340 acttttgat gttcatcgtt catgtctcct ttttatgta ctgtgttagc ggtctgcttc    5400
ttccagccct cctgtttgaa gatggcaagt tagttacgca caataaaaaa agacctaaaa    5460
tatgtaaggg gtgacgccaa agtatacact ttgcccttta cacattttag gtcttgcctg    5520
ctttatcagt aacaaacccg cgcgatttac ttttcgacct cattctatta gactctcgtt    5580
tggattgcaa ctggtctatt ttcctctttt gtttgataga aaatcataaa aggatttgca    5640
gactacgggc ctaaagaact aaaaaatcta tctgtttctt ttcattctct gtatttttta    5700
tagtttctgt tgcatgggca taaagttgcc ttttttaatca caattcagaa aatatcataa    5760
tatctcattt cactaaataa tagtgaacgg caggtatatg tgatgggtta aaaaggatcg    5820
gcggccgctc gatttaaatc tcgagaggcc tgacgtcggg                         5860
```

<210> SEQ ID NO 69
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Old38

<400> SEQUENCE: 69
acatccatgg tggccgttac cctgcgaat                                      29

<210> SEQ ID NO 70
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Old 39

<400> SEQUENCE: 70

```
tgtatgtcct cctggacttc                                                 20

<210> SEQ ID NO 71
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Old40

<400> SEQUENCE: 71
gaagtccagg aggacataca atgaccaaca tccgcgtagc                           40

<210> SEQ ID NO 72
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Old 37

<400> SEQUENCE: 72
gaaaccacac tgtttccttg c                                               21

<210> SEQ ID NO 73
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Old 32

<400> SEQUENCE: 73
atcaacgcgt cgacaccaca tcatcaatca c                                    31

<210> SEQ ID NO 74
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: Old33

<400> SEQUENCE: 74
atcaccatgg gttcttgtaa tcctccaaaa ttg                                  33

<210> SEQ ID NO 75
<211> LENGTH: 6187
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: internal designation: pCIS Peftu ddh (pCLiK int
      sacB Peftu ddh)

<400> SEQUENCE: 75
tcgagctaaa ttagacgtcg cgtgcgatca gatcgtccaa gttctctggg gagagcaggt      60
atggagcaac ttcgaggacg gtgaaagctc cgctttggcc ctgctgcttc atgcggtgag     120
```

```
ctgcgcgacc gaaagcgatc tgtgaggaag cggtgaaatc tgggtttcgg tccagcttga    180
ggatgtattc cacggtgtgg ttgaagccac cggtgtcgcc ggtggtaatc acgtggccac    240
cgtgtggcat gccggtgtgc tcggagtcga aggttgcttc gtcgatgaag ttgacttcga    300
cttcgtagcc aacgaagtaa tcaggcatgg tgcggatgtc gttttcgatg cgctcgtgat    360
cggccgcgtc ggcaaccacg aagcattggc gcttgtgggt ttgctttccg gtaaggtcgc    420
cggcttcgcc gcggcgggcc ttttccaggg cgtcttcgga tgggagggtg tactggactg    480
ccttttgaac gccagggatg cgtcgcaaag catcggagtg gccctgtgac aaacctgggc    540
cccagaaggt gtgctgctgg tgctcggcta agactgccgc tgcgtagacg cggttgatgg    600
agaacattcc tggatcccag ccggtagaga ccagtgcaac gttgccggct gcggtggcgg    660
cttcgttcat gacctggcgg tggcgtggga tgtcgcggtg gttgtcgtag gtgtctacgg    720
tgcaggcgaa ctgcgcgaac tttggtgcct gctcagggat gtcggtggcg gagcccatgc    780
acaggaacag cacgtccacg tcgtcggcgt gcttgtccac gtcggcgaca tcaaagactg    840
gcgtctttgt gtcgagggtg gcccggcgcg agaagattcc tacaaggtcc atgtcgggct    900
gcttggcaat aagcttttcg acgctgcgtc ccaggtttcc gtagcccacg atagctacgc    960
ggatgttggt cattgtatgt cctcctggac ttcgtggtgg ctacgacttt cgcagccacg    1020
aattggtttt gctttcactg tgataagcag cctggaagac tgagcacaca gatctagcgc    1080
attacaaaat gtgccagtta ctgaatccta agggcaacgg cgttgatttt caaactacca    1140
gctaccctgt ggacattcgc agggtaacgg ccaccatggg ttcttgtaat cctccaaaat    1200
tgtggtggca ctgtcctggt cgagcttacc gagatgcata cttagatgat gattcaggga    1260
catctctttc atcaggaccg aaagcgaacg tttcgtattg ttgagccttt tggttccacc    1320
acggatgcgc tgatctattt tcatggctcc cagcagtcag gatctgtggg gcgcagcttc    1380
accaacagga cttttgatcc gttgccgttc atggtggttt atccggatgg ggtggatcag    1440
cattggaatg atgcgcggtt gggtttggat gaaaataccc gccatttagg cattgatgat    1500
gtggggttct tgtaaaaact cgccacgcac ttgggcaaca cgtatggcat caagaggatc    1560
tttattgttg gctattccaa cggtgggcag atggtgttgc ggctcatgca tgaggttccc    1620
aagatgctca gtggcgctgc aaccattgca tccaacatgc cagttgcaga gaatacgctg    1680
ccgcaggtga aaaccttcaa gacacatccg gtgccttatt ggcgatggc tggaactgcc    1740 gatacttttt caccgtatga gggtggcgat gccggtattg gtcgcgaaca ccgccgtggc    1800
gtgggcatgt ccgcctttga ttcagctgcc tatattgccg cccgaaacgg actgaccgaa    1860
caccgccacg acgtgattga tgatgtggtg tcgacgcgtc atatgactag ttcggaccta    1920
gggatatcgt cgacatcgat gctcttctgc gttaattaac aattgggatc ctctagaccc    1980
gggatttaaa tcgctagcgg gctgctaaag gaagcggaac acgtagaaag ccagtccgca    2040
gaaacggtgc tgaccccgga tgaatgtcag ctactgggct atctggacaa gggaaaacgc    2100
aagcgcaaag agaaagcagg tagcttgcag tgggcttaca tggcgatagc tagactgggc    2160
ggttttatgg acagcaagcg aaccggaatt gccagctggg gcgccctctg gtaaggttgg    2220
gaagccctgc aaagtaaact ggatggcttt cttgccgcca aggatctgat ggcgcagggg    2280
atcaagatct gatcaagaga caggatgagg atcgtttcgc atgattgaac aagatggatt    2340
gcacgcaggt tctccggccg cttgggtgga gaggctattc ggctatgact gggcacaaca    2400
gacaatcggc tgctctgatg ccgccgtgtt ccggctgtca gcgcagggc gcccggttct    2460 ttttgtcaag accgacctgt ccggtgccct gaatgaactg caggacgagg cagcgcggct    2520
```

```
atcgtggctg gccacgacgg gcgttccttg cgcagctgtg ctcgacgttg tcactgaagc    2580
gggaagggac tggctgctat tgggcgaagt gccggggcag gatctcctgt catctcacct    2640
tgctcctgcc gagaaagtat ccatcatggc tgatgcaatg cggcggctgc atacgcttga    2700
tccggctacc tgcccattcg accaccaagc gaaacatcgc atcgagcgag cacgtactcg    2760
gatggaagcc ggtcttgtcg atcaggatga tctggacgaa gagcatcagg gctcgcgcc    2820 agccgaactg ttcgccaggc tcaaggcgcg catgcccgac ggcgaggatc tcgtcgtgac    2880
ccatggcgat gcctgcttgc cgaatatcat ggtggaaaat ggccgctttt ctggattcat    2940
cgactgtggc cggctgggtg tggcggaccg ctatcaggac atagcgttgg ctacccgtga    3000
tattgctgaa gagcttggcg gcgaatgggc tgaccgcttc ctcgtgcttt acggtatcgc    3060
cgctcccgat tcgcagcgca tcgccttcta tcgccttctt gacgagttct tctgagcggg    3120
actctggggt tcgaaatgac cgaccaagcg acgcccaacc tgccatcacg agatttcgat    3180
tccaccgccg ccttctatga aaggttgggc ttcggaatcg ttttccggga cgccggctgg    3240
atgatcctcc agcgcgggga tctcatgctg gagttcttcg cccacgctag cggcgcgccg    3300 gccgcccgg tgtgaaatac cgcacagatg cgtaaggaga aaataccgca tcaggcgctc    3360
ttccgcttcc tcgctcactg actcgctgcg ctcggtcgtt cggctgcggc gagcggtatc    3420
agctcactca aaggcggtaa tacggttatc cacagaatca ggggataacg caggaaagaa    3480
catgtgagca aaaggccagc aaaaggccag gaaccgtaaa aaggccgcgt tgctggcgtt    3540
tttccatagg ctccgccccc ctgacgagca tcacaaaaat cgacgctcaa gtcagaggtg    3600
gcgaaacccg acaggactat aaagatacca ggcgtttccc cctggaagct ccctcgtgcg    3660
ctctcctgtt ccgaccctgc cgcttaccgg atacctgtcc gcctttctcc cttcgggaag    3720
cgtggcgctt tctcatagct cacgctgtag gtatctcagt tcggtgtagg tcgttcgctc    3780
caagctgggc tgtgtgcacg aaccccccgt tcagcccgac cgctgcgcct tatccggtaa    3840
ctatcgtctt gagtccaacc cggtaagaca cgacttatcg ccactggcag cagccactgg    3900
taacaggatt agcagagcga ggtatgtagg cggtgctaca gagttcttga agtggtggcc    3960
taactacggc tacactagaa ggacagtatt tggtatctgc gctctgctga agccagttac    4020
cttcggaaaa agagttggta gctcttgatc cggcaaacaa accaccgctg gtagcggtgg    4080
tttttttgtt tgcaagcagc agattacgcg cagaaaaaaa ggatctcaag aagatccttt    4140
gatcttttct acggggtctg acgctcagtg gaacgaaaac tcacgttaag ggattttggt    4200
catgagatta tcaaaaagga tcttcaccta gatccttta aaggccggcc gcggccgcca    4260
tcggcatttt cttttgcgtt tttatttgtt aactgttaat tgtccttgtt caaggatgct    4320
gtctttgaca acagatgttt tcttgccttt gatgttcagc aggaagctcg gcgcaaacgt    4380
tgattgtttg tctgcgtaga atcctctgtt tgtcatatag cttgtaatca cgacattgtt    4440
tcctttcgct tgaggtacag cgaagtgtga gtaagtaaag gttacatcgt taggatcaag    4500 atccatttt aacacaaggc cagttttgtt cagcggcttg tatgggccag ttaaagaatt    4560
agaaacataa ccaagcatgt aaatatcgtt agacgtaatg ccgtcaatcg tcattttga    4620 tccgcgggag tcagtgaaca ggtaccattt gccgttcatt ttaaagacgt tcgcgcgttc    4680
aatttcatct gttactgtgt tagatgcaat cagcggtttc atcactttt tcagtgtgta    4740 atcatcgttt agctcaatca taccgagagc gccgtttgct aactcagccg tgcgtttttt    4800
atcgctttgc agaagttttt gactttcttg acggaagaat gatgtgcttt tgccatagta    4860
tgctttgtta aataaagatt cttcgccttg gtagccatct tcagttccag tgtttgcttc    4920
```

-continued

```
aaatactaag tatttgtggc ctttatcttc tacgtagtga ggatctctca gcgtatggtt    4980
gtcgcctgag ctgtagttgc cttcatcgat gaactgctgt acattttgat acgtttttcc    5040
gtcaccgtca aagattgatt tataatcctc tacaccgttg atgttcaaag agctgtctga    5100
tgctgatacg ttaacttgtg cagttgtcag tgtttgtttg ccgtaatgtt taccggagaa    5160
atcagtgtag aataaacgga ttttttccgtc agatgtaaat gtggctgaac ctgaccattc    5220
ttgtgtttgg tcttttagga tagaatcatt tgcatcgaat ttgtcgctgt ctttaaagac    5280
gcggccagcg ttttttccagc tgtcaataga agtttcgccg acttttttgat agaacatgta    5340 aatcgatgtg tcatccgcat ttttaggatc tccggctaat gcaaagacga tgtggtagcc    5400
gtgatagttt gcgacagtgc cgtcagcgtt ttgtaatggc cagctgtccc aaacgtccag    5460
gccttttgca gaagagatat ttttaattgt ggacgaatca aattcagaaa cttgatattt    5520 ttcattttttt tgctgttcag ggatttgcag catatcatgg cgtgtaatat gggaaatgcc    5580
gtatgtttcc ttatatggct tttggttcgt ttctttcgca aacgcttgag ttgcgcctcc    5640
tgccagcagt gcggtagtaa aggttaatac tgttgcttgt tttgcaaact ttttgatgtt    5700
catcgttcat gtctccttttt ttatgtactg tgttagcggt ctgcttcttc cagccctcct    5760
gtttgaagat ggcaagttag ttacgcacaa taaaaaaaga cctaaaatat gtaaggggtg    5820
acgccaaagt atacactttg ccctttacac attttaggtc ttgcctgctt tatcagtaac    5880
aaacccgcgc gatttacttt tcgacctcat tctattagac tctcgtttgg attgcaactg    5940
gtctattttc ctcttttgtt tgatagaaaa tcataaagg atttgcagac tacgggccta    6000
aagaactaaa aaatctatct gtttctttc attctctgta ttttttatag tttctgttgc    6060
atgggcataa agttgccttt ttaatcacaa ttcagaaaat atcataatat ctcatttcac    6120
taaataatag tgaacggcag gtatatgtga tgggttaaaa aggatcggcg gccgctcgat    6180
ttaaatc                                                              6187
```

<210> SEQ ID NO 76
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: CK461

<400> SEQUENCE: 76
cctgacgtcg caatataggc agctgaatc                                        29

<210> SEQ ID NO 77
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: CK466

<400> SEQUENCE: 77
gcccaattgg ttcttgtaat cctccaaaa                                        29

<210> SEQ ID NO 78
<211> LENGTH: 26
<212> TYPE: DNA
<213> ORGANISM: Artificial Sequence

```
<220> FEATURE:
<223> OTHER INFORMATION: Primer
<220> FEATURE:
<221> NAME/KEY: misc_feature
<223> OTHER INFORMATION: internal designation: CK426

<400> SEQUENCE: 78
cgccaattgt cgagggccgt taccct                                        26

<210> SEQ ID NO 79
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: CK463

<400> SEQUENCE: 79
gctacgcgga tgttggtcat gggtaaaaaa tcctttcgta                          40

<210> SEQ ID NO 80
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal designation: CK464

<400> SEQUENCE: 80
tacgaaagga tttttacccc atgaccaaca tccgcgtagc                          40

<210> SEQ ID NO 81
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal desigation: CK467

<400> SEQUENCE: 81
agacccgggt tagacgtcgc gtgcgatca                                      29

<210> SEQ ID NO 82
<211> LENGTH: 6233
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<223> OTHER INFORMATION: internal designation: pCIS PeftuPsod ddh =
      pClik int sacB PeftuPs od ddh

<400> SEQUENCE: 82
gggatttaaa tcgctagcgg gctgctaaag gaagcggaac acgtagaaag ccagtccgca    60
gaaacggtgc tgaccccgga tgaatgtcag ctactgggct atctggacaa gggaaaacgc   120
aagcgcaaag agaaagcagg tagcttgcag tgggcttaca tggcgatagc tagactgggc   180
ggttttatgg acagcaagcg aaccggaatt gccagctggg gcgccctctg gtaaggttgg   240
gaagccctgc aaagtaaact ggatggcttt cttgccgcca aggatctgat ggcgcagggg   300
atcaagatct gatcaagaga caggatgagg atcgtttcgc atgattgaac aagatggatt   360
```

```
gcacgcaggt tctccggccg cttgggtgga gaggctattc ggctatgact gggcacaaca      420
gacaatcggc tgctctgatg ccgccgtgtt ccggctgtca gcgcaggggc gcccggttct      480
ttttgtcaag accgacctgt ccggtgccct gaatgaactg caggacgagg cagcgcggct      540
atcgtggctg gccacgacgg gcgttccttg cgcagctgtg ctcgacgttg tcactgaagc      600
gggaagggac tggctgctat tgggcgaagt gccggggcag gatctcctgt catctcacct      660
tgctcctgcc gagaaagtat ccatcatggc tgatgcaatg cggcggctgc atacgcttga      720
tccggctacc tgcccattcg accaccaagc gaaacatcgc atcgagcgag cacgtactcg      780
gatggaagcc ggtcttgtcg atcaggatga tctggacgaa gagcatcagg gctcgcgcc       840 agccgaactg ttcgccaggc tcaaggcgcg catgcccgac ggcgaggatc tcgtcgtgac      900
ccatggcgat gcctgcttgc cgaatatcat ggtggaaaat ggccgctttt ctggattcat      960
cgactgtggc cggctgggtg tggcggaccg ctatcaggac atagcgttgg ctacccgtga     1020
tattgctgaa gagcttggcg gcgaatgggc tgaccgcttc ctcgtgcttt acggtatcgc     1080
cgctcccgat tcgcagcgca tcgccttcta tcgccttctt gacgagttct tctgagcggg     1140
actctggggt tcgaaatgac cgaccaagcg acgcccaacc tgccatcacg agatttcgat     1200
tccaccgccg ccttctatga aaggttgggc ttcggaatcg ttttccggga cgccggctgg     1260
atgatcctcc agcgcgggga tctcatgctg gagttcttcg cccacgctag cggcgcgccg     1320
gccggcccgg tgtgaaatac cgcacagatg cgtaaggaga aaataccgca tcaggcgctc     1380
ttccgcttcc tcgctcactg actcgctgcg ctcggtcgtt cggctgcggc gagcggtatc     1440
agctcactca aaggcggtaa tacggttatc cacagaatca ggggataacg caggaaagaa     1500
catgtgagca aaaggccagc aaaaggccag gaaccgtaaa aaggccgcgt tgctggcgtt     1560
tttccatagg ctccgccccc ctgacgagca tcacaaaaat cgacgctcaa gtcagaggtg     1620
gcgaaacccg acaggactat aaagatacca ggcgtttccc cctggaagct ccctcgtgcg     1680
ctctcctgtt ccgaccctgc cgcttaccgg atacctgtcc gcctttctcc cttcgggaag     1740
cgtggcgctt tctcatagct cacgctgtag gtatctcagt tcggtgtagg tcgttcgctc     1800
caagctgggc tgtgtgcacg aaccccccgt tcagcccgac cgctgcgcct tatccggtaa     1860
ctatcgtctt gagtccaacc cggtaagaca cgacttatcg ccactggcag cagccactgg     1920
taacaggatt agcagagcga ggtatgtagg cggtgctaca gagttcttga agtggtggcc     1980
taactacggc tacactagaa ggacagtatt tggtatctgc gctctgctga agccagttac     2040
cttcggaaaa agagttggta gctcttgatc cggcaaacaa accaccgctg gtagcggtgg     2100
tttttttgtt tgcaagcagc agattacgcg cagaaaaaaa ggatctcaag aagatccttt     2160
gatcttttct acggggtctg acgctcagtg gaacgaaaac tcacgttaag ggattttggt     2220
catgagatta tcaaaaagga tcttcaccta gatccttta aaggccgcc gcggccgcca      2280 tcggcatttt cttttgcgtt tttatttgtt aactgttaat tgtccttgtt caaggatgct     2340
gtctttgaca acagatgttt tcttgccttt gatgttcagc aggaagctcg gcgcaaacgt     2400
tgattgtttg tctgcgtaga atcctctgtt tgtcatatag cttgtaatca cgacattgtt     2460
tcctttcgct tgaggtacag cgaagtgtga gtaagtaaag gttacatcgt taggatcaag     2520
atccattttt aacacaaggc cagttttgtt cagcggcttg tatgggccag ttaaagaatt     2580
agaaacataa ccaagcatgt aaatatcgtt agacgtaatg ccgtcaatcg tcattttga      2640 tccgcgggag tcagtgaaca ggtaccattt gccgttcatt ttaaagacgt tcgcgcgttc     2700
aatttcatct gttactgtgt tagatgcaat cagcggtttc atcactttt tcagtgtgta     2760
```

```
atcatcgttt agctcaatca taccgagagc gccgtttgct aactcagccg tgcgtttttt    2820
atcgctttgc agaagttttt gactttcttg acggaagaat gatgtgcttt tgccatagta    2880
tgctttgtta aataaagatt cttcgccttg gtagccatct tcagttccag tgtttgcttc    2940
aaatactaag tatttgtggc ctttatcttc tacgtagtga ggatctctca gcgtatggtt    3000
gtcgcctgag ctgtagttgc cttcatcgat gaactgctgt acattttgat acgttttcc     3060 gtcaccgtca aagattgatt tataatcctc tacaccgttg atgttcaaag agctgtctga    3120
tgctgatacg ttaacttgtg cagttgtcag tgtttgtttg ccgtaatgtt taccggagaa    3180
atcagtgtag aataaacgga ttttccgtc  agatgtaaat gtggctgaac ctgaccattc    3240
ttgtgtttgg tcttttagga tagaatcatt tgcatcgaat ttgtcgctgt ctttaaagac    3300
gcggccagcg ttttccagc  tgtcaataga agtttcgccg acttttgat  agaacatgta    3360 aatcgatgtg tcatccgcat ttttaggatc tccggctaat gcaaagacga tgtggtagcc    3420
gtgatagttt gcgacagtgc cgtcagcgtt ttgtaatggc cagctgtccc aaacgtccag    3480
gccttttgca gaagagatat ttttaattgt ggacgaatca aattcagaaa cttgatattt    3540 ttcattttt  tgctgttcag ggatttgcag catatcatgg cgtgtaatat gggaaatgcc    3600
gtatgtttcc ttatatggct tttggttcgt tctttcgca  aacgcttgag ttgcgcctcc    3660
tgccagcagt gcggtagtaa aggttaatac tgttgcttgt tttgcaaact ttttgatgtt    3720
catcgttcat gtctcctttt ttatgtactg tgttagcggt ctgcttcttc cagccctcct    3780
gtttgaagat ggcaagttag ttacgcacaa taaaaaaga  cctaaaatat gtaaggggtg    3840
acgccaaagt atacactttg cccttacac  attttaggtc ttgcctgctt tatcagtaac    3900
aaacccgcgc gatttacttt tcgacctcat tctattagac tctcgtttgg attgcaactg    3960
gtctattttc ctcttttgtt tgatagaaaa tcataaaagg atttgcagac tacgggccta    4020
aagaactaaa aaatctatct gtttcttttc attctctgta ttttttatag tttctgttgc    4080
atgggcataa agttgccttt ttaatcacaa ttcagaaaat atcataatat ctcatttcac    4140
taaataatag tgaacggcag gtatatgtga tgggttaaaa aggatcggcg gccgctcgat    4200
ttaaatctcg agaggcctga cgtcgcaata taggcagctg aatcaaaggc ggacatgccc    4260
acgccacggc ggtgttcgcg accaataccg gcatcgccac cctcatacgg tgaaaaagta    4320
tcggcagttc cagccatcgc caaataaggc accggatgtg tcttgaaggt tttcacctgc    4380
ggcagcgtat tctctgcaac tggcatgttg gatgcaatgg ttgcagcgcc actgagcatc    4440
ttgggaacct catgcatgag ccgcaacacc atctgcccac cgttggaata gccaacaata    4500
aagatcctct tgatgccata cgtgttgccc aagtgcgtgg cgagttttac aaagaacccc    4560
acatcatcaa tgcctaaatg gcgggtattt tcatccaaac ccaaccgcgc atcattccaa    4620
tgctgatcca ccccatccgg ataaaccacc atgaacggca acggatcaaa agtcctgttg    4680
gtgaagctgc gccccacaga tcctgactgc tgggagccat gaaaatagat cagcgcatcc    4740
gtggtggaac caaaaggctc aacaatacga aacgttcgct tcggtcctg  atgaaagaga    4800 tgtccctgaa tcatcatcta agtatgcatc tcggtaagct cgaccaggac agtgccacca    4860 caatttgga  ggattacaag aaccaattgt cgagggccgt taccctgcga atgtccacag    4920
ggtagctggt agtttgaaaa tcaacgccgt tgcccttagg attcagtaac tggcacattt    4980
tgtaatgcgc tagatctgtg tgctcagtct tccaggctgc ttatcacagt gaaagcaaaa    5040
ccaattcgtg gctgcgaaag tcgtagccac actagtagct gccaattatt ccgggcttgt    5100
gacccgctac ccgataaata ggtcggctga aaaatttcgt tgcaatatca acaaaaaggc    5160
```

```
ctatcattgg gaggtgtcgc accaagtact tttgcgaagc gccatctgac ggattttcaa    5220
aagatgtata tgctcggtgc ggaaacctac gaaaggattt tttacccatg accaacatcc    5280
gcgtagctat cgtgggctac ggaaacctgg gacgcagcgt cgaaaagctt attgccaagc    5340
agcccgacat ggaccttgta ggaatcttct cgcgccgggc caccctcgac acaaagacgc    5400
cagtctttga tgtcgccgac gtggacaagc acgccgacga cgtggacgtg ctgttcctgt    5460
gcatgggctc cgccaccgac atccctgagc aggcaccaaa gttcgcgcag ttcgcctgca    5520
ccgtagacac ctacgacaac caccgcgaca tcccacgcca ccgccaggtc atgaacgaag    5580
ccgccaccgc agccggcaac gttgcactgg tctctaccgg ctgggatcca ggaatgttct    5640
ccatcaaccg cgtctacgca gcggcagtct tagccgagca ccagcagcac accttctggg    5700
gcccaggttt gtcacagggc cactccgatg ctttgcgacg catccctggc gttcaaaagg    5760
cagtccagta caccctccca tccgaagacg ccctggaaaa ggcccgccgc ggcgaagccg    5820
gcgaccttac cggaaagcaa acccacaagc gccaatgctt cgtggttgcc gacgcggccg    5880
atcacgagcg catcgaaaac gacatccgca ccatgcctga ttacttcgtt ggctacgaag    5940
tcgaagtcaa cttcatcgac gaagcaacct tcgactccga gcacaccggc atgccacacg    6000
gtggccacgt gattaccacc ggcgacaccg gtggcttcaa ccacaccgtg aatacatcc     6060 tcaagctgga ccgaaaccca gatttcaccg cttcctcaca gatcgctttc ggtcgcgcag    6120
ctcaccgcat gaagcagcag ggccaaagcg gagctttcac cgtcctcgaa gttgctccat    6180
acctgctctc cccagagaac ttggacgatc tgatcgcacg cgacgtctaa ccc           6233

<210> SEQ ID NO 83
<211> LENGTH: 7
<212> TYPE: DNA
<213> ORGANISM: Corynebacterium glutamicum
<220> FEATURE:
<221> NAME/KEY: misc_feature
<223> OTHER INFORMATION: ribosome binding sequence

<400> SEQUENCE: 83 aggagga                                                                 7

<210> SEQ ID NO 84
<211> LENGTH: 1365
<212> TYPE: DNA
<213> ORGANISM: Corynebacterium glutamicum
<220> FEATURE:
<221> NAME/KEY: misc_feature
<223> OTHER INFORMATION: RAX077

<400> SEQUENCE: 84
atgaatgatg agaatattca agctccaac tatcagccat tcccgagttt tgacgattgg        60
aaacagatcg aggtgtcgct cttagatgtc atcgaatcct cacgccattt ttctgatttg     120
aaagatagca ctgatcgttc tgcgttagat gctgcgctag agagagcaaa aagagctgcc     180
gcagttgata ccaatgccat agaaggaatc ttccaaactg atcgcggttt tacccataca     240
gttgcaacgc aggtaggggc ttgggagcaa caaatggcga tgaaaggcaa acatgttaag    300
cctgcgtttg acgatactct agaaggcttt gagtatgttc tcgatgcagt aactggtaga    360
actccaatct ctcagcaatg gattagaaat ttgcacgccg tcattctgcg gagccaagaa    420
agccacgagg ttttttacagc cgttggagtc caaaatcagg cgcttcagaa aggcgagtat    480
aaaactcagc caaatagtcc acagcgctca gatggatctg tacatgcata cgccccagtt    540
gaagatactc ctgctgaaat ggctagattt atttcagaac ttgaatctaa ggaattctta    600
```

-continued

```
gcagccgaga aggttattca agctgcctat gcccactatg ctttcgtatg tattcatcct      660
tttgcagatg ggaatggacg agttgcacga gccttggcta gtgtttttct atacaaagat      720
cctggtgtcc ctctcgtaat ctaccaagat caacgcagag attacatcca tgctctagaa      780
gcagcggaca agaataaccc gctcctgctg attagattct ttgctgaacg agtgaccgat      840
actattaact ctattatcgt tgatctcact accccgatcg cgggtaaatc tggttcggct      900
aagctttcgg atgcgctacg ccccactcgc gtattaccag aattacatga tgctgcacat      960
aggctccaag aaagtttatt tacagaaatc cgatctcgat tggatgaaga aggaaaaagg     1020
aatgggttgg agtttctact tcaacggatt tttatcggtt ccccattcaa tctgccagag     1080
ggctataacg ctttccctga tagctattgt ctgaccttag ctttcaatag caactctcca     1140
aaacaaatct tccacccgct atccatagta atagcagctc gagatgggaa aagagcgagc     1200
agcgacctcg tggcagctac ttctattgga tacaactttc acgcttacgg acgtgaagtc     1260
gagcctgttg ttactgaaag ctttcgagaa cgtgtgaaaa tttacgccga cgggattgta     1320
gatcacttct taaccgaact ggctaaaaag tttcaacaga attaa                     1365
```